(12) United States Patent
Johansson et al.

(10) Patent No.: US 7,943,639 B2
(45) Date of Patent: May 17, 2011

(54) COMPOUNDS

(75) Inventors: Gary Johansson, Uppsala (SE); Annika Jenmalm-Jensen, Uppsala (SE); Katarina Beierlein, Uppsala (SE)

(73) Assignee: Proximagen Limited (GB)

( * ) Notice: Subject to any disclaimer, the term of this patent is extended or adjusted under 35 U.S.C. 154(b) by 2083 days.

(21) Appl. No.: 10/465,034

(22) Filed: Jun. 19, 2003

(65) Prior Publication Data
US 2004/0024210 A1 Feb. 5, 2004

Related U.S. Application Data

(60) Provisional application No. 60/406,120, filed on Aug. 26, 2002, provisional application No. 60/434,010, filed on Dec. 17, 2002, provisional application No. 60/464,701, filed on Apr. 23, 2003.

(30) Foreign Application Priority Data

| Jun. 20, 2002 | (SE) | 0201925 |
| Jul. 11, 2002 | (SE) | 0202181 |
| Oct. 1, 2002 | (SE) | 0202908 |
| Feb. 10, 2003 | (SE) | 0300357 |

(51) Int. Cl.
*A61K 31/47* (2006.01)
*C07D 215/00* (2006.01)

(52) U.S. Cl. ........ 514/312; 546/153
(58) Field of Classification Search ........ 546/153; 544/363; 514/312, 252.13
See application file for complete search history.

(56) References Cited

U.S. PATENT DOCUMENTS

| 4,808,595 A | 2/1989 | Hoffman, Jr. ......... 514/302 |
| 2003/0158202 A1 | 8/2003 | Caldirola et al. |

FOREIGN PATENT DOCUMENTS

| EP | 0 701 819 | 3/1996 |
| EP | 0 815 861 | 1/1998 |
| EP | 1 020 445 | 7/2000 |
| EP | 1020445 A1 * | 7/2000 |
| GB | 947606 | 1/1964 |
| WO | WO 84/01151 | 3/1984 |
| WO | WO 94/21619 | 9/1994 |
| WO | WO 98/27081 * | 6/1998 |
| WO | WO 99/02502 | 1/1999 |
| WO | WO 99/37623 | 7/1999 |
| WO | WO 99/42465 | 8/1999 |
| WO | WO 00/12073 | 3/2000 |
| WO | WO 00/55159 | 9/2000 |
| WO | WO-01/32646 A2 * | 5/2001 |
| WO | WO 01/32646 A2 | 5/2001 |
| WO | WO 01/32660 A1 | 5/2001 |
| WO | WO 01/85722 | 11/2001 |
| WO | WO 01/96336 | 12/2001 |
| WO | WO 02/32863 | 4/2002 |
| WO | WO 02/092585 | 11/2002 |
| WO | WO 02/098857 | 12/2002 |
| WO | WO 02/100822 | 12/2002 |

OTHER PUBLICATIONS

STN International, file CAPLUS, CAPLUS Accession No. 1970:509549, document No. 73:109549, Werbel, Leslie M. et al: *Synthetic schistosomicides*. . . J. Med. Chem 13(4):592-598, 1970.

Methvin Isaac et al., "6-Bicyclopiperazinyl-1-arylsulfonylindoles and 6-Bicyclopiperidinyl-1-arylsulfonylindoles Derivatives as Novel, Potent, and Selective 5-HT$_6$ Receptor Antagonists", *Bioorganic & Medicinal Chemistry Letters*, 10, pp. 1719-1721 (2000).

* cited by examiner

*Primary Examiner* — Kamal A Saeed
(74) *Attorney, Agent, or Firm* — Fish & Richardson P.C.

(57) ABSTRACT

The present invention relates to compounds of the general formula (I),

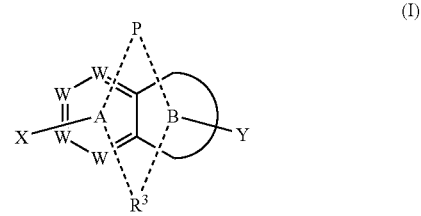

(I)

wherein P is sulfone or sulfonamide; and
A, B, W, X, Y and $R^3$ are as defined in the description;
to pharmaceutical compositions comprising these compounds, and to the use of the compounds for the prophylaxis and treatment of medical conditions relating to obesity, type II diabetes, and/or CNS disorders, to achieve reduction of body weight and of body weight gain.

41 Claims, No Drawings

COMPOUNDS

RELATED APPLICATIONS

This application claims priority to Swedish application number 0201925-5, filed on Jun. 20, 2002, Swedish application number 0202908-0, filed on Oct. 1, 2002, Swedish application number 0202181-4, filed on Jul. 11, 2002, Swedish application number 0300357-1, filed on Feb. 10, 2003, U.S. provisional application No. 60/406,120, filed on Aug. 26, 2002, U.S. provisional application No. 60/434,010, filed on Dec. 17, 2002, and U.S. provisional application No. 60/464,701, filed on Apr. 23, 2003, the contents of which are incorporated herein by reference.

TECHNICAL FIELD

The present invention relates to substituted sulphone and sulphonamide compounds, to pharmaceutical compositions comprising these compounds, and to the use of the compounds for the prophylaxis and treatment of medical conditions relating to obesity, type 2 diabetes, and/or disorders of the central nervous system (CNS), to achieve reduction of body weight and of body weight gain, as well as for cosmetic use.

BACKGROUND ART

Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type 2 diabetes. Searching for compounds, which reduce body weight has been going on for many decades. One line of research has been activation of serotoninergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulates a wide range of physiological and pathological functions, including anxiety, sleep regulation, aggression, feeding and depression. Multiple serotonin receptor subtypes have been identified and cloned. One of these, the $5\text{-HT}_6$ receptor, was cloned by several groups in 1993 (Ruat, M. et al. (1993) Biochem. Biophys. Res. Commun. 193: 268-276; Sebben, M. et al. (1994) NeuroReport 5: 2553-2557). This receptor is positively coupled to adenylyl cyclase and displays affinity for antidepressants such as clozapine. Recently, the effect of $5\text{-HT}_6$ antagonist and $5\text{-HT}_6$ antisense oligonucleotides to reduce food intake in rats has been reported (Bentley, J. C. et al. (1999) Br J Pharmac. Suppl. 126, P66; Bentley, J. C. et al. (1997) J. Psychopharmacol. Suppl. A64, 255; Woolley M. L. et al. (2001) Neuropharmacology).

Compounds with enhanced affinity and selectivity for the $5\text{-HT}_6$ receptor have been identified, e.g. in WO 00/34242 and by Isaac, M. et al. (2000) 6-Bicyclopiperazinyl-1-arylsulfonylindoles and 6-Bicyclopiperidinyl-1-arylsulfonylindoles derivatives as novel, potent and selective $5\text{-HT}_6$ receptor antagonists. Bioorganic & Medicinal Chemistry Letters 10: 1719-1721 (2000).

INFORMATION DISCLOSURE

J. Med. Chem. 1970, 13(4), 592-598 describes N-(4-{[2-(diethylamino)ethyl]amino}-1-naphthyl)amides; N-{5,6,7,8-Tetrahydro-4-[(3-piperidinopropyl)amino]-1-naphthyl}amides and related amides and urea derivatives as schistosomicides.

WO 99/42465 discloses sulphonamides derivatives that bind to the $5\text{-HT}_6$ receptor and that can be used for the treatment of CNS disorders such as anxiety, depression, epilepsy, obsessive compulsive disorders, cognitive disorders, ADHD, anorexia and bulimia schizophrenia, drug abuse.

WO 01/32646 A1 discloses compounds that bind to the $5\text{-HT}_6$ receptor and that are used for the treatment of CNS disorders and which inter alia may be used for the treatment of eating disorders.

WO 99/37623 A2 discloses compounds that bind to the $5\text{-HT}_6$ receptor and that are used for the treatment of CNS disorders and which inter alia may be used for the treatment of eating disorders.

WO 99/42465 A3 discloses compounds that bind to the $5\text{-HT}_6$ receptor and that are used for the treatment of CNS disorders and which inter alia may be used for the treatment of eating disorders.

EP 0 815 861 A1 discloses compounds that bind to the $5\text{-HT}_6$ receptor and that are used for the treatment of CNS disorders.

WO 99/02502 A2 discloses compounds that bind to the $5\text{-HT}_6$ receptor and that are used for the treatment of CNS disorders and which inter alia may be used for the treatment of eating disorders.

WO 98/27081 A1 discloses compounds that bind to the $5\text{-HT}_6$ receptor and that are used for the treatment of CNS disorders and which inter alia may be used for the treatment of eating disorders.

EP 0701819 discloses compounds that bind to the $5\text{-HT}_{1D}$ receptor and that are used for the treatment of CNS disorders and obesity.

U.S. Pat. No. 6,191,141 and WO 01/12629 disclose compounds that bind to the $5\text{-HT}_6$ receptor and that are used for the treatment of CNS disorders.

DISCLOSURE OF THE INVENTION

It has surprisingly been found that the compounds of formula (I) show affinity for the $5\text{-HT}_6$ receptor as antagonists at low nanomolar range. Compounds according to the invention and their pharmaceutically acceptable salts have $5\text{-HT}_6$ receptor antagonist, agonist and partial agonist activity and are believed to be of potential use in the treatment or prophylaxis of obesity and type 2 diabetes, to achieve reduction of body weight and of body weight gain, as well as in the treatment or prophylaxis of disorders of the central nervous system such as anxiety, depression, panic attacks, memory disorders, cognitive disorders, sleep disorders, migraine, anorexia, bulimia, binge disorders, obsessive compulsive disorders, psychoses, Alzheimer's disease, Parkinson's disease, Huntington's chorea and/or schizophrenia, Attention Deficit Hyperactive Disorders (ADHD), drug abuse. The reduction of body weight and of body weight gain (e.g. treating bodyweight disorders) is achieved inter alia by reduction of food intake. As used herein, the term "body weight disorders" refers to the disorders caused by an imbalance between energy intake and energy expenditure, resulting in abnormal body (e.g., excessive) weight. Such body weight disorders include obesity.

Definitions

Unless otherwise stated or indicated, the term "$C_{1-6}$ alkyl" (or "$C_{2-6}$ alkenyl") denotes a straight or branched hydrocarbon chain group having from 1 to 6 carbon atoms (or 2 to 6 carbon atoms). Examples of said lower alkyl include methyl, ethyl, n-propyl, iso-propyl, n-butyl, iso-butyl, sec-butyl, t-butyl and straight- and branched-chain pentyl and hexyl. Alkenyl groups have one or more double carbon-carbon bonds in the chain.

Unless otherwise stated or indicated, the term "$C_{1-6}$ alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term "$C_{1-6}$ alkoxyalkyl" denotes a straight or branched alkoxyalkyl group having from 1 to 6 carbon atoms. Examples of said lower alkoxyalkyl include methoxymethyl, ethoxymethyl, iso-propoxymethyl, n-butoxymethyl, t-butoxyethyl and straight- and branched-chain pentoxymethyl.

The expression "$C_{2-6}$ alkenyl" as used herein refers to straight-chained and branched alkenyl groups containing from 2 to 6 carbon atoms. Typical examples include vinyl, allyl, 2,3-dimethylallyl, 1-butenyl groups, 1-pentenyl, and 1-hexenyl groups.

The expression "$C_{2-6}$ alkynyl" as used herein refers to straight-chained and branched alkynyl groups containing from 2 to 6 carbon atoms. Typical examples include ethynyl, 1-propynyl, 1-butynyl, 1-pentynyl, and 1-hexynyl groups.

Unless otherwise stated or indicated, the term "halogen" shall mean fluorine, chlorine, bromine or iodine.

The term "alkylhalide" refers to an alkyl group substituted with one or more halogen groups (e.g., F, Cl, Br, I).

The term "$C_{3-7}$ cycloalkyl" denotes a cyclic alkyl group having a ring size from $C_3$ to $C_7$, which can be saturated or partially unsaturated. Examples of said cycloalkyl include cyclopropyl, cyclobutyl, cyclopentyl, cyclopentenyl, cyclopentadienyl, cyclohexyl, methylcyclohexyl, cyclohexenyl, cyclohexadienyl, and cycloheptyl.

The term "$C_{5-10}$ cycloalkenyl" denotes a cyclic alkenyl group having a ring size from $C_5$ to $C_{10}$. Examples of said cycloalkenyl include 1-cyclopentyl, 2-cyclopentenyl, 1-cyclohexenyl, 1-cycloheptenyl, 1-cyclooctenyl, 1-cyclononenyl, and 1-cyclodecenyl groups.

The term "heterocyclic" refers to a hydrocarbon ring system containing 4 to 8 ring members that have at least one heteroatom (e.g., S, N, or O) as part of the ring. It includes saturated, unsaturated, aromatic, and nonaromatic heterocycles. Suitable heterocyclic groups include thienyl, furyl, pyridyl, pyrrolidinyl, imidazolyl, pyrazolyl, piperidyl, azepinyl, morpholinyl, pyranyl, dioxanyl, pyridazinyl, pyrimidinyl, and piperazinyl groups.

Unless otherwise stated or indicated, the term "aryl" refers to a hydrocarbon ring system having at least one aromatic ring. Examples of aryl groups include phenyl, cinnamyl, pentalenyl, indenyl, 1-naphthyl, 2-naphthyl, anthryl and phenanthryl.

The term "heteroaryl" refers to a hydrocarbon ring system having at least one aromatic ring which contains at least one heteroatom such as O, N, or S. Examples of heteroaryl groups include furyl, pyrrolyl, thienyl, oxazolyl, imidazolyl, thiazolyl, pyridinyl, pyrimidinyl, quinazolinyl, and indolyl groups.

Compounds of Formula (I)

One object of the present invention is a compound having the general formula (I):

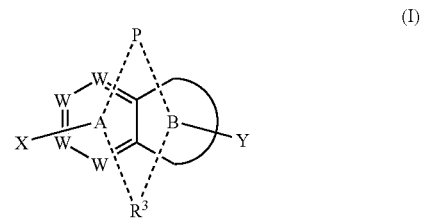

(I)

or a pharmaceutically acceptable salt thereof, wherein:
ring B is

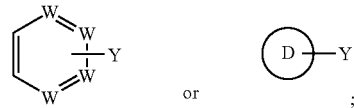

in which D is a five-membered heterocyclic or heteroaryl ring, said heteroaryl ring comprising one or two atoms selected from the group consisting of nitrogen, sulfur and oxygen, with the proviso that when D contains an oxygen atom, D is heteroaryl;

each W is independently —N—, —(CH)—, or —C— provided that not more than three groups W are —N— in both rings A and B together;

P is any one of formula (a), (b) or (c)

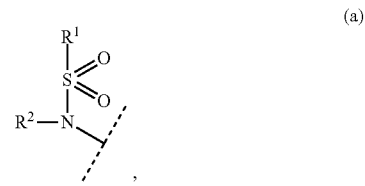

(a)

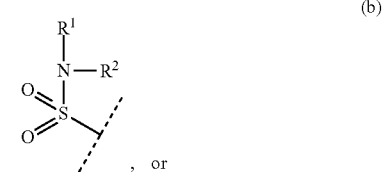

(b)

(c)

wherein x=0, 1, or 2 and y=0, 1, or 2;

and P and $R^3$ can be attached to any carbon atom that allows the substitution in one of either the A- or B-ring, or when ring A contains at least one nitrogen atom and P is (c), then P can also be attached to any nitrogen in ring B that allows the substitution;

the dashed bonds denote that P and $R^3$, respectively, may be attached to either the A or B ring; but each P or $R^3$ may not be simultaneously bound to both rings A and B;

$R^1$ is
- (a) $C_{1-6}$ alkyl,
- (b) $C_{1-6}$ alkoxyalkyl,
- (c) straight-chained or branched $C_{1-6}$ hydroxyalkyl,
- (d) straight-chained or branched $C_{1-6}$ alkylhalides,
- (e) aryl carbonylmethyl,
- (f) $C_{3-7}$ cycloalkyl, which is optionally partially unsaturated,
- (g) $C_{3-7}$ cycloalkyl-$C_{1-6}$ alkyl, wherein the cyclic ring is optionally partially unsaturated, or
- (h) a group Ar;

wherein Ar is
- (a) phenyl,
- (b) 1-naphthyl,
- (c) 2-naphthyl,
- (d) aryl-$C_{1-6}$ alkyl,
- (e) cinnamyl,
- (f) a 5 to 7-membered, optionally aromatic, partially saturated or completely saturated, mono- or bi-cyclic heterocyclic ring, each containing 1 to 4 heteroatoms, selected from oxygen, sulfur, and nitrogen,
- (g) a bicyclic ring system comprising at least one heterocyclic ring according to (f) and a group Ar,
  wherein the group Ar is substituted in one or more positions with
  - (a) H, X or Y, or
  - (b) a 5 to 7-membered, optionally aromatic, partially saturated or completely saturated, heterocyclic ring each containing 1 to 4 heteroatoms selected from oxygen, nitrogen or sulfur;

$R^2$ is
- (a) H,
- (b) $C_{1-6}$ alkyl,
- (c) $C_{2-6}$ alkoxyalkyl,
- (d) straight or branched $C_{1-6}$ hydroxyalkyl, or
- (e) straight or branched $C_{1-6}$ alkylhalides;
- (f) a group Ar, or $R^1$ and $R^2$ are linked to form a group —CH$_2$CH$_2$OCH$_2$CH$_2$— or

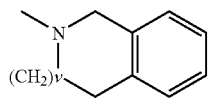

wherein v is 0-2,

X and Y are independently
- (a) H,
- (b) halogen,
- (c) $C_{1-6}$ alkyl,
- (d) $CF_3$,
- (e) hydroxy,
- (f) $C_{1-6}$ alkoxy,
- (g) $C_{2-6}$ alkenyl,
- (h) phenyl,
- (i) phenoxy,
- (j) benzyloxy,
- (k) benzoyl,
- (l) —$OCF_3$,
- (m) —CN,
- (n) straight or branched $C_{1-6}$ hydroxyalkyl,
- (o) straight or branched $C_{1-6}$ alkylhalides,
- (p) —$NH_2$,
- (q) —$NHR^4$,
- (r) —$NR^4R^5$,
- (s) —$NO_2$,
- (t) —$CONR^4R^5$,
- (u) —$NHSO_2R^4$,
- (v) —$NR^4COR^5$,
- (x) —$SO_2NR^4R^5$,
- (z) —C(=O)$R^4$,
- (aa) —$CO_2R^4$,
- (ab) —S(O)$_n R^4$, wherein n is 0, 1, 2 or 3,
- (ac) —S—($C_{1-6}$) alkyl, or
- (ad) —$SCF_3$; and $R^4$ and $R^5$ are independently
- (a) H,
- (b) $C_{1-6}$ alkyl,
- (c) $C_{3-7}$ cycloalkyl, or
- (d) Ar, as defined above for $R^1$;

alternatively, $R^4$ and $R^5$ are linked to form a group —CH$_2$OCH$_2$—, —CH$_2$CH$_2$OCH$_2$CH$_2$— or (CH$_2$)$_{3-5}$;

$R^3$ is a group selected from any one of

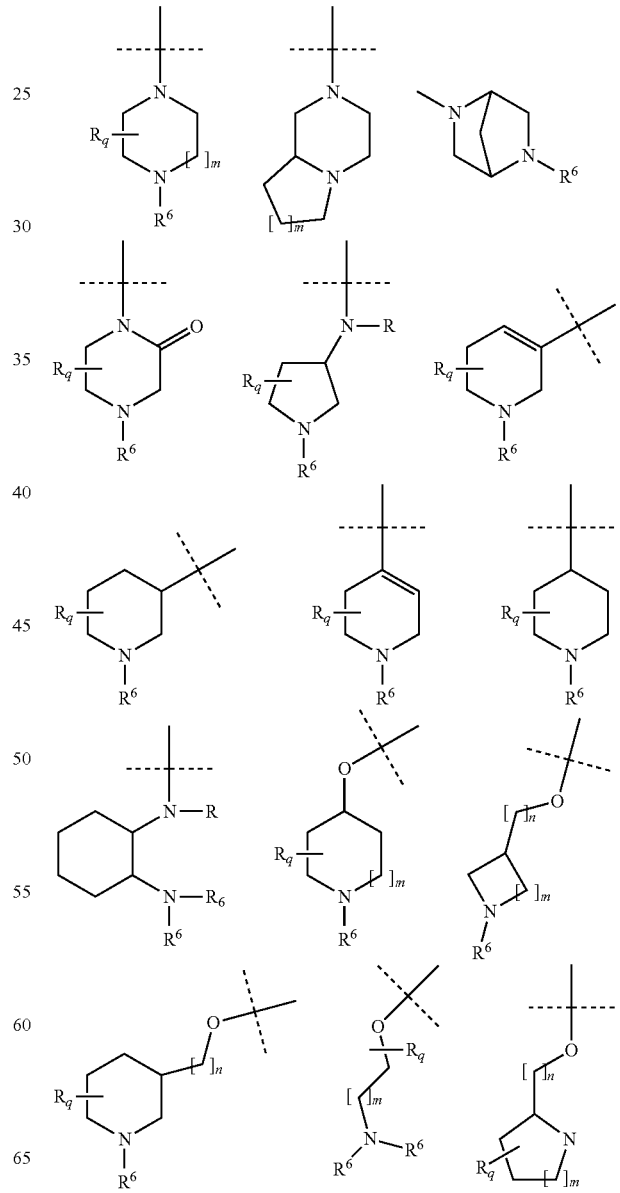

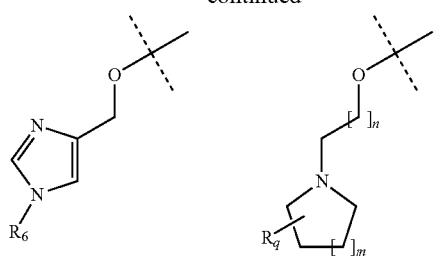
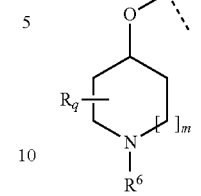
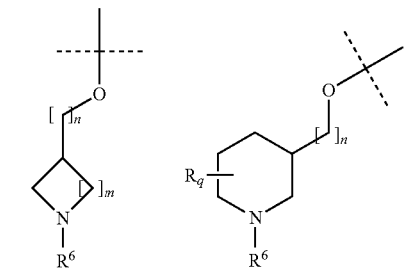

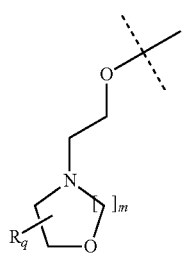
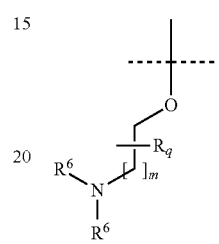
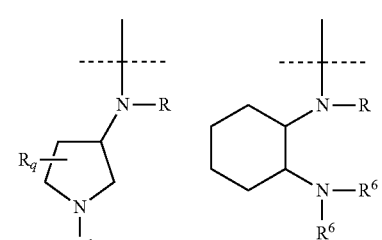

wherein R³ is optionally substituted on each carbon atom that allows the substitution with Rq groups, wherein Rq is independently H, or (C$_{1-6}$) alkyl, and wherein two Rq groups can be present on the same carbon atom simultaneously, wherein q=1, 2, 3, 4, 5 or 6, m=1 or 2, and n=0, 1 or 2;

R is independently (a) H, (b) linear or branched C$_{1-6}$ alkyl, (c) benzyl, (d) —CH$_2$—CH$_2$—OH, or (e) —CH$_2$—CH$_2$—O—C$_{1-6}$ alkyl;

P and R³ can be attached to the same ring or to different rings of rings A and B;

provided that when P is

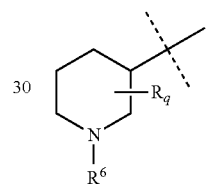
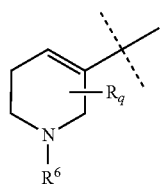

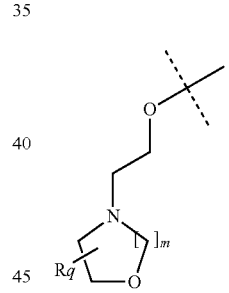
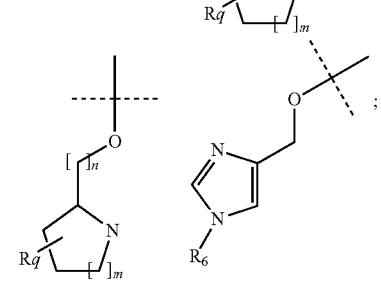

(a)

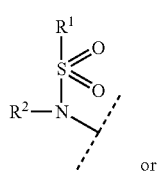

or (b)

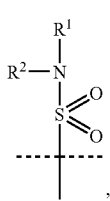

and P and R³ both are attached to ring A in the meta- or para-position relative to one another then R³ is selected from any one of when ring B is

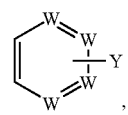

and P is (a)

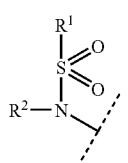

then P and R³ are simultaneously attached to the same ring A or B;
when ring B is

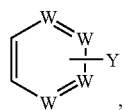

and P is

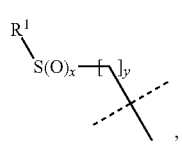

wherein y=0 then P and R³ are attached to the different rings of rings A and B;
when the ring system A+B is benzofurane or benzothiophene, and P is

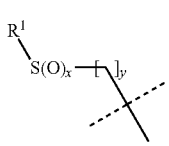 (c)

and attached to position 3 in the A+B ring system, and R³ is a group selected from any one of

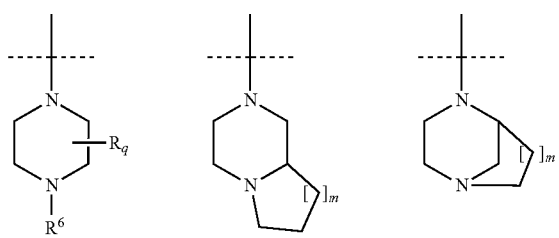

and attached to position 7 in the A+B ring system, then y=1 or 2;
when the ring system A+B is indole, and P is

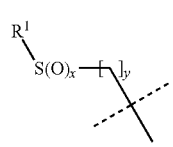 (c)

and P is attached to position 3 in the A+B ring system, and R³ is a group selected from any one of

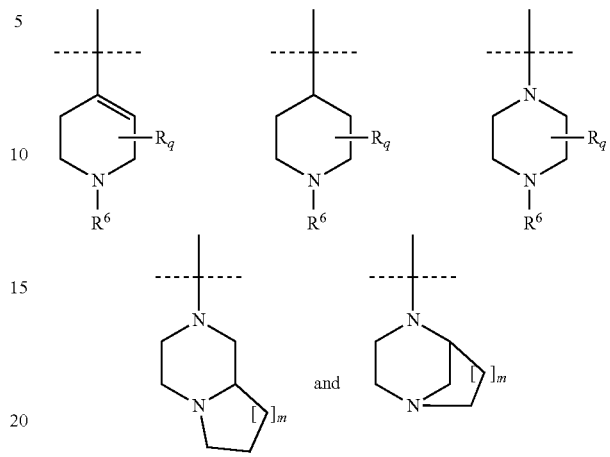

and R³ is attached to any one of positions 5, 6 or 7 in the A+B ring system, then y=1 or 2; or
when ring B is

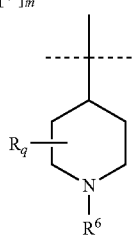

and R¹=Ar is partially saturated bi-cyclic heterocyclic ring containing a N atom, the N atom in Ar cannot be attached to the S atom in P;
with the proviso that:
when rings A and B are both phenyl, P is any one of formula (a) or (c) substituted in position 7 on the naphthalene ring, then R³ is not substituted in position 1 on the naphthalene ring; and
with the proviso that:
when ring D is a pyrrole ring, P is of the formula (c), then R³ is not of the formula

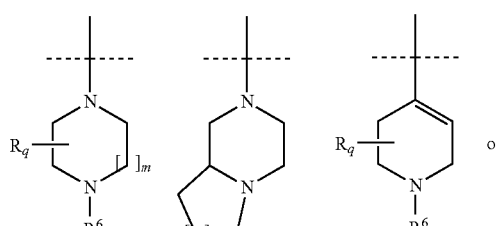

substituted in position 3 on the pyrrole ring.

A naphthalene ring has the following position numbers:

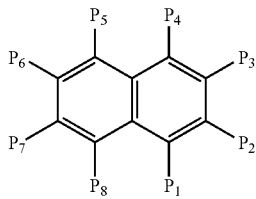

wherein $P_1$—$P_8$ denote the position on the naphthalene ring.

A pyrrole ring, as connected to an A ring, has the following position numbers:

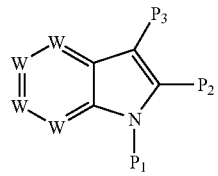

wherein $P_1$—$P_3$ denote the position on the pyrrole ring.

It is preferred that:

$R^1$ is
- (a) $C_{1-6}$ alkyl, or
- (e) a group Ar;

Ar is
- (a) phenyl,
- (b) 1-naphthyl,
- (c) 2-naphthyl, or
- (f) a 5 to 7-membered, optionally aromatic, partially saturated or completely saturated, heterocyclic ring containing 1 to 4 heteroatoms, selected from oxygen, nitrogen and sulfur, wherein the group Ar is substituted in one or more positions with
- (a) H,
- (b) halogen,
- (c) $C_{1-6}$ alkyl,
- (d) —$CF_3$,
- (f) $C_{1-6}$ alkoxy,
- (g) $C_{2-6}$ alkenyl (preferably $C_{2-4}$ alkenyl),
- (l) —$OCF_3$,
- (m) straight or branched $C_{1-6}$ hydroxyalkyl,
- (n) phenyloxy,
- (o) benzyloxy,
- (v) —$NR^4COR^5$,
- (x) —$SO_2NR^4R^5$,
- (z) —C(=O)$R^4$,
- (ab) —S(O)$_n R^4$, wherein n is 0, 1, 2 or 3;
- (ac) —S—($C_{1-6}$) alkyl, or
- (ad) —$SCF_3$;

$R^2$ is
- (a) H, or
- (b) $C_{1-6}$ alkyl;

or $R^1$ and $R^2$ are linked to form a group —$CH_2CH_2OCH_2CH_2$—;

X and Y are H;
$R^4$ and $R^5$ are each independently H or $C_{1-3}$ alkyl; and
$R^3$ is selected from any one of

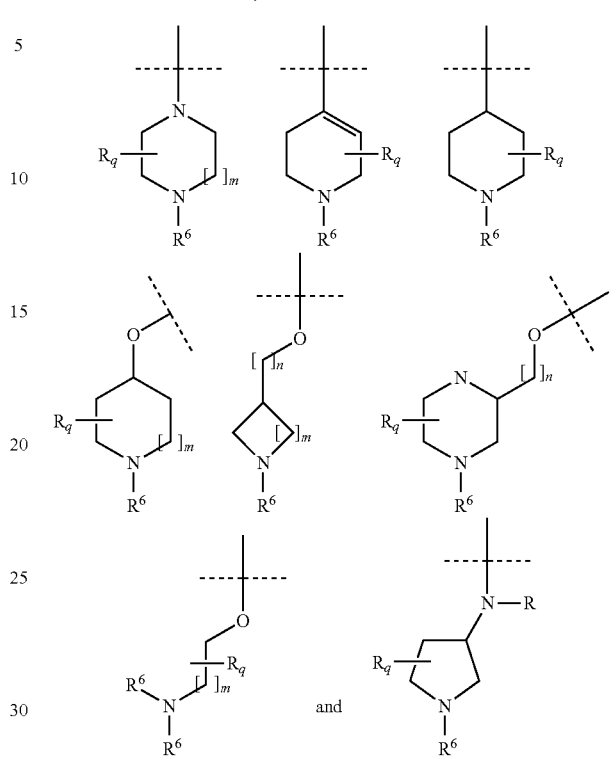

wherein $R^3$ can be substituted on each carbon atom that allows the substitution with Rq groups, wherein Rq is independently H, or $C_{1-6}$ alkyl, and wherein two Rq groups can be present on the same carbon atom simultaneously, wherein
q=1 or 2,
m=1 or 2,
n=0, and $R^6$ is independently
- (a) H,
- (b) $C_{1-6}$ alkyl (preferably $C_{1-3}$ alkyl), in particular methyl,
- (d) —$CH_2$—$CH_2$—OH, or
- (e) —$CH_2$—$CH_2$—$OCH_3$.

It is especially preferred that $R^3$ is selected from any one of

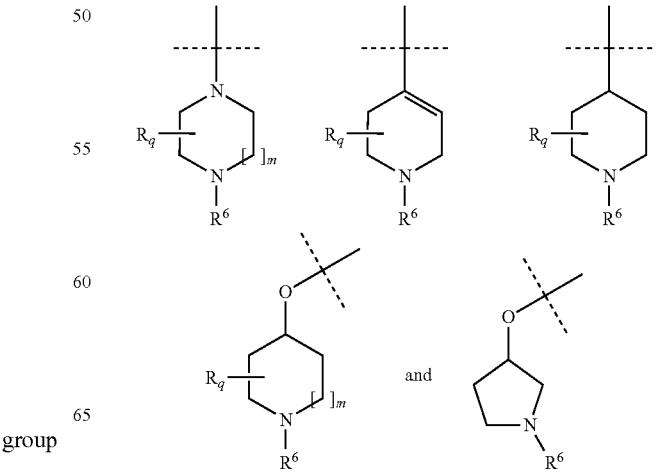

wherein $R^3$ can be substituted on each carbon atom that allows the substitution with Rq groups, wherein Rq is independently H, or $C_{1-2}$ alkyl, and wherein two Rq groups can be present on the same carbon atom simultaneously, wherein q=1 or 2, m=1 or 2; and $R^6$ is independently (a) H, (b) $C_{1-3}$ alkyl, (d) —$CH_2$—$CH_2$—OH, or (e) —$CH_2$—$CH_2$—$OCH_3$.

It is also preferred that $R^3$ is selected from any one of

[structures]

wherein $R^3$ can be substituted on each carbon atom that allows the substitution with Rq groups, wherein Rq is independently H, or $C_{1-6}$ alkyl, and wherein two Rq groups can be present on the same carbon atom simultaneously, wherein q=1 or 2, m=1 or 2, n=0, and $R^6$ is independently (a) H, (b) $C_{1-3}$ alkyl, (d) —$CH_2$—$CH_2$—OH, or (e) —$CH_2$—$CH_2$—$OCH_3$.

It is also preferred that $R^3$ is selected from any one of

[structures]

$R^6$ is independently (a) H, (b) $C_{1-3}$ alkyl, (d) —$CH_2$—$CH_2$—OH, or (e) —$CH_2$—$CH_2$—$OCH_3$.

It is preferred that $R^6$ is H or methyl.

It is also preferred that $R^3$ is piperazine; homopiperazine; 2,6-dimethylpiperazine; 3,5-dimethylpiperazine; 2,5-dimethylpiperazine; 2-methylpiperazine; 3-methylpiperazine; 2,2-dimethylpiperazine; 3,3-dimethylpiperazine; piperidine; 1,2,3,6-tetrahydro-pyrazine; or 4-pyrrolidin-3-yloxy.

It is preferred that the groups Y and X are attached to any unsubstituted carbon atom.

It is preferred that D is pyrrolyl, thienyl or furanyl.

It is preferred that P is (c)

[structure with $R^1$, $S(O)_x$, y]

wherein $R^1$, x, and y are as defined in claim 1.

It is also preferred that P is (a)

[structure]

or (b)

[structure]

wherein $R^1$ and $R^2$ are as defined in claim 1.

It is preferred that $R^2$ is H.

Another object of the present invention is a compound of the general formula (II)

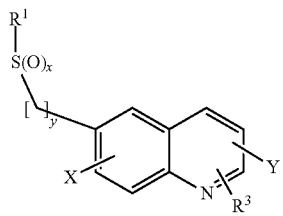
(II)

wherein R¹, x, y, X, and Y are as defined in claim 1, and R³ is as defined in claim 2.

It is preferred that y=0 and x=2.

Another object of the present invention is a compound of the general formula (III)

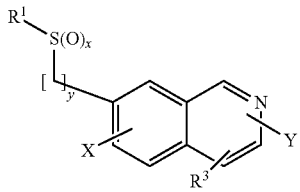
(III)

wherein R¹, x, y, X, and Y are as defined in claim 1, and R³ is as defined in claim 2.

It is preferred that y=0 and x=2

Another object of the present invention is a compound of the general formula (IV)

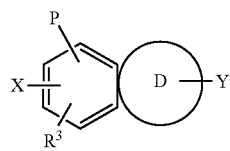
(IV)

wherein P is of the formula (c), R¹, x, y, X, and Y are as defined in claim 1, and R³ is as defined in claim 2, and wherein D is a five-membered heteroaryl ring, said ring comprising one or two atoms selected from the group consisting of nitrogen, sulfur and oxygen; and when the heteroaryl ring comprises one or two nitrogen atoms, a group R⁶ is attached at any nitrogen atom which allows the substitution.

It is preferred that D is a thiophene and P is attached to the D ring, giving a skeleton as any of the following:

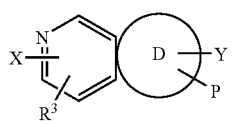

It is also preferred that D is pyrrole and P is attached to the nitrogen atom in the D ring, giving a skeleton as any of the following:

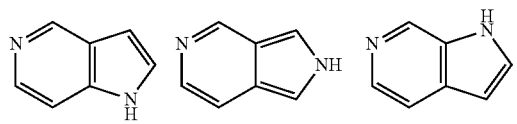

It is also preferred that D is furan and P is attached to the D ring, giving a skeleton as any of the following:

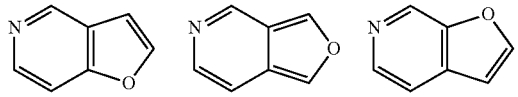

Another object of the present invention is a compound of the general formula (V)

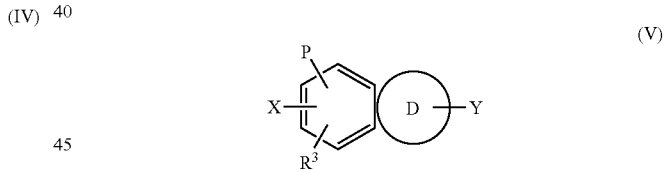
(V)

wherein P is of the formula (c) as defined in claim 1, R¹, x, y, X, Y, and R³ are as defined in claim 1, and wherein D is a five-membered heteroaryl ring, said heteroaryl ring comprising one or two atoms selected from the group consisting of nitrogen, sulfur and oxygen; and when the heteroaryl ring comprises one or two nitrogen atoms, a group R⁶ is attached at any nitrogen atom which allows the substitution.

Another object of the present invention is a compound of the general formula (V)

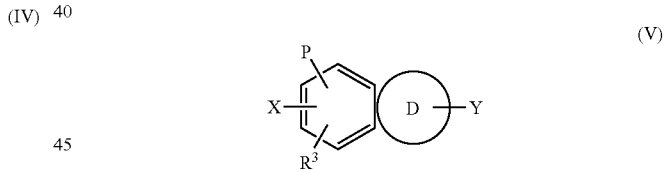
(V)

wherein P is of the formula (a) or (b) as defined in claim 1, preferably wherein R² is H, X, Y, and R³ are as defined in claim 1, and wherein D is a five-membered heteroaryl ring, said heteroaryl ring comprising one or two atoms selected from the group consisting of nitrogen, sulfur and oxygen; and when the heteroaryl ring comprises one or two nitrogen atoms, a group R⁶ is attached at any nitrogen atom which allows the substitution.

Another object of the present invention is a compound of the general formula (VI)

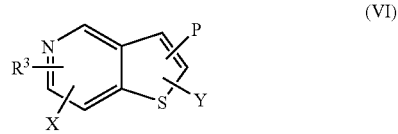
(VI)

wherein P is of the formula (a) or (b) as defined in claim 1, preferably wherein $R^2$ is H, X and Y are as defined in claim 1, and $R^3$ is as defined in claim 2.

Another object of the present invention is a compound of the general formula (VII)

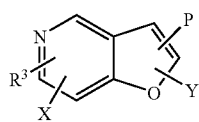

(VII)

wherein P is of the formula (a) or (b) as defined in claim 1, preferably wherein $R^2$ is H, X and Y are as defined in claim 1, and $R^3$ is as defined in claim 4.

Another object of the present invention is a compound of the general formula (VIII)

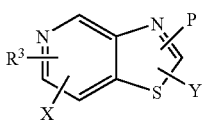

(VIII)

wherein P is of the formula (a) or (b) as defined in claim 1, preferably wherein $R^2$ is H, X, Y, and $R^3$ are as defined in claim 1.

Another object of the present invention is a compound of the general formula (IX)

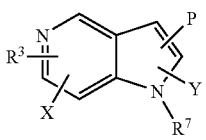

(IX)

wherein $R^7$ in formula (IX) is:
(a) H,
(b) $C_{1-6}$ alkyl,
(c) benzyl,
(d) —$CH_2$—$CH_2$—OH, or
(e) $CH_2$—$CH_2$—O—$CH_3$, and wherein P is of the formula (a) or (b) as defined in claim 1, preferably wherein $R^2$ is H, X, Y, and $R^3$ are as defined in claim 1.

Another object of the present invention is a compound of the general formula (X)

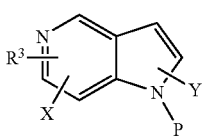

(X)

wherein P is of the formula (a) or (b) as defined in claim 1, preferably wherein $R^2$ is H, X, Y, and $R^3$ are as defined in claim 1.

Another object of the present invention is a compound of the general formula (XI)

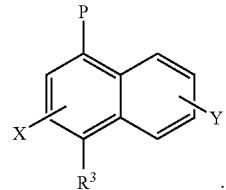

(XI)

wherein P is of the formula (a) or (b) as defined in claim 1, preferably wherein $R^2$ is H, X and Y are as defined in claim 1, and $R^3$ is as defined in claim 4.

Another object of the present invention is a compound of the general formula (XII):

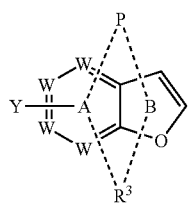

(XII)

or a pharmaceutically acceptable salt thereof, wherein P and $R^3$ are attached to the same ring or to different rings of rings A and B, wherein A, B, Y, P, and $R_3$ are as defined in claim 1.

Preferred compounds of the formula (II) are
6-Benzenesulfonyl-4-piperazin-1-yl-quinoline hydrochloride;
6-[(2-Fluorophenyl)sulfonyl]-4-piperazin-1-ylquinoline hydrochloride;
6-(1-Naphthylsulfonyl)-4-piperazin-1-ylquinoline hydrochloride;
6-[(3,4-Dichlorophenyl)sulfonyl]-4-piperazin-1-ylquinoline hydrochloride;
6-[(3,5-Dimethylphenyl)sulfonyl]-4-piperazin-1-ylquinoline hydrochloride;
6-[(2-Chloro-6-methylphenyl)sulfonyl]-4-piperazin-1-ylquinoline hydrochloride;
6-[(4-Chlorophenyl)sulfonyl]-4-piperazin-1-ylquinoline hydrochloride;
6-[(2-Methyl,4-tert-butyl-phenyl)sulfonyl]-4-piperazin-1-ylquinoline hydrochloride;
6-[(3,4-Dimethylphenyl)sulfonyl]-4-piperazin-1-ylquinoline hydrochloride;
6-[(2,3-Dichlorophenyl)sulfonyl]-4-piperazin-1-ylquinoline hydrochloride;
6-[(4-tert-Butylphenyl)sulfonyl]-4-piperazin-1-ylquinoline hydrochloride;
6-[(4-Isopropylphenyl)sulfonyl]-4-piperazin-1-ylquinoline hydrochloride;
(4-Piperazin-1-yl-6-{[4-(trifluoromethyl)phenyl]sulfonyl}quinoline hydrochloride;
6-[(4-tert-Butylphenyl)sulfonyl]-4-(1,4-diazepan-1-yl)quinoline hydrochloride; and
4-(1,4-Diazepan-1-yl)-6-[(4-isopropylphenyl)sulfonyl]quinoline hydrochloride.

Preferred compounds of the formula (III) are
7-(2-Chloro-6-methyl-benzenesulfonyl)-1-piperazin-1-yl-isoquinoline hydrochloride;

7-(2-t-Butyl-benzenesulfonyl)-1-piperazin-1-yl-isoquinoline hydrochloride;
7-(3,4-Dichloro-benzenesulfonyl)-1-piperazin-1-yl-isoquinoline hydrochloride;
7-(2,4-Dimethyl-benzenesulfonyl)-1-piperazin-1-yl-isoquinoline hydrochloride;
7-(2,5-Dimethyl-benzenesulfonyl)-1-piperazin-1-yl-isoquinoline hydrochloride;
7-(p-Chloro-benzenesulfonyl)-1-piperazin-1-yl-isoquinoline hydrochloride;
7-Benzenesulfonyl-1-[1,4]diazepan-1-yl-isoquinoline hydrochloride;
7-(4-tert-Butyl-benzenesulfonyl)-1-[1,4]diazepan-1-yl]-isoquinoline, hydrochloride;
7-(2-Chloro-6-methyl-benzenesulfonyl)-1-[1,4]diazepan-1-yl]-isoquinoline hydrochloride;
7-(3,5-Dimethyl-benzenesulfonyl)-1-[1,4]diazepan-1-yl]-isoquinoline hydrochloride;
7-(3,4-Dichloro-benzenesulfonyl)-1-[1,4]diazepan-1-yl]-isoquinoline hydrochloride;
7-(4-Chloro-benzenesulfonyl)-1-[1,4]diazepan-1-yl]-isoquinoline hydrochloride;
7-(3,4-Dimethyl-benzenesulfonyl)-1-[1,4]diazepan-1-yl]-isoquinoline hydrochloride;
7-(2-tert-Butyl-benzenesulfonyl)-1-[1,4]diazepan-1-yl]-isoquinoline hydrochloride;
7-Benzenesulfonyl-1-piperazin-yl-isoquinoline hydrochloride; and
7-(4-tert-Butyl-benzenesulfonyl-1-piperazin-yl-isoquinoline hydrochloride
Preferred compounds of the formula (IV) are
4-(1,4-Diazepan-1-yl)-2-(phenylsulfonyl)thieno[3,2-c]pyridine hydrochloride;
4-(1,4-Diazepan-1-yl)-2-[(3,4-dichlorophenyl)sulfonyl]thieno[3,2-c]pyridine hydrochloride;
4-(1,4-Diazepan-1-yl)-2-[4-tert-butylphenylsulfonyl)thieno[3,2-c]pyridine hydrochloride;
4-(1,4-Diazepan-1-yl)-2-[4-tert-butylphenylsulfonyl)thieno[3,2-c]pyridine hydrochloride;
4-(1,4-Diazepan-1-yl)-2-[3,4-dimethylphenylsulfonyl)thieno[3,2-c]pyridine hydrochloride;
2-[(4-Bromophenyl)sulfonyl]-4-(1,4-diazepan-1-yl)thieno[3,2-c]pyridine hydrochloride;
2-(Phenylsulfonyl)-4-piperazin-1-ylthieno[3,2-c]pyridine hydrochloride;
2-(3-Methoxy-benzenesulfonyl)-4-piperazin-1-yl-thieno[3,2-c]pyridine hydrochloride;
2-(4-Methoxy-benzenesulfonyl)-4-piperazin-1-yl-thieno[3,2-c]pyridine hydrochloride;
4-Piperazin-1-yl-2-{[4-trifluoromethyl)phenyl]sulfonyl}thieno[3,2-c]pyridine hydrochloride;
2-[[2-tert-Butylphenyl)sulfonyl]-4-piperazin-1-ylthieno[3,2-c]pyridine hydrochloride;
2-[(3,4-Dichlorophenyl)sulfonyl]-4-piperazin-1-ylthieno[3,2-c]pyridine-2-sulfonamide hydrochloride;
2-[(4-tert-Butylphenyl)sulfonyl]-4-piperazin-1-ylthieno[3,2-c]pyridine hydrochloride;
2-(1-Naphthyl sulfonyl)-4-piperazin-1-ylthieno[3,2-c]pyridine hydrochloride;
2-[(3-Fluorophenyl)sulfonyl]-4-piperazin-1-ylthieno[3,2-c]pyridine-2-sulfonamide hydrochloride;
2-(Mesitylsulfonyl)-4-piperazin-1-ylthieno[3,2-c]pyridine hydrochloride;
2-[(2-Methoxyphenyl)sulfonyl]-4-piperazin-1-ylthieno[3,2-c]pyridine hydrochloride;
2-[(2,4-Dimethoxyphenyl)sulfonyl]-4-piperazin-1-ylthieno[3,2-c]pyridine hydrochloride;
2-[(2,4-Dimethylphenyl)sulfonyl]-4-piperazin-1-ylthieno[3,2-c]pyridine hydrochloride;
2-[(2,5-Dimethylphenyl)sulfonyl]-4-piperazin-1-ylthieno[3,2-c]pyridine hydrochloride;
2-[(2-Ethylphenyl)sulfonyl]-4-piperazin-1-ylthieno[3,2-c]pyridine hydrochloride;
4-(Piperazinyl)-2-(3-methoxybenzyl-sulfonyl)-thienopyridine hydrochloride;
2-(Benzylsulfonyl)-4-piperazin-1-ylthieno[3,2-c]pyridine hydrochloride;
4-Piperazin-1-yl-2-{[4-(trifluoromethyl)benzyl]sulfonyl}thieno[3,2-c]pyridine hydrochloride;
2-[(3-Bromobenzyl)sulfonyl]-4-piperazin-1-ylthieno[3,2-c]pyridine hydrochloride;
2-[(2,3-Difluorobenzyl)sulfonyl]-4-piperazin-1-ylthieno[3,2-c]pyridine hydrochloride;
2-[(4-Bromobenzyl)sulfonyl]-4-piperazin-1-ylthieno[3,2-c]pyridine hydrochloride;
2-{[2,5-bis(Trifluoromethyl)benzyl]sulfonyl}-4-piperazin-1-ylthieno[3,2-c]pyridine hydrochloride;
2-[(4-Methylbenzyl)sulfonyl]-4-piperazin-1-ylthieno[3,2-c]pyridine hydrochloride;
2-{[5-Chloro-2-(trifluoromethyl)benzyl]sulfonyl}-4-piperazin-1-ylthieno[3,2-c]pyridine hydrochloride;
2-[(3,5-Dimethoxybenzyl)sulfonyl]-4-piperazin-1-ylthieno[3,2-c]pyridine hydrochloride;
2-[(2-Naphthylmethyl)sulfonyl]-4-piperazin-1-ylthieno[3,2-c]pyridine hydrochloride;
4-Piperazin-1-yl-2-{[4-(1,2,3-thiadiazol-4-yl)benzyl]sulfonyl}thieno[3,2-c]pyridine hydrochloride;
1-(4-Pyrrolidin-1-ylphenyl)-2-[(4-piperazine-1-ylthieno[3,2-c]pyridin-2-yl)sulfonyl]ethanone hydrochloride; and
1-[4-(Diethylamino)phenyl]-2-[(4-piperazine-1-ylthieno[3,2-c]pyridin-2-yl)sulfonyl]ethanone hydrochloride.
Also preferred compounds of the formula (IV) are
1-(4-Methylphenylsulphonyl)-4-piperazin-1-yl-1H-pyrrolo[3,2-c]pyridine hydrochloride;
1-(3-Chloro-2-methylphenylsulphonyl)-4-piperazin-1-yl-1H-pyrrolo[3,2-c]pyridine hydrochloride;
1-(3,4-Dimethoxyphenylsulphonyl)-4-piperazin-1-yl-1H-pyrrolo[3,2-c]pyridine hydrochloride;
4-(4-Piperazin-1-yl-pyrrolo[3,2-c]pyridine-1-sulfonyl)-benzonitrile hydrochloride;
1-(4,5-Dichloro-thiophene-2-sulfonyl)-4-piperazin-1-yl-1H-pyrrolo[3,2-c]pyridine hydrochloride;
1-(2-Chloro-4-fluorophenylsulphonyl)-4-piperazin-1-yl-1H-pyrrolo[3,2-c]pyridine hydrochloride;
1-Phenylmethanesulfonyl-4-piperazin-1-yl-1H-pyrrolo[3,2-c]pyridine hydrochloride;
1-(5-Chloro-thiophene-2-sulfonyl)-4-piperazin-1-yl-1H-pyrrolo[3,2-c]pyridine hydrochloride;
1-(4-Butyl-benzenesulfonyl)-4-piperazin-1-yl-1H-pyrrolo(3,2-c)pyridine hydrochloride;
1-(4-Phenoxy-benzenesulfonyl)-4-piperazin-1-yl-1H-pyrrolo(3,2-c)pyridine hydrochloride;
1-(Phenylsulfonyl)-4-piperazin-1-yl-1H-pyrrolo[3,2-c]pyridine hydrochloride;
1-[(4-Chlorophenyl)sulfonyl]-4-piperazin-1-yl-1H-pyrrolo[3,2-c]pyridine hydrochloride;
1-[(4-Methoxyphenyl)sulfonyl]-4-piperazin-1-yl-1H-pyrrolo[3,2-c]pyridine hydrochloride;
1-[(2-Methoxy-5-methylphenyl)sulfonyl]-4-piperazin-1-yl-1H-pyrrolo[3,2-c]pyridine hydrochloride; and
4-Piperazin-1-yl-1-{[2-(trifluoromethyl)phenyl]sulfonyl}-1H-pyrrolo[3,2-c]pyridine hydrochloride.
Preferred compounds of the formula (VI) are N-(4-Methylphenyl)-4-(4-methylpiperazin-1-yl)thieno[3,2-c]pyridine-2-sulfonamide hydrochloride;
2-Bromo-4-(4-methyl-piperazin-1-yl)-thieno[3,2-c]pyridine-3-sulfonic acid p-tolylamide hydrochloride;
4-(4-Methylpiperazin-1-yl)-n-phenylthieno[3,2-c]pyridine-2-sulfonamide hydrochloride;
4-Piperazin-1-yl-thieno[3,2-c]pyridine-2-sulfonic acid (3-fluoro-5-trifluoromethyl-phenyl)amide hydrochloride;
4-Piperazin-1-yl-thieno[3,2-c]pyridine-2-sulfonic acid (4-chloro-phenyl)-amide hydrochloride;
4-Piperazin-1-yl-thieno[3,2-c]pyridine-2-sulfonic acid (4-isopropyl-phenyl)-amide hydrochloride;
4-Piperazin-1-yl-thieno[3,2-c]pyridine-2-sulfonic acid p-tolylamide hydrochloride;
4-(4-Methylpiperazin-1-yl)-N-(2-cyclohex-1-en-1-ylethyl)thieno[3,2-c]pyridine-2-sulfonamide hydrochloride;
2-(4-(4-Methylpiperazin-1-yl)thieno[3,2-c]pyridin-2-ylsulfonyl)-1,2,3,4-tetrahydroisoquinoline hydrochloride;
4-(4-Methylpiperazin-1-yl)-N-(2-thien-2-ylethyl)thieno[3,2-c]pyridine-2-sulfonamide hydrochloride;
4-(4-Methylpiperazin-1-yl)-N-[1-(1-naphthyl)ethyl]thieno[3,2-c]pyridine-2-sulfonamide hydrochloride;
4-(4-Methylpiperazin-1-yl)-N-(4-hexylphenyl)thieno[3,2-c]pyridine-2-sulfonamide hydrochloride;
N-(3-Chlorobenzyl)-4-(4-methylpiperazin-1-yl)thieno[3,2-c]pyridine-2-sulfonamide;
4-(4-Methylpiperazin-1-yl)-N-[1-(4-fluorophenyl)ethyl]thieno[3,2-c]pyridine-2-sulfonamide hydrochloride;
N-(2,3-Difluorobenzyl)-4-(4-methylpiperazin-1-yl)thieno[3,2-c]pyridine-2-sulfonamide hydrochloride;
4-(4-Methylpiperazin-1-yl)-N-(4-chloro-2,5-dimethoxyphenyl)thieno[3,2-c]pyridine-2-sulfonamide hydrochloride;
2-Bromo-4-(4-methylpiperazin-1-yl)-N-(2-cyclohex-1-en-1-ylethyl)thieno[3,2-c]pyridine-3-sulfonamide hydrochloride;
2-Bromo-4-(4-methylpiperazin-1-yl)-N-[(1S)-1-(2-naphthyl)ethyl]thieno[3,2-c]pyridine-3-sulfonamide hydrochloride;
2-Bromo-4-(4-methylpiperazin-1-yl)-N-[1-(4-fluorophenyl)ethyl]thieno[3,2-c]pyridine-3-sulfonamide hydrochloride;
2-Bromo-4-(4-methylpiperazin-1-yl)-N-(2,4,5-trimethoxyphenyl)thieno[3,2-c]pyridine-3-sulfonamide;
N-(3,4-Dichlorophenyl)-4-piperazin-1-ylthieno[3,2-c]pyridine-2-sulfonamide hydrochloride;
N-(2,4-Difluorophenyl)-4-piperazin-1-ylthieno[3,2-c]pyridine-2-sulfonamide hydrochloride;
4-Piperazin-1-yl-N-[-3-(trifluoromethyl)phenyl]thieno[3,2-c]pyridine-2-sulfonamide hydrochloride;
N-(3-Ethylphenyl)-4-piperazin-1-ylthieno[3,2-c]pyridine-2-sulfonamide hydrochloride;
N-(3,4-Dimethoxyphenyl)-4-piperazin-1-ylthieno[3,2-c]pyridine-2-sulfonamide hydrochloride;
N-(4-Bromo-2-methylphenyl)-4-piperazin-1-ylthieno[3,2-c]pyridine-2-sulfonamide hydrochloride;
2-(4-Piperazin-1-yl-thieno[3,2-c]pyridine-2-sulfonyl)-1,2,3,4-tetrahydro-isoquinoline hydrochloride;
4-Piperazin-1-yl-thieno[3,2-c]pyridine-2-sulfonic acid (2-thiophen-2-yl-ethyl)-amide hydrochloride;
4-Piperazin-1-yl-thieno[3,2-c]pyridine-2-sulfonic acid (4-chloro-2,5-dimethoxy-phenyl)amide hydrochloride;
4-Piperazin-1-yl-thieno[3,2-c]pyridine-2-sulfonic acid phenethyl-amide hydrochloride;
4-Piperazin-1-yl-thieno[3,2-c]pyridine-2-sulfonic acid (2,6-diethyl-phenyl)-amide hydrochloride;
4-Piperazin-1-yl-thieno[3,2-c]pyridine-2-sulfonic acid (3-phenyl-propyl)-amide hydrochloride;
4-Piperazin-1-yl-thieno[3,2-c]pyridine-2-sulfonic acid (3,3-diphenyl-propyl)-amide hydrochloride;
4-Piperazin-1-yl-thieno[3,2-c]pyridine-2-sulfonic acid [2-(5-methoxy-1H-indol-3-yl)-ethyl]-amide hydrochloride;
4-Piperazin-1-yl-thieno[3,2-c]pyridine-2-sulfonic acid 4-trifluoromethyl-benzylamide hydrochloride;
4-Piperazin-1-yl-thieno[3,2-c]pyridine-2-sulfonic acid benzyl-ethyl-amide hydrochloride;
N-(3-Ethylphenyl)-4-piperazin-1-ylthieno[3,2-c]pyridine-3-sulfonamide hydrochloride;
N-(4-Isopropylphenyl)-4-piperazin-1-ylthieno[3,2-c]pyridine-3-sulfonamide hydrochloride;
N-(4-Methylphenyl)-4-(pyrrolidin-3-yloxy)thieno[3,2-c]pyridine-2-sulfonamide hydrochloride;
N-(4-Methylphenyl)-4-(piperidin-4-yloxy)thieno[3,2-c]pyridine-2-sulfonamide hydrochloride;
N-(2,3-Difluorobenzyl)-4-piperazin-1-ylthieno[3,2-c]pyridine-2-sulfonamide hydrochloride;
N-(3-Chlorobenzyl)-4-piperazin-1-ylthieno[3,2-c]pyridine-2-sulfonamide hydrochloride;
4-Piperazin-1-yl-thieno[3,2-c]pyridine-2-sulfonic acid phenylamide hydrochloride;
4-Piperazin-1-yl-thieno[3,2-c]pyridine-2-sulfonic acid (4-tert-butyl-phenyl)-amide hydrochloride;
4-(4-Methyl-piperazin-1-yl)-thieno[3,2-c]pyridine-2-sulfonic acid phenylamide hydrochloride;
4-(4-Methyl-piperazin-1-yl)-thieno[3,2-c]pyridine-2-sulfonic acid (3-chloro-phenyl)-amide hydrochloride;
2-Bromo-4-(4-methyl-piperazin-1-yl)-thieno[3,2-c]pyridine-3-sulfonic acid phenylamide hydrochloride;
4-(4-Methyl-piperazin-1-yl)-thieno[3,2-c]pyridine-3-sulfonic acid (4-methylphenyl)-amide hydrochloride; and
N-Phenyl-7-piperazin-1-ylthieno[2,3-c]pyridine-2-sulfonamide hydrochloride.

Preferred compounds of the formula (VII) are
N-(4-methylphenyl)-4-piperazin-1-ylfuro[3,2-c]pyridine-2-sulfonamide hydrochloride;
N-phenyl-4-piperazin-1-ylfuro[3,2-c]pyridine-2-sulfonamide hydrochloride; and
N-phenyl-7-piperazin-1-ylfuro[2,3-c]pyridine-2-sulfonamide hydrochloride.

A preferred compound of the formula (VIII) is
4-Piperazin-1-yl-thiazolo[4,5-c]pyridine-2-sulfonic acid phenylamide hydrochloride.

Preferred compounds of the formula (IX) are
N-(4-methylphenyl)-4-piperazin-1-yl-1H-pyrrolo[3,2-c]pyridine-2-sulfonamide hydrochloride;
N-phenyl-4-piperazin-1-yl-1H-pyrrolo[3,2-c]pyridine-2-sulfonamide hydrochloride; and
N-phenyl-7-piperazin-1-yl-1H-pyrrolo[2,3-c]pyridine-2-sulfonamide hydrochloride.

Preferred compounds of the formula (X) are
4-Chloro-N-[4-(pyrrolidin-3-yloxy)-1-naphthyl]benzenesulfonamide hydrochloride;
4-Methoxy-N-[4-(pyrrolidin-3-yloxy)-1-naphthyl]benzenesulfonamide hydrochloride;
5-Chloro-N-[4-(pyrrolidin-3-yloxy)-1-naphthyl]thiophene-2-sulfonamide hydrochloride;
4-Chloro-N-[4-(piperidin-3-yloxy)-1-naphthyl]benzenesulfonamide hydrochloride;
4-Methoxy-N-[4-(piperidin-3-yloxy)-1-naphthyl]benzenesulfonamide hydrochloride;
5-Fluoro-2-methyl-N-[4-(piperidin-4-yloxy)-1-naphthyl]benzenesulfonamide hydrochloride;
5-Chloro-N-[4-(piperidin-4-yloxy)-1-naphthyl]thiophene-2-sulfonamide hydrochloride;

4-Chloro-N-{4-[(3S)-pyrrolidin-3-yloxy]-1-naphthyl}benzenesulfonamide hydrochloride; and
4-Chloro-N-{4-[(3R)-pyrrolidin-3-yloxy]-1-naphthyl}benzenesulfonamide hydrochloride.

Another object of the present invention is a process for the preparation of a compound above, said method comprising the steps of:
(a) Mitsonobu reaction of 4-nitro-1-naphthol with boc-protected 3-hydroxypyrrolidine or 4-hydroxypiperidine;
(b) reduction of the nitro group in the nitronaphthalene obtained in step (a) to form an aminonaphthalene derivative; and
(c) synthesis of a sulfonamide by reacting the aminonaphthalene obtained in step (b) with a suitable sulfonyl chloride.

Another object of the present invention is a process for the preparation of a compound above, wherein P is

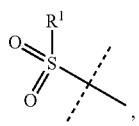

said method comprising the steps of:
preparation of the heteroaromatic 5-member ring fused halogen-substituted pyridine, reduction of an aromatic nitro group; aromatic nucleophilic substitution with a thiol via a diazointermediate; oxidation of the thiol derivative to a sulphone; introduction of a halogen atom by electrophilic aromatic substitution; aromatic nucleophilic substitution of the halogen with a diamine.

Another object of the present invention is a process for the preparation of a compound above, wherein P is

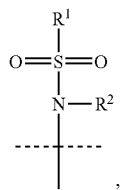

said method comprising the steps of: preparation of the heteroaromatic 5-member ring fused pyridine; introduction of a carboxylic moiety; conversion of the carboxylic moiety to amine by Curtius rearrangement; reaction of the amine group with a sulphonylchloride.

Another object of the present invention is a process for the preparation of a compound above, wherein P is

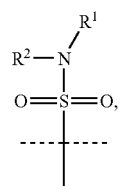

said method comprising the steps of: preparation of the heteroaromatic 5-member ring fused pyridine; introduction of sulfonylchloride moiety by nucleophilic addition; reaction of sulphonylchloride moiety with an aniline to obtained a sulfonamide; aromatic nucleophilic substitution of the chloro with a diamine.

All diastereomeric forms possible (pure enantiomers, tautomers, racemic mixtures and unequal mixtures of two enantiomers) are within the scope of the invention. Such compounds can also occur as cis- or trans-, E- or Z-double bond isomer forms. All isomeric forms are contemplated.

The compounds of the formulae (I) to (XII) may be used as such or, where appropriate, as pharmacologically acceptable salts (acid or base addition salts) thereof.

The pharmacologically acceptable addition salts as mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

Another object of the present invention is a compound above for use in therapy.

Another object of the present invention is a compound above, and for the case when rings A and B are both phenyl, P is any one of formula (a) or (c) substituted in position 7 on the naphthalene ring, and $R^3$ is substituted in position 1 on the naphthalene ring, for use in the treatment or prophylaxis of a 5-HT$_6$ receptor related disorder, such as obesity, type II diabetes, and/or disorders of the central nervous system, to achieve reduction of body weight and of body weight gain.

Another object of the present invention is a compound above for use in the treatment or prophylaxis of disorders of the central nervous system.

Another object of the present invention is a compound above, for the case when rings A and B are both phenyl, P is any one of formula (a) or (c) substituted in position 7 on the naphthalene ring, and $R^3$ is substituted in position 1 on the naphthalene ring, and for the case when ring D is a pyrrole ring, P is of the formula (c) and R³ is of the formula

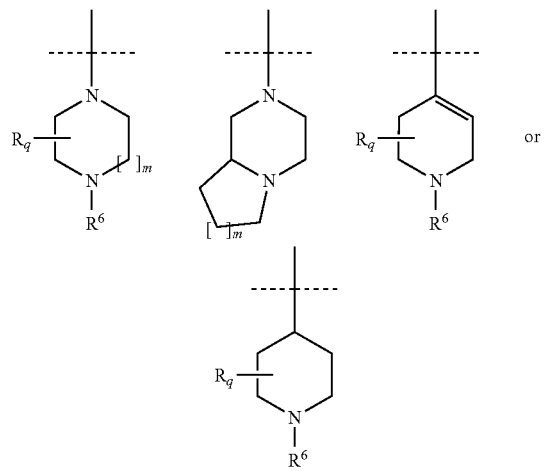

substituted in position 3 on the pyrrole ring, for use in the treatment or prophylaxis of type II diabetes.

Another object of the present invention is a compound above, and for the case when ring D is a pyrrole ring, P is of the formula (c) and R³ is of the formula

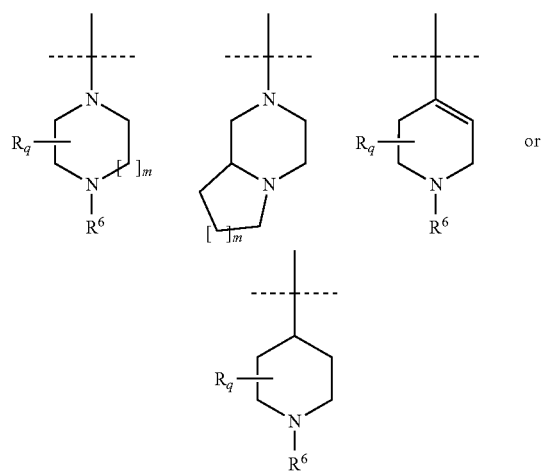

substituted in position 3 on the pyrrole ring, for use in the treatment or prophylaxis of obesity, to achieve reduction of body weight and of body weight gain.

Another object of the present invention is a pharmaceutical formulation comprising a compound above as an active ingredient, in combination with a pharmaceutically acceptable diluent or carrier.

Another object of the present invention is a pharmaceutical formulation comprising a compound above, and for the case when rings A and B are both phenyl, P is any one of formula (a) or (c) substituted in position 7 on the naphthalene ring, and R³ is substituted in position 1 on the naphthalene ring, as an active ingredient, for use in the treatment or prophylaxis of a 5-HT$_6$ receptor related disorder, such as obesity, type II diabetes, and/or disorders of the central nervous system, to achieve reduction of body weight and of body weight gain.

Another object of the present invention is a compound above as an active ingredient, for use in the treatment or prophylaxis of disorders of the central nervous system.

Another object of the present invention is a pharmaceutical formulation comprising a compound above, for the case when rings A and B are both phenyl, P is any one of formula (a) or (c) substituted in position 7 on the naphthalene ring, and R³ is substituted in position 1 on the naphthalene ring, and for the case when ring D is a pyrrole ring, P is of the formula (c) and R³ is of the formula

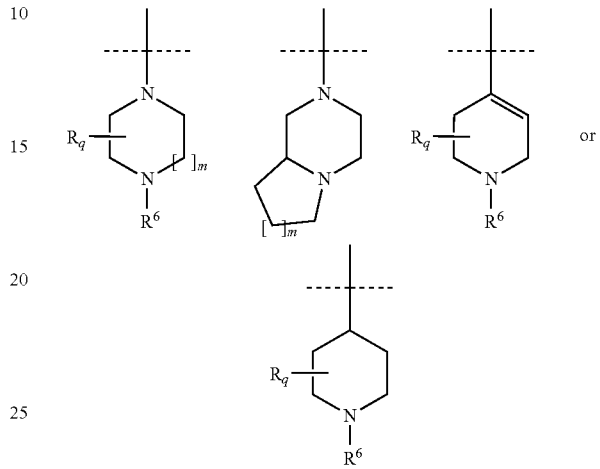

substituted in position 3 on the pyrrole ring, as an active ingredient, for use in the treatment or prophylaxis of type II diabetes.

Another object of the present invention is a pharmaceutical formulation comprising a compound above, and for the case when ring D is a pyrrole ring, P is of the formula (c) and R³ is of the formula

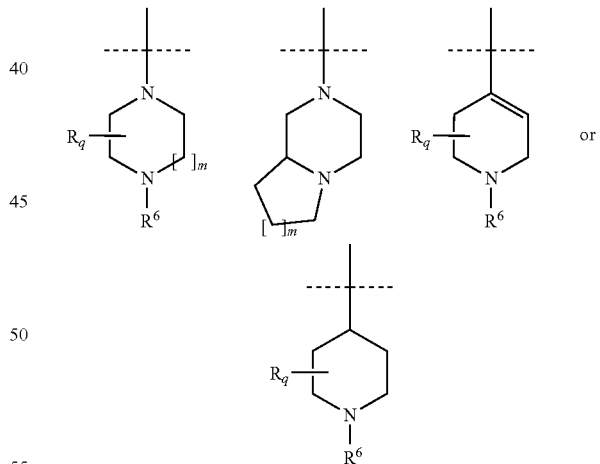

substituted in position 3 on the pyrrole ring, as an active ingredient, for use in the treatment or prophylaxis of obesity, to achieve reduction of body weight and of body weight gain.

Another object of the present invention is a method for the treatment or prophylaxis of a 5-HT$_6$ receptor related disorder, such as obesity, type II diabetes, and/or disorders of the central nervous system, to achieve reduction of body weight and of body weight gain, which comprises administering to a subject (e.g., a mammal, a human, a horse, a dog, or a cat) in need of such treatment an effective amount of one or more compounds of any of the formulae described above, their salt forms or compositions that include the compounds or their salt forms, and for the case when rings A and B are both phenyl, P is any one of formula (a) or (c) substituted in position 7 on the naphthalene ring, and R³ is substituted in position 1 on the naphthalene ring.

Another object of the present invention is a method for the treatment or prophylaxis of disorders of the central nervous system, which comprises administering to a subject in need of such treatment an effective amount of one or more compounds of any of the formulae described above, their salt forms or compositions that include the compounds or their salt forms.

Another object of the present invention is a method for the treatment or prophylaxis of type II diabetes, which comprises administering to a subject in need of such treatment an effective amount of one or more compounds of any of the formulae described above, their salt forms or compositions that include the compounds or their salt forms, for the case when rings A and B are both phenyl, P is any one of formula (a) or (c) substituted in position 7 on the naphthalene ring, and R³ is substituted in position 1 on the naphthalene ring, and for the case when ring D is a pyrrole ring, P is of the formula (c) and R³ is of the formula

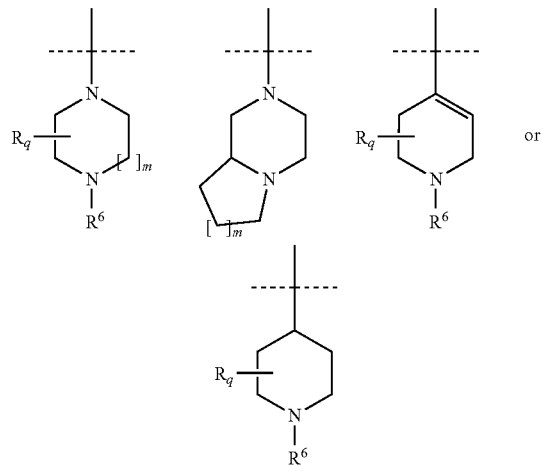

substituted in position 3 on the pyrrole ring.

Another object of the present invention is a method for the treatment or prophylaxis of obesity, which comprises administering to a subject in need of such treatment an effective amound of one or more compounds of any of the formulae described above, their salt forms or compositions that include the compounds or their salt forms, and for the case when ring D is a pyrrole ring, P is of the formula (c) and R³ is of the formula

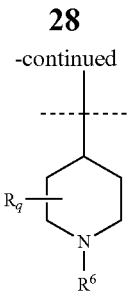

substituted in position 3 on the pyrrole ring.

Another object of the present invention is a method for modulating 5-HT₆ receptor activity, comprising administering to a subject in need thereof an effective amount of one or more compounds of any of the formulae described above, their salt forms or compositions that include the compounds or their salt forms.

A subject "in need of such treatment" or "in need thereof" can include a subject identified as in need of a particular treatment or treatments. The identification can be in the judgement of a subject or a health care professional and can be subjective (e.g., opinion) or objective (e.g., measurable by a test or a diagnostic method). The methods delineated herein can also include the step of identifying that the subject is in need of treatment of obesity, type II diabetes, or disorders of the central nervous system.

Another object of the present invention is the use of one or more compounds of any of the formulae described above, their salt forms or compositions that include the compounds or their salt forms, and for the case when rings A and B are both phenyl, P is any one of formula (a) or (c) substituted in position 7 on the naphthalene ring, and R³ is substituted in position 1 on the naphthalene ring, for the manufacture of a medicament for use in the treatment or prophylaxis of a 5-HT₆ receptor related disorder, such as obesity, type II diabetes, and/or disorders of the central nervous system, to achieve reduction of body weight and of body weight gain.

Another object of the present invention is the use of one or more compounds of any of the formulae described above, their salt forms or compositions that include the compounds or their salt forms for the manufacture of a medicament for use in the treatment or prophylaxis of disorders of the central nervous system.

Another object of the present invention is the use of one or more compounds of any of the formulae described above, their salt forms or compositions that include the compounds or their salt forms, for the case when rings A and B are both phenyl, P is any one of formula (a) or (c) substituted in position 7 on the naphthalene ring, and R³ is substituted in position 1 on the naphthalene ring, and for the case when ring D is a pyrrole ring, P is of the formula (c) and R³ is of the formula

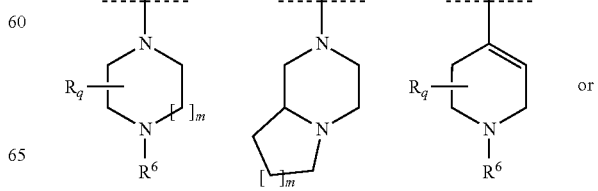

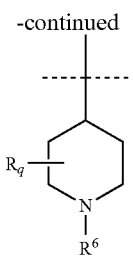

substituted in position 3 on the pyrrole ring, for the manufacture of a medicament for use in the treatment or prophylaxis of type II diabetes.

Another object of the present invention is the use of one or more compounds of any of the formulae described above, their salt forms or compositions that include the compounds or their salt forms, and for the case when ring D is a pyrrole ring, P is of the formula (c) and $R^3$ is of the formula

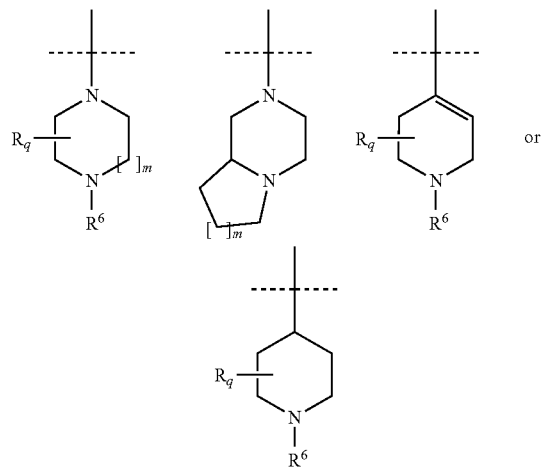

substituted in position 3 on the pyrrole ring, for the manufacture of a medicament for use in the treatment or prophylaxis of obesity, to achieve reduction of body weight and of body weight gain.

The methods delineated herein can also include the step of identifying that the subject is in need of treatment of obesity, type II diabetes, or disorders of the central nervous system, or in need of reducing body weight and of body weight gain.

The invention further relates to cosmetic use of one or more compounds of any of the formulae described herein, for causing loss of weight, as well as cosmetic compositions containing said compounds.

Still further, the invention relates to a non-therapeutic metod for impriving the bodily appearance of a mammal, including a human, in which the method comprises orally administering to said mammal one or more compounds of any of the formulae described herein.

"An effective amount" refers to an amount of a compound that confers a therapeutic effect on the treated subject. The therapeutic effect may be objective (i.e., measurable by some test or marker) or subjective (i.e., subject gives an indication of or feels an effect).

For clinical use, the compounds of the invention are formulated into pharmaceutical formulations for oral, rectal, parenteral or other mode of administration. Usually the amount of active compounds is between 0.1-95% by weight of the preparation, preferably between 0.2-20% by weight in preparations for parenteral use and preferably between 1 and 50% by weight in preparations for oral administration.

The typical daily dose of the active substance varies within a wide range and will depend on various factors such as, for example, the individual requirement of each patient and the route of administration. In general, oral and parenteral dosages will be in the range of 5 to 1000 mg per day of active substance, preferably 50 to 150 mg per day.

Processes for Preparation

In a further aspect the invention relates to methods of making compounds of any of the formulae herein comprising reacting any one or more of the compounds of the formulae delineated herein, including any processes delineated herein. The compounds of the formulae above may be prepared by, or in analogy with, conventional methods, and especially according to or in analogy with the following methods.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the compounds of any of the formulae described above, their salt forms, or compositions that include the compounds or their salt forms. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Methods $^1$H nuclear magnetic resonance (NMR) and $^{13}$C NMR were recorded on a Bruker Advance DPX 400 spectrometer at 400.1 and 100.6 MHz, respectively. All spectra were recorded using residual solvent or tetramethylsilane (TMS) as internal standard. IR spectra were recorded on a Perkin-Elmer Spectrum 1000 FT-IR spectrophotometer. Ionspray mass spectrometry (MS) spectra were obtained on a Perkin-Elmer API 150EX mass spectrometer. Accurate mass measurements were performed on a Micromass LCT dual probe. Preparative HPLC/MS was performed on a Waters/Micromass Platform ZQ system equipped with System A: ACE 5 C8 column (19×50 mm), eluents: MilliQ water, MeCN and MilliQ/MeCN/0.1% TFA and system B: Xterra MS C18, 5 μm column (19×50 mm), eluents: MilliQ water, MeCN and $NH_4HCO_3$ (100 mM). Analytical HPLC were performed on Agilent 1100, column: ACE 3 C8 (system A) or column: YMC-Pack (system B), eluents: MilliQ/0.1% TFA and MeCN. Elemental analyses were performed on a Vario E1 instrument. Preparative flash chromatography was performed on Merck silica gel 60 (230-400 mesh).

TABLE 1

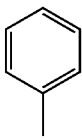

| EXAMPLE | | R⁶ | R⁴ |
|---|---|---|---|
| 1 | 6-Benzenesulfonyl-4-piperazin-1-yl-quinoline hydrochloride | 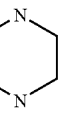 | 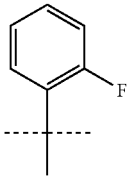 |
| 2 | 6-[(2-Fluorophenyl)sulfonyl]-4-piperazin-1-ylquinoline hydrochloride | 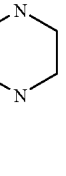 | 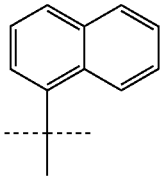 |
| 3 | 6-(1-Naphthylsulfonyl)-4-piperazin-1-ylquinoline hydrochloride | 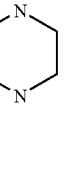 | 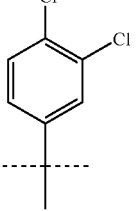 |
| 4 | 6-[(3,4-Dichlorophenyl)sulfonyl]-4-piperazin-1-ylquinoline hydrochloride | 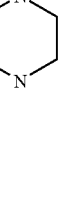 | 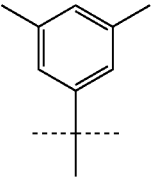 |
| 5 | 6-[(3,5-Dimethylphenyl)sulfonyl]-4-piperazin-1-ylquinoline hydrochloride | 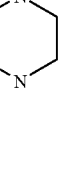 | 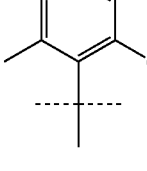 |
| 6 | 6-[(2-Chloro-6-methylphenyl)sulfonyl]-4-piperazin-1-ylquinoline hydrochloride | 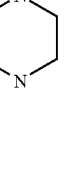 | 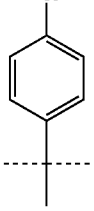 |
| 7 | 6-[(4-Chlorophenyl)sulfonyl]-4-piperazin-1-ylquinoline hydrochloride | 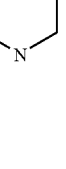 | |

TABLE 1-continued

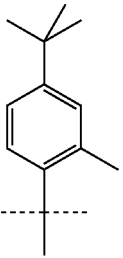

| EXAMPLE | | R⁶ | R⁴ |
|---|---|---|---|
| 8 | 6-[(2-Methyl,4-tert-butyl-phenyl)sulfonyl]-4-piperazin-1-ylquinoline hydrochloride |  | 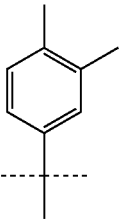 |
| 9 | 6-[(3,4-Dimethylphenyl)sulfonyl]-4-piperazin-1-ylquinoline hydrochloride |  | 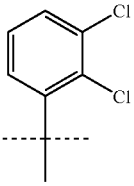 |
| 10 | 6-[(2,3-Dichlorophenyl)sulfonyl]-4-piperazin-1-ylquinoline hydrochloride |  | 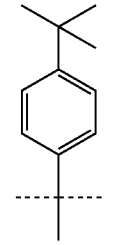 |
| 11 | 6-[(4-tert-Butylphenyl)sulfonyl]-4-piperazin-1-ylquinoline hydrochloride |  | 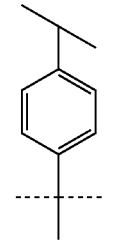 |
| 12 | 6-[(4-Isopropylphenyl)sulfonyl]-4-piperazin-1-ylquinoline hydrochloride |  | |

TABLE 1-continued
| EXAMPLE | | R⁶ | R⁴ |
|---|---|---|---|
| 13 | (4-piperazin-1-yl-6-{[4-(trifluoromethyl)phenyl]sulfonyl}quinoline hydrochloride | 4-(trifluoromethyl)phenyl | piperazin-1-yl |
| 14 | 6-[(4-tert-Butylphenyl)sulfonyl]-4-(1,4-diazepan-1-yl)quinoline hydrochloride | 4-tert-butylphenyl | 1,4-diazepan-1-yl |
| 15 | 4-(1,4-Diazepan-1-yl)-6-[(4-isopropylphenyl)sulfonyl]quinoline hydrochloride | 4-isopropylphenyl | 1,4-diazepan-1-yl |
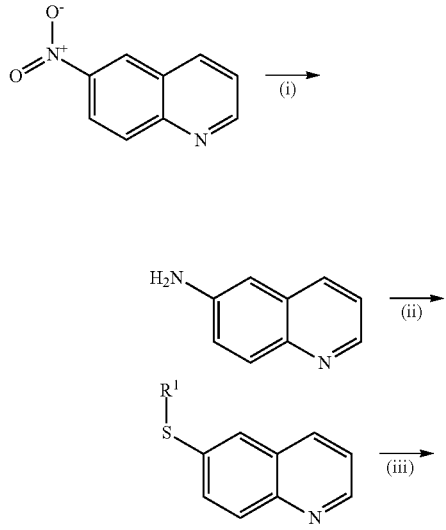
Scheme 1
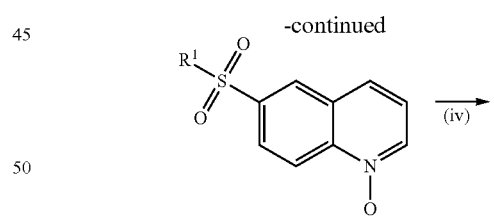
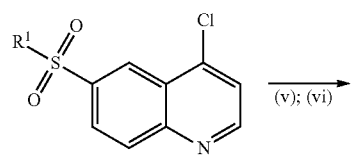

-continued

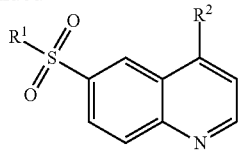

Legend to Scheme 1: i) Hydrogen gas, Pd/C, Methanol; ii) Sodium nitrite, Sulphuric acid, diverse thiols (R[1]—SH), 3h; iii) meta-chloroperoxybenzoic acid (m-CPBA), dichloromethane (CH$_2$Cl$_2$), overnight; iv) phosphorus oxylchloride (POCl$_3$), acetonitrile (CH$_3$CN), 80° C., 2h; v) aliphatic cyclic amines (R[2]), 80° C., CH$_3$CN; vi) HCl in diethyl ether.

Methods

The assigned structures were confirmed by standard spectroscopical methods and elemental analysis and/or high resolution MS.

NMR spectra were obtained on Bruker 500 MHz or JEOL 270 MHz spectrometers at 25° C., and the chemical shift values are reported as parts per million (6). MS spectra were acquired on a 2690 Separation Module (Waters) with a Platform LCZ (Micromass). Flash chromatography was performed on Silica gel 60 (Merck) or LiChroprep RP-18 (Merck). HPLC analysis were accomplished on a HP Series1100, with a GROM-SIL 100 ODS-0 AB column, 4.6×50 mm. The HPLC purifications were performed on preparative HPLC/Mass system using YMC Combi prep ODS-AQ column, 56×20 mm, Gilson pumps, Dynamax UV-1 detector and Finnigan Mass detector. The used eluents were H$_2$O and CH$_3$CN, both with 0.1% TFA. The purity of the compounds was determined by HPLC. Elemental analysis was performed at Structural Chemistry Department, Biovitrum AB, Stockholm. Melting points, when given, were obtained on a Büchi or a Gallenkamp melting point apparatus and are uncorrected.

INTERMEDIATE 1

Synthesis of 6-Amino-quinoline

A suspension of 6-nitro-quinoline (8.7 g, 5 mmol), palladium on charcoal (10%) (0.1 g) in methanol (0.2 L) was hydrogenated at room temperature for 24 with stirring. The catalyst was filtered and the solvent evaporated to yield a yellow solid. Crystallisation from ethyl acetate yielded the pure title compound as a pale yellow solid (3.3 g, 46%). MS m/z: 145 [M+H+]. $^1$H NMR (270 MHz, CHCl$_3$-d) δ ppm 3.89 (s, 2H) 6.87 (d, J=2.64 Hz, 1H) 7.14 (dd, J=8.97, 2.64 Hz, 1H) 7.25 (dd, J=8.44, 4.22 Hz, 1H) 7.88 (dd, J=7.92, 1.58 Hz, 1H) 7.90 (d, J=8.97 Hz, 1H) 8.63 (dd, J=4.22, 1.58 Hz, 1H).

INTERMEDIATE 2

Synthesis of 6-phenylsulfanyl-quinoline

A solution of sodium nitrite (1 g, 14 mmol) in water (6 mL) was slowly added to a stirred solution of 6-amino-quinoline (1.44 g, 10 mmol) in sulfuric acid (50%) (8 mL). The temperature was kept below 5° C. during the addition. The reaction mixture was poured into a solution of potassium hydroxide (9 g, 16 mmol) and thiophenol (1 mL, 9 mmol) in water (30 mL). The reaction mixture was refluxed for 3 h, cooled and extracted with diethyl ether. The insoluble material was eliminated by filtration. During filtration most of the material was trapped in the solid phase. The filtrate was evaporated and the residue was purified by column chromatography (SiO$_2$, ethyl acetate:hexane, 1:2) to yield a colorless oil (100 mg, 4% PS: the low yield is due to the loss of the material during the filtration procedure). MS m/z: 238 [M+H+]. $^1$H NMR (270 MHz, CD$_3$Cl) δ ppm 7.34 (m, 4H) 7.42 (m, 2H) 7.57 (dd, J=8.97, 2.11 Hz, 1H) 7.67 (d, J=2.11 Hz, 1H) 7.99 (m, 2H) 8.84 (dd, J=4.22, 1.58 Hz, 1H).

INTERMEDIATE 3

Synthesis of 6-benzenesulfonyl-quinoline 1-oxid

A solution of m-chloroperbenzoic acid (1 g, 5.8 mmol) in DCM (10 mL) was added to a stirred solution of 6-phenylsulfanyl-quinoline (0.25 g, 1 mmol) and NaHCO$_3$ (0.5 g) in DCM (10 mL). The reaction was left stirring over night, washed with water, NaHCO$_3$ solution and evaporated. Trituration of the residue in diethyl ether gave the pure title product as a slightly yellow solid (0.14 g, 30%). MS m/z: 287 [M+H+].

INTERMEDIATE 4

Synthesis of 6-benzenesulfonyl-4-chloro-quinoline

A solution of 6-benzenesulfonyl-quinoline 1-oxid (135 mg, 0.47 mmol) in POCl$_3$ (4 mL) was heated at 90° C. for 2 h after which the solution was poured on ice, ammonium hydroxide was added and extraction with DCM. The organic phase was dried (NaSO$_4$), the volatiles were evaporated and the residue was purified by column chromatography (SiO$_2$, ethyl acetate:petroleum ether, 1:1) to yield a white solid (39 mg, 27%). MS m/z: 305 [M+H+].

EXAMPLE 1

Synthesis of 6-benzenesulfonyl-4-piperazin-1-yl-quinoline hydrochloride

A solution of 6-benzenesulfonyl-4-chloro-quinoline (35 mg, 0.11 mmol) and piperazine (0.5 g, 2.5 mmol) in acetonitrile (2 mL) was heated at 80° C. over night. The mixture was extracted with toluene and water. The organic phase was purified by chromatography on silica gel eluted with CHCl$_3$ saturated with NH$_3$ (gas). The pure product was dissolved in ethyl acetate and HCl (gas) in diethyl ether was added. The resulting oily residue was dissolved in methanol and ethyl acetate and evaporated to yield a white solid (24 mg, 77%). MS m/z: 354 [M+H+]. $^1$H NMR (270 MHz, CH$_3$OH-D$_4$) δ ppm 3.52 (m, 4H) 4.13 (m, 4H) 7.36 (d, J=7.18 Hz, 1H) 7.57 (m, 3H) 8.01 (m, J=12.25, 8.54 Hz, 3H) 8.28 (d, J=8.91 Hz, 1H) 8.63 (d, J=6.68 Hz, 1H) 8.69 (s, 1H).

Scheme 2

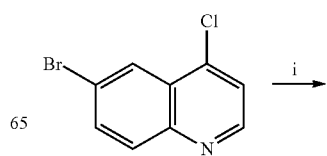

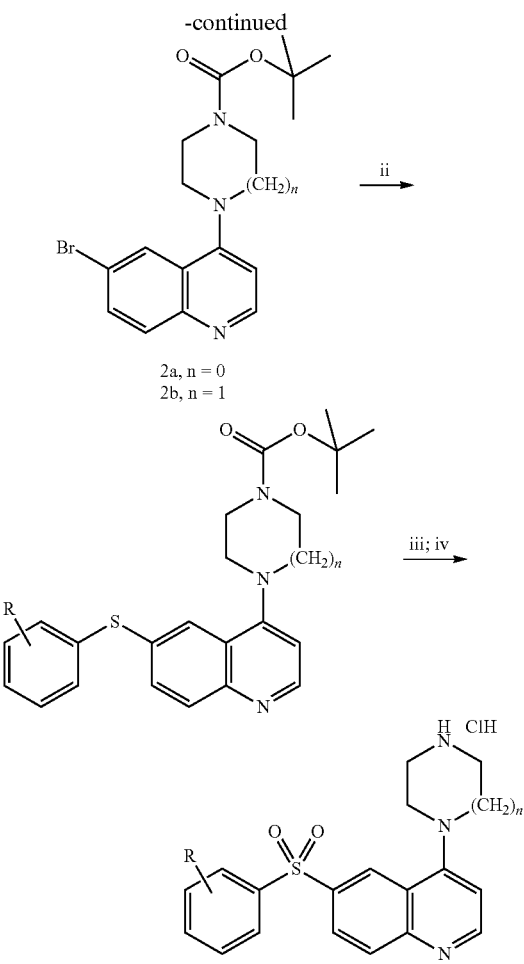

2a, n = 0
2b, n = 1

Legend for Scheme 2: i) NatBuO, Pd(PPh₃)₄, n-BuOH, BOC-protected diamines; ii) tert-butyl piperazine-1-carboxylate or tert-butyl 1,4-diazepane-1-carboxylate, triethylamine or K₂CO₃, DMSO, thiols; iv) TFA, H₂O₂, NaOH; iv) HCl.

Method A
Preparation of Thiol Derivatives tert-Butyl 4-(6-bromoquinolin-4-yl)-1,4-diazepane-1-carboxylate (0.5 g, 1.23 mmol) was mixed with the thiol (1 equiv.), NaOtBu (2 equiv.), Pd(PPh₃)₄ (0.05 equiv.) and n-BuOH (5 mL) in a reaction tube. N₂ (g) was flushed through the mixture for 30 minutes. The reaction mixture was heated to 120° C. overnight. The precipitate was filtrated and the reaction mixture concentrated in vacuo. The residue was dissolved in EtOAc and washed with H₂O, dried (MgSO₄) and evaporated. Purification by flash chromatography using DCM: MeOH 98:2 as eluent afforded the title product that was used in the next step without further purification.

Method B
Oxidation of Thiol Derivatives to Sulphone Derivatives

The appropriate thiophenols derivatives are dissolved in TFA (5 mL) and stirred for 15 minutes at room temperature. H₂O₂ (2 mL) was added and the reaction was left stirring overnight. The reaction mixtures are evaporated and the residues are portioned between diethyl ether and water. The layers are separated and the water layer is extracted with diethyl ether and made basic by adding NaOH 1M. Extraction with DCM, drying with MgSO₄ and evaporation gives the free bases of the products which are dissolved in MeOH, excess of HCl/ether (2M) was added and the solvent evaporated. The residues are purified on preparative HPLC/MS (Xterra MS C18, 5 μm column) using a 10 to 40% MeCN-water gradient (containing 0.1% HOAc) over 10 minutes. The pure fractions are pooled and lyophilised. The residues are dissolved in MeOH and treated with excess of HCl/ether (2M). After evaporation of solvent, a solid is obtained and triturated with diethyl ether giving the desired products as HCl-salts.

INTERMEDIATE 5 tert-Butyl 4-(6-bromoquinolin-4-yl)piperazine-1-carboxylate

6-Bromo-4-chloroquinoline (5.0 g, 20.6 mmol), tert-butyl-1-piperazine (4.1 g, 22 mmol), triethylamine (3 mL, 22 mmol) and DMSO (20 mL) were mixed and heated overnight in an oil bath at 100° C. The reaction was cooled and diluted with diethyl ether and washed with water (5×), dried (MgSO₄) and evaporated. The residue was filtered through a short column of silica (2.5-5%) MeOH in CH₂Cl₂ and evaporated. Yield 8.02 g. (97%). Brown liquid. HPLC 98%, $R_T$=3.01 (System A1, 10-97% MeCN over 3 min). ¹H NMR (400 MHz, CDCl₃) δ ppm 1.52 (s, 9H) 3.12-3.17 (m, 4H) 3.69-3.75 (m, 4H) 6.86 (d, J=5.0 Hz, 1H) 7.72 (dd, J=9.0, 2.26 Hz, 1H) 7.92 (d, J=8.8 Hz, 1H) 8.14 (d, J=2.3 Hz, 1H) 8.73 (d, J=5.0 Hz, 1H). MS (ESI+) for $C_{18}H_{22}BrN_3O_2$ m/z 392.2 (M+H⁺)

EXAMPLE 2

6-[(2-fluorophenyl)sulfonyl]-4-piperazin-1-ylquinoline hydrochloride

A total amount of 2.25 mmol, of the appropriate thiophenol was used and the reaction was prolonged with 8 hours. The oxidation step was completed after 24 hours at ambient temperature. Purification by column chromatography on silica gel 10-20% MeOH in DCM gave the free amine that was additionally purified by preparative HPLC. Yield 15 mg (4%) Yellow solid. HPLC 95%, $R_T$=2.33 (System A1, 10-97% MeCN over 3 min). ¹H NMR (400 MHz, DMSO-d₆) δ ppm 3.30-3.42 (m, 4H) 3.51-3.62 (m, 4H) 7.28 (d, J=5.27 Hz, 1H) 7.42 (dd, J=10.29, 8.78 Hz, 1H) 7.52 (t, J=7.28 Hz, 1H) 7.77-7.84 (m, 1H) 8.04-8.21 (m, 3H) 8.62 (s, 1H) 8.87 (d, J=5.27 Hz, 1H) 9.82 (br s, 2H). MS (ESI+) for $C_{19}H_{18}FN_3O_2S$ m/z 372.0 (M+H⁺). HRMS for $C_{19}H_{18}FN_3O_2S$: calcd, 371.1104; found, 371.1102.

EXAMPLE 3

6-(1-Naphthylsulfonyl)-4-piperazin-1-ylquinoline hydrochloride

A total amount of 2.25 mmol, of the appropriate thiophenol was used and the reaction was prolonged with 8 hours. The oxidation step was completed after 24 hours at ambient temperature. Purification by column chromatography on silica gel 10-20% MeOH in DCM gave the free amine that was converted to the HCl-salt. Yield 14 mg (4%). Grey solid. HPLC 95%, $R_T$=2.54 (System A1, 10-97% MeCN over 3 min). ¹H NMR (400 MHz, DMSO-d₆) δ ppm 3.33 (s, 4H) 4.06 (s, 4H) 7.38 (d, J=6.78 Hz, 1H) 7.65 (d, J=7.53 Hz, 1H) 7.69-7.75 (m, 1H) 7.82 (t, J=7.78 Hz, 1H) 8.12 (d, J=8.03 Hz, 1H) 8.21-8.30 (m, 2H) 8.38 (d, J=8.03 Hz, 1H) 8.56 (t, J=8.53 Hz, 2H) 8.74-8.79 (m, 2H) 10.05 (s, 2H). MS (ESI+) for $C_{23}H_{21}N_3O_2S$ m/z 404.4 (M+H⁺) HRMS for $C_{23}H_{21}N_3O_2S$: calcd, 403.1354; found, 403.1365.

EXAMPLE 4

6-[(3,4-Dichlorophenyl)sulfonyl]-4-piperazin-1-ylquinoline hydrochloride

A total amount of 2.25 mmol, of the appropriate thiophenol was used and the reaction was prolonged with 8 hours. The oxidation step was completed after 24 hours at ambient temperature. Purification by column chromatography on silica gel 10-20% MeOH in DCM gave the free amine which was converted to the HCl-salt giving yellow solid. Yield 15 mg (3%). Yellow solid. $^1$H NMR (400 MHz, DMSO-$d_6$) δ ppm 3.35-3.41 (m, 4H) 4.06-4.15 (m, 4H) 7.40 (d, J=6.78 Hz, 1H) 7.93 (d, J=8.53 Hz, 1H) 8.04 (dd, J=8.53, 2.01 Hz, 1H) 8.27 (d, J=9.03 Hz, 1H) 8.32 (d, J=2.01 Hz, 1H) 8.36-8.42 (m, 1H) 8.73 (d, J=1.51 Hz, 1H) 8.82 (d, J=6.53 Hz, 1H) 9.86 (s, 2H). MS (ESI+) for $C_{19}H_{17}Cl_2N_3O_2S$ m/z 422.2 (M+H$^+$). HRMS for $C_{19}H_{17}Cl_2N_3O_2S$: calcd, 421.0419; found, 421.0422. HPLC 95%, $R_T$=20.69 (System A1, 10-97% MeCN over 3 min)

EXAMPLE 5

6-[(3,5-Dimethylphenyl)sulfonyl]-4-piperazin-1-ylquinoline hydrochloride

The oxidation step was completed after 2 hours at ambient temperature. Purification by column chromatography on silica gel 10-20% MeOH in DCM gave the free amine which was converted to the HCl-salt giving grey solid. Yield 0.007 g (2%). Yellow solid. HPLC 90%, $R_T$=2.57 (System A1, 10-97% MeCN over 3 min). MS (ESI+) for $C_{21}H_{23}FN_3O_2S$ m/z 382.2. HRMS for $C_{21}H_{23}FN_3O_2S$: calcd, 381.1511; found, 381.1521.

EXAMPLE 6

6-[(2-Chloro-6-methylphenyl)sulfonyl]-4-piperazin-1-ylquinoline hydrochloride A total amount of 2.25 mmol, of the appropriatethiophenol was used and the reaction was prolonged with 8 hours. Additional $H_2O_2$ (1 mL) was added and the reaction mixture was stirred at 50° C. for another 48 hours. Purification by column chromatography on silica gel 10-20% MeOH in DCM gave the free amine that was converted to the HCl-salt. Yield 33 mg (7.5%). White solid. $^1$H NMR (400 MHz, DMSO-$d_6$) δ ppm 2.13 (s, 3H) 2.98 (s, 4H) 3.72 (s, 4H) 7.06 (d, J=6.78 Hz, 1H) 7.14 (dd, J=11.54, 8.03 Hz, 2H) 7.23 (t, J=7.78 Hz, 1H) 7.89 (d, J=8.78 Hz, 1H) 7.94-8.00 (m, 1H) 8.24 (s, 1H) 8.45 (d, J=6.78 Hz, 1H) 9.68 (s, 2H). MS (ESI+) for $C_{20}H_{20}ClN_3O_2S$ m/z 402.2 (M+H$^+$). HRMS for $C_{20}H_{20}ClN_3O_2S$: calcd, 401.965; found, 401.967. HPLC 95%, $R_T$=20.55 (System A1, 10-97% MeCN over 3 min).

EXAMPLE 7

6-[(4-Chlorophenyl)sulfonyl]-4-piperazin-1-ylquinoline hydrochloride

A total amount of 2.25 mmol, of the appropriate thiophenol was used and the reaction was prolonged for another 8 hours. The oxidation step was completed after 24 h at ambient temperature. Purification by column chromatography on silica gel 10-20% MeOH in DCM gave the free amine that was converted to the HCl-salt. Yield 14 mg (3%). Yellow solid. HPLC 95%, $R_T$=2.66 (System A1, 10-97% MeCN over 3 min). MS (ESI+) for $C_{19}H_{18}ClN_3O_2S$ m/z 388.2 (M+H$^+$). HRMS for $C_{19}H_{18}ClN_3O_2S$: calcd, 387.0808; found, 387.0821.

EXAMPLE 8

6-[(2-Methyl,4-tert-butyl-phenyl)sulfonyl]-4-piperazin-1-ylquinoline hydrochloride The oxidation step was completed after 2 hours at ambient temperature. Purification by column chromatography on silica gel 10-20% MeOH in DCM gave the free amine which was converted to the HCl-salt giving gray solid. Yield 17 mg (4%). HPLC 95%, $R_T$=2.81 (System A1, 10-97% MeCN over 3 min). MS (ESI+) for $C_{24}H_{29}N_3O_2S$ m/z 424.2 (M+H$^+$). HRMS for $C_{24}H_{29}N_3O_2S$: calcd, 423.1980; found, 423.1969.

EXAMPLE 9

6-[(3,4-Dimethylphenyl)sulfonyl]-4-piperazin-1-ylquinoline hydrochloride

The oxidation step was completed after 2 hours at ambient temperature. Purification by column chromatography on silica gel 10-20% MeOH in DCM gave the free amine which was converted to the HCl-salt. Yield 33 mg (8%). Yellow solid. $^1$H NMR (400 MHz, DMSO-$d_6$) δ ppm 2.27 (d, J=6.27 Hz, 6H) 3.34 (s, 4H) 4.12 (s, 4H) 7.39 (dd, J=7.40, 2.13 Hz, 2H) 7.75 (d, J=7.78 Hz, 1H) 7.81 (s, 1H) 8.32 (s, 2H) 8.61 (s, 1H) 8.78 (d, J=6.78 Hz, 1H) 10.18 (s, 2H). MS (ESI+) for $C_{21}H_{23}N_3O_2S$ m/z 382.2 (M+H$^+$). HRMS for $C_{21}H_{23}N_3O_2S$: calcd, 381.1511; found, 381.1519. HPLC 95%, $R_T$=2.54 (System A1, 10-97% MeCN over 3 min).

EXAMPLE 10

6-[(2,3-Dichlorophenyl)sulfonyl]-4-piperazin-1-ylquinoline hydrochloride

A total amount of 2.25 mmol, of the appropriate thiophenol was used and the reaction was prolonged for another 8 hours. The oxidation step was completed after 24 hours at ambient temperature. Purification by column chromatography on silica gel 10-20% MeOH in DCM gave the free amine which was converted to the HCl-salt. Yield 15 mg (3%). Yellow solid. $^1$H NMR (400 MHz, DMSO-$d_6$) δ ppm 3.36 (m, 4H) 4.10 (m, 4H) 7.42 (d, J=6.78 Hz, 1H) 7.75 (t, J=8.03 Hz, 1H) 8.07 (d, J=8.03 Hz, 1H) 8.24 (d, J=9.04 Hz, 1H) 8.33 (dd, J=13.93, 8.41 Hz, 2H) 8.70 (s, 1H) 8.82 (d, J=6.78 Hz, 1H) 10.00 (s, 2H). MS (ESI+) for $C_{19}H_{17}Cl_2N_3O_2S$ m/z 422.2 (M+H$^+$). HRMS for $C_{19}H_{17}Cl_2N_3O_2S$: calcd, 421.0419; found, 421.0408. HPLC 95%, $R_T$=2.50 (System A1, 10-97% MeCN over 3 min).

EXAMPLE 11

6-[(4-tert-Butylphenyl)sulfonyl]-4-piperazin-1-ylquinoline hydrochloride tert-Butyl 4-{6-[(4-tert-butylphenyl)thio]quinolin-4-yl}piperazine-1-carboxylate (0.60 g, 1.3 mmol) was dissolved in TFA (12 mL) and stirred for 30 minutes before $H_2O_2$ (0.65 mL, 6.3 mmol) was added. The mixture was stirred for 2 hours and water (5 mL) was added. The mixture was evaporated and the residue was taken up in water and washed with diethyl ether (2×). The aqueous phase was adjusted to pH 10 with 1 N NaOH and the mixture was extracted with $CH_2Cl_2$ (2×), dried ($MgSO_4$) and evaporated. The residue was diluted with $CH_2Cl_2$ and 1.3 mL 2N HCl in diethyl ether was added under vigorous stirring and the mixture was evaporated and washed with diethyl ether (2×) and dried. Yield: 0.40 g (69%). Grey solid. HPLC 95%, $R_T$=2.77 (System A1, 10-97% MeCN over 3 min). $^1$H NMR (400 MHz, DMSO-$d_6$) δ ppm 1.23 (s, 9H) 3.38 (s, 4H) 4.08 (s, 4H) 7.39 (d, J=7.03 Hz, 1H) 7.65 (d, J=8.53 Hz, 2H) 7.96 (d, J=8.53 Hz, 2H) 8.25 (d, J=8.78 Hz, 1H) 8.30-8.36 (m, 1H) 8.66 (d, J=1.76 Hz, 1H) 8.81 (d, J=7.03 Hz, 1H) 9.85 (br. s, 2H), MS (ESI+) for $C_{23}H_{27}N_3O_2S$ m/z 410.4 (M+H$^+$).

EXAMPLE 12

6-[(4-Isopropylphenyl)sulfonyl]-4-piperazin-1-ylquinoline hydrochloride

4-Isopropylthiophenol (0.152 g, 1.0 mmol) was added dropwise to a suspension of tert-butyl 4-(6-bromo-quinolin-4-yl)-piperazine-1-carboxylate (0.2 g, 0.51 mmol), Na-t-butoxide (0.192 g, 2.0 mmol) and Pd[P(Ph)$_3$]$_4$ (0.030 g, 0.025 mmol) in ethanol (3 mL) at 90° C. and the mixture was stirred for 18 h. The mixture was diluted with THF and filtered through a plug of silica and evaporated. The crude product was dissolved in TFA (5 mL) and stirred for 15 minutes before 30% $H_2O_2$ (1 mL) was added. The mixture was stirred for 2 hours and evaporated. The residue was dissolved in water and washed with $CH_2Cl_2$ (2×) and 2 N NaOH was added until pH reached 10 and the mixture was extracted with $CH_2Cl_2$ (3×), dried ($MgSO_4$) and evaporated. The crude product was purified by preparative HPLC 5-95 water/acetonitrile collecting on m/z 395.2. After evaporation the free amine was dissolved in $CH_2Cl_2$ and excess of HCl in diethyl ether was added and the mixture was evaporated. Yield 0.015 g (7%). $^1$H NMR (400 MHz, DMSO-$d_6$) δ ppm 1.17 (d, J=7.03 Hz, 6H) 2.90-3.02 (m, 1H) 3.34-3.42 (m, 4H) 4.03-4.12 (m, 4H) 7.39 (d, J=6.78 Hz, 1H) 7.51 (d, J=8.28 Hz, 2H) 7.96 (d, J=8.53 Hz, 2H) 8.26 (d, J=9.03 Hz, 1H) 8.29-8.36 (m, 1H) 8.66 (s, 1H) 8.80 (d, J=6.78 Hz, 1H) 9.85-9.97 (m, 2H). HPLC 95%, $R_T$=2.65 (System A1, 10-97% MeCN over 3 min).

EXAMPLE 13

4-Piperazin-1-yl-6-{[4-(trifluoromethyl)phenyl]sulfonyl}quinoline hydrochloride

4-Trifluoromethylthiophenol (0.178 g, 1.0 mmol) was added dropwise to a suspension of tert-butyl 4-(6-bromo-quinolin-4-yl)-piperazine-1-carboxylate (0.2 g, 0.51 mmol), Sodium-t-butoxide (0.192 g, 2.0 mmol) and Pd[P(Ph)$_3$]$_4$ (0.030 g, 0.025 mmol) in ethanol (3 mL) at 90° C. and the mixture was stirred for 18 h. The mixture was diluted with THF and filtered through a plug of silica and evaporated. The crude product was dissolved in TFA (5 mL) and stirred for 15 minutes before 30% $H_2O_2$ (1 mL) was added. The mixture was stirred for 2 hours and evaporated. The residue was dissolved in water and washed with $CH_2Cl_2$ (2×) and 2 N NaOH was added until pH reached 10 and the mixture was extracted with $CH_2Cl_2$ (3×) dried ($MgSO_4$) and evaporated. The crude was purified by preparative HPLC 5-95 water/acetonitrile collecting on m/z 421.1. After evaporation the free amine was dissolved in $CH_2Cl_2$ and excess of HCl in diethyl ether was added and the mixture was evaporated. Yield 0.024 g (10%). $^1$H NMR (400 MHz, DMSO-$d_6$) δ ppm 3.33-3.40 (m, 4H) 4.13-4.21 (m, 4H) 7.42 (d, J=7.03 Hz, 1H) 8.02 (d, J=8.53 Hz, 2H) 8.25-8.35 (m, 3H) 8.37-8.53 (m, 1H) 8.76 (d, J=1.76 Hz, 1H) 8.80 (d, J=7.03 Hz, 1H) 9.95-10.05 (m, 2H). Yellow oil. HPLC 95%, $R_T$=2.66 (System A1, 10-97% MeCN over 3 min).

INTERMEDIATE 6 tert-Butyl 4-(6-bromoquinolin-4-yl)-1,4-diazepane-1-carboxylate

6-Bromo-4-chloroquinoline (3.5 g, 14.5 mmol) was reacted with tert-butyl 1,4-diazepane-1-carboxylate (3.7 g, 18.8 mmol) and $K_2CO_3$ (4 g, 29 mmol) in DMSO at 100° C. overnight. After cooling the mixture was poured into water and extracted with DCM. The organic layer was washed with water, dried ($MgSO_4$) and evaporated. The residue was purified by flash chromatography using a gradient of EtOAc: hexane 1:1 to 2:1 giving 2.1 g (36%) of yellow oil. $^1$H NMR (400 MHz, CDCl$_3$) δ ppm 1.47 (d, J=5.5 Hz, 9H) 2.08-2.16 (m, 2H) 3.35-3.44 (m, 4H) 3.60-3-73 (m, 4H) 6.87 (d, J=5.5 Hz, 1H) 7.69 (dd, J=9.0, 2.0 Hz, 1H) 7.88 (d, J=8.5 Hz, 1H) 8.16 (s, 1H) 8.65 (d, J=5.0 Hz, 1H). MS (ESI+) for $C_{19}H_{24}BrN_3O_2$ m/z 406.4 (M+H)$^+$. HRMS (EI) calcd for $C_{19}H_{24}BrN_3$: 405.1052, found 405.1045.

INTERMEDIATE 7 tert-Butyl-4{3-[(4-tert-butylphenyl)thio]quinolin-5-yl}-1,4-diazepane-1-carboxylate (General Method A)

The compound was prepared from tert-butyl 4-(6-bromo-quinolin-4-yl)-1,4-diazepane-1-carboxylate (0.5 g, 1.23 mmol) and p-tert-butylbenzenethiol (0.2 g, 1.23 mmol). Yield: 0.27 g (44%) of the title compound. HPLC 89%, $R_T$: 3.76 min (5-99% MeCN containing 0.1% TFA over 3 min).

INTERMEDIATE 8 tert-Butyl-4{3-[(4-isopropylphenyl)thio]quinolin-5-yl}-1,4-diazepane-1-carboxylate (General Method A)

The compound was prepared from tert-butyl 4-(6-bromo-quinolin-4-yl)-1,4-diazepane-1-carboxylate (0.5 g, 1.23 mmol) and 4-isopropylbenzenethiol (0.19 g, 1.23 mmol). Yield: 0.27 g (46%) of the title compound that was used in the next step without further purification. HPLC 89%, $R_T$: 3.67 min (5-99% MeCN containing 0.1% TFA over 3 min); MS (ESI+) for $C_{28}H_{35}N_3O_2S$ m/z 478.2 (M+H)$^+$.

EXAMPLE 14

6-[(4-tert-Butylphenyl)sulfonyl]-4-(1,4-diazepan-1-yl)quinoline hydrochloride (General Method B)

The compound was synthesized from tert-butyl-4{3-[(4-tert-butylphenyl)thio]quinolin-5-yl}-1,4-diazepane-1-carboxylate (0.27 g, 0.55 mmol).

Yield: 20 mg (8%) of the title compound; $^1$H NMR (270 MHz, DMSO-$d_6$) δ ppm 1.25 (s, 9H) 2.31 (br s, 2H) 3.25 (br s, 2H) 3.49 (br s, 2H) 4.11 br s, 2H) 4.26 (br s, 2H) 7.16 (d, J=7.1 Hz, 1H) 7.65 (d, J=8.2 Hz, 2H) 7.94 (d, J=8.2 Hz, 2H) 8.19 (d, J=8.7 Hz, 1H) 8.26 (d, J=8.7 1H) 8.62 (d, J=6.3 Hz, 1H) 8.75 (s, 1H) 9.65 (br s, 2H); MS (ESI+) for $C_{24}H_{29}N_3O_2S$ m/z 424.2 (M+H)$^+$. HPLC 93%, $R_T$: 2.79 min (5-99% MeCN over 3 min).

EXAMPLE 15

4-(1,4-Diazepan-1-yl)-6-[(4-isopropylphenyl)sulfonyl]quinoline hydrochloride (General Method B)

The compound was prepared from tert-Butyl-4{3-[(4-isopropylphenyl)thio]quinolin-5-yl}-1,4-diazepane-1-carboxylate (0.27 g, 0.57 mmol). Yield: 15 mg (6%) of the title compound; $^1$H NMR (270 MHz, DMSO-$d_6$) δ ppm 1.16 (d, J=6.9 Hz, 6H) 2.31 (br s, 2H) 2.96 (m, 1H) 3.25 (br s, 2H) 3.49 (br s, 2H) 4.11 (br s, 2H) 4.26 (br s, 2H) 7.16 (d, J=6.9 Hz, 1H) 7.51 (d, J=8.2 Hz, 2H) 7.94 (d, J=8.2 Hz, 2H) 8.18 (d, J=8.7 Hz, 1H) 8.30 (d, J=8.4 Hz, 1H) 8.62 (d, J=6.1 Hz, 1H) 8.75 (s, 1H) 9.62 (br s, 2H); MS (ESI+) for $C_{23}H_{27}N_3O_2S$ m/z 410.4 (M+H)$^+$. HPLC 93%, $R_T$: 2.70 min (5-99% MeCN over 3 min).

TABLE 2

| EXAMPLE | | $R^7$ | $R^1$ |
|---|---|---|---|
| 16 | 7-(2-Chloro-6-methyl-benzenesulfonyl)-1-piperazin-1-yl-isoquinoline hydrochloride | 2-chloro-6-methylphenyl | piperazin-1-yl |
| 17 | 7-(2-t-Butyl-benzenesulfonyl)-1-piperazin-1-yl-isoquinoline hydrochloride | 2-t-butylphenyl | piperazin-1-yl |
| 18 | 7-(3,4-Dichloro-benzenesulfonyl)-1-piperazin-1-yl-isoquinoline hydrochloride | 3,4-dichlorophenyl | piperazin-1-yl |

TABLE 2-continued

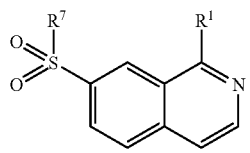

| EXAMPLE | | R⁷ | R¹ |
|---|---|---|---|
| 19 | 7-(3,4-Dimethyl-benzenesulfonyl)-1-piperazin-1-yl-isoquinoline hydrochloride | 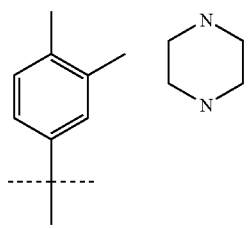 | |
| 20 | 7-(2,5-Dimethyl-benzenesulfonyl)-1-piperazin-1-yl-isoquinoline hydrochloride | 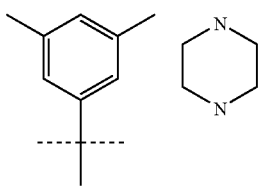 | |
| 21 | 7-(p-Chloro-benzenesulfonyl)-1-piperazin-1-yl-isoquinoline hydrochloride | 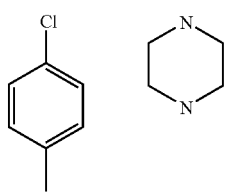 | |
| 22 | 7-Benzenesulfonyl-1-[1,4]diazepan-1-yl-isoquinolin, hydrochloride | 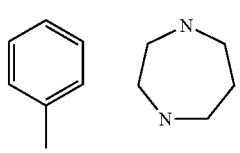 | |
| 23 | 7-(4-tert-Butyl-benzenesulfonyl)-1-[1,4]diazepan-1-yl]-isoquinoline, hydrochloride | 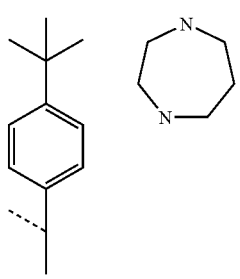 | |
| 24 | 7-(2-Chloro-6-methyl-benzenesulfonyl)-1-[1,4]diazepan-1-yl]-isoquinoline hydrochloride | 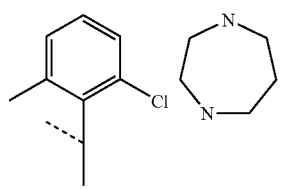 | |

TABLE 2-continued

| EXAMPLE | | R⁷ | R¹ |
|---|---|---|---|
| 25 | 7-(3,5-Dimethyl-benzenesulfonyl)-1-[1,4]diazepan-1-yl]-isoquinoline hydrochloride | 3,5-dimethylphenyl | [1,4]diazepan-1-yl |
| 26 | 7-(3,4-Dichloro-benzenesulfonyl)-1-[1,4]diazepan-1-yl]-isoquinoline hydrochloride | 3,4-dichlorophenyl | [1,4]diazepan-1-yl |
| 27 | 7-(4-Chloro-benzenesulfonyl)-1-[1,4]diazepan-1-yl]-isoquinoline hydrochloride | 4-chlorophenyl | [1,4]diazepan-1-yl |
| 28 | 7-(3,4-Dimethyl-benzenesulfonyl)-1-[1,4]diazepan-1-yl]-isoquinoline hydrochloride | 3,4-dimethylphenyl | [1,4]diazepan-1-yl |
| 29 | 7-(2-tert-Butyl-benzenesulfonyl)-1-[1,4]diazepan-1-yl]-isoquinoline hydrochloride | 2-tert-butylphenyl | [1,4]diazepan-1-yl |
| 30 | 7-Benzenesulfonyl-1-piperazin-yl-isoquinoline hydrochloride | phenyl | piperazin-1-yl |

TABLE 2-continued
| EXAMPLE | | R⁷ | R¹ |
|---|---|---|---|
| 31 | 7-(4-tert-Butyl-benzenesulfonyl-1-piperazin-yl-isoquinoline hydrochloride | | |
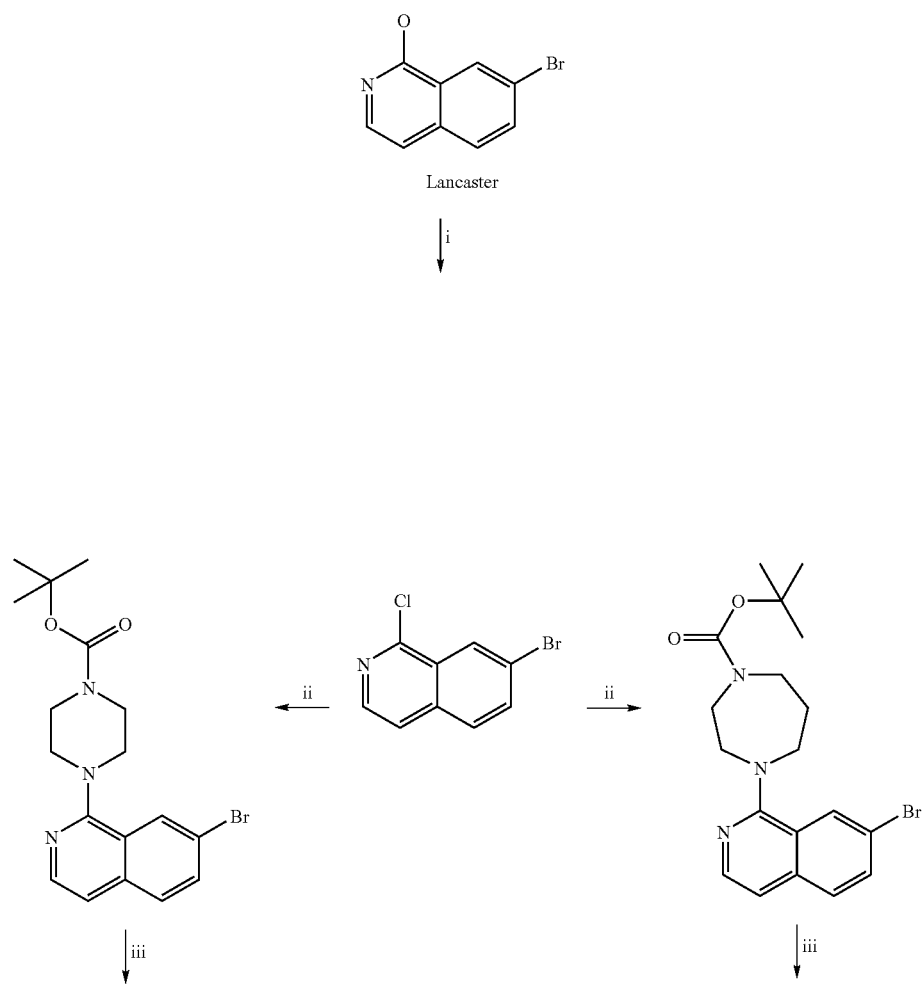
Scheme 3

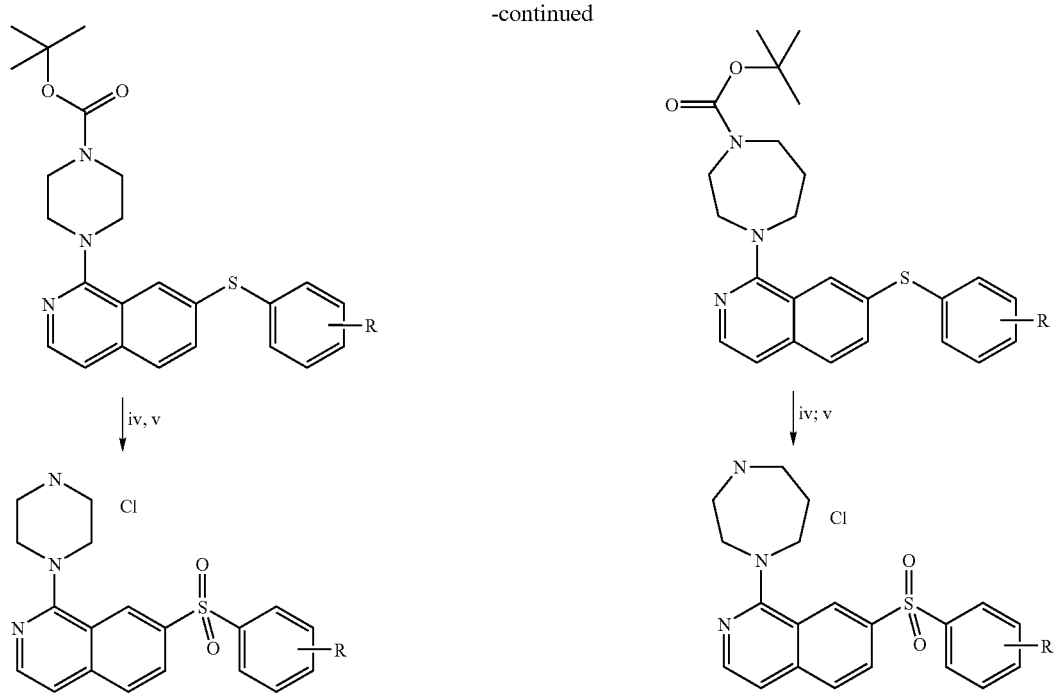

Legend to Scheme 3: i) POCl₃; ii) K₂CO₃, DMF, BOC-diamines; iii) Nat-BuO, thiophenols, Pd(PPh₃)₄; n-BuOH; iv) TFA, H₂O₂; v) HCl in diethyl ether.

INTERMEDIATE 9

7-Bromo-1-Chloroisoquinoline

To phosphorus oxychloride (46.6 mL, 0.5 mol) at room temperature was added, portionwise, 7-bromo-1-hydroxyisoquinoline (11.2 g, 0.05 mol). The mixture was heated to 100° C. for 90 min with rapid stirring. On cooling to room temperature, the mixture was poured, cautiously onto ice/water (200 mL). Dropwise addition of aqueous ammonia raised the pH=8 and the resulting precipitate was collected by filtration, washing with cold water. The solid was dried under reduced vacuum at 45° C. for 12 h. 13.86 g (115%) Beige solid isolated. $^1$H NMR (DMSO-d$_6$) δ 8.4 (s, 1H), 8.34-8.38 (d, J=6 Hz, 1H), 8.03-8.07 (m, 2H), 7.91-7.96 (d, J=6 Hz, 1H); HPLC: 96%; LCMS: 242, 244, 246.

Nucleophilic Displacement of Chlorine

INTERMEDIATE 10

4-(7-Bromo-isoquinoline-1-yl)-piperazine-1-carboxylic acid, tert-butyl ester To a suspension of 7-bromo-1-chloroisoquinoline (3.14 g, 13 mmol) in DMSO (20 mL) at room temperature was added either carboxylic acid tert-butyl (BOC)piperazine (7.23 g, 38.8 mmol) or BOC-homopiperazine (7.77 g, 38.8 mmol) and then potassium carbonate (5.36 g, 39 mmol). The mixture was heated to 110° C. for 24 h. On cooling, the mixture was poured onto ice/water (50 mL) and extracted with ethyl acetate (3×50 mL). The combined organic phases were washed with water 50 mL) and brine (50 mL). Before drying over anhydrous sodium sulfate. Removal of solvent under reduced pressure gave crude product. Purification was performed by applying the crude material to a plug of silica in a filter funnel and eluting with heptane/ethyl acetate (2:1) and gave 2.73 g (54%) yellow oil. $^1$H NMR (CDCl$_3$) δ 8.20-8.22 (m, 1H), 8.13-8.18 (d, J=6 Hz, 1H), 7.65-7.71 (dd, J=12, 3 Hz, 1H), 7.59-7.65 (d, J=12 Hz, 1H), 7.21-7.25 (m, 1H), 3.64-3.73 (m, 4H), 7.27-7.36 (m, 4H), 1.49 (s, 9H); LCMS: 392, 394, 395.

INTERMEDIATE 11

4-(7-Bromo-isoquinoline-1-yl)-[1,4]diazepane-1-carboxylic acid, tert-butyl ester 2.75 g (52%) yellow oil isolated $^1$H NMR (CDCl$_3$) δ 8.19-8.24 (m, 1H), 8.06-8.12 (d, J=9 Hz, 1H), 7.54-7.68 (m, 2H), 7.11 (m, 1H), 3.47-3.74 (m, 8H), 1.98-2.16 (m, 2H), 1.48 (s, 9H); LCMS: 406, 407, 408.

Palladium-Catalysed Aryl Thiol Coupling

To 7-bromo-1-chloroisoquinoline (1 mmol) in butan-1-ol (20 mL) at room temperature was added sodium tert-butoxide (481 mg, 5 mmol), thiol (1.5 mmol) and tetrakis triphenylphosphine palladium (60 mg, catalytic). The mixture was heated to 120° C. for 16 h. On cooling to room temperature, the mixture was filtered through silica eluting with THF. Removal of solvent under reduced pressure gave the crude product which was used without further purification in the subsequent step.

INTERMEDIATE 12

4-[7-(2-Chloro-6-methyl-phenylsulfanyl)-isoquinolin-1-yl]-piperazine-1-carboxylic acid tert-butyl ester A mixture of 4-(7-bromo-isoquinoline-1-yl)-piperazine-1-carboxylic acid, tert-butyl ester (0.5 g, 1.3 mmol), 2-chloro-6-methyl-thiophenol (0.206 g, 1.3 mmol), NatBuO (0.44 g, 4.5 mmol), Pd(PPh$_3$)$_4$ (74 mg, 0.065 mmol) in nBuOH (10 mL) was heated at 110° C., 3 h. The reaction mixture was filtered. The filtrate was concentrated and the residue was dissolved in ethyl acetate. The organic phase was washed with water (50 mL×3), separated and dried (MgSO$_4$), filtered. The volatiles were evaporated and the residue was purified by flash column chromatography (SiO$_2$, n-heptane: ethyl acetate 8:2) to give 530 mg of the title compound as colourless oil (yield 86.4%). $^1$H NMR (CDCl$_3$) δ 8.05 (d, 1H), 7.65 (d, 1H), 7.20-7.45 (m, 5H), 7.15 (d, 1H), 3.26-3.40 (m, 4H), 3.10-3.20 (m, 4H), 2.5 (s, 3H), 1.38 (s, 9H).

INTERMEDIATE 13

4-[7-(2-t-butyl-phenylsulfanyl)-isoquinolin-1-yl]-piperazine-1-carboxylic acid tert-butyl ester A mixture of 4-(7-bromo-isoquinoline-1-yl)-piperazine-1-carboxylic acid, tert-butyl ester (0.5 g, 1.3 mmol), 2-t-butyl-thiophenol (0.216 g, 1.3 mmol), Nat-BuO (0.44 g, 4.5 mmol), Pd(PPh$_3$)$_4$ (74 mg, 0.065 mmol) in n-BuOH (10 mL) was heated at 110° C., 3 h. The reaction mixture was filtered. The filtrate was concentrated and the residue was dissolved in ethyl acetate. The organic phase was washed with water (50 mL×3), separated and dried (MgSO$_4$), filtered. The volatiles were evaporated and the residue was purified by flash column chromatography (SiO$_2$, n-heptane: ethyl acetate 8:2) to give 440 mg of the title compound as colorless oil (yield 71%). $^1$H NMR (CDCl$_3$) δ 8.00-8.10 (m, 2H), 7.15-7.65 (m, 7H), 3.60-3.70 (m, 1H), 3.30-3.45 (m, 4H), 3.05-3.20 (m, 3H), 1.55 (s, 9H), 1.50 (s, 9H).

INTERMEDIATE 14

4-[7-(3,4-Dichloro-phenylsulfanyl)-isoquinolin-1-yl]-piperazine-1-carboxylic acid tert-butyl ester A mixture of 4-(7-bromo-isoquinoline-1-yl)-piperazine-1-carboxylic acid, tert-butyl ester (0.5 g, 1.3 mmol), 3,4-dichloro-thiophenol (165 uL, 1.3 mmol), NatBuO (0.44 g, 4.5 mmol), Pd(PPh$_3$)$_4$ (74 mg, 0.065 mmol) in n-BuOH (10 mL) was heated at 110° C., 3 h. The reaction mixture was filtered. The filtrate was concentrated and the residue was dissolved in ethyl acetate. The organic phase was washed with water (50 mL×3), separated and dried (MgSO$_4$), filtered. The volatiles were evaporated and the residue was purified by flash column chromatography (SiO$_2$, n-pentane:ethyl acetate 9.5:0.5→8:2) to give 230 mg of the title compound as colorless oil (yield 36%). $^1$H NMR (CDCl$_3$) δ 8.10-8.20 (m, 2H), 7.90 (bs, 1H), 7.65-7.75 (m, 2H), 7.10-7.55 (m, 3H), 3.50-3.65 (m, 4H), 3.20-3.30 (m, 4H), 1.50 (s, 9H).

INTERMEDIATE 15

4-[7-(3,4-Dimethyl-phenylsulfanyl)-isoquinolin-1-yl]-piperazine-1-carboxylic acid tert-butyl ester A mixture of 4-(7-bromo-isoquinoline-1-yl)-piperazine-1-carboxylic acid, tert-butyl ester (0.5 g, 1.3 mmol), 3,4-dimethyl-thiophenol (175 uL, 1.3 mmol), NatBuO (0.44 g, 4.5 mmol), Pd(PPh$_3$)$_4$ (74 mg, 0.065 mmol) in n-BuOH (10 mL) was heated at 110° C., 3 h. The reaction mixture was filtered. The filtrate was concentrated and the residue was dissolved in ethyl acetate. The organic phase was washed with water (50 mL×3), separated and dried (MgSO$_4$), filtered. The volatiles were evaporated and the residue was purified by flash column chromatography (SiO$_2$, n-pentane:ethyl acetate 9.5:0.5→8:2) to give 260 mg of the title compound as colorless oil (yield 44%). $^1$H NMR (CDCl$_3$) δ 8.00-8.10 (m, 2H), 7.55-7.65 (m, 3H), 7.40-7.50 (m, 1H), 7.10-7.30 (m, 2H), 3.30-3.40 (m, 4H), 3.10-3.20 (m, 4H), 2.30 (s, 3H), 2.25 (s, 3H), 1.50 (s, 9H).

INTERMEDIATE 16

4-[7-(3,5-Dimethyl-phenylsulfanyl)-isoquinolin-1-yl]-piperazine-1-carboxylic acid tert-butyl ester A mixture of 4-(7-bromo-isoquinoline-1-yl)-piperazine-1-carboxylic acid, tert-butyl ester (0.5 g, 1.3 mmol), 3,5-dimethyl-thiophenol (180 mg, 1.3 mmol), NatBuO (0.44 g, 4.5 mmol), Pd(PPh$_3$)$_4$ (74 mg, 0.065 mmol) in nBuOH (10 mL) was heated at 110° C., 3 h. The reaction mixture was filtered. The filtrate was concentrated and the residue was dissolved in ethyl acetate. The organic phase was washed with water (50 mL×3), separated and dried (MgSO$_4$), filtered. The volatiles were evaporated and the residue was purified by flash column chromatography (SiO$_2$, n-pentane:ethyl acetate 9.8:0.2→8:2) to give 380 mg of the title compound as colourless oil (yield 65%). $^1$H NMR (CDCl$_3$) δ 8.05-8.10 (m, 1H), 7.80-7.85 (m, 1H), 7.60-7.75 (m, 1H), 7.17-7.25 (m, 1H), 7.10 (bs, 2H), 7.00 (bs, 1H), 3.40-3.50 (m, 4H), 3.10-3.20 (m, 4H), 2.25 (bs, 6H), 1.50 (s, 9H).

INTERMEDIATE 17

4-[7-(p-Chloro-phenylsulfanyl)-isoquinolin-1-yl]-piperazine-1-carboxylic acid tert-butyl ester A mixture of 4-(7-bromo-isoquinoline-1-yl)-piperazine-1-carboxylic acid, tert-butyl ester (0.5 g, 1.3 mmol), p-chloro-thiophenol (188 mg, 1.3 mmol), NatBuO (0.44 g, 4.5 mmol), Pd(PPh$_3$)$_4$ (74 mg, 0.065 mmol) in nBuOH (10 mL) was heated at 110° C., 3 h. The reaction mixture was filtered. The filtrate was concentrated and the residue was dissolved in ethyl acetate. The organic phase was washed with water (50 mL×3), separated and dried (MgSO$_4$), filtered. The volatiles were evaporated and the residue was purified by flash column chromatography (SiO$_2$, n-pentane:ethyl acetate 9.5:0.5→8:2) to give 300 mg of the title compound as colourless oil (yield 50%). $^1$H NMR (CDCl$_3$) δ 8.05-8.15 (m, 2H), 7.60-7.70 (m, 2H), 7.40-7.50 (m, 2H), 7.15-7.30 (m, 3H), 3.45-3.55 (m, 4H), 3.10-3.15 (m, 4H), 1.50 (s, 9H).

INTERMEDIATE 18

4-(7-Phenylsulfanyl-isoquinoline-1-yl)-piperazine-1-carboxylic acid, tert-butyl ester

LCMS: 422, 423.

INTERMEDIATE 19

4-[7-(4-tert-Butyl-phenylsulfanyl)-isoquinoline-1-yl]-piperazine-1-carboxylic acid, tert-butyl ester

LCMS: 478, 479.

INTERMEDIATE 20

4-(7-Phenylsulfanyl-isoquinoline-1-yl)-[1,4]diazepane-1-carboxylic acid, tert-butyl ester

MS: 368, 369, 370.

INTERMEDIATE 21

4-[7-(4-tert-Butyl-phenylsulfanyl)-isoquinoline-1-yl]-[1,4]diazepane-1-carboxylic acid, tert-butyl ester

MS: 424, 425, 426.

INTERMEDIATE 22

4-[7-(2-Chloro-6-methyl-phenylsulfanyl)-isoquinoline-1-yl]-[1,4]diazepane-1-carboxylic acid, tert-butyl ester

MS: 416, 417, 418.

INTERMEDIATE 23

4-[7-(3,4-Dimethyl-phenylsulfanyl)-isoquinoline-1-yl]-[1,4]diazepane-1-carboxylic acid, tert-butyl ester

MS: 396, 397, 398.

INTERMEDIATE 24

4-[7-(3,4-Dichloro-phenylsulfanyl)-isoquinoline-1-yl]-[1,4]diazepane-1-carboxylic acid, tert-butyl ester

MS: 436, 437, 438.

INTERMEDIATE 25

4-[7-(4-Chloro-phenylsulfanyl)-isoquinoline-1-yl]-[1,4]diazepane-1-carboxylic acid, tert-butyl ester

MS: 402, 404.

INTERMEDIATE 26

4-[7-(3,4-Dimethyl-phenylsulfanyl)-isoquinoline-1-yl]-[1,4]diazepane-1-carboxylic acid, tert-butyl ester

LCMS: 464, 465, 466.

INTERMEDIATE 27

4-[7-(2-tert-Butyl-phenylsulfanyl)-isoquinoline-1-yl]-[1,4]diazepane-1-carboxylic acid, tert-butyl ester

LCMS: 492, 493, 494.

BOC Deprotection and Oxidation of Thiols to Sulphone Derivatives

Each thiol (0.2-1.14 mmol) was dissolved in trifluoroacetic acid (1.5 mL) at 0° C. and stirred for 15 mins at this temperature. To this was added 33% aqueous hydrogen peroxide solution (5-100 mL). The resulting mixture was stirred at room temperature for 90 min and then treated with sodium hydroxide solution (1M, 25 mL). Extraction of this mixture with ethyl acetate (3×50 mL) was followed by the washing of the combined organic layers with brine (50 mL). The organic extracts were dried over anhydrous sodium sulfate and then the solvent was removed under reduced pressure. The crude product was purified by preparative LCMS. Treatment of the purified material with HCl/Ether (1M, 1 mL) gave the final product as a white solid.

EXAMPLE 16

7-(2-Chloro-6-methyl-benzenesulfonyl)-1-piperazin-1-yl-isoquinoline hydrochloride A mixture of 4-[7-(2-chloro-6-methyl-phenylsulfanyl)-isoquinolin-1-yl]-piperazine-1-carboxylic acid tert-butyl ester (160 mg, 0.340 mmol), $H_2O_2$ (30% in water, 200 uL), trifluoroacetic acid (2 mL) was heated at 50° C., 2 h. A water solution of NaOH (1N) was added (pH=14), ethyl acetate was added and the organic phase was separated, dried ($MgSO_4$), filtered. The filtrated was concentrated and the residue was purified by flash column chromatography ($SiO_2$, dichloromethane:methanol 8:2) to lead to 77 mg of the product compound as free base (yield 56%). The free base was converted into hydrochloride by treatment with HCl in diethyl ether. $^1$H NMR ($CH_3OH-d_4$) δ 8.88 (bs, 1H), 8.05-8.20 (m, 3H), 7.65 (d, 1H), 7.35-7.55 (m, 3H), 3.85-3.95 (m, 4H), 3.00-3.15 (m, 4H), 2.95 (s, 3H).

EXAMPLE 17

7-(2-t-Butyl-benzenesulfonyl)-1-piperazin-1-yl-isoquinoline hydrochloride

A mixture of 4-[7-(2-tbutyl-phenylsulfanyl)-isoquinolin-1-yl]-piperazine-1-carboxylic acid tert-butyl ester (273 mg, 0.571 mmol), $H_2O_2$ (30% in water, 1 mL), trifluoroacetic acid (3 mL) was heated at 50° C., 2 h. The reaction was continued overnight at 35° C. A water solution of NaOH (1N) was added (pH=14), ethyl acetate was added and the organic phase was separated, dried ($MgSO_4$), filtered. The filtrated was concentrated and the residue was purified by flash column chromatography ($SiO_2$, dichloromethane:methanol 8:2) to lead to 50 mg of the title compound as free base (yield 56%). The free base was converted into hydrochloride by treatment with HCl in diethyl ether. $^1$H NMR ($CH_3OH-d_4$) δ 8.55 (d, 1H), 8.25 (d, 1H), 7.95-8.10 (m, 3H), 7.55 (d, 1H), 7.55-7.65 (m, 2H), 7.4 (d, 1H), 3.60-3.75 (m, 4H), 3.40-3.50 (m, 4H), 1.55 (s, 9H).

EXAMPLE 18

7-(3,4-Dichloro-benzenesulfonyl)-1-piperazin-1-yl-isoquinoline hydrochloride

A mixture of 4-[7-(3,4-dichloro-phenylsulfanyl)-isoquinolin-1-yl]-piperazine-1-carboxylic acid tert-butyl ester (230 mg, 0.47 mmol), $H_2O_2$ (30% in water, 0.5 mL), trifluoroacetic acid (1.5 mL) was heated at 50° C., 2 h. The reaction was continued overnight at 35° C. A water solution of NaOH (1N) was added (pH=14), ethyl acetate was added and the organic phase was separated, dried ($MgSO_4$), filtered. The filtrated was concentrated and the residue was purified by flash column chromatography ($SiO_2$, dichloromethane:methanol 9:1) The free base was converted into hydrochloride by treatment with HCl in diethyl ether to obtained 45 mg of the title compound. $^1$H NMR ($CH_3OH-d_4$) δ 8.75-8.85 (m, 1H), 8.10-8.30 (m, 4H), 7.90-8.00 (m, 1H), 7.75-7.85 (m, 1H), 7.50-7.60 (m, 1H), 3.85-3.90 (m, 4H), 3.50-3.70 (m, 4H).

EXAMPLE 19

7-(3,4-Dimethyl-benzenesulfonyl)-1-piperazin-1-yl-isoquinoline hydrochloride A mixture of 4-[7-(3,4-dimethyl-phenylsulfanyl)-isoquinolin-1-yl]-piperazine-1-carboxylic acid tert-butyl ester (260 mg, 0.58 mmol), $H_2O_2$ (30% in water, 0.5 mL), trifluoroacetic acid (1.5 mL) was heated at 50° C., 2 h. The reaction was continued overnight at 35° C. A water solution of NaOH (1N) was added (pH=14), ethyl acetate was added and the organic phase was separated, dried ($MgSO_4$), filtered. The filtrated was concentrated and the residue was purified by flash column chromatography ($SiO_2$, dichloromethane:methanol 9:1) The free base was converted into hydrochloride by treatment with HCl in diethyl ether to obtained 20 mg of the title compound. $^1$H NMR ($CH_3OH-d_4$) δ 8.75-8.80 (m, 1H), 8.10-8.25 (m, 3H), 7.70-7.85 (m, 2H), 7.60-7.70 (m, 1H), 7.35-7.40 (m, 1H), 3.90-4.00 (m, 4H), 3.55-3.65 (m, 4H), 2.35 (bs, 6H).

EXAMPLE 20

7-(2,5-Dimethyl-benzenesulfonyl)-1-piperazin-1-yl-isoquinoline hydrochloride A mixture of 4-[7-(2,5-dimethyl-phenylsulfanyl)-isoquinolin-1-yl]-piperazine-1-carboxylic acid tert-butyl ester (380 mg, 0.846 mmol), $H_2O_2$ (30% in water, 0.5 mL), trifluoroacetic acid (3 mL) was heated at 50° C., 2 h. The reaction was continued overnight at 35° C. A water solution of NaOH (1N) was added (pH=14), ethyl acetate was added and the organic phase was separated, dried ($MgSO_4$), filtered. The filtrated was concentrated and the residue was purified by flash column chromatography ($SiO_2$, dichloromethane:methanol 9.8:0.2→9.5:0.5) The free base was converted into hydrochloride by treatment with HCl in diethyl ether to obtained 120 mg of the title compound. $^1$H NMR ($CH_3OH-d_4$) δ 8.75-8.80 (m, 1H), 8.25-8.30 (m, 1H), 8.05-8.20 (m, 2H), 7.60-7.70 (m, 3H), 7.30-7.35 (m, 1H), 4.00-4.10 (m, 4H), 3.60-3.70 (m, 4H), 2.30-1.35 (bs, 6H).

EXAMPLE 21

7-(p-Chloro-benzenesulfonyl)-1-piperazin-1-yl-isoquinoline hydrochloride

A mixture of 4-[7-(p-chloro-phenylsulfanyl)-isoquinolin-1-yl]-piperazine-1-carboxylic acid tert-butyl ester (297 mg, 0.65 mmol), $H_2O_2$ (30% in water, 0.5 mL), trifluoroacetic acid (3 mL) was heated at 50° C., 2 h. The reaction was continued overnight at 35° C. A water solution of NaOH (1N) was added (pH=14), ethyl acetate was added and the organic phase was separated, dried ($MgSO_4$), filtered. The filtrated was concentrated and the residue was purified by flash column chromatography ($SiO_2$, dichloromethane:methanol 9.5:0.5→9.0:1.0) The free base was converted into hydrochloride by treatment with HCl in diethyl ether to obtained 70 mg of the title compound. $^1$H NMR ($CH_3OH-d_4$) δ 8.75-8.85 (m, 2H), 8.10-8.25 (m, 3H), 8.00-8.08 (m, 2H), 7.60-7.68 (m, 3H), 3.85-3.95 (m, 4H), 3.55-3.65 (m, 4H).

EXAMPLE 22

7-Benzenesulfonyl-1-[1,4]diazepan-1-yl-isoquinoline hydrochloride 30 mg. $^1$H NMR (DMSO-$d_6$) δ 9.3 (s, 1H), 8.58 (s, 1H), 8.26-8.30 (d, J=9 Hz, 1H), 8.1-8.13 (m, 2H), 8.01-8.06 (d, J=6 Hz, 1H), 7.6-7.76 (m, 3H), 7.53-7.58 (d, J=6 Hz, 1H), 3.70-3.90 (m, 4H) 3.58-3.66 (m, 2H), 3.29-3.40 (m, 2H); LCMS: 368, 369 HPLC: 98%.

EXAMPLE 23

7-(4-tert-Butyl-benzenesulfonyl)-1-[1,4]diazepan-1-yl]-isoquinoline hydrochloride Isolated 69 mg. $^1$H NMR (DMSO-$d_6$) δ 9.2 (s, 1H), 8.65 (s, 1H), 8.09-8.15 (d, J=6 Hz, 1H), 8.03-8.08 (d, J=15 Hz, 1H), 7.89-7.96 (d, J=9 Hz, 2H), 7.60-7.67 (d, J=9 Hz, 2H), 7.33-7.38 (d, J=9 Hz, 1H), 4.01-4.09 (m, 2H), 3.83-3.91 (m, 2H), 3.43-3.52 (m, 2H), 3.23-3.33 (m, 2H), 1.25 (s, 9H); LCMS: 424, 425, HPLC: 97%.

EXAMPLE 24

7-(2-Chloro-6-methyl-benzenesulfonyl)-1-[1,4]diazepan-1-yl]-isoquinoline hydrochloride Isolated 27 mg $^1$H NMR (DMSO-$d_6$) δ 8.81 (s, 1H), 8.28 (m, 1H), 8.10-8.18 (d, J=6 Hz, 1H), 7.94-8.08 (m, 2H), 7.45-7.62 (m, 3H), 7.36-7.42 (d, J=6 Hz, 1H), 3.75-3.86 (m, 2H), 3.41-3.51 (m, 2H), 3.18-3.32 (m, 2H), 2.86 (s, 3H), 2.14-2.19 (m 2H); LCMS: 416, 418 HPLC: 98%.

EXAMPLE 25

7-(3,5-Dimethyl-benzenesulfonyl)-1-[1,4]diazepan-1-yl]-isoquinoline hydrochloride Isolated 62 mg. $^1$H NMR (DMSO-$d_6$) δ 9.35 (s, 1H), 8.67 (m, 1H), 8.00-8.18 (m, 3H), 7.58-7.69 (m, 2H), 7.45-7.41 (d, J=6 Hz, 1H), 7.30-7.35 (m, 1H), 4.06-4.14 (m, 2H), 3.86-3.97 (m, 2H), 3.42-3.52 (m, 2H), 3.23-3.31 (m, 2H), 2.33 (s, 6H) 2.23-2.25 (m 2H); LCMS: 436, 438, HPLC: 95%.

EXAMPLE 26

7-(3,4-Dichloro-benzenesulfonyl)-1-[1,4]diazepan-1-yl]-isoquinoline, hydrochloride Isolated 11 mg. $^1$H NMR ($CD_3OD$) δ 8.88 (m, 1H), 8.23-8.29 (d, J=12 Hz, 1H), 8.13-8.16 (d, J=3 Hz, 1H), 8.04-8.10 (d, J=9 Hz, 1H), 7.88-7.94 (d, J=9 Hz, 1H), 7.79-7.84 (d, J=6 Hz, 1H), 7.67-7.73 (d, J=9 Hz, 1H), 7.42-7.46 (d, J=6 Hz, 1H), 4.28-4.35 (m, 2H), 4.09-4.16 (m, 2H), 3.69-3.75 (m, 2H), 2.33-2.46 (m, 2H); LCMS: 368, 369; HPLC: 97%.

EXAMPLE 27

7-(4-Chloro-benzenesulfonyl)-1-[1,4]diazepan-1-yl]-isoquinoline, hydrochloride Isolated 41 mg. $^1$H NMR (DMSO-$d_6$) δ 9.27 (s, 1H), 8.68 (m, 1H), 7.99-8.17 (m, 5H), 7.66-7.75 (d, J=9 Hz, 2H), 7.33-7.39 (d, J=6 Hz, 1H), 4.03-4.11 (m, 2H), 3.83-3.93 (m, 2H), 3.43-3.53 (m, 2H), 3.23-3.32 (m, 2H), 2.19-2.30 (m, 2H); LCMS: 402, 404; HPLC: 98%.

EXAMPLE 28

7-(3,4-Dimethyl-benzenesulfonyl)-1-[1,4]diazepan-1-yl]-isoquinoline, hydrochloride Isolated 10 mg. $^1$H NMR (DMSO-$d_6$) δ 9.41 (s, 1H), 8.67 (s, 1H), 8.00-8.16 (m, 3H), 7.76-7.82 (m, 1H), 7.68-7.77 (d, J=9 Hz, 1H), 7.32-7.42 (d, J=9 Hz, 2H), 3.99-4.40 (m, 4H), 3.49 (m, 2H), 3.33 (m, 2H), 2.29 (s, 3H), 2.25 (s, 3H); LCMS: 396, 397; HPLC: 92%.

EXAMPLE 29

7-(2-tert-Butyl-benzenesulfonyl)-1-[1,4]diazepan-1-yl]-isoquinoline, hydrochloride Isolated 5 mg. $^1$H NMR (DMSO-$d_6$) δ 9.27 (s, 1H), 8.52 (s, 1H), 8.06-8.16 (m, 2H), 7.97-7.97 (m, 2H), 7.72-7.78 (m, 1H), 7.61-7.70 (m, 1H), 7.40-7.45 (d, J=9 Hz, 2H), 3.69-3.99 (m, 4H), 3.43 (s, 2H), 3.25 (s, 2H), 2.05-2.26 (m, 2H); 1.52 (s, 9H); LCMS: 424, 425; HPLC: 90%.

EXAMPLE 30

7-Benzenesulfonyl-1-piperazin-yl-isoquinoline, hydrochloride

Isolated 10 mg. $^1$H NMR (DMSO-$d_6$) δ 9.04 (s, 1H), 8.65 (s, 1H), 8.12-8.16 (d, J=6 Hz, 1H), 7.98-8.05 (m, 5H), 7.58-7.72 (m, 2H), 7.32-7.36 (d, J=6 Hz, 1H), 3.98-4.04 (m, 4H), 3.80-3.86 (m, 4H); LCMS: 354, 355; HPLC: 98%.

EXAMPLE 31

7-(4-tert-Butyl-benzenesulfonyl-1-piperazin-yl-isoquinoline, hydrochloride

Isolated 10 mg. $^1$H NMR (DMSO-$d_6$) δ 9.33 (s, 1H), 8.57 (s, 1H), 8.24-8.29 (d, J=9 Hz, 1H), 8.11 (m, 2H), 7.91-7.97 (d, J=9 Hz, 2H), 7.60-7.66 (d, J=12 Hz, 2H), 7.52-7.57 (d, J=6 Hz, 1H), 3.59-3.68 (m, 4H), 3.29-3.40 (m, 4H), 1.24 (s, 9H); LCMS: 410, 411 HPLC: 90

TABLE 3

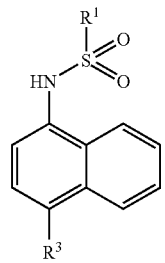

| EXAMPLE | NAME | R$^1$ | R$^3$ |
|---|---|---|---|
| 32 | 4-Chloro-N-[4-(pyrrolidin-3-yloxy)-1-naphthyl]benzenesulfonamide hydrochloride | 4-chlorophenyl | pyrrolidin-3-yloxy |
| 33 | 4-Methoxy-N-[4-(pyrrolidin-3-yloxy)-1-naphthyl]benzenesulfonamide hydrochloride | 4-methoxyphenyl | pyrrolidin-3-yloxy |
| 34 | 5-Chloro-N-[4-(pyrrolidin-3-yloxy)-1-naphthyl]thiophene-2-sulfonamide hydrochloride | 5-chlorothiophen-2-yl | pyrrolidin-3-yloxy |

TABLE 3-continued

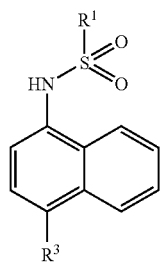

| EXAMPLE | NAME | R¹ | R³ |
|---|---|---|---|
| 35 | 4-Chloro-N-[4-(piperidin-3-yloxy)-1-naphthyl]benzenesulfonamide hydrochloride | 4-chlorophenyl | piperidin-3-yloxy |
| 26 | 4-Methoxy-N-[4-(piperidin-3-yloxy)-1-naphthyl]benzenesulfonamide hydrochloride | 4-methoxyphenyl | piperidin-3-yloxy |
| 37 | 5-Fluoro-2-methyl-N-[4-(piperidin-4-yloxy)-1-naphthyl]benzenesulfonamide hydrochloride | 5-fluoro-2-methylphenyl | piperidin-4-yloxy |
| 38 | 5-Chloro-N-[4-(piperidin-4-yloxy)-1-naphthyl]thiophene-2-sulfonamide hydrochloride | 5-chlorothiophen-2-yl | piperidin-4-yloxy |
| 39 | 4-Chloro-N-{4-[(3S)-pyrrolidin-3-yloxy]-1-naphthyl}benzenesulfonamide hydrochloride | 4-chlorophenyl | (3S)-pyrrolidin-3-yloxy |

TABLE 3-continued

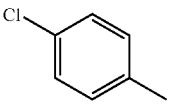

| EXAMPLE | NAME | R¹ | R³ |
|---|---|---|---|
| 40 | 4-Chloro-N-{4-[(3R)-pyrrolidin-3-yloxy]-1-naphthyl}benzenesulfonamide hydrochloride | | |

Scheme 4

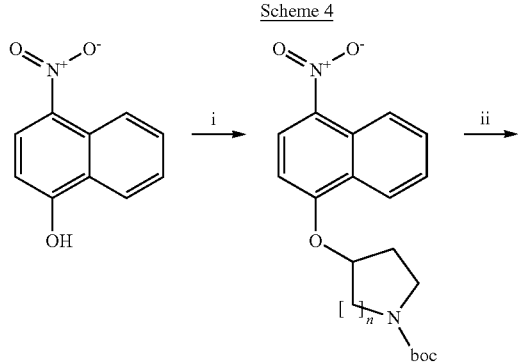

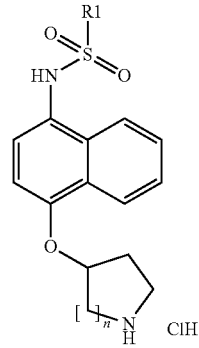

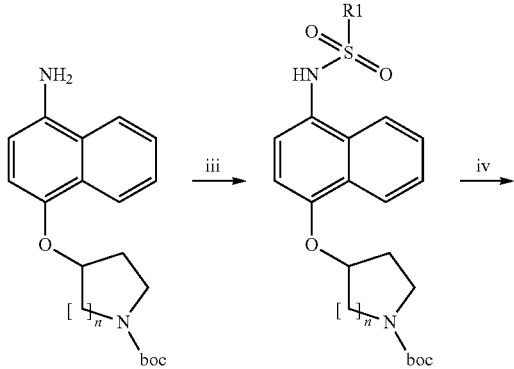

Legend to Scheme 4: (i) tert-butyl 3-hydroxypyrrolidine-1-carboxylate or tert-butyl 4-hydroxypiperidine-1-carboxylate, PPh₃, DEAD, THF; (ii) H₂(g), Pd/C, MeOH; (iii) R₁—SO₂—Cl, pyridine, CH₂Cl₂; (iv) HCl in diethyl ether General Method C Mitsonobu reaction of 4-nitro-1-naphthol with boc-protected 3-hydroxypyrrolidine and 4-hydroxypiperidine 4-Nitro-1-naphthol (1 equiv.) was dissolved in THF (3 mL/mmol), tert-butyl 3-hydroxypyrrolidine-1-carboxylate (2 equiv.) was added followed by PPh₃ (2 equiv.). The solution was kept under N₂-atmosphere and cooled with ice-bath. Diethylazodicarboxylate (DEAD; 2 equiv.) was added dropwise. The ice-bath was removed after 10 min and the reaction mixture was stirred at ambient temperature overnight. The solvent was evaporated and the residue was re-dissolved in EtOAc. The formed precipitate was collected by filtration. The solution was concentrated in vacuo and purified by flash chromatography (SiO₂, EtOAc:iso-hexane 2:8→EtOAc)

General Method D

Reduction of Nitronaphthalene Derivatives

To a solution of corresponding nitronaphthalenes (1 equiv.) (prepared by General method A) in MeOH (2 mL/mmol), was added Pd/C (10%) and the reaction mixture was stirred overnight under hydrogen (1 atm). The reaction mixture was filtered and the filtrate was concentrated in vacuo to give corresponding aminonaphthalene derivatives.

General Method E

Reaction of Aminonaphthalene Derivatives with Sulfonyl Chlorides

To a solution of the aminonaphthalene derivatives (1 equiv.) in $CH_2Cl_2$ (8 mL/mmol) was added pyridine (3 equiv.) followed by the corresponding sulfonyl chloride (1.2 equiv.). The mixtures were stirred at ambient temperature overnight, washed with HCl (1M) (2 mL) and dried ($MgSO_4$). The volatiles were eliminated under vacuo and gave the crude product which were purified by flash chromatography ($SiO_2$, EtOAc:iso-hexane 1:4) to give desired sulfonamide.

General Method F

Deprotection of Boc-Group

The sulfonamide derivatives (prepared by General Method C) were dissolved in a small amount of MeOH and treated with an excess of HCl in diethyl ether (1M). Stirring at ambient temperature overnight resulted in a precipitate which were collected by filtration giving the title compounds as its hydrochloride salts.

General Method G

3-Hydroxypyrrolidine (1 equiv.) was dissolved in MeOH (1 mL/mmol) and cooled on ice-bath. $(BOC)_2O$ (1.1 equiv.) was added and the mixture was stirred for 2 h at ambient temperature. Pyridine/water (10/10 mL) was added and the mixture was stirred overnight. Evaporation of solvents and co-evaporation with toluene provided the desired boc-protected 3-hydroxypyrrolidine.

INTERMEDIATE 28 tert-Butyl 3-[(4-nitro-1-naphthyl)oxy]pyrrolidine-1-carboxylate (General Method C)

The crude product was purified by column chromatography. The compound was prepared from 4-nitro-1-naphthol (2.85 g, 15.1 mmol). The material thus obtained was dissolved in small amount of EtOAc and iso-hexane was added. The formed solid was collected by filtration and triturated with MeOH to give the pure title compound 4.6 g (85%). HPLC 99%, $R_T$=2.70 (System A1, 10-97% MeCN over 3 min). $^1$H NMR (400 MHz, $CDCl_3$) δ ppm 1.46 (d, J=7.03 Hz, 9H) 2.26-2.38 (m, 2H) 3.60-3.81 (m, 4H) 5.20 (br s, 1H) 6.76 (d, J=8.53 Hz, 1H) 7.58 (t, J=7.53 Hz, 1H) 7.73 (t, J=7.53 Hz, 1H) 8.34 (dd, J=20.33, 8.78 Hz, 2H) 8.75 (d, J=9.04 Hz, 1H). MS (ESI+) for $C_{19}H_{22}N_2O_5$ m/z 376.2 $(M+NH)^+$, 359.2 $(M+H)^+$, 303.2 $(M-tBu)^+$. HPLC 99%, $R_T$=2.78 min (System B1, 10-90% MeCN over 3 min).

INTERMEDIATE 29 tert-Butyl 3-[(4-amino-1-naphthyl)oxy]pyrrolidine-1-carboxylate (General Method D)

The compound was prepared from intermediate 1 (2.6 g, 7.2 mmol), Yield: 2.1 g (87%) of the title compound as purple solid. HPLC 96%, $R_T$=1.768 min (System A1, 10-97% MeCN over 3 min). HPLC 95%, $R_T$=1.604 min (System B1, 10-90% MeCN over 3 min). $^1$H NMR (400 MHz, DMSO-$d_6$) δ ppm 1.37 (d, J=22.59 Hz, 9H) 2.12 (s, 2H) 3.43-3.46 (m, 4H) 4.96 (s, 1H) 5.50 (s, 2H) 6.63 (d, J=8.03 Hz, 1H) 6.81 (d, J=8.03 Hz, 1H) 7.41 (dd, J=6.02, 3.01 Hz, 2H) 7.94-8.01 (m, 2H). MS (ESI+) for $C_{19}H_{24}N_2O_3$ m/z 329.2 $(M+H)^+$, 273.2 $(M-tBu)^+$, 229.2 $(M-Boc)^+$.

INTERMEDIATE 30 tert-Butyl 3-[(4-{[(4-chlorophenyl)sulfonyl]amino}-1-naphthyl)oxy]pyrrolidine-1-carboxylate (General Method E)

The compound was prepared from intermediate 2 (0.2 g, 0.61 mmol). The crude material was triturated with $CH_3CN$ to give 0.14 g (46%) of the title compound as a pale pink solid. HPLC 97%, $R_T$=2.703 min (System A1, 10-97% MeCN over 3 min). $^1$H NMR (400 MHz, $CDCl_3$) δ ppm 1.46 (d, J=4.02 Hz, 9H) 2.18-2.30 (m, 2H) 3.54-3.76 (m, 4H) 5.05 (br s, 1H) 6.62-6.65 (m, 1H) 6.74-6.76 (m, 1H) 7.17-7.23 (m, 1H) 7.32 (d, J=9.04 Hz, 2H) 7.39-7.45 (m, 2H) 7.62 (d, J=8.53 Hz, 2H) 7.68-7.72 (m, 1H) 8.16-8.19 (m, 1H). MS (ESI+) for $C_{25}H_{27}ClN_2O_5S$ m/z 520.2 $(M+NH_4)^+$, 447.0 $(M-tBu)^+$. HPLC 98%, $R_T$=2.738 min (System B1, 10-90% MeCN over 3 min).

INTERMEDIATE 31 tert-Butyl 3-[(4-{[(4-methoxyphenyl)sulfonyl]amino}-1-naphthyl)oxy]pyrrolidine-1-carboxylate (General Method E)

The compound was prepared from intermediate 2 (0.2 g, 0.61 mmol), Yield: 0.2 g (66%) of the title compound as a pink oil. HPLC 98%, $R_T$=2.617 min (System A1, 10-97% MeCN over 3 min). $^1$H NMR (400 MHz, $CDCl_3$) δ ppm 1.45 (d, J=5.02 Hz, 9H) 2.14-2.31 (m, 2H) 3.54-3.76 (m, 4H) 3.79 (s, 3H) 5.04 (br s, 1H) 6.60-6.65 (m, 2H) 6.81 (d, J=8.53 Hz, 2H) 7.15-7.24 (m, 1H) 7.38-7.44 (m, 2H) 7.60-7.64 (m, 2H) 7.71-7.76 (m, 1H) 8.14-8.18 (m, 1H). MS (ESI+) for $C_{26}H_{30}N_2O_6S$ m/z 516.4 $(M+NH_4)^+$, 443.0 $(M-tBu)^+$, 399.2 $(M-Boc)^+$.

INTERMEDIATE 32 tert-Butyl 3-[(4-{[(5-chloro-2-thienyl)sulfonyl]amino}-1-naphthyl)oxy]pyrrolidine-1-carboxylate (General Method E)

The compound was prepared from intermediate 2 (0.2 g, 0.61 mmol), Yield: 0.21 g (68%) of the title compound as a yellow solid. HPLC 99%, $R_T$=2.777 min (System B1, 10-90% MeCN over 3 min). $^1$H NMR (400 MHz, $CDCl_3$) δ ppm 1.46 (d, J=6.02 Hz, 9H) 2.16-2.30 (m, 2H) 3.55-3.74 (m, 4H) 5.07 (br s, 1H) 6.67-6.70 (m, 1H) 6.75 (d, J=4.02 Hz, 1H) 6.77 (br s, 1H) 7.13 (br s, 1H) 7.28-7.35 (m, 1H) 7.46-7.48 (m, 2H) 7.75-7.79 (m, 1H) 8.19-8.22 (m, 1H). MS (ESI+) for $C_{23}H_{25}ClN_2O_5S_2$ m/z 526.2 $(M+NH_4)^+$, 453.0 $(M-tBu)^+$, 409.2 $(M-Boc)^+$. HPLC 99%, $R_T$=2.767 min (System A1, 10-97% MeCN over 3 min).

INTERMEDIATE 33 tert-Butyl 4-[(4-nitro-1-naphthyl)oxy]piperidine-1-carboxylate (General Method C)

The compound was prepared from 4-nitro-1-naphthol (2 g, 10.6 mmol). The material obtained after flash chromatography was not pure according to NMR. Recrystallization from EtOAc/iso-hexane gave 2.3 g (62%) of the title compound as a yellow solid. HPLC 98%, $R_T$=2.842 min (System A1, 10-97% MeCN over 3 min $^1$H NMR (400 MHz, $CDCl_3$) δ ppm 1.48 (s, 9H) 1.99 (m, 4H) 3.54 (m, 2H) 3.70 (m, 2H) 4.87 (m, 1H) 6.82 (d, J=9.04 Hz, 1H) 7.59 (m, 1H) 7.74 (m, 1H)

8.38 (d, J=8.53 Hz, 2H) 8.77 (d, J=8.53 Hz, 1H). MS (ESI+) for $C_{20}H_{24}N_2O_5$ m/z 373.0 (M+H)$^+$, 390.2 (M+NH$_4$)$^+$, 317.0 (M−tBu)$^+$. HPLC 98%, $R_T$=2.973 min (System B1, 10-90% MeCN over 3 min).

INTERMEDIATE 34 tert-Butyl 4-[(4-amino-1-naphthyl)oxy]piperidine-1-carboxylate (General Method C)

The compound was prepared from intermediate 6 (2.3 g, 7.0 mmol), Yield: 2 g (95%) as pink oil. HPLC 94%, $R_T$=2.885 min (System B1, 10-90% MeCN over 3 min). $^1$H NMR (400 MHz, CDCl$_3$) δ ppm 1.46 (s, 9H) 1.80-1.98 (m, 4H) 3.35-3.41 (m, 2H) 3.46 (s, 3H) 3.69-3.75 (m, 2H) 3.88 (br s, 1H) 4.50-4.54 (m, 1H) 7.45-7.50 (m, 2H) 7.79-7.81 (m, 1H) 8.22-8.24 (m, 1H). MS (ESI+) for $C_{20}H_{26}N_2O_3$ m/z 343.2 (M+H)$^+$. HPLC 94%, $R_T$=2.735 min (System A1, 10-97% MeCN over 3 min).

INTERMEDIATE 35 tert-Butyl 4-[(4-{[(4-chlorophenyl)sulfonyl]amino}-1-naphthyl)oxy]piperidine-1-carboxylate (General Method E)

The compound was prepared from intermediate 7 (0.25 g, 0.73 mmol), Yield: 0.29 g (77%). HPLC 98%, $R_T$=2.906 min (System A1, 10-97% MeCN over 3 min). $^1$H NMR (400 MHz, CDCl$_3$) δ ppm 1.47 (s, 9H) 1.88 (m, 2H) 1.98 (m, 2H) 3.47 (m, 2H) 3.68 (m, 2H) 4.69 (m, 1H) 6.61 (s, 1H) 6.70 (d, J=8.03 Hz, 1H) 7.17 (d, J=8.03 Hz, 1H) 7.32 (m, 2H) 7.43 (m, 2H) 7.62 (m, 2H) 7.70 (m, 1H). MS (ESI+) for $C_{26}H_{29}ClN_2O_5S$ m/z 534.0 (M+NH$_4$)$^+$, 461.2 (M−tBu)$^+$. HPLC 98%, $R_T$=2.843 min (System B1, 10-90% MeCN over 3 min).

INTERMEDIATE 36 tert-Butyl 4-[(4-{[(4-methoxyphenyl)sulfonyl]amino}-1-naphthyl)oxy]piperidine-1-carboxylate (General Method E)

The compound was prepared from intermediate 7 (0.25 g, 0.73 mmol). Yield: 0.21 g (56%) of the title compound as pink solid. HPLC 100%, $R_T$=2.755 min (System A1, 10-97% MeCN over 3 min). $^1$H NMR (400 MHz, CDCl$_3$) δ ppm 1.47 (s, 9H) 1.86-2.01 (m, 4H) 3.43-3.49 (m, 2H) 3.65-3.71 (m, 2H) 3.79 (s, 3H) 4.65-4.70 (m, 1H) 6.58 (s, 1H) 6.69 (d, J=8.53 Hz, 1H) 6.83-6.79 (m, 2H) 7.17 (d, J=8.03 Hz, 1H) 7.39-7.44 (m, 2H) 7.61-7.64 (m, 2H) 7.75-7.77 (m, 1H) 8.21-8.24 (m, 1H). MS (ESI+) for $C_{27}H_{32}N_2O_6S$ m/z 530.2 (M+NH$_4$)$^+$, 457.2 (M−tBu)$^+$, 413.4 (M−Boc)$^+$. HPLC 99%, $R_T$=2.668 min (System B1, 10-90% MeCN over 3 min).

INTERMEDIATE 37 tert-Butyl 4-[(4-{[(5-fluoro-2-methylphenyl)sulfonyl]amino}-1-naphthyl)oxy]piperidine-1-carboxylate (General Method E)

The compound was prepared from tert-butyl 4-[(4-amino-1-naphthyl)oxy]piperidine-1-carboxylate (0.25 g, 0.73 mmol). Yield: 0.24 g (64%) of the title compound as a pink solid. HPLC 99%, $R_T$=2.809 min (System B1, 10-90% MeCN over 3 min). $^1$H NMR (400 MHz, CDCl$_3$) δ ppm 1.46 (s, 9H) 1.83-1.98 (m, 4H) 2.54 (s, 3H) 3.42-3.48 (m, 2H) 3.63-3.69 (m, 2H) 4.64-4.68 (m, 1H) 6.64-6.68 (m, 2H) 7.03 (d, J=8.53 Hz, 1H) 7.10 (m, 1H) 7.22 (dd, J=8.53, 5.02 Hz, 1H) 7.44-7.48 (m, 2H) 7.55 (dd, J=8.53, 2.51 Hz, 1H) 7.83-7.86 (m, 1H) 8.24 (m, 1H). MS (ESI+) for $C_{27}H_{31}FN_2O_5S$ m/z 532.2 (M+NH$_4$)$^+$, 459.2 (M−tBu)$^+$, 415.2 (M−Boc)$^+$. HPLC 100%, $R_T$=2.877 min (System A1, 10-97% MeCN over 3 min).

INTERMEDIATE 38 tert-Butyl 4-[(4-{[(5-chloro-2-thienyl)sulfonyl]amino}-1-naphthyl)oxy]piperidine-1-carboxylate (General Method E)

The compound was prepared from tert-butyl 4-[(4-amino-1-naphthyl)oxy]piperidine-1-carboxylate (0.25 g, 0.73 mmol). Yield: 0.25 g (65%) of the title compound as a pink solid. HPLC 98%, $R_T$=2.827 min (System B1, 10-90% MeCN over 3 min). $^1$H NMR (400 MHz, CDCl$_3$) δ ppm 1.47 (s, 9H) 1.86-2.03 (m, 4H) 3.45-3.51 (m, 2H) 3.66-3.72 (m, 2H) 4.69-4.74 (m, 1H) 6.66 (s, 1H) 6.74-6.76 (m, 2H) 7.14 (d, J=4.02 Hz, 1H) 7.30 (d, J=8.03 Hz, 1H) 7.45-7.50 (m, 2H) 7.76-7.79 (m, 1H) 8.25-8.28 (m, 1H) MS (ESI+) for $C_{24}H_{27}ClN_2O_5S_2$ m/z 540.4 (M+NH$_4$)$^+$, 467.2 (M−tBu)$^+$. HPLC 99%, $R_T$=2.910 min (System A1, 10-97% MeCN over 3 min).

INTERMEDIATE 39 tert-Butyl (3R)-3-hydroxypyrrolidine-1-carboxylate (General Method G)

The compound was prepared from (3R)-3-hydroxypyrrolidine (5 g, 57.4 mmol). Yield: 9.6 g (90%) of the title compound. $^1$H NMR (400 MHz, CDCl$_3$) δ ppm 1.43 (s, 9H) 1.90-1.98 (m, 2H) 3.27-3.47 (m, 4H) 4.40 (br s, 1H).

INTERMEDIATE 40 tert-Butyl (3S)-3-hydroxypyrrolidine-1-carboxylate (General Method G)

The compound was prepared from (3S)-3-hydroxypyrrolidine (5 g, 57.4 mmol). Yield: 8 g (86%) of the title compound. $^1$H NMR (400 MHz, CDCl$_3$) δ ppm 1.40 (s, 9H) 1.86-1.91 (m, 2H) 3.24-3.42 (m, 4H) 4.36 (br s, 1H).

INTERMEDIATE 41 tert-Butyl (3S)-3-[(4-nitro-1-naphthyl)oxy]pyrrolidine-1-carboxylate (General Method C)

The compound was prepared from tert-butyl (3R)-3-hydroxypyrrolidine-1-carboxylate (3.56 g, 19 mmol) and 4-nitro-1-naphthol (3 g, 15.9 mmol). Yield: 5 g (88%) of the title compound as yellow oil. $^1$H NMR (400 MHz, CDCl$_3$) δ ppm 1.45 (d, J=7.03 Hz, 9H) 2.22-2.38 (m, 2H) 3.54-3.83 (m, 4H) 5.18 (br s, 1H) 6.74 (d, J=8.53 Hz, 1H) 7.56 (t, J=7.78 Hz, 1H) 7.71 (t, J=7.78 Hz, 1H) 8.29 (d, J=8.53 Hz, 1H) 8.33 (d, J=8.53 Hz, 1H) 8.72 (d, J=8.53 Hz, 1H). MS (ESI+) for $C_{19}H_{22}N_2O_5$ m/z 376.2 (M+NH$_4$)$^+$, 303.2 (M−tBu)$^+$. HPLC 100%, $R_T$=2.768 min (System A1, 10-97% MeCN over 3 min).

INTERMEDIATE 42 tert-Butyl (3R)-3-[(4-nitro-1-naphthyl)oxy]pyrrolidine-1-carboxylate (General Method C)

The compound was prepared from tert-butyl (3S)-3-hydroxypyrrolidine-1-carboxylate (3.56 g, 19 mmol) and 4-nitro-1-naphthol (3 g, 15.9 mmol). Yield: 2.8 g (49%) of the title compound as yellow oil. $^1$H NMR (400 MHz, CDCl$_3$) δ ppm 1.46 (d, J=7.03 Hz, 9H) 2.26-2.38 (m, 2H) 3.55-3.81 (m, 4H) 5.20 (br s, 1H) 6.77 (d, J=8.53 Hz, 1H) 7.59 (t, J=7.53 Hz, 1H) 7.72-7.76 (m, 1H) 8.32 (d, J=8.03 Hz, 1H) 8.37 (d, J=8.53 Hz, 1H) 8.76 (d, J=8.53 Hz, 1H). HPLC 95%, $R_T$=2.775 min (System A1, 10-97% MeCN over 3 min).

INTERMEDIATE 43 tert-Butyl (3S)-3-[(4-amino-1-naphthyl)oxy]pyrrolidine-1-carboxylate (General Method D)

The compound was prepared from tert-butyl (3S)-3-[(4-nitro-1-naphthyl)oxy]pyrrolidine-1-carboxylate (5 g, 14 mmol). Yield: 3.5 g (76%) of the title compound as dark pink solid. $^1$H NMR (400 MHz, CDCl$_3$) δ ppm 1.46 (d, J=14.56 Hz, 9H) 2.08-2.13 (m, 1H) 2.27-2.30 (m, J=13.05 Hz, 1H) 3.54-3.77 (m, 4H) 3.88 (br s, 2H) 4.96 (br s, 1H) 6.65-6.70 (m, 2H) 7.45-7.51 (m, 2H) 7.79-7.81 (m, 1H) 8.15-8.19 (m, 1H). MS (ESI+) for $C_{19}H_{24}N_2O_3$ m/z 329.2 (M+H)$^+$, 273.2 (M−tBu)$^+$, 229.2 (M−Boc)$^+$. HPLC 95%, $R_T$=1.854 min (System A1, 10-97% MeCN over 3 min).

INTERMEDIATE 44 tert-Butyl (3R)-3-[(4-amino-1-naphthyl)oxy]pyrrolidine-1-carboxylate (General Method D)

The compound was prepared from tert-butyl (3R)-3-[(4-nitro-1-naphthyl)oxy]pyrrolidine-1-carboxylate (2.8 g, 7.8 mmol). Yield: 1.8 g (72%) of the title compound as dark pink solid. $^1$H NMR (400 MHz, CDCl$_3$) δ ppm 1.46 (d, J=14.56 Hz, 9H) 2.07-2.14 (m, 1H) 2.27-2.30 (m, 1H) 3.54-3.77 (m, 4H) 3.93 (br s, 2H) 4.96 (br s, 1H) 6.65-6.70 (m, 2H) 7.45-7.51 (m, 2H) 7.79-7.81 (m, 1H) 8.16-8.18 (m, 1H). MS (ESI+) for $C_{19}H_{24}N_2O_3$ m/z 329.2 (M+H)$^+$, 273.2 (M−tBu)$^+$, 229.2 (M−Boc)$^+$. HPLC 94%, $R_T$=1.751 min (System A1, 10-97% MeCN over 3 min).

INTERMEDIATE 45 tert-Butyl (3S)-3-[(4-{[(4-chlorophenyl)sulfonyl]amino}-1-naphthyl)oxy]pyrrolidine-1-carboxylate (General Method E)

The compound was prepared from tert-butyl (3S)-3-[(4-nitro-1-naphthyl)oxy]pyrrolidine-1-carboxylate (0.3 g, 0.9 mmol) and 4-chloro-phenylsulfonylchloride (0.23 g, 1.1 mmol). Yield: 0.23 g (50%) of the title compound. $^1$H NMR (400 MHz, CDCl$_3$) δ ppm 1.46 (d, J=4.52 Hz, 9H) 2.15-2-34 (m, 2H) 3.54-3.74 (m, 4H) 5.05 (br s, 1H) 6.62-6.71 (m, 2H) 7.17-7.23 (m, 1H) 7.33 (d, J=8.53 Hz, 1H) 7.39-7.43 (m, 2H) 7.62-7.64 (m, 2H) 7.65-7.70 (m, J=6.02 Hz, 1H) 8.18 (d, J=8.53 Hz, 1H) MS (ESI+) for $C_{25}H_{27}ClN_2O_5S$ m/z 520.2 (M+NH$_4$)$^+$, 447.0 (M−tBu)$^+$. HPLC 100%, $R_T$=2.772 min (System A1, 10-97% MeCN over 3 min).

INTERMEDIATE 46 tert-Butyl (3R)-3-[(4-{[(4-chlorophenyl)sulfonyl]amino}-1-naphthyl)oxy]pyrrolidine-1-carboxylate (General Method E)

The compound was prepared from tert-butyl (3R)-3-[(4-nitro-1-naphthyl)oxy]pyrrolidine-1-carboxylate (0.3 g, 0.9 mmol) and 4-chloro-phenylsulfonylchloride (0.23 g, 1.1 mmol). Yield: 0.4 g (87%) of the title compound. $^1$H NMR (400 MHz, CDCl$_3$) δ ppm 1.46 (d, J=4.52 Hz, 9H) 2.15-2-34 (m, 2H) 3.54-3.74 (m, 4H) 5.05 (br s, 1H) 6.60-6.66 (m, 2H) 7.17-7.23 (m, 1H) 7.33 (d, J=8.53 Hz, 1H) 7.39-7.43 (m, 2H) 7.62-7.64 (m, 2H) 7.65-7.70 (m, J=6.02 Hz, 1H) 8.18 (d, J=8.53 Hz, 1H) MS (ESI+) for $C_{25}H_{27}ClN_2O_5S$ m/z 520.2 (M+NH$_4$)$^+$, 447.0 (M−tBu)$^+$. HPLC 100%, $R_T$=2.769 min (System A1, 10-97% MeCN over 3 min).

EXAMPLE 32

4-Chloro-N-[4-(pyrrolidin-3-yloxy)-1-naphthyl]benzenesulfonamide hydrochloride (General Method F)

The compound was prepared from intermediate 3 (0.13 g, 0.26 mmol). The solid was further purified by trituration with diethyl ether giving 0.11 g (95%) of the title compound as white solid. HPLC 98%, $R_T$=1.810 min (System A1, 10-97% MeCN over 3 min). $^1$H NMR (400 MHz, DMSO-d$_6$) δ ppm 2.21-2.26 (m, 2H) 3.32-3.37 (m, 2H) 3.48-3.50 (m, 2H) 5.28 (br s, 1H) 6.91-6.98 (m, 2H) 7.44-7.50 (m, 2H) 7.56-7.64 (m, 4H) 7.88-7.90 (m, 1H) 8.20-8.23 (m, 1H). MS (ESI+) for $C_{20}H_{19}ClN_2O_3S$ m/z 401.2 (M+H)$^+$. HPLC 98%, $R_T$=1.651 min (System B1, 10-90% MeCN over 3 min).

EXAMPLE 33

4-Methoxy-N-[4-(pyrrolidin-3-yloxy)-1-naphthyl]benzenesulfonamide hydrochloride (General Method F)

The compound was prepared from intermediate 4 (0.18 g, 0.36 mmol), Yield: 0.12 g (76%) of the title compound as a white solid. HPLC 100%, $R_T$=1.490 min (System B1, 10-90% MeCN over 3 min). $^1$H NMR (400 MHz, DMSO-d$_6$) δ ppm 2.20-2.25 (m, 2H) 3.31-3.53 (m, 4H) 3.78 (s, 3H) 5.27 (br s, 1H) 6.90-6.97 (m, 2H) 7.00 (d, J=8.53 Hz, 2H) 7.43-7.48 (m, 2H) 7.57 (d, J=8.53 Hz, 2H) 7.93-7.96 (m, 1H) 8.19-8.22 (m, 1H) 9.63 (br s, 2H). MS (ESI+) for $C_{21}H_{22}N_2O_4S$ m/z 409.2 (M+H)$^+$. HPLC 100%, $R_T$=1.639 min (System A1, 10-97% MeCN over 3 min).

EXAMPLE 34

5-Chloro-N-[4-(pyrrolidin-3-yloxy)-1-naphthyl]thiophene-2-sulfonamide hydrochloride (General Method F)

The compound was prepared from intermediate 5 (0.20 g, 0.39 mmol), Yield: 0.14 g (80%) of the title compound as a pale white solid. HPLC 99%, $R_T$=1.651 min (System B11, 10-90% MeCN over 3 min). $^1$H NMR (400 MHz, DMSO-d$_6$) δ ppm 2.23-2.26 (m, 2H) 3.28-3.39 (m, 2H) 3.40-3.56 (m, 2H) 5.32 (br s, 1H) 6.99 (d, J=8.53 Hz, 1H) 7.13 (d, J=8.03 Hz, 1H) 7.15 (d, J=4.02 Hz, 1H) 7.26 (d, J=4.02 Hz, 1H) 7.48-7.52 (m, 2H) 7.92 (dd, J=6.53, 3.01 Hz, 1H) 8.25 (dd, J=6.53, 3.01 Hz, 1H) 9.60 (s, 1H). MS (ESI+) for $C_{18}H_{17}ClN_2O_3S_2$ m/z 409.2 (M+H)$^+$. HPLC 99%, $R_T$=1.818 min (System A1, 10-97% MeCN over 3 min).

EXAMPLE 35

4-Chloro-N-[4-(piperidin-3-yloxy)-1-naphthyl]benzenesulfonamide hydrochloride (General Method F)

The compound was prepared from intermediate 8 (0.26 g, 0.50 mmol), Yield: 0.12 g (53%) of the title compound as a white solid. HPLC 100%, $R_T$=1.872 min (System A1, 10-97% MeCN over 3 min). $^1$H NMR (400 MHz, DMSO-$d_6$) δ ppm 1.95-1.99 (m, 2H) 2.14-2.19 (m, 2H) 3.11 (br s, 2H) 3.26 (br s, 2H) 4.84 (br s, 1H) 6.92-6.99 (m, 2H) 7.44-7.51 (m, 2H) 7.57-7.65 (m, 4H) 7.91 (d, J=7.53 Hz, 1H) 8.17 (d, J=7.03 Hz, 1H) 8.94 (br s, 1H) 9.05 (br s, 1H) 10.11 (s, 1H). MS (ESI+) for $C_{21}H_{21}ClN_2O_3S$ m/z 415.2 (M+H)$^+$. HPLC 99%, $R_T$=0.657 min (System B1, 10-90% MeCN over 3 min).

EXAMPLE 36

4-Methoxy-N-[4-(piperidin-3-yloxy)-1-naphthyl]benzenesulfonamide hydrochloride (General Method F)

The compound was prepared from intermediate 9 (0.19 g, 0.37 mmol). Yield: 0.15 g (90%) of the title compound as a white solid. HPLC 97%, $R_T$=1.508 min (System B1, 10-90% MeCN over 3 min). $^1$H NMR (400 MHz, DMSO-$d_6$) δ ppm 1.96 (m, 2H) 2.16 (m, 2H) 3.10 (m, 2H) 3.26 (m, J=6.02 Hz, 2H) 3.78 (s, 3H) 4.82 (m, 1H) 6.95 (q, J=8.20 Hz, 1H) 7.01 (d, J=9.04 Hz, 2H) 7.47 (m, 2H) 7.57 (m, 2H) 7.96 (m, 1H) 8.16 (m, 1H) 8.96 (s, 1H) 9.07 (s, 1H) 9.81 (s, 1H). MS (ESI+) for $C_{22}H_{24}N_2O_4S$ m/z 413.4 (M+H)$^+$. HPLC 97%, $R_T$=1.713 min (System A1, 10-97% MeCN over 3 min).

EXAMPLE 37

5-Fluoro-2-methyl-N-[4-(piperidin-4-yloxy)-1-naphthyl]benzenesulfonamide hydrochloride (General Method F)

The compound was prepared from intermediate 10 (0.24 g, 0.47 mmol). Yield: 0.21 g (99%) of the title compound as an off-white solid. HPLC 100%, $R_T$=1.823 min (System A1, 10-97% MeCN over 3 min). $^1$H NMR (400 MHz, CH$_3$OH-$d_4$) δ ppm 2.13 (m, 4H) 2.42 (s, 3H) 3.18 (m, 2H) 3.37 (m, 2H) 4.83 (m, 1H) 6.81 (d, J=8.53 Hz, 1H) 6.97 (d, J=8.03 Hz, 1H) 7.10 (m, 1H) 7.24 (m, J=8.53, 5.52 Hz, 1H) 7.35 (m, 3H) 7.83 (m, 1H). MS (ESI+) for $C_{22}H_{23}FN_2O_3S$ m/z 415.2 (M+H)$^+$. HPLC 96%, $R_T$=1.628 min (System B1, 10-90% MeCN over 3 min).

EXAMPLE 38

5-Chloro-N-[4-(piperidin-4-yloxy)-1-naphthyl]thiophene-2-sulfonamide hydrochloride (General Method F)

The compound was prepared from tert-butyl 4-[(4-{[(5-fluoro-2 methylphenyl)sulfonyl]amino}-1-naphthyl)oxy]piperidine-1-carboxylate (0.24 g, 0.46 mmol). Yield: 0.16 g (76%) of the title compound as a white solid. $^1$H NMR (400 MHz, DMSO-$d_6$) δ ppm 1.96-2.03 (m, 2H) 2.16-2.22 (m, 2H) 3.09-3.14 (m, 2H) 3.25-3.31 (m, 2H) 4.86-4.89 (m, 1H) 7.04-7.11 (m, 2H) 7.16 (d, J=4.02 Hz, 1H) 7.26 (d, J=4.02 Hz, 1H) 7.48-7.53 (m, 2H) 7.92-7.94 (m, 1H) 8.19-8.21 (m, 1H) 9.06 (br s, 1H) 10.36 (br s, 1H). MS (ESI+) for $C_{19}H_{19}ClN_2O_3S_2$ m/z 423.0 (M+H)$^+$. HPLC 99%, $R_T$=1.861 min (System A1, 10-97% MeCN over 3 min).

EXAMPLE 39

4-Chloro-N-{4-[(3S)-pyrrolidin-3-yloxy]-1-naphthyl}benzenesulfonamide hydrochloride (General Method F)

The compound was prepared from tert-butyl (3S)-3-[(4-{[(4-chlorophenyl)sulfonyl]amino}-1-naphthyl)oxy]pyrrolidine-1-carboxylate (0.22 g, 0.44 mmol). Yield: 0.15 g (78%) of the title compound as a yellow solid. $^1$H NMR (400 MHz, CH$_3$OH-$d_4$) δ ppm 2.37-2.49 (m, 2H) 3.52-3.56 (m, 2H) 3.61-3.71 (m, 2H) 5.37 (br s, 1H) 6.87 (d, J=8.03 Hz, 1H) 7.14 (d, J=8.03 Hz, 1H) 7.38-7.47 (m, 4H) 7.61 (d, J=8.53 Hz, 2H) 7.83 (d, J=8.03 Hz, 1H) 8.22 (d, J=8.03 Hz, 1H). MS (ESI+) for $C_{20}H_{19}ClN_2O_3S$ m/z 403.2 (M+H)$^+$. HPLC 100%, $R_T$=1.826 min (System A1, 10-97% MeCN over 3 min).

EXAMPLE 40

4-Chloro-N-{4-[(3R)-pyrrolidin-3-yloxy]-1-naphthyl}benzenesulfonamide hydrochloride (General Method F)

The compound was prepared from tert-butyl (3R)-3-[(4-{[(4-chlorophenyl)sulfonyl]amino}-1-naphthyl)oxy]pyrrolidine-1-carboxylate (0.37 g, 0.74 mmol). Yield: 0.27 g (82%) of the title compound as a off-white solid. $^1$H NMR (400 MHz, CH$_3$OH-$d_4$) δ ppm 2.37-2.49 (m, 2H) 3.52-3.56 (m, 2H) 3.61-3.71 (m, 2H) 5.37 (br s, 1H) 6.88 (d, J=8.53 Hz, 1H) 7.15 (d, J=8.03 Hz, 1H) 7.39-7.47 (m, 4H) 7.60-7.62 (m, 2H) 7.83 (d, J=7.53 Hz, 1H) 8.22 (d, J=8.03 Hz, 1H). MS (ESI+) for $C_{20}H_{19}ClN_2O_3S$ m/z 403.2 (M+H)$^+$. HPLC 100%, $R_T$=1.815 min (System A1, 10-97% MeCN over 3 min).

TABLE 4

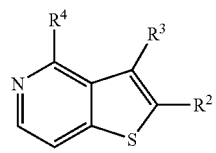

| EXAMPLE | | $R^2$ | $R^3$ | $R^4$ |
|---|---|---|---|---|
| 41 | N-(4-Methylphenyl)-4-(4-methylpiperazin-1-yl)thieno[3,2-c]pyridine-2-sulfonamide hydrochloride | 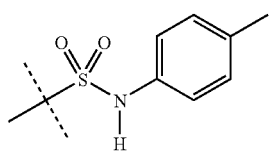 | H | 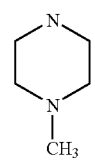 |

TABLE 4-continued

| EXAMPLE | | R² | R³ | R⁴ |
|---|---|---|---|---|
| 42 | 2-Bromo-4-(4-methyl-piperazin-1-yl)-thieno[3,2-c]pyridine-3-sulfonic acid p-tolylamide hydrochloride | Br | *p-tolyl-NH-SO₂-* (sulfonamide with 4-methylphenyl) | 4-methylpiperazin-1-yl |
| 43 | 4-(4-Methylpiperazin-1-yl)-N-phenylthieno[3,2-c]pyridine-2-sulfonamide hydrochloride | *phenyl-NH-SO₂-* | H | 4-methylpiperazin-1-yl |
| 44 | 4-Piperazin-1-yl-thieno[3,2-c]pyridine-2-sulfonic acid (3-fluoro-5-trifluoromethyl-phenyl)-amide hydrochloride | *(3-F,5-CF₃-phenyl)-NH-SO₂-* | H | piperazin-1-yl |
| 45 | 4-Piperazin-1-yl-thieno[3,2-c]pyridine-2-sulfonic acid (4-chloro-phenyl)-amide hydrochloride | *(4-Cl-phenyl)-NH-SO₂-* | H | piperazin-1-yl |
| 46 | 4-Piperazin-1-yl-thieno[3,2-c]pyridine-2-sulfonic acid (4-isopropyl-phenyl)-amide hydrochloride | *(4-iPr-phenyl)-NH-SO₂-* | H | piperazin-1-yl |
| 47 | 4-Piperazin-1-yl-thieno[3,2-c]pyridine-2-sulfonic acid p-tolylamide hydrochloride | *(4-methylphenyl)-NH-SO₂-* | H | piperazin-1-yl |
| 48 | 4-(4-Methylpiperazin-1-yl)-N-(2-cyclohex-1-en-1-ylethyl) thieno[3,2-c]pyridine-2-sulfonamide hydrochloride | *(2-cyclohex-1-en-1-ylethyl)-NH-SO₂-* | H | 4-methylpiperazin-1-yl |

TABLE 4-continued

| EXAMPLE | | R² | R³ | R⁴ |
|---|---|---|---|---|
| 49 | 2-(4-(4-Methylpiperazin-1-yl) thieno [3,2-c] pyridin-2-ylsulfonyl)-1,2,3,4-tetrahydroisoquinoline hydrochloride | *sulfonyl-tetrahydroisoquinoline* | H | *4-methylpiperazin-1-yl* |
| 50 | 4-(4-Methylpiperazin-1-yl)-N-(2-thien-2-ylethyl) thieno [3,2-c] pyridine-2-sulfonamide hydrochloride | *sulfonamide-N-(2-thien-2-ylethyl)* | H | *4-methylpiperazin-1-yl* |
| 51 | 4-(4-Methylpiperazin-1-yl)-N-[1-(1-naphthyl) ethyl] thieno [3,2-c] pyridine-2-sulfonamide hydrochloride | *sulfonamide-N-[1-(1-naphthyl)ethyl]* | H | *4-methylpiperazin-1-yl* |
| 52 | 4-(4-Methylpiperazin-1-yl)-N-(4-hexylphenyl) thieno [3,2-c] pyridine-2-sulfonamide hydrochloride | *sulfonamide-N-(4-n-hexylphenyl)* | H | *4-methylpiperazin-1-yl* |
| 53 | N-(3-Chlorobenzyl)-4-(4-methylpiperazin-1-yl) thieno [3,2-c] pyridine-2-sulfonamide | *sulfonamide-N-(3-chlorobenzyl)* | H | *4-methylpiperazin-1-yl* |
| 54 | 4-(4-Methylpiperazin-1-yl)-N-[1-(4-fluorophenyl) ethyl] thieno [3,2-c] pyridine-2-sulfonamide hydrochloride | *sulfonamide-N-[1-(4-fluorophenyl)ethyl]* | H | *4-methylpiperazin-1-yl* |

TABLE 4-continued

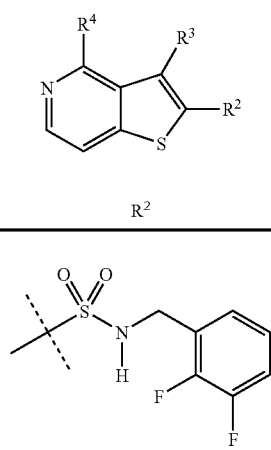

| EXAM-PLE | | R² | R³ | R⁴ |
|---|---|---|---|---|
| 55 | N-(2,3-Difluorobenzyl)-4-(4-methylpiperazin-1-yl) thieno [3,2-c] pyridine-2-sulfonamide hydrochloride | 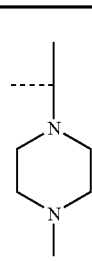 | H | 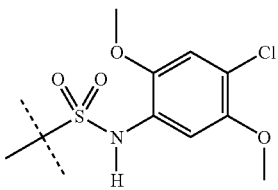 |
| 56 | 4-(4-Methylpiperazin-1-yl)-N-(4-chloro-2,5-dimethoxyphenyl) thieno [3,2-c] pyridine-2-sulfonamide hydrochloride | 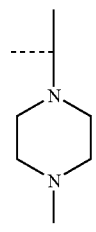 | H | 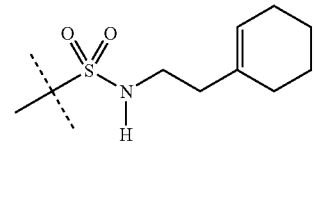 |
| 57 | 2-Bromo-4-(4-methylpiperazin-1-yl)-N-(2-cyclohex-1-en-1-ylethyl) thieno [3,2-c] pyridine-3-sulfonamide hydrochloride | Br | 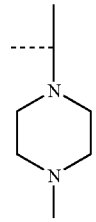 | 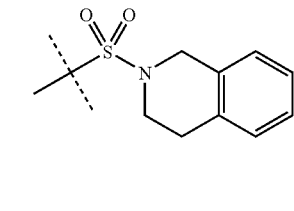 |
| 58 | 2-[2-Bromo-4-(4-methyl-piperazin-1-yl)-benzo[b]thiophene-3-sulfonyl]-1,2,3,4-tetrahydro-isoquinoline | Br | 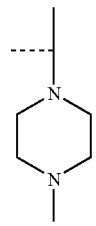 | 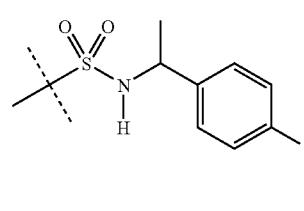 |
| 59 | 2-Bromo-4-(4-methylpiperazin-1-yl)-N-[1-(4-fluorophenyl) ethyl] thieno [3,2-c] pyridine-3-sulfonamide hydrochloride | Br | 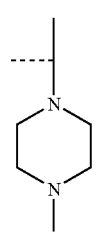 | 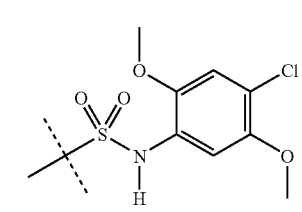 |
| 60 | 2-Bromo-4-(4-methylpiperazin-1-yl)-N-(4-chloro)-(2,5-dimethoxyphenyl) thieno [3,2-c] pyridine-3-sulfonamide hydrochloride | Br | 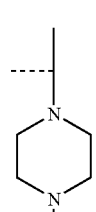 | |

TABLE 4-continued

[Structure: thieno[3,2-c]pyridine core with R² at 2-position, R³ at 3-position, R⁴ at 4-position]

| EXAMPLE | | R² | R³ | R⁴ |
|---|---|---|---|---|
| 61 | N-(3,4-Dichlorophenyl)-4-piperazin-1-ylthieno[3,2-c]pyridine-2-sulfonamide hydrochloride | sulfonamide-NH-(3,4-dichlorophenyl) | H | piperazin-1-yl |
| 62 | N-(2,4-Difluorophenyl)-4-piperazin-1-ylthieno[3,2-c]pyridine-2-sulfonamide hydrochloride | sulfonamide-NH-(2,4-difluorophenyl) | H | piperazin-1-yl |
| 63 | 4-Piperazin-1-yl-N-[-3-(trifluoromethyl)phenyl]thieno[3,2-c]pyridine-2-sulfonamide hydrochloride | sulfonamide-NH-(3-trifluoromethylphenyl) | H | piperazin-1-yl |
| 64 | N-(3-Ethylphenyl)-4-piperazin-1-ylthieno[3,2-c]pyridine-2-sulfonamide hydrochloride | sulfonamide-NH-(3-ethylphenyl) | H | piperazin-1-yl |
| 65 | N-(3,4-Dimethoxyphenyl)-4-piperazin-1-ylthieno[3,2-c]pyridine-2-sulfonamide hydrochloride | sulfonamide-NH-(3,4-dimethoxyphenyl) | H | piperazin-1-yl |
| 66 | N-(4-Bromo-2-methylphenyl)-4-piperazin-1-ylthieno[3,2-c]pyridine-2-sulfonamide hydrochloride | sulfonamide-NH-(4-bromo-2-methylphenyl) | H | piperazin-1-yl |
| 67 | 2-(4-Piperazin-1-yl-thieno[3,2-c]pyridine-2-sulfonyl)-1,2,3,4-tetrahydro-isoquinoline hydrochloride | sulfonyl-(1,2,3,4-tetrahydroisoquinolin-2-yl) | H | piperazin-1-yl |
| 68 | 4-Piperazin-1-yl-thieno[3,2-c]pyridine-2-sulfonic acid (2-thiophen-2-yl-ethyl)-amide hydrochloride | sulfonamide-NH-CH₂CH₂-(thiophen-2-yl) | H | piperazin-1-yl |

TABLE 4-continued

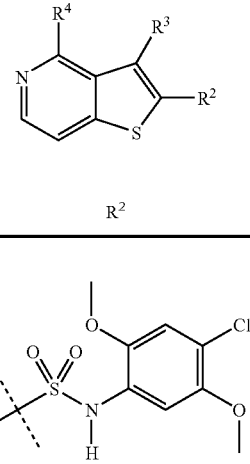

| EXAMPLE | | R² | R³ | R⁴ |
|---|---|---|---|---|
| 69 | 4-Piperazin-1-yl-thieno[3,2-c]pyridine-2-sulfonic acid (4-chloro-2,5-dimethoxy-phenyl)-amide hydrochloride | 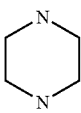 | H | 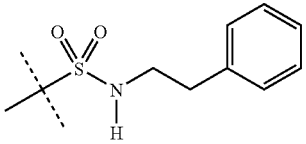 |
| 70 | 4-Piperazin-1-yl-thieno[3,2-c]pyridine-2-sulfonic acid phenethyl-amide hydrochloride | 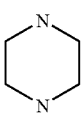 | H | 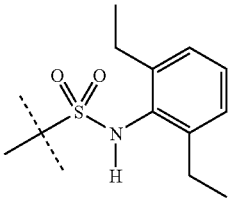 |
| 71 | 4-Piperazin-1-yl-thieno[3,2-c]pyridine-2-sulfonic acid (2,6-diethyl-phenyl)-amide hydrochloride | 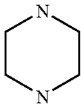 | H | 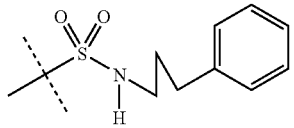 |
| 72 | 4-Piperazin-1-yl-thieno[3,2-c]pyridine-2-sulfonic acid (3-phenyl-propyl)-amide hydrochloride | 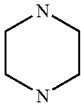 | H | 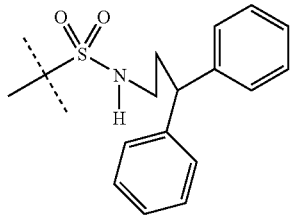 |
| 73 | 4-Piperazin-1-yl-thieno[3,2-c]pyridine-2-sulfonic acid (3,3-diphenyl-propyl)-amide hydrochloride | 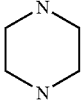 | H | 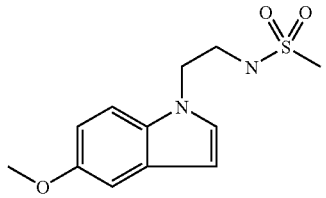 |
| 74 | 4-Piperazin-1-yl-thieno[3,2-c]pyridine-2-sulfonic acid [2-(5-methoxy-1H-indol-3-yl)-ethyl]-amide hydrochloride | 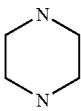 | H | 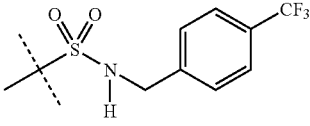 |
| 75 | 4-Piperazin-1-yl-thieno[3,2-c]pyridine-2-sulfonic acid 4-trifluoromethyl-benzylamide hydrochloride | 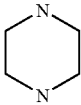 | H |  |

TABLE 4-continued

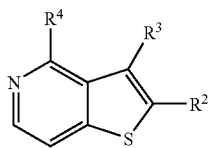

| EXAMPLE | | R² | R³ | R⁴ |
|---|---|---|---|---|
| 76 | 4-Piperazin-1-yl-thieno[3,2-c]pyridine-2-sulfonic acid benzyl-ethyl-amide hydrochloride | 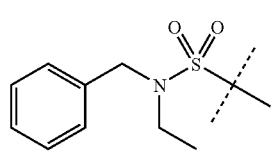 | H | 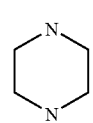 |
| 77 | N-(3-Ethylphenyl)-4-piperazin-1-ylthieno[3,2-c]pyridine-3-sulfonamide hydrochloride | H | 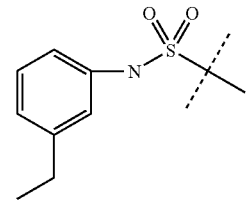 | 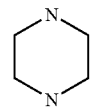 |
| 78 | N-(4-Isopropylphenyl)-4-piperazin-1-ylthieno[3,2-c]pyridine-3-sulfonamide hydrochloride | H | 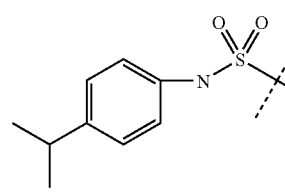 | 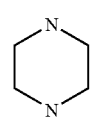 |
| 79 | N-(4-Methylphenyl)-4-(pyrrolidin-3-yloxy)thieno[3,2-c]pyridine-2-sulfonamide hydrochloride | 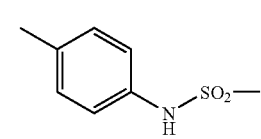 | H | 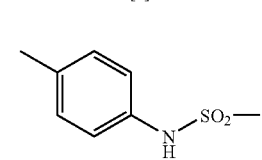 |
| 80 | N-(4-Methylphenyl)-4-(piperidin-4-yloxy)thieno[3,2-c]pyridine-2-sulfonamide hydrochloride | 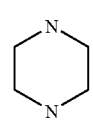 | H |  |
| 81 | N-(2,3-Difluorobenzyl)-4-piperazin-1-ylthieno[3,2-c]pyridine-2-sulfonamide hydrochloride |  | H |  |

TABLE 4-continued

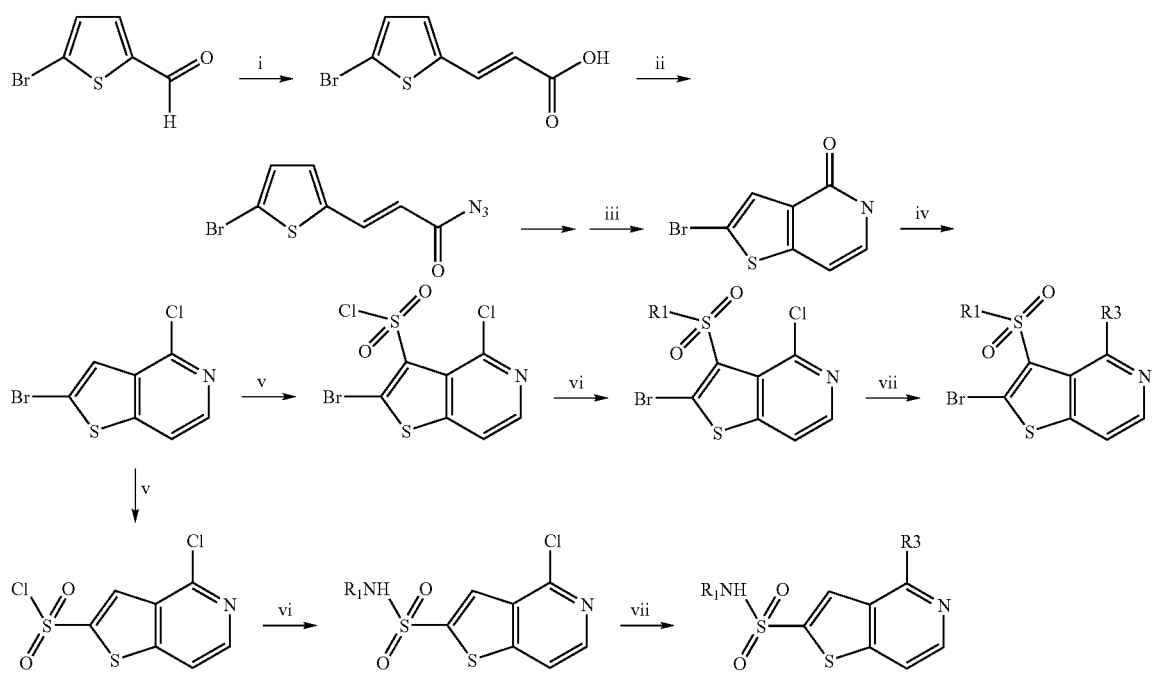

| EXAMPLE | | R² | R³ | R⁴ |
|---|---|---|---|---|
| 82 | N-(3-Chlorobenzyl)-4-piperazin-1-ylthieno[3,2-c]pyridine-2-sulfonamide hydrochloride | [?] | H | (piperazine) |

Scheme 5

Legend to Scheme 5: i) Malonic acid, pyridine, piperidine, heat; ii) ethylchloroformate, acetone, NaN₃ -10° C.; iii) diphenyl ether, 220 ° C.; iv) POCl₃, heat; v) gas SO₂, n-BuLi, N-chlorosuccinimide, CH₂Cl₂; vi) R¹—NH₂, pyridine; vii) HR₃, K₂CO₃, DMSO, heat.

INTERMEDIATE 47

(2E)-3-(5-Bromothien-2-yl) Acrylic Acid

Malonic acid (44.40 g, 426.7 mmol) was added to a mixture of 5-bromothiophene-2-carbaldehyde (50 g, 261.7 mmol), piperidine (2.84 mL) and pyridine (150 mL). The mixture was refluxed for 1 h at 80° C. and than at 100° C. over night. The volatiles were evaporated and the residue was dissolved in water and acidified with hydrochloric acid (pH 2). The crude product was crystallized in ethanol. Yield: 55.24 g (90.5%). $^1$H NMR (270 MHz, CH₃OH-d₄) δ ppm 6.14 (d, J=15.83 Hz, 1H) 7.11-7.16 (m, 2H) 7.68 (d, J=16.36 Hz, 1H); MS 233.1 (M−H)⁺; Purity (HPLC) 94%.

INTERMEDIATE 48

(2E)-3-(5-Bromothien-2-yl) acryloyl azide

Thionyl chloride (1.04 mL) was added to a solution of (2E)-3-(5-bromothien-2-yl) acrylic acid (1.04 g, 4.46 mmol) in chloroform (20 mL) and the mixture was refluxed for 2 h at 75° C. and than used in the next step. The above solution was added drop wise to a stirred suspension of sodium azide (0.58 g, 8.93 mmol), dioxane (3 mL) and water (3 mL) in an ice bath. After 10 min a precipitate appeared which was filtered off and washed with water. The residue was dissolved in dichloromethane, dried with MgSO$_4$, filtered and the solvent was removed to afford: 0.96 g (83.4%). $^1$H NMR (270 MHz CH$_3$OH-d$_4$) δ ppm 6.20 (d, J=15.57 Hz, 1H) 7.15-7.25 (m, 2H) 7.80 (d, J=15.57 Hz, 1H); MS 258.1 (M–H)$^+$; Purity (HPLC) 65%.

INTERMEDIATE 49

2-Bromothieno[3,2-c]pyridin-4 (5H)-one

A solution of (2E)-3-(5-bromothien-2-yl) acryloyl azide (18.00 g, 69.7 mmol) solved in dichloromethane (100 mL) was added dropwise to diphenyl ether (90 mL) at 150° C. The temperature was increased to 220° C. for 1 h. The mixture was cooled to room temperature followed by the addition of ether. The solid precipitated and was separated by filtration. Yield: 13.58 g (84.6%). $^1$H NMR (270 MHz, DMSO-d$_6$) δ ppm 6.82 (d, J=7.13 Hz, 1H) 7.27 (d, J=6.86 Hz, 1H) 7.54 (s, 1H) 11.55 (s, 1H); MS 230.1 (M–H)$^+$; Purity (HPLC) 92%.

INTERMEDIATE 50

2-Bromo-4-chloro-thieno[3,2-c]pyridine

Phosphorus oxychloride (4.08 g, 26.6 mmol) was added dropwise to 2-bromothieno[3,2-c]pyridin-4 (5H)-one (2.04 g, 8.87 mmol) at 0° C. The mixture was heated at 135° C. for 2.5 h, then carefully poured over ice water. The precipitated was collected by filtration and dried to yield 1.78 g (80.7%) of title product. $^1$H NMR (270 MHz, CH$_3$OH-d$_4$) δ ppm 7.67 (d, 1H) 7.88 (dddd, J=6.33 Hz, 2H) 8.19 (d, J=5.54 Hz, 1H); MS 248.0 (M–H)$^+$; Purity (HPLC) 100

INTERMEDIATE 51 AND INTERMEDIATE 52

4-Chlorothieno[3,2-c]pyridine-2-sulfonyl chloride
and
2-bromo-4-chlorothieno[3,2-c]pyridine-3-sulfonyl chloride n-Butyl lithium (1.5 mL, 2.4 mmol) was added to 2-bromo-4-chlorothieno[3,2-c]pyridine (0.5 g, 2 mmol) dissolved in dry THF (15 ml) at –78° C. under nitrogen. The mixture was stirred for 40 min. The above solution was added to a dry ether saturated with SO$_2$ (gas) at –78° C. The mixture was warmed to room temperature, followed by the addition of ether. The precipitate was separated by filtration. The two title products were obtained and taken to the next step without further purification as follows: N-chlorosuccinimide (2.07 g, 10.3 mmol) was added to [(4-chlorothieno[3,2-c]pyridin-2-yl)sulfonyl]lithium and [(2-bromo-4-chlorothieno[3,2-c]pyridin-3-yl)sulfonyl]lithium in dichloromethane (150 mL) at 0° C. The mixture was heated at 60° C. for 2 h, extracted with water (3×50 mL). The organic phase was separated, dried with MgSO$_4$, filtrated and the volatiles were eliminated by vacuum distillation. The crude products were used in the next step without further purification.

INTERMEDIATE 53 AND INTERMEDIATE 54

4-Chloro-2-thieno[3,2-c]pyridine-2-sulfonic acid p-tolylamide and 2-bromo-4-chlorothieno[3,2-c]pyridine-3-sulfonic acid p-tolylamide p-Toludine (30 mg, 2.87 mmol) was added to a solution of 4-chlorothieno[3,2-c]pyridine-2-sulfonyl chloride and 2-bromo-4-chlorothieno[3,2-c]pyridine-3-sulfonyl chloride (0.07 g, 0.26 mmol) in dichloromethane and pyridine (0.19 mL). The reaction was stirred at room temperature for 2 h. The solvent was removed and the crude mixture was taken to the next step without further purification.

EXAMPLE 41 AND EXAMPLE 42

4-(4-Methyl-piperazin-1-yl)-thieno[3,2-c]pyridine-2-sulfonic acid p-tolylamide hydrochloride and 2-bromo-4-(4-methyl-piperazin-1-yl)-thieno[3,2-c]pyridine-3-sulfonic acid p-tolylamide hydrochloride A mixture of 4-chloro-2-thieno[3,2-c]pyridine-2-sulfonic acid p-tolylamide and 2-bromo-4-chloro-thieno[3,2-c]pyridine-3-sulfonic acid p-tolylamide (70 mg, 0.21 mmol) in DMSO (2 mL), 1-methyl piperazine (0.344 mL, 3.1 mmol) and K$_2$CO$_3$ (28.5 mg, 0.21 mmol) was heated to 100° C. over night. The reaction mixture was dissolved in water and extracted with ethyl acetate (3×10 mL). The organic layers were collected and the solvent was removed. The products were purified by HPLC to afford 1.9 mg of 4-(4-Methyl-piperazin-1-yl)-thieno[3,2-c]pyridine-2-sulfonic acid p-tolylamide. The free base was converted into the hydrochloride salt by treatment with HCl in ether: $^1$H NMR (270 MHz, Methanol-d$_4$) δ ppm 2.26 (s, 3H) 2.98 (s, 3H) 3.40-3.55 (m, 8H) 7.02-7.10 (m, 6H) 7.55 (d, J=5.81 Hz, 1H) 7.69 (s, 1H) 8.13 (d, J=5.81 Hz, 1H); LC-MS 403 (M+H)$^+$; Purity (LC-MS) 92% and 3.8 mg 2-bromo-4-(4-methyl-piperazin-1-yl)-thieno[3,2-c]pyridine-3-sulfonic acid p-tolylamide. The free base was converted into the hydrochloride salt by treatment with HCl in ether: $^1$H NMR (270 MHz, Methanol-d$_4$) δ ppm 2.21 (s, 1H) 3.00 (d, 3H) 3.50-3.77 (m, 8H) 7.00-7.10 (m, 6H) 7.63 (d, J=5.81 Hz, 1H) 8.19 (d, J=5.81 Hz, 1H); LC-MS 481 (M+H)$^+$; Purity (LC-MS) 98%.

Reaction of Sulfonyl Chloride with Amines (Method H)

To a solution of the amine (1.3 equiv.) and pyridine (8 equiv.) in DCM was added the sulfonyl chloride (1 equiv.) and the reaction mixture was stirred over night. After addition of Trisamine™ (ca 2 equiv.), the mixture was gently shaken for additional 3 h. The suspension was then filtered through a short silica plug by the aid of DCM and ethyl acetate. The solvent was evaporated, and the residue was dissolved in DCM and washed with 1 M aqueous HCl (2 times). The combined organic phases were dried (MgSO$_4$), filtered, and the solvent was removed to give the sulfonamide product. In cases of low-purity material, the products were purified by silica gel flash chromatography. The products are used in the next step (Procedure B).

Coupling with Aromatic Amines (Method I)

To the reaction mixtures from the Method H, dissolved in DMSO (2 mL), amines (15 equiv.) and K$_2$CO$_3$ (1 equiv.) are added. The reactions are stirred at 100° C. for 24 and than concentrated. The products are purified by LC-MS. The solvents are removed under vacuum by SpeedVac and purified by preparative LC/MS. The products that were not pure enough (Purity ≦90%) were purified by preparative chromatography using acetonitrile-water gradients containing 0.1% triflouroacetic acid. After HPLC analysis fractions that were ≧90% pure were collected and concentrated. Deprotection of the amine in the piperazine was performed by first dissolving the substance in methanol and adding portions of 1M HCl/ether. The reactions are analyzed by TLC. The solvents were concentrated under vacuum by a SpeedVac.

Deprotection of BOC-Group (Method L)

The sulfone or sulfonamide derivative (prepared by Methods H and I) were dissolved in a small amount of MeOH/DCM 1:1 and treated with an excess of 1 M HCl in diethyl ether. Stirring at ambient temperature overnight resulted in a precipitate which were collected by filtration to give the products as their corresponding hydrochloride salts.

EXAMPLE 43

4-(4-Methylpiperazin-1-yl)-N-phenylthieno[3,2-c]pyridine-2-sulfonamide hydrochloride The synthesis was preformed essentially as described in Method H-L. Yield: 8.1 mg (33.8%). $^1$H NMR (270 MHz, CH$_3$OH-d$_4$) δ ppm 8.13 (d, J=5.81 Hz, 1H) 7.67 (s, 1H) 7.54 (d, J=5.81 Hz, 1H) 7.55-7.53 (m, 5H) 2.97 (s, 3H) (4H obscured by solvent signal); LC-MS 389 (M−H)$^+$; Purity (HPLC) 100%.

EXAMPLE 44

4-Piperazin-1-yl-thieno[3,2-c]pyridine-2-sulfonic acid (3-fluoro-5-trifluoromethylphenyl)-amide hydrochloride 4-[2-(3-Fluoro-5-trifluoromethyl-phenylsulfamoyl)-thieno[3,2-c]pyridin-4-yl]-piperazine-1-carboxylic acid tert-butyl ester (0.235 mmol, 1 equiv.) was used as the thienopyridine in Method H-L. Yield: 25.7 mg HPLC: t$_R$=3.395 (System: 5% to 50% ACN in 3 min, C8), Purity: 100%, LC/MS: t$_R$=1.375 (System: 30% to 60% ACN in 1.5 min, Hypersil BDS), Purity: 99%. MS: 461 (M+1) $^1$H NMR (270 MHz, CH$_3$OH-d$_4$) δ ppm 3.47 (m, 4H) 3.53 (s, 1H) 3.87 (m, 4H) 7.21 (m, 1H) 7.29 (m, 1H) 7.33 (s, 1H) 7.66 (d, J=6.33 Hz, 1H).

EXAMPLE 45

4-Piperazin-1-yl-thieno[3,2-c]pyridine-2-sulfonic acid (4-chloro-phenyl)-amide hydrochloride 4-Chloro-thieno[3,2-c]pyridine-2-sulfonic acid (3-fluoro-5-trifluoromethyl-phenyl)-amide (0.208 mmol, 1 equiv.) was used as the thienopyridine in Method H-L. Yield: 7.2 mg HPLC: t$_R$=3.039 (System: 5% to 50% ACN in 3 min, C8), Purity: 100%, LC/MS: t$_R$=0.905 (System: 30% to 60% ACN in 1.5 min, Hypersil BDS), Purity: 97%. MS: 409 (M+1). $^1$H NMR (270 MHz, CH$_3$OH-d$_4$) δ ppm 3.50 (m, 4H) 3.91 (m, 4H) 7.25 (m, 4H) 7.71 (dd, J=6.33, 0.53 Hz, 1H) 7.96 (d, J=0.79 Hz, 1H) 8.04 (d, J=6.33 Hz, 1H).

EXAMPLE 46

4-Piperazin-1-yl-thieno[3,2-c]pyridine-2-sulfonic acid (4-isopropyl-phenyl)-amide hydrochloride 4-Chloro-thieno[3,2-c]pyridine-2-sulfonic acid (4-isopropyl-phenyl)-amide (0.201 mmol, 1 equiv.) was used as the thienopyridine in Method H-L. Yield: 6.9 mg HPLC: t$_R$=3.255 (System: 5% to 50% ACN in 3 min, C8), Purity: 95%, LC/MS: t$_R$=1.255 (System: 30% to 60% ACN in 1.5 min, Hypersil BDS), Purity: 98%. MS: 417 (M+1). $^1$H NMR (270 MHz, CH$_3$OH-d$_4$) δ ppm 1.18 (d, J=6.86 Hz, 6H) 2.83 (m, 2H) 3.52 (m, 4H) 4.00 (m, 4H) 7.14 (m, 3H) 7.75 (d, J=6.60 Hz, 1H) 8.02 (m, 1H).

EXAMPLE 47

4-Piperazin-1-yl-thieno[3,2-c]pyridine-2-sulfonic acid p-tolylamide hydrochloride To a solution of 4-chloro-thieno[3,2-c]pyridine-2-sulfonyl chloride (0.640 g, 2.39 mmol) in DCM (20 mL) was added pyridine (1.9 mL, 23.9 mmol) followed by p-tolylamine (0.307 g, 2.86 mmol). The reaction mixture was stirred at room temperature for 16 hours. The mixture was concentrated and re-dissolved in DMSO (10 mL), piperazine-1-carboxylic acid tert-butyl ester (1.34 g, 7.17 mmol) and K$_2$CO$_3$ (0.989 g, 7.17 mmol) were added. The mixture was stirred at 100° C. for 16 hours and then concentrated. The crude reaction mixture was dissolved in EtOAc (100 mL) and washed with brine (2×50 mL). The organic phase was dried (Na$_2$SO$_4$) and concentrated. The crude intermediate was purified by column chromatography on silica using EtOAc/n-pentane (1:1) as eluent. The intermediate was dissolved in EtOAc/MeOH and diethyl ether saturated with HCl (g) was added. The mixture was stirred at room temperature for 16 hours. The precipitate was collected by filtration and washed with diethyl ether/n-pentane to give 0.475 g of the crude product. Purification by preparative reversed phase HPLC gave 0.133 g of the pure product: $^1$H NMR (DMSO-d$_6$, 25° C., 270.17 MHz) δ 10.61 (br s, 1H), 9.23 (br s, 2H), 8.13 (d, J=5.80 Hz, 1H), 7.91 (s, 1H); 7.67 (d, J=5.80 Hz, 1H), 7.09-7.07 (m, 4H), 3.68-3.59 (m, 4H), 3.33-3.22 (m, 4H), 2.20 (s, 3H); m/z (posESI) 399 (M+H).

EXAMPLE 48

4-(4-Methylpiperazin-1-yl)-N-(2-cyclohex-1-en-1-ylethyl)thieno[3,2-c]pyridine-2-sulfonamide hydrochloride The synthesis was preformed essentially as described in Method H-L. Yield: 25.6 mg $^1$H NMR (270 MHz, DMSO-d$_6$) δ ppm 10.49-10.48 (m, 1H) 8.23-7.95 (m, 3H) 7.72-7.71 (m, 1H) 5.34-5.33 (m, 1H) 4.14-4.11 (m, 2H) 3.53-3.51 (m, 2H) 3.29-3.25 (m, 2H) 2.98-2.97 (m, 2H) 2.85 (s, 3H) 2.04-1.81 (m, 4H) 1.57-1.15 (m, 8H); LC-MS 420.17 (M−H)$^+$; Purity (LC-MS) 97%.

EXAMPLE 49

2-(4-(4-Methylpiperazin-1-yl)thieno[3,2-c]pyridin-2-ylsulfonyl)-1,2,3,4-tetrahydroisoquinoline hydrochloride The synthesis was preformed essentially as described in Method H-L. Yield: 15.5 mg $^1$H NMR (270 MHz, DMSO-d$_6$) δ ppm 10.49-10.48 (m, 1H) 8.17-8.15 (m, 1H) 7.86-7.85 (m, 1H) 7.70-7.65 (m, 2H) 7.28-7.12 (m, 3H) 3.97-3.94 (m, 2H) 3.87-3.85 (m, 2H) 3.25-3.18 (m, 2H) 2.84 (s, 3H) 1.67-1.65 (m, 2H) 3.51-3.34 (6H obscured by solvent signal); LC-MS 428.13 (M−H)$^+$; Purity (LC-MS) 99%.

EXAMPLE 50

4-(4-Methylpiperazin-1-yl)-N-(2-thien-2-ylethyl)thieno[3,2-c]pyridine-2-sulfonamide hydrochloride The synthesis was preformed essentially as described in Method H-L. Yield: 29.5 mg $^1$H NMR (270 MHz, DMSO-d$_6$) δ ppm 10.28-10.27 (m, 1H) 8.34-8.33 (m, 1H) 8.19-8.17 (m, 1H) 8.01-8.00 (m, 1H) 7.71-7.69 (m, 1H) 7.31-7.30 (m, 1H)

6.91-6.87 (m, 1H) 4.13-4.10 (m, 2H) 3.53-3.51 (m, 2H) 3.29-3.25 (m, 2H) 3.17-3.16 (m, 2H) 2.99-2.95 (m 4H) 2.86 (s, 3H); LC-MS 422.09 (M–H)$^+$; Purity (LC-MS) 99%.

EXAMPLE 51

4-(4-Methylpiperazin-1-yl)-N-[1-(1-naphthyl)ethyl]thieno[3,2-c]pyridine-2-sulfonamide hydrochloride The synthesis was preformed essentially as described in Method H-L. 20.1 mg $^1$H NMR (270 MHz, DMSO-d$_6$) δ ppm 10.28-10.27 (m, 1H) 8.85-8.84 (m, 1H) 8.02-8.01 (m, 1H) 7.67-7.60 (m, 4H) 7.53-7.50 (m, 2H) 7.39-7.36 (m, 2H) 4.72-4.70 (m, 1H) 3.87-3.84 (m, 1H) 3.72-3.70 (m, 1H) 3.23-3.13 (m, 4H) 2.84 (s, 3H) 1.42-1.40 (m 3H); LC-MS 466.15 (M–H)$^+$; Purity (LC-MS) 99%.

EXAMPLE 52

4-(4-Methylpiperazin-1-yl)-N-(4-hexylphenyl)thieno[3,2-c]pyridine-2-sulfonamide hydrochloride The synthesis was preformed essentially as described in Method H-L. 8.0 mg $^1$H NMR (270 MHz, DMSO-d$_6$) δ ppm 10.39-10.38 (m, 1H) 8.16-8.15 (m, 1H) 7.90-7.89 (m, 1H) 7.66-7.65 (m, 1H) 7.09-7.08 (m, 4H) 4.00-3.98 (m, 2H) 3.51-3.48 (m, 2H) 3.26-3.22 (m, 2H) 2.85 (s, 3H) 2.49-2.45 (m, 2H) 1.48-1.46 (m, 2H) 1.24-1.22 (m, 8H) 0.82-0.81 (m, 3H); LC-MS 472.20 (M–H)$^+$; Purity (LC-MS) 98%.

EXAMPLE 53

N-(3-Chlorobenzyl)-4-(4-methylpiperazin-1-yl)thieno[3,2-c]pyridine-2-sulfonamide hydrochloride The synthesis was preformed essentially as described in Method H-L. 30.7 mg $^1$H NMR (270 MHz, DMSO-d$_6$) δ ppm 10.25-10.24 (m, 1H) 8.78-8.77 (m, 1H) 8.18-8.17 (m, 1H) 7.91-7.90 (m, 1H) 7.68-7.67 (m, 1H) 7.26-7.19 (m, 3H) 4.21-4.20 (m, 2H) 4.08-4.05 (m, 2H) 3.54-3.51 (m, 2H) 3.28-3-23 (m, 2H) 2.87 (s, 3H) 2.84-2.60 (2H obscured by solvent signal); LC-MS 436.08 (M–H)$^+$; Purity (LC-MS) 94%

EXAMPLE 54

4-(4-Methylpiperazin-1-yl)-N-[1-(4-fluorophenyl)ethyl]thieno[3,2-c]pyridine-2-sulfonamide hydrochloride The synthesis was preformed essentially as described in Method H-L. 32.9 mg $^1$H NMR (270 MHz, DMSO-d$_6$) δ ppm 10.16-10.15 (m, 1H) 8.75-8.73 (m, 1H) 7.63-7.62 (m, 2H) 7.25-7.24 (m, 2H) 6.91-6.88 (m, 2H) 4.58-4.55 (m, 1H) 4.02-3.95 (m, 2H) 3.55-3.53 (m, 2H) 3.25-3-21 (m, 2H) 2.68 (s, 3H) 1.31-1.30 (m, 3H) 2.70-2.64 (2H obscured by solvent signal); LC-MS 434.12 (M–H)$^+$; Purity (LC-MS) 92%.

EXAMPLE 55

N-(2,3-Difluorobenzyl)-4-(4-methylpiperazin-1-yl)thieno[3,2-c]pyridine-2-sulfonamide hydrochloride The synthesis was preformed essentially as described in Method H-L. 26.7 mg $^1$H NMR (270 MHz, DMSO-d$_6$) δ ppm 10.36-10.35 (m, 1H) 8.82-8.81 (m, 1H) 7.96-7.95 (m, 1H) 7.69-7.68 (m, 1H) 7.27-7.10 (m, 2H) 4.26-4.25 (m, 2H) 4.11-4.08 (m, 2H) 3.54-3.52 (m, 2H) 3.28-3-24 (m, 2H) 2.68 (s, 3H) 2.86-2.60 (2H obscured by solvent signal); LC-MS 438.10 (M–H)$^+$; Purity (LC-MS) 93%.

EXAMPLE 56

4-(4-Methylpiperazin-1-yl)-N-(4-chloro-2,5-dimethoxyphenyl)thieno[3,2-c]pyridine-2-sulfonamide hydrochloride The synthesis was preformed essentially as described in Method H-L. 14.6 mg $^1$H NMR (270 MHz, DMSO-d$_6$) δ ppm 10.27-10.26 (m, 1H) 10.14-10.13 (m, 1H) 8.18-8.17 (m, 1H) 7.83-7.82 (m, 1H) 7.69-7.68 (m, 1H) 7.09-7.07 (m, 2H) 4.00 (s 2H) 3.76-3.75 (m, 2H) 3.51-3.48 (m, 2H) 3.24-3.22 (m, 2H) 2.85 (s, 3H); LC-MS 482.08 (M–H)$^+$; Purity (LC-MS) 95%.

EXAMPLE 57

2-Bromo-4-(4-methylpiperazin-1-yl)-N-(2-cyclohex-1-en-1-ylethyl)thieno[3,2-c]pyridine-3-sulfonamide hydrochloride The synthesis was preformed essentially as described in Method H-L. 4.6 mg $^1$H NMR (270 MHz, DMSO-d$_6$) δ ppm 10.30-10.29 (m, 1H) 8.31-8.27 (m, 2H) 7.89-7.88 (m, 1H) 5.27-5.26 (m, 1H) 3.68-3.52 (m, 4H) 3.05-3.04 (m, 2H) 2.88-2.87 (m, 3H) 2.04-2.03 (m, 2H) 2.77-1.81 (m, 2H) 1.54-1.15 (m, 101H); LC-MS 498.08 (M–H)$^+$; Purity (LC-MS) 93%.

EXAMPLE 58

2-[2-Bromo-4-(4-methyl-piperazin-1-yl)-benzo[b]thiophene-3-sulfonyl]-1,2,3,4-tetrahydro-isoquinoline hydrochloride The synthesis was preformed essentially as described in Method H-L. Yield: 3.7 mg $^1$H NMR (270 MHz, DMSO-d$_6$) δ ppm 10.30-10.29 (m, 1H) 9.24-9.22 (m, 1H) 8.09-8.08 (m, 1H) 7.67-7.35 (m, 7H) 4.69-4.66 (m, 1H) 2.86-2.85 (m, 3H) 1.50-1.48 (m, 3H) 3.23-2.51 (8H obscured by solvent signal); LC-MS 544.06 (M–H)$^+$; Purity (LC-MS) 92%.

EXAMPLE 59

2-Bromo-4-(4-methylpiperazin-1-yl)-N-[1-(4-fluorophenyl)eth-2-yl]thieno[3,2-c]pyridine-3-sulfonamide hydrochloride The synthesis was preformed essentially as described in Method H-L. Yield: 4.3 mg $^1$H NMR (270 MHz, DMSO-d$_6$) δ ppm 10.35-10.34 (m, 1H) 9.16-9.14 (m, 1H) 8.23-8.22 (m, 1H) 7.80-7.79 (m, 1H) 7.26-7.25 (m, 1H) 4.55-4.52 (m, 1H) 3.54-3.52 (m, 2H) 2.88-2.87 (m, 3H) 1.38-1.36 (m, 3H) 3.17-2.83 (6H obscured by solvent signal); LC-MS 512.04 (M–H)$^+$; Purity (LC-MS) 93%

EXAMPLE 60

2-Bromo-4-(4-methylpiperazin-1-yl)-N-(4-chloro)-(2,5-dimethoxyphenyl)thieno[3,2-c]pyridine-3-sulfonamide hydrochloride The synthesis was preformed essentially as described in Method H-L. Yield: 0.7 mg, LC-MS 561.91 (M–H)$^+$; Purity (LC-MS) 95%.

EXAMPLE 61

N-(3,4-dichlorophenyl)-4-piperazin-1-ylthieno[3,2-c]pyridine-2-sulfonamide hydrochloride 3,4-Dichloroaniline (0.49 mmol), was dissolved in acetonitrile (1 mL) and pyridine (0.440 mL, 4.03 mmol) was added to a solution of 4-chlorothieno[3,2-c]pyridine-2-sulfonyl chloride (0.445 mmol) dissolved in acetonitrile (1 mL). The reaction was shaken for 1 h, controlled with HPLC and the solvent was removed. The crude product was used in the next step without further purification. To the reaction mixture from the previous step, dissolved in DMSO (1 mL), piperazine (15 equiv.) and $K_2CO_3$ (1 equiv.) was added. The reaction was stirred at 100° C. for 24 and than concentrated. The product was purified by LC-MS and gave 5.8 mg (2.6%) of the title product. $^1$H NMR (270 MHz, $CH_3OH-d_4$) δ ppm 8.07-8.05 (m, 2H) 7.73 (d, J=6.60 Hz, 1H) 7.46-7.41 (m, 2H) 7.16 (dd, J=8.71, 2.38 Hz, 1H) 3.94-3.90 (m, 4H) 3.92 (m, 4H) 3.53-3.50 (m, 4H); LC-MS 443 (M−H)$^+$; Purity (HPLC) 95%.

EXAMPLE 62

N-(2,4-Difluorophenyl)-4-piperazin-1-ylthieno[3,2-c]pyridine-2-sulfonamide hydrochloride The synthesis was preformed essentially as described in Method H-L. Yield: 4.3 mg (2.1%). $^1$H NMR (270 MHz, $CH_3OH-d_4$) δ ppm 8.22 (s, 1H) 8.07-8.01 (m, 2H) 7.79-7.72 (m, 1H) 7.55-7.47 (m, 1H) 7.04-6.94 (m, 2H) 4.00-3.96 8 m, 4H) 3.53-3.43 (m, 4H) 2.66 (s, 1H); LC-MS 411 (M−H)$^+$; Purity (HPLC) 98%.

EXAMPLE 63

4-Piperazin-1-yl-N-[-3-(trifluoromethyl)phenyl]thieno[3,2-c]pyridine-2-sulfonamide hydrochloride The synthesis was preformed essentially as described in Method H-L. Yield: 2.6 mg (1.2%). $^1$H NMR (270 MHz, $CH_3OH-d_4$) δ ppm 8.05 (d, J=6.60 Hz, 2H) 7.81-7.60 (m, 3H) 7.50-7.47 (m, 2H) 3.94-3.90 (m, 4H) 3.56-3.49 (m, 4H); LC-MS 443 (M−H)$^+$; Purity (HPLC) 99%.

EXAMPLE 64

N-(3-Ethylphenyl)-4-piperazin-1-ylthieno[3,2-c]pyridine-2-sulfonamide hydrochloride The synthesis was preformed essentially as described in Method H-L. Yield: 1.4 mg (0.7%). $^1$H NMR (270 MHz, $CH_3OH-d_4$) δ ppm 8.35 (s, 1H) 7.58-6.92 (m, 7H) 3.54-3.44 (m, 2H) 3.01-2.95 (m, 4H) 2.66 (s, 1H) 2.18-2.01 (m, 3H)); LC-MS 403 (M−H)$^+$; Purity (HPLC) 100

EXAMPLE 65

N-(3,4-Dimethoxyphenyl)-4-piperazin-1-ylthieno[3,2-c]pyridine-2-sulfonamide hydrochloride The synthesis was preformed essentially as described in Method H-L. Yield: 7.7 mg (3.6%). $^1$H NMR (270 MHz, $CH_3OH-d_4$) δ ppm 8.04 (d, J=6.60 Hz, 1H) 7.77-7.75/m, 2H) 6.85-6.83 (m, 2H) 6.68-6.83 (m, 1H) 3.87-3.85 (m, 4H) 3.77-3.75 (m, 6H) 3.49-3.45 (m, 4H) 2.65 (s, 1H); LC-MS 435 (M−H)$^+$; Purity (HPLC) 98%.

EXAMPLE 66

N-(4-Bromo-2-methylphenyl)-4-piperazin-1-ylthieno[3,2-c]pyridine-2-sulfonamide hydrochloride The synthesis was preformed essentially as described in Method H-L. Yield: 12.2 mg (5.3%). $^1$H NMR (270 MHz, $CH_3OH-d_4$) δ ppm 8.07 (d, J=6.33 Hz, 1H) 7.86-7.79 (m, 2H) 7.40 (d, J=1.58 Hz, 1H) 7.30-7.29 (m, 1H) 7.08 (d, J=8.71 Hz, 1H) 3.96-3.92 (m, 4H) 3.53-3.51 (4H) 2.66 (s, 1H) 2.11 (s, 3H); LC-MS 467 (M−H)$^+$; Purity (HPLC) 90%.

EXAMPLE 67

2-(4-Piperazin-1-yl-thieno[3,2-c]pyridine-2-sulfonyl)-1,2,3,4-tetrahydro-isoquinoline hydrochloride The synthesis was preformed essentially as described in Method H-L from 4-[2-(3,4-dihydro-1H-isoquinoline-2-sulfonyl)-thieno[3,2-c]pyridin-4-yl]-piperazine-1-carboxylic acid tert-butyl ester (0.235 mmol, 1 equiv.). Yield: 4.0 mg. LC/MS: $t_R$=0.801 (System: 30% to 60% ACN in 1.5 min, Hypersil BDS), Purity: 92%. MS: 415 (M+1) $^1$H NMR (270 MHz, $DMSO-d_6$) δ ppm 2.87 (t, J=5.81 Hz, 2H) 3.30 (s, 4H) 4.43 (s, 2H) 7.15 (m, 4H) 7.70 (d, J=5.54 Hz, 1H) 8.12 (s, 1H) 8.18 (d, J=5.54 Hz, 1H) 6 aliphatic protons were obscured by the water-peak in the spectra and so could not be analyzed.

EXAMPLE 68

4-Piperazin-1-yl-thieno[3,2-c]pyridine-2-sulfonic acid (2-thiophen-2-yl-ethyl)-amide hydrochloride The synthesis was preformed essentially as described in Method H-L from 4-[2-(2-thiophen-2-yl-ethylsulfamoyl)-thieno[3,2-c]pyridin-4-yl]-piperazine-1-carboxylic acid tert-butyl ester (0.235 mmol, 1 equiv.). Yield: 8.7 mg. LC/MS: $t_R$=0.430 (System: 30% to 60% ACN in 1.5 min, Hypersil BDS), Purity: 93%. MS: 409 (M+1) $^1$H NMR (270 MHz, $DMSO-d_6$) δ ppm 2.25 (s, 1H) 2.75 (s, 1H) 2.96 (t, J=6.99 Hz, 1H) 3.16 (q, J=6.51 Hz, 1H) 3.31 (s, 4H) 3.70 (s, 4H) 6.90 (m, 1H) 7.32 (t, J=5.54 Hz, 1H) 7.70 (d, J=5.81 Hz, 1H) 8.04 (d, J=1.85 Hz, 1H) 8.18 (d, J=5.54 Hz, 1H) 8.36 (m, 1H) 9.05 (s, 1H).

EXAMPLE 69

4-Piperazin-1-yl-thieno[3,2-c]pyridine-2-sulfonic acid (4-chloro-2,5-dimethoxy-phenyl)amide hydrochloride The synthesis was preformed essentially as described in Method H-L from 4-[2-(4-chloro-2,5-dimethoxy-phenylsulfamoyl)-thieno[3,2-c]pyridin-4-yl]-piperazine-1-carboxylic acid tert-butyl ester (0.112 mmol, 1 equiv.) was used as the thienopyridine in Method C. Yield: 14.7 mg. LC/MS: $t_R$=0.610 (System: 30% to 60% ACN in 1.5 min, YMC), Purity: 92%. MS: 469 (M+1) $^1$H NMR (270 MHz, $DMSO-d_6$) δ ppm 3.17 (s, 1H) 3.27 (s, 4H) 3.38 (s, 3H) 3.58 (d, J=4.22 Hz, 4H) 3.77 (s, 3H) 7.08 (s, 1H) 7.69 (d, J=5.81 Hz, 1H) 7.81 (s, 1H) 8.16 (d, J=5.81 Hz, 1H) 9.07 (s, 1H) 10.17 (s, 1H).

EXAMPLE 70

4-Piperazin-1-yl-thieno[3,2-c]pyridine-2-sulfonic acid phenethyl-amide hydrochloride The synthesis was preformed essentially as described in Method H-L from 4-(2-phenethylsulfamoyl-thieno[3,2-c]pyridin-4-yl)-piperazine-1-carboxylic acid tert-butyl ester (0.112 mmol, 1 equiv.). Yield: 3.8 mg. LC/MS: $t_R$=0.410 (System: 30% to 60% ACN in 1.5 min, YMC), Purity: 91%. MS: 403 (M+1) $^1$H NMR (270 MHz, CH$_3$OH-d$_4$) δ ppm 1.44 (d, J=7.13 Hz, 2H) 3.51 (d, J=4.75 Hz, 4H) 3.54 (s, 2H) 3.94 (m, 4H) 7.05 (m, 4H) 7.16 (m, 1H) 7.62 (s, 1H) 7.72 (d, J=6.60 Hz, 1H) 8.00 (d, J=6.60 Hz, 1H).

EXAMPLE 71

4-Piperazin-1-yl-thieno[3,2-c]pyridine-2-sulfonic acid (2,6-diethyl-phenyl)-amide hydrochloride The synthesis was preformed essentially as described in Method H-L from 4-[2-(2,6-dethylphenylsulfamoyl)-thieno[3,2-c]pyridin-4-yl]-piperazine-1-carboxylic acid tert-butyl ester (0.112 mmol, 1 equiv.). Yield: 9.0 mg. LC/MS: $t_R$=0.830 (System: 30% to 60% ACN in 1.5 min, YMC), Purity: 92%. MS: 431 (M+1) $^1$H NMR (270 MHz, DMSO-D6) δ ppm 0.96 (t, J=7.52 Hz, 6H) 2.25 (m, 1H) 2.43 (s, 2H) 2.75 (t, J=1.72 Hz, 1H) 3.26 (s, 4H) 3.62 (s, 4H) 7.09 (s, 1H) 7.12 (s, 1H) 7.23 (m, 1H) 7.73 (d, J=5.81 Hz, 1H) 7.77 (s, 1H) 8.19 (d, J=5.81 Hz, 1H) 9.04 (s, 1H) 9.95 (s, 1H).

EXAMPLE 72

4-Piperazin-1-yl-thieno[3,2-c]pyridine-2-sulfonic acid (3-phenyl-propyl)-amide hydrochloride The synthesis was preformed essentially as described in Method H-L from 4-[2-(3-phenylpropylsulfamoyl)-thieno[3,2-c]pyridin-4-yl]-piperazine-1-carboxylic acid tert-butyl ester (0.112 mmol, 1 equiv.). Yield: 13.0 mg. LC/MS: $t_R$=0.726 (System: 30% to 60% ACN in 1.5 min, YMC), Purity: 91%. MS: 417 (M+1) $^1$H NMR (270 MHz, CH$_3$OH-d$_4$) δ ppm 1.82 (m, 2H) 2.63 (m, 2H) 3.04 (t, J=6.86 Hz, 2H) 3.55 (s, 4H) 4.09 (s, 4H) 7.16 (m, 4H) 7.82 (d, J=6.60 Hz, 1H) 8.05 (d, J=6.33 Hz, 1H) 8.14 (s, 1H).

EXAMPLE 73

4-Piperazin-1-yl-thieno[3,2-c]pyridine-2-sulfonic acid (3,3-diphenyl-propyl)-amide hydrochloric acid The synthesis was preformed essentially as described in Method H-L from 4-[2-(3,3-diphenylpropylsulfamoyl)-thieno[3,2-c]pyridin-4-yl]-piperazine-1-carboxylic acid tert-butyl ester (0.112 mmol, 1 equiv.). Yield: 14.4 mg. LC/MS: $t_R$ 1.109 (System: 30% to 60% ACN in 1.5 min, YMC), Purity: 93%. MS: 493 (M+1) $^1$H NMR (270 MHz, DMSO-d$_6$) δ ppm 2.20 (m, 2H) 2.80 (m, 2H) 3.29 (s, 4H) 3.67 (d, J=5.01 Hz, 4H) 4.01 (m, 1H) 7.14 (m, 8H) 7.71 (d, J=5.81 Hz, 1H) 7.95 (s, 1H) 8.18 (d, J=5.81 Hz, 1H) 8.27 (m, 2H) 9.13 (s, 2H).

EXAMPLE 74

4-Piperazin-1-yl-thieno[3,2-c]pyridine-2-sulfonic acid [2-(5-methoxy-1H-indol-3-yl)ethyl]-amide hydrochloride The synthesis was preformed essentially as described in Method H-L from 4-{2-[2-(5-methoxy-1H-indol-3-yl)-ethylsulfamoyl]-thieno[3,2-c]pyridin-4-yl}-piperazine-1-carboxylic acid tert-butyl ester (0.112 mmol, 1 equiv.). Yield: 6.1 mg. LC/MS: $t_R$=0.364 (System: 30% to 60% ACN in 1.5 min, YMC), Purity: 91%. MS: 472 (M+1) $^1$H NMR (270 MHz, CH$_3$OH-d$_4$) δ ppm 2.85 (t, J=6.20 Hz, 2H) 3.48 (t, J=6.20 Hz, 2H) 3.55 (m, 4H) 3.80 (s, 3H) 4.02 (m, 4H) 6.44 (dd, J=8.71, 2.37 Hz, 1H) 6.80 (m, 2H) 6.97 (s, 1H) 7.64 (s, 1H) 7.67 (s, 1H) 7.97 (d, J=6.60 Hz, 1H).

EXAMPLE 75

4-Piperazin-1-yl-thieno[3,2-c]pyridine-2-sulfonic acid 4-trifluoromethyl-benzylamide hydrochloride The synthesis was preformed essentially as described in Method H-L from 4-[2-(4-trifluoromethyl-benzylsulfamoyl)-thieno[3,2-c]pyridin-4-yl]-piperazine-1-carboxylic acid tert-butyl ester (0.112 mmol, 1 equiv.) was used as the thienopyridine in Method C. Yield: 1.9 mg. LC/MS: $t_R$=0.771 (System: 30% to 60% ACN in 1.5 min, YMC), Purity: 91%. MS: 457 (M+1) $^1$H NMR (270 MHz, CH$_3$OH-d$_4$) δ ppm 3.54 (m, 4H) 3.98 (m, 4H) 4.36 (s, 2H) 7.49 (m, 4H) 7.74 (d, J=6.86 Hz, 1H) 8.02 (s, 1H) 8.07 (d, J=6.60 Hz, 1H).

EXAMPLE 76

4-Piperazin-1-yl-thieno[3,2-c]pyridine-2-sulfonic acid benzyl-ethyl-amide hydrochloride The synthesis was preformed essentially as described in Method H-L from 4-[2-(benzyl-ethyl-sulfamoyl)-thieno[3,2-c]pyridin-4-yl]-piperazine-1-carboxylic acid tert-butyl ester (0.112 mmol, 1 equiv.). Yield: 6.4 mg. LC/MS: $t_R$=0.930 (System: 30% to 60% ACN in 1.5 min, YMC), Purity: 95%. MS: 417 (M+1) $^1$H NMR (270 MHz, CH$_3$OH-d$_4$) δ ppm 1.03 (t, J=7.13 Hz, 3H) 3.37 (m, 2H) 3.57 (s, 2H) 3.75 (m, 2H) 4.11 (s, 2H) 4.50 (s, 2H) 5.80 (s, 1H) 7.32 (m, 5H) 7.84 (d, J=6.60 Hz, 1H) 8.07 (d, J=6.60 Hz, 1H) 8.14 (s, 1H).

INTERMEDIATE 55 tert-Butyl-4-(3-{[(3-ethylphenyl)amino]sulfonyl}thieno[3,2-c]pyridin-4-yl)piperazine-1-carboxylate Prepared from tert-butyl 4-[3-(chlorosulfonyl)thieno[3,2-c]pyridin-4-yl]piperazine-1-carboxylate (90.0 mg, 0.215 mmol) and 3-ethylaniline (33.9 mg, 0.28 mmol) to give the title compound as an off-white solid (82.7 mg, 76%). $^1$H NMR (400 MHz, CDCl$_3$) δ 1.03 (t, J=7.5 Hz, 3H), 1.48 (s, 9H), 2.47 (q, J=7.7 Hz, 2H), 3.00-3.53 (m, 6H), 4.02-4.44 (m, 2H), 6.66 (d, J=8.0 Hz, 1H), 6.75 (s, 1H), 6.66 (d, J=8.0 Hz, 1H), 7.02 (t, J=7.8 Hz, 1H), 7.67 (d, J=5.5 Hz, 1H), 8.24 (s, 1H), 8.39 (d, J=5.5 Hz, 1H), 9.80 (s, 1H). MS (ESI+) m/z 503.2 (M+H)$^+$. HPLC 97%, R$_T$: 3.93 min (5-99% MeCN over 3 min).

EXAMPLE 77

N-(3-Ethylphenyl)-4-piperazin-1-ylthieno[3,2-c]pyridine-3-sulfonamide hydrochloride Prepared from tert-butyl 4-(3-{[(3-ethylphenyl)amino]sulfonyl}thieno[3,2-c]pyridin-4-yl)piperazine-1-carboxylate (81.1 mg, 0.161 mmol) which afforded 19 mg (98%) of the product as a white solid (38.0 mg, 54%). $^1$H NMR (400 MHz, CH$_3$OH-d$_4$) δ 1.09 (t, J=7.5 Hz, 3H), 2.51 (q, J=7.5 Hz, 2H), 3.59 (br. s, 8H), 6.89-6.92 (m, 3H), 7.12-7.14 (m, 1H), 8.06 (d, J=6.0 Hz, 1H), 8.36 (d, J=6.0 Hz, 1H), 8.49 (s, 1H). MS (ESI+) m/z 403.2 (M+H)⁺. HPLC 95%, $R_T$: 3.02 min (5-99% MeCN over 3 min).

INTERMEDIATE 56 tert-Butyl 4-(3-bromothieno[3,2-c]pyridin-4-yl)piperazine-1-carboxylate

A mixture of 3-bromo-4-chlorothieno[3,2-c]pyridine (729 mg, 2.93 mmol), tert-butyl piperazine-1-carboxylate (1.64 g, 8.80 mmol) and $K_2CO_3$ (811 mg, 5.87 mmol) in DMSO (45 mL) was stirred for 5 days at 100° C. After addition of $H_2O$ and ethyl acetate, the layers were separated. The water phase was extracted twice with ethyl acetate, and the combined organic phases were washed with water and brine and dried ($MgSO_4$). After filtration and removal of the solvent, the residue was purified by silica gel flash chromatography (pentane/ethyl acetate, 8:2) to give the product as a white powder (398 mg, 34%). HPLC 99%, $R_T$: 3.27 min (5-99% MeCN over 3 min). ¹H NMR (400 MHz, $CH_3OH$-$d_4$) δ 1.48 (s, 9H), 3.21 (br. s, 4H), 3.71 (s br., 4H), 7.61 (d, J=6.1 Hz, 1H), 7.72 (s, 1H), 8.08 (d, J=5.6 Hz, 1H). MS (ESI+) m/z 398.2 (M+H)⁺.

INTERMEDIATE 57

{4-[4-(tert-Butoxycarbonyl)piperazin-1-yl]thieno[3,2-c]pyridin-3-yl}sulfonyl)lithium To a suspension of tert-Butyl 4-(3-bromothieno[3,2-c]pyridin-4-yl)piperazine-1-carboxylate (4.055 g, 10.18 mmol) in diethyl ether (30 mL) at −78° C. under $N_2$ atmosphere was added dropwise an 1.6 M solution of n-BuLi in hexanes (9.5 mL, 15.2 mmol). After 1 h of stirring, a saturated solution of $SO_2$ in THF (25 mL) at −78° C. was transferred via a cannula to the mixture. The reaction was allowed to gradually increase to ambient temperature over night. The solvent was evaporated, and the residue was washed with several portions of diethyl ether and then dried under vacuum to give 4.094 g of an off-white solid consisting of 66% of the title compound and 34% of (n-butylsulfonyl)lithium as by-product. This mixture was used without any further purification in the next step. ¹H NMR (400 MHz, $CH_3OH$-$d_4$) δ 1.48 (s, 9H), 3.22 (br. s, 4H), 3.72 (s br., 4H), 7.60 (d, J=5.5 Hz, 1H), 8.06 (d, J=5.5 Hz, 1H), 8.14 (s, 1H). MS (ESI+) m/z 384.0 (M+H)⁺. HPLC $R_T$: 2.62 min (5-99% MeCN over 3 min).

INTERMEDIATE 58 tert-Butyl-4-[3-(chlorosulfonyl)thieno[3,2-c]pyridin-4-yl]piperazine-1-carboxylate To a suspension of ({4-[4-(tert-butoxycarbonyl)piperazin-1-yl]thieno[3,2-c]pyridin-3-yl}sulfonyl)lithium (2.751 g, 7.06 mmol (3.126 g of the crude product mixture)) in DCM (40 mL) at 0° C. was added N-chlorosuccinimide (1.338 g, 10.0 mmol). After 20 minutes, the temperature was raised to ambient, and the reaction mixture was stirred for an additional 2.5 h. The resulting product solution was washed with water, and the water phase was extracted with DCM. The combined organic extracts were washed with brine and dried over $MgSO_4$. After filtration and evaporation of the solvent, the residue was washed with several portions of pentane to yield the product as an off-white solid (2.024 g, 69%). ¹H NMR (400 MHz, $CH_3OH$-$d_4$) δ 1.47 (s, 9H), 3.11 (br. s, 4H), 3.2-4.3 (s br., 4H), 7.68 (d, J=5.5 Hz, 1H), 8.45 (d, J=5.5 Hz, 1H), 8.60 (s, 1H). MS (ESI+) m/z 418.2 (M+H)⁺. HPLC 92%, $R_T$: 3.76 min (5-99% MeCN over 3 min).

INTERMEDIATE 59 tert-Butyl-4-(3-{[(4-isopropylphenyl)amino]sulfonyl}thieno[3,2-c]pyridin-4-yl)piperazine-1-carboxylate Prepared from tert-butyl 4-[3-(chlorosulfonyl)thieno[3,2-c]pyridin-4-yl]piperazine-1-carboxylate (90.0 mg, 0.215 mmol) and 4-isopropylaniline (37.9 mg, 0.28 mmol) to give the title compound as an off-white solid (58.3 mg, 52%). ¹H NMR (400 MHz, $CDCl_3$) δ 1.12 (d, J=7.0 Hz, 6H), 1.47 (s, 9H), 2.76 (sept., J=6.9 Hz, 2H), 3.01-3.53 (m, 6H), 4.04-4.41 (m, 2H), 6.79 (d, J=8.5 Hz, 2H), 6.66 (d, J=8.5 Hz, 2H), 7.69 (d, J=5.5 Hz, 1H), 8.23 (s, 1H), 8.40 (d, J=5.5 Hz, 1H), 9.90 (s, 1H). MS (ESI+) m/z 517.2 (M+H)⁺. HPLC 97%, $R_T$: 4.01 min (5-99% MeCN over 3 min).

EXAMPLE 78

N-(4-Isopropylphenyl)-4-piperazin-1-ylthieno[3,2-c]pyridine-3-sulfonamide hydrochloride Prepared from tert-butyl 4-(3-{[(4-isopropylphenyl)amino]sulfonyl}thieno[3,2-c]pyridin-4-yl)piperazine-1-carboxylate (60.0 mg, 0.116 mmol) which afforded 19 mg (98%) of the product as a white solid (25.8 mg, 49%) according to Method H-L. ¹H NMR (400 MHz, $CH_3OH$-$d_4$) δ 1.16 (d, J=7.0 Hz, 6H), 2.81 (sept., J=6.8 Hz, 1H), 3.59 (s, br., 8H), 7.00 (d, J=8.0 Hz, 2H), 7.10 (d, J=8.0 Hz, 2H), 8.07 (s, br., 1H), 8.37 (s, br., 1H), 8.50 (s, 1H). MS (ESI+) m/z 417.2 (M+H)⁺. HPLC 94%, $R_T$: 3.14 min (5-99% MeCN over 3 min).

EXAMPLE 79

N-(4-Methylphenyl)-4-(pyrrolidin-3-yloxy)thieno[3,2-c]pyridine-2-sulfonamide hydrochloride 4-Chloro-N-(4-methylphenyl)thieno[3,2-c]pyridine-2-sulfonamide (60.0 mg, 0.17 mmol) in dry DMF (1 mL) and NaH (5.1 mg, 0.21 mmol) was added to pyrrolidin-3-ol (18.5 mg, 0.21 mmol) under nitrogen. The mixture was heated in the microwave at 200° C. in 5 min. The product was purified by preparative HPLC. Yield: 29.9 mg (43.4%). ¹H NMR (270 MHz, $CH_3OH$-$d_4$) δ ppm 8.09 (s, 1H) 7.71 (d, J=6.93 Hz, 1H) 7.46 (d, J=6.93 Hz, 1H) 7.47-7.44 (m, 4H) 4.67 (d, J=3.22 Hz, 1H) 3.97 (s, 2H) 2.26 (s, 3H). LC-MS 390 (M−H)⁺; Purity (HPLC) 99%.

EXAMPLE 80

N-(4-Methylphenyl)-4-(piperidin-4-yloxy)thieno[3,2-c]pyridine-2-sulfonamide hydrochloride The synthesis was preformed essentially as described for compound of N-(4-methylphenyl)-4-(pyrrolidin-3-yloxy)thieno[3,2-c]pyridine-2-sulfonamide hydrochloride. Yield: 16.2 mg (22.7%). ¹H NMR (270 MHz, $CH_3OH$-$d_4$) δ ppm 7.81-7.78 (m, 2H) 7.62 (d, J=6.93 Hz, 1H) 7.13-7.04 (m, 4H) 4.05-3.94 (m, 1H) 3.90-3.88 (m, 2H) 3.63-3.58 (m, 2H), 2.27 (s, 3H) 2.06-2.03 (m, 2H) 2.01-1.71 (m, 2H); LC-MS 404 (M–H)$^+$; Purity (HPLC) 99%.

EXAMPLE 81

N-(2,3-Difluorobenzyl)-4-piperazin-1-ylthieno[3,2-c]pyridine-2-sulfonamide hydrochloride Yield: 74.4 mg (39.2%). $^1$H NMR (270 MHz, CH$_3$OH-d$_4$) δ ppm 8.10-8.03 (m, 2H) 7.81 (d, J=6.68 Hz, 1H) 7.16-7.05 (m, 3H) 4.37 (s, 2H) 4.11-4.07 (m, 4H) 3.59-3.53 (m, 4H); LC-MS 425 (M–H)$^+$; Purity (HPLC) 90%.

EXAMPLE 82

N-(3-Chlorobenzyl)-4-piperazin-1-ylthieno[3,2-c]pyridine-2-sulfonamide hydrochloride Yield: 74.4 mg (44.7%). $^1$H NMR (270 MHz, CH$_3$OH-d$_4$) δ ppm 8.04-8.01 7.85 (d, J=6.93 Hz, 1H) 7.22-7.15 (m, 4H) 4.30 (s, 2H) 4.14-4.10 (m, 4H) 3.60-3.54 (m, 4H); LC-MS 423 (M–H)$^+$; Purity (HPLC) 90%.

TABLE 5

| EXAMPLE | | R$^2$ | R$^4$ |
|---|---|---|---|
| 83 | 4-(1,4-Diazepan-1-yl)-2-(phenylsulfonyl)thieno[3,2-c]pyridine hydrochloride | phenyl | 1,4-diazepan-1-yl |
| 84 | 4-(1,4-Diazepan-1-yl)-2-[(3,4-dichlorophenyl)sulfonyl]thieno[3,2-c]pyridine hydrochloride | 3,4-dichlorophenyl | 1,4-diazepan-1-yl |
| 85 | 4-(1,4-Diazepan-1-yl)-2-[1-naphthylsulfonyl]thieno[3,2-c]pyridine hydrochloride | 1-naphthyl | 1,4-diazepan-1-yl |
| 86 | 4-(1,4-Diazepan-1-yl)-2-[4-tert-butylphenylsulfonyl]thieno[3,2-c]pyridine hydrochloride | 4-tert-butylphenyl | 1,4-diazepan-1-yl |
| 87 | 4-(1,4-Diazepan-1-yl)-2-[3,4-dimethylphenylsulfonyl)thieno[3,2-c]pyridine hydrochloride | 3,4-dimethylphenyl | 1,4-diazepan-1-yl |
| 88 | 2-[(4-Bromophenyl)sulfonyl]-4-(1,4-diazepan-1-yl)thieno[3,2-c]pyridine hydrochloride | 4-bromophenyl | 1,4-diazepan-1-yl |

TABLE 5-continued

| EXAMPLE | | R² | R⁴ |
|---|---|---|---|
| 89 | 2-(Phenylsulfonyl)-4-piperazin-1-ylthieno[3,2-c]pyridine hydrochloride | phenyl | piperazinyl |
| 90 | 2-(3-Methoxy-benzenesulfonyl)-4-piperazin-1-yl-thieno[3,2-c]pyridine hydrochloride | 3-methoxyphenyl | piperazinyl |
| 91 | 2-(4-Methoxy-benzenesulfonyl)-4-piperazin-1-yl-thieno[3,2-c]pyridine hydrochloride | 4-methoxyphenyl | piperazinyl |
| 92 | 4-piperazin-1-yl-2-{[4-trifluoromethyl)phenyl]sulfonyl}thieno[3,2-c]pyridine hydrochloride | 4-(trifluoromethyl)phenyl | piperazinyl |
| 93 | 2-[[2-tert-Butylphenyl)sulfonyl]-4-piperazin-1-ylthieno[3,2-c]pyridine hydrochloride | 2-tert-butylphenyl | piperazinyl |
| 94 | 2-[(3,4-Dichlorophenyl)sulfonyl]-4-piperazin-1-ylthieno[3,2-c]pyridine-2-sulfonamide hydrochloride | 3,4-dichlorophenyl | piperazinyl |
| 95 | 2-[(4-tert-Butylphenyl)sulfonyl]-4-piperazin-1-ylthieno[3,2-c]pyridine hydrochloride | 4-tert-butylphenyl | piperazinyl |
| 96 | 2-(1-Naphthyl sulfonyl)-4-piperazin-1-ylthieno[3,2-e]pyridine hydrochloride | 1-naphthyl | piperazinyl |

TABLE 5-continued

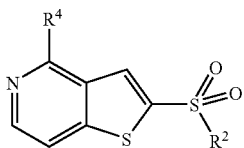

| EXAMPLE | | R² | R⁴ |
|---|---|---|---|
| 97 | 2-[(3-Fluorophenyl)sulfonyl]-4-piperazin-1-ylthieno[3,2-c]pyridine-2-sulfonamide hydrochloride | 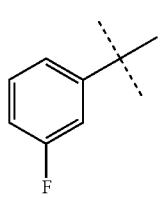 | 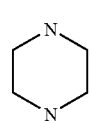 |
| 98 | 2-(Mesitylsulfonyl)-4-piperazin-1-ylthieno[3,2-c]pyridine hydrochloride | 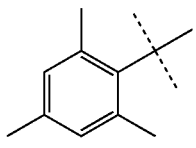 | 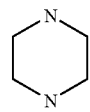 |
| 99 | 2-[(2-Methoxyphenyl)sulfonyl]-4-piperazin-1-ylthieno[3,2-c]pyridine hydrochloride | 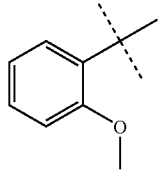 | 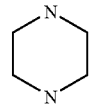 |
| 100 | 2-[(2,4-Dimethoxyphenyl)sulfonyl]-4-piperazin-1-ylthieno[3,2-c]pyridine hydrochloride | 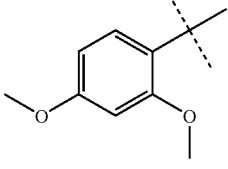 | 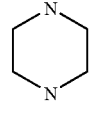 |
| 101 | 2-[(2,4-Dimethylphenyl)sulfonyl]-4-piperazin-1-ylthieno[3,2-c]pyridine hydrochloride | 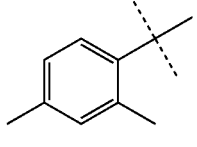 | 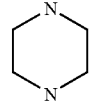 |
| 102 | 2-[(2,5-Dimethylphenyl)sulfonyl]-4-piperazin-1-ylthieno[3,2-c]pyridine hydrochloride | 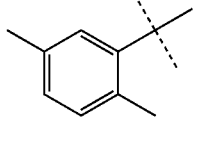 | 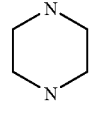 |
| 103 | 2-[(2-Ethylphenyl)sulfonyl]-4-piperazin-1-ylthieno[3,2-c]pyridine hydrochloride | 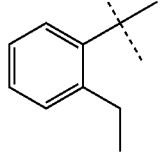 | 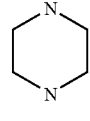 |
| 104 | 4-(Piperazinyl)-2-(3-methoxybenzyl-sulfonyl)-thienopyridine hydrochloride | 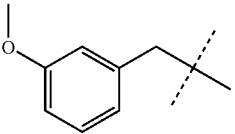 | 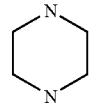 |

TABLE 5-continued

| EXAMPLE | | R² | R⁴ |
|---|---|---|---|
| 105 | 2-(Benzylsulfonyl)-4-piperazin-1-ylthieno[3,2-c]pyridine hydrochloride | benzyl | piperazin-1-yl |
| 106 | 4-Piperazin-1-yl-2-{[4-(trifluoromethyl)benzyl]sulfonyl}thieno[3,2-c]pyridine hydrochloride | 4-(trifluoromethyl)benzyl | piperazin-1-yl |
| 107 | 2-[(3-Bromobenzyl)sulfonyl]-4-piperazin-1-ylthieno[3,2-c]pyridine hydrochloride | 3-bromobenzyl | piperazin-1-yl |
| 108 | 2-[(2,3-Difluorobenzyl)sulfonyl]-4-piperazin-1-ylthieno[3,2-c]pyridine hydrochloride | 2,3-difluorobenzyl | piperazin-1-yl |
| 109 | 2-[(4-Bromobenzyl)sulfonyl]-4-piperazin-1-ylthieno[3,2-c]pyridine hydrochloride | 4-bromobenzyl | piperazin-1-yl |
| 110 | 2-{[2,5-bis(Trifluoromethyl)benzyl]sulfonyl}-4-piperazin-1-ylthieno[3,2-c]pyridine hydrochloride | 2,5-bis(trifluoromethyl)benzyl | piperazin-1-yl |
| 111 | 2-[(4-Methylbenzyl)sulfonyl]-4-piperazin-1-ylthieno[3,2-c]pyridine hydrochloride | 4-methylbenzyl | piperazin-1-yl |
| 112 | 2-{[5-Chloro-2-(trifluoromethyl)benzyl]sulfonyl}-4-piperazin-1-ylthieno[3,2-c]pyridine hydrochloride | 5-chloro-2-(trifluoromethyl)benzyl | piperazin-1-yl |
| 113 | 2-[(3,5-Dimethoxybenzyl)sulfonyl]-4-piperazin-1-ylthieno[3,2-c]pyridine hydrochloride | 3,5-dimethoxybenzyl | piperazin-1-yl |

TABLE 5-continued

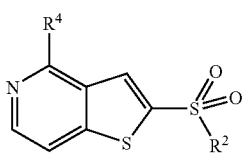

| EXAMPLE | | R² | R⁴ |
|---|---|---|---|
| 114 | 2-[(2-Naphthylmethyl)sulfonyl]-4-piperazin-1-ylthieno[3,2-c]pyridine hydrochloride | 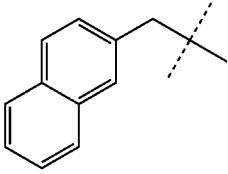 | 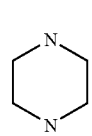 |
| 115 | 4-Piperazin-1-yl-2-{[4-(1,2,3-thiadiazol-5-yl)benzyl]sulfonyl}thieno[3,2-c]pyridine hydrochloride | 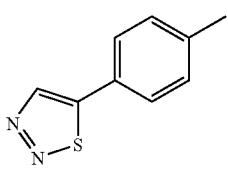 | 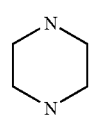 |
| 116 | 1-(4-Pyrrolidin-1-ylphenyl)-2-[(4-piperazine-1-ylthieno{3,2-c]pyridin-2-yl) sulfonyl] propanone hydrochloride | 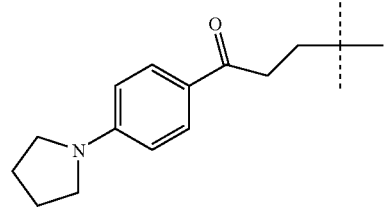 | 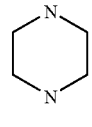 |
| 117 | 1-[4-(Diethylamino)phenyl]-2-[(4-piperazine-1-ylthieno[3,2-c]pyridin-2-yl) sulfonyl] propanone hydrochloride | 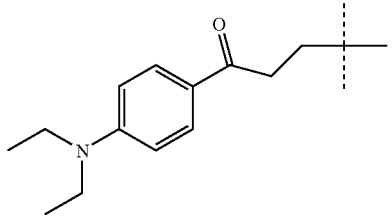 | 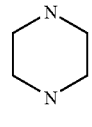 |
| 118 | 1-(4-Bromophenyl)-2-[(4-piperazin-1-ylthieno[3,2-c]pyridin-2-yl) sulfonyl] propanone | 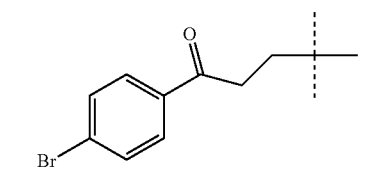 | 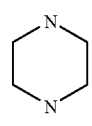 |
| 119 | 1-(3-Methoxyphenyl)-2-[(4-piperazin-1-ylthieno[3,2-c]pyridin-2-yl) sulfonyl] propanone | 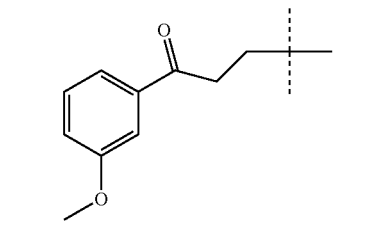 | 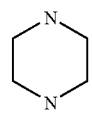 |
| 120 | 1-Phenyl-2-[(4-piperazin-1-ylthieno[3,2-c]pyridin-2-yl)sulfonyl]propanone | 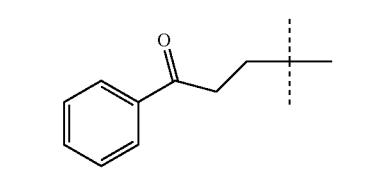 | 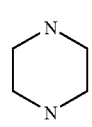 |

Scheme 6

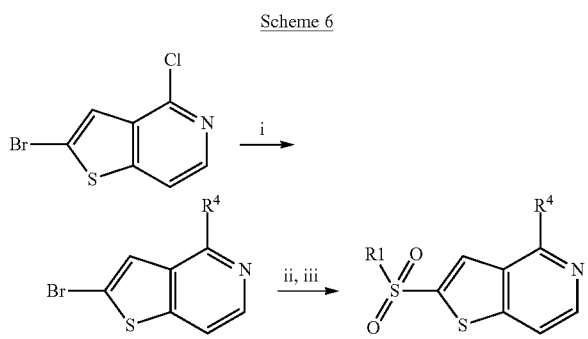

Legend to Scheme 6: i) BOC protected amines (R⁴), K₂CO₃, DMSO; ii) thiophenols (R¹—SH), Cu₂(I)O, DMF; iii) NaOAc, oxone, water; iv) a. TFA, b. HCl, methanol

INTERMEDIATE 60 tert-Butyl 4-(2-bromothieno[3,2-c]pyridin-4-yl)piperazine-1-carboxylate

2-Bromo-4-chlorothieno[3,2-c]pyridine (5.0 g, 20.24 mmol) and K$_2$CO$_3$ (13.97 g, 101.2 mmol) was stirred in DMSO (20 mL) followed by addition of tert-butyl piperazine-1-carboxylate (4.14 g, 22.26 mmol). The reaction mixture was stirred at 100° C. for 6 days. The reaction mixture was filtered to eliminate the carbonate and addition of water (50 mL) and ethyl was followed. The phases were separated and the aqueous phase was extracted with ethyl acetate. The combined organic phases were dried (MgSO$_4$) and the solvent was evaporated. The crude product was purified by flash chromatography using ethyl acetate/hexanes (2/8) as eluent to give 2 g of the desired product, yield 25%, 99% pure. $^1$H NMR (270 MHz, CDCl$_3$) δ 1.48 (s, 9H), 1.52-1.63 (m, 1H), 3.42-3.47 (m, 4H), 3.61-3.64 (m, 4H), 7.22 (dd, J=5.4, 1 Hz, 1H), 7.35 (d, J=1 Hz, 1H), 8.04 (d, J=5.4 Hz, 1H). m/z=398.91 (M+H), bromide pattern.

INTERMEDIATE 61 tert-butyl 4-(2-bromothieno[3,2-c]pyridin-4-yl)-1,4-diazepane-1-carboxylate

The same procedure above intermediate was used starting from 2-bromo-4-chlorothieno[3,2-c]pyridine (7.5 g, 30.45 mmol), K$_2$CO$_3$ (6.7 g, 33.5 mmol) and tert-butyl 1,4-diazepane-1-carboxylate (21.0 g, 152.2 mmol) in DMSO (30 mL). Purification by flash chromatography 3.04 g of the title compound (Yield 25%). HPLC purity 92%; $^1$H NMR (270 MHz, CDCl$_3$) δ 1.38 (s, 4.5H), 1.43 (s, 4.5H), 1.96-2.11 (m, 2H), 3.36-3.41 (m, 1H), 3.46-3.51 (m, 1H), 3.65-3.87 (m, 6H), 7.02-7.04 (m, 1H), 7.40-7.42 (m, 1H), 7.94 (d, J=5.4 Hz, 1H). m/z=411.97 (M+H).

Coupling with Thiophenols (Method M)

INTERMEDIATE 62 tert-butyl 4-(2-phenylthio)thieno[3,2-c]pyridin-4-yl)-1,4-diazepane-1-carboxylate tert-Butyl 4-(2-bromothieno[3,2-c]pyridin-4-yl)-1,4-diazepane-1-carboxylate (0.31 g, 0.752 mmol), pulverized KOH (0.084 g, 1.5 mmol) and Cu$_2$(I)O (0.1 g, 0.75 mmol) was mixed with DMF (1 mL) before the addition of a solution of benzenethiol (0.016 g, 1.5 mmol) in DMF (1 mL). The reaction mixture was heated to 120° C. for 15 h. The reaction mixture was poured in a silica plug and eluted with chloroform, to give the crude product. The crude product was purified by flash chromatography using ethyl acetate/hexanes (2/8) as eluent to give 0.21 g of the desired product, yield 64%, 90% pure. $^1$H NMR (270 MHz, CDCl$_3$) δ 1.37 (s, 4.5H), 1.43 (s, 4.5H), 1.97-2.10 (m, 2H), 3.36-3.43 (m, 1H), 3.46-3.53 (m, 1H), 3.64-3.73 (m, 2H), 3.78-3.96 (m, 4H), 7.05 (d, J=5.4 Hz, 1H), 7.22-7.32 (m, 5H), 7.59-7.63 (m, 1H), 7.97 (d, J=5.4 Hz, 1H). m/z=442.15 (M+H).

Oxidation of Thio-Derivatives (Method N)

INTERMEDIATE 63 tert-Butyl 4-(2-phenylsulfonyl)thieno[3,2-c]pyridin-4-yl)-1,4-diazepane-1-carboxylate A solution of tert-Butyl 4-(2-phenylthio)thieno[3,2-c]pyridin-4-yl)-1,4-diazepane-1-carboxylate (0.21 g, 0.48 mmol) and NaOAc (0.5 g) in ethanol (10 mL), (pH ~5) followed by the addition of Oxone (0.64 g, 1.04 mmol) dissolved in water (1 mL). The reaction mixture was stirred at RT for 16 h. Additional Oxone (0.32 g) in water (1 mL) was added. Full conversion of the SM was obtained after 8 h. Water (50 mL) and chloroform (30 mL) were added. The phases were separated and the aqueous phase was extracted with chloroform. The combined organic phases were dried over (MgSO$_4$), the solvent was evaporated to give the crude product which was purified by reverse-phase chromatography (10→90), to give 0.191 g of the desired product as yellow oil (Yield 86%) 98% pure. $^1$H NMR (270 MHz, CDCl$_3$) δ 1.28 (s, 4.5H), 1.38 (s, 4.5H), 1.99-2.03 (m, 2H), 3.31-3.40 (m, 1H), 3.42-3.47 (m, 1H), 3.63-3.69 (m, 2H), 3.85-3.98 (m, 4H), 7.02 (d, J=5.4 Hz, 1H), 7.48-7.61 (m, 3H), 7.76-8.01 (m, 3H), 8.06-8.08 (m, 1H). m/z 474.01 (M+H).

Removal of the t-butyl-carboxylate Protecting Group (Method O)

EXAMPLE 83

4-(1,4-Diazepan-1-yl)-2-(phenylsulfonyl)thieno[3,2-c]pyridine hydrochloride tert-Butyl 4-(2-phenylsulfonyl)thieno[3,2-c]pyridin-4-yl)-1,4-diazepane-1-carboxylate (0.165 g, 0.348 mmol) was dissolved in DCM (2 mL) and TFA (1 mL) was added. The reaction mixture was stirred for 2 h. The solvent was evaporated. Methanol and HCl in ether was added (×3) to give 0.118 g of the desired HCl salt, yield 85%, 98% pure. $^1$H NMR (270 MHz, CHOH-d$_4$) δ 2.45-2.52 (m, 2H), 3.45-3.52 (m, 2H), 3.70-3.79 (m, 2H), 4.18-4.22 (m, 2H), 4.30-4.40 (m, 2H), 7.62-7.76 (m, 5H), 7.91 (d, J=5.4 Hz, 1H), 8.11 (dd, J=5.4, 1 Hz, 1H), 8.41 (d, J=1 Hz, 1H). m/z=374.09 (M+H−HCl).

INTERMEDIATE 64 tert-Butyl 4-[2-(4-tert-butylphenyl)thio]thieno[3,2-c]pyridin-4-yl)-1,4-diazepane-1-carboxylate The product was prepared according to Method M. Purification by flash chromatography using ethyl acetate/hexanes (2/8) as eluent gave 0.035 g, 99% pure. $^1$H NMR (270 MHz, CDCl$_3$) δ 1.28 (s, 9H), 1.38 (s, 4.5H), 1.43 (s, 4.5H), 1.98-2.03 (m, 2H), 3.35-3.41 (m, 1H), 3.46-3.52 (m, 1H), 3.62-3.72 (m, 2H), 3.77-3.93 (4H), 7.04 (d, J=5.4 Hz, 1H), 7.27-7.34 (m, 4H), 7.54-7.56 (m, 1H), 7.95 (d, J=5.4 Hz, 1H). m/z=498.0 (M+H).

INTERMEDIATE 65 tert-Butyl 4-[2-(4-tert-butylphenyl)sulfonyl]thieno[3,2-c]pyridin-4-yl)-1,4-diazepane-1-carboxylate Procedure B from tert-butyl 4-[2-(4-tert-butylphenyl)thio]thieno[3,2-c]pyridin-4-yl)-1,4-diazepane-1-carboxylate (0.035 g, 0.070 mmol), Oxone (0.17 g, 0.28 mmol), NaOAc (0.5 g) in EtOH (2 mL followed by reversed phase chromatography (40→70), gave 6 mg of the product. Yield 17%, 98% pure. $^1$H NMR (270 MHz, CDCl$_3$) δ 1.32 (s, 9H), 1.35 (s, 9H), 2.05-2.15 (m, 2H), 3.45-3.62 (m, 2H), 3.75-4.13 (m, 6H), 7.20-7.27 (m, 5H), 7.58 (d, J=10.8 Hz, 1H), 7.93 (d, J=10.8 Hz, 1H). m/z=530.0 (M+H).

INTERMEDIATE 66 tert-Butyl 4-[2-(3,4-dimethylphenyl)thio]thieno[3,2-c]pyridin-4-yl)-1,4-diazepane-1-carboxylate The title compound was obtained according to Method M. Purification by flash chromatography using ethyl acetate/hexanes (2/8) as eluent gave 0.022 g, 95% pure. $^1$H NMR (270 MHz, CDCl$_3$) δ 1.38 (s, 4.5H), 1.43 (s, 4.5H), 1.96-2.04 (m, 2H), 2.21 (s, 3H), 2.22 (s, 3H), 3.37-3.45 (m, 2H), 3.47-3.50 (m, 2H), 3.77-3.95 (m, 4H), 7.01-7.12 (m, 3H), 7.16 (s, 1H), 7.53 (dd, J=5.4, 1 Hz, 1H), 7.94 (d, J=5.4 Hz, 1H). m/z=470.3 (M+H).

INTERMEDIATE 67 tert-Butyl 4-[2-(3,4-dimethylphenyl)sulfonyl]thieno[3,2-c]pyridin-4-yl)-1,4-diazepane-1-carboxylate Procedure B from tert-Butyl 4-[2-(3,4-dimethylphenyl)thio]thieno[3,2-c]pyridin-4-yl)-1,4-diazepane-1-carboxylate (0.022 g, 0.047 mmol); OXONE (0.11 g, 0.19 mmol); NaOAc (0.5 g) in EtOH (2 mL) followed by reversed phase chromatography (40→70), 9 mg of the product. Yield 38%, 92% pure. $^1$H NMR (270 MHz, CDCl$_3$) δ 1.35 (s, 9H), 2.08-2.20 (m, 2H), 2.33 (s, 6H), 3.52-3.59 (m, 2H), 3.83-3.88 (m, 2H), 4.08-4.18 (m, 4H), 7.21-7.28 (m, 2H), 7.31-7.35 (m, 1H), 7.73-7.75 (m, 2H), 8.02 (d, J=5.4 Hz, 1H). m/z=502.21 (M+H).

INTERMEDIATE 68 tert-Butyl 4-[2-(1-naphthyl)thio]thieno[3,2-c]pyridin-4-yl)-1,4-diazepane-1-carboxylate The title compound was obtained according to Method M. Purification by flash chromatography using ethyl acetate/hexanes (2/8) as eluent gave 0.055 g. HPLC purity 99%; $^1$H NMR (270 MHz, CDCl$_3$) δ 1.37 (s, 4.5H), 1.43 (s, 4.5H), 1.89-2.20 (m, 2H), 3.30-3.40 (m, 1H), 3.43-3.50 (m, 1H), 3.60. 3.90 (m, 6H), 6.99 (d, J=5.4 Hz, 1H), 7.39 (dd, J=8.1, 1 Hz, 1H), 7.50-7.61 (m, 5H), 7.79-7.88 (m, 2H), 7.92 (d, J=5.4 Hz, 1H), 8.40-8.44 (m, 1H). m/z 498.26 (M+H).

INTERMEDIATE 69 tert-Butyl 4-[2-(1-naphthyl)sulfonyl]thieno[3,2-c]pyridin-4-yl)-1,4-diazepane-1-carboxylate Procedure B from tert-Butyl 4-[2-(1-naphthyl)thio]thieno[3,2-c]pyridin-4-yl)-1,4-diazepane-1-carboxylate (0.055 g, 0.112 mmol); Oxone (0.27 g, 0.448 mmol); NaOAc (0.5 g) in EtOH (2 mL) followed reversed phase chromatography (40→70) gave 15 mg of the product. Yield 26%, 93% pure. $^1$H NMR (270 MHz, CDCl$_3$) δ 1.34 (s, 9H), 2.06-2.10 (m, 2H), 3.48-3.62 (m, 2H), 3.78-3.86 (m, 2H), 3.95-4.16 (m, 4H), 7.19-7.31 (m, 2H), 7.60-7.75 (m, 3H), 7.92-7.99 (m, 2H), 8.18 (m, J=8.1 Hz, 1H), 8.50-8.53 (m, 1H), 8.77-8.80 (m, 1H). m/z=524.22 (M+H);

EXAMPLE 84

4-(1,4-Diazepan-1-yl)-2-[(3,4-dichlorophenyl)sulfonyl]thieno[3,2-c]pyridine hydrochloride tert-Butyl 4-{2-[(3,4-dichlorophenyl)sulfonyl]thieno[3,2-c]pyridin-4-yl}-1,4-diazepane-1-carboxylate was prepared from 3,4-dichlorothiophenol (60 mg, 15%), as a beige solid, by the application of the general procedures A and B described above. $^1$H NMR (CDCl$_3$) δ 8.27-8.14 (m, 1H), 8.11-8.04 (m, 2H), 7.87-7.80 (m, 1H), 7.67-7.62 (m, 1H), 7.26-7.20 (m, 1H), 4.18-3.98 (m, 4H), 3.87-3.74 (m, 2H), 3.61-3.44 (m, 2H), 2.20-2.00 (m, 2H), 1.33 (s, 9H); MS m/z 542 (M+1). The title compound (50 mg, 95%) was obtained as a beige solid, by the application of the general procedure C described above. $^1$H NMR (270 MHz, CH$_3$OH-d$_4$) δ 8.48 (s, 1H), 8.30 (d, J=1.85 Hz, 1H), 8.05 (dd, J=8.58, 1.98 Hz, 1H), 7.92 (d, J=6.86 Hz, 1H), 7.83 (d, J=8.44 Hz, 1H), 7.69 (d, J=6.86 Hz, 1H), 4.4.41-4.34 (m, 2H), 4.24-4.16 (m, 2H), 3.76-3.69 (m, 2H), 3.51-3.43 (m, 2H), 2.52-2.42 (m, 2H); MS m/z 442 (M+1).

EXAMPLE 85

4-(1,4-Diazepan-1-yl)-2-[1-naphthylsulfonyl)thieno[3,2-c]pyridine hydrochloride

The title compound was obtained from tert-butyl 4-[2-(1-naphthyl)sulfonyl]thieno-[3,2-c]pyridin-4-yl)-1,4-diazepane-1-carboxylate (15 mg, 0.029 mmol) following Method O to give 12 mg of the desired product yield 90%, 95% pure. $^1$H NMR (270 MHz, CH$_3$OH-d$_4$) δ 2.40-2.50 (m, 2H), 3.45-3.55 (m, 2H), 3.65-3.75 (m, 2H), 4.06-4.26 (m, 2H), 4.27-4.46 (m, 2H), 7.58-7.80 (m, 4H), 7.83-7.86 (m, 1H), 8.06 (d, J=8.1 Hz, 1H), 8.20 (d, J=8.1 Hz, 1H), 8.48 (s, 1H), 8.53-8.56 (m, 1H), 8.83-8.86 (m, 1). m/z=424.06 (M+H–HCl).

EXAMPLE 86

4-(1,4-Diazepan-1-yl)-2-[4-tert-butylphenylsulfonyl)thieno[3,2-c]pyridine hydrochloride The title compound was obtained from tert-butyl 4-[2-(4-tert-butylphenyl)sulfonyl]thieno[3,2-c]pyridin-4-yl)-1,4-diazepane-1-carboxylate (6 mg, 11.3 mmol) following Method O to give 4 mg of the desired product, yield 76%, 88% pure. $^1$H NMR (270 MHz, CH$_3$OH-d$_4$) δ 1.33 (s, 9H), 2.41-2.47 (m, 2H), 3.41-3.49 (m, 2H), 3.65-3.78 (m, 2H), 4.15-4.25 (m, 2H), 4.29-4.40 (m, 2H), 7.65-7.70 (m, 3H), 7.90 (d, J=5.4 Hz, 1H), 8.00-8.04 (m, 2H), 8.37 (s, 1H). m/z=430.06 (M+H–

EXAMPLE 87

4-(1,4-Diazepan-1-yl)-2-[3,4-dimethylphenylsulfonyl)thieno[3,2-c]pyridine hydrochloride The title compound was obtained from tert-butyl 4-[2-(3,4 dimethylphenyl)sulfonyl]thieno[3,2-c]pyridin-4-yl)-1,4-diazepane-1-carboxylate (6 mg, 0.012 mmol) following Method O to give 6 mg of the desired product, yield 88%, 89% pure. $^1$H NMR (270 MHz, CH$_3$OH-d$_4$) δ 2.34 (s, 6H), 2.45-2.55 (m, 2H), 3.42-3.51 (m, 2H), 3.67-3.76 (m, 2H), 4.10-4.20 (m, 2H), 3.58-3.70 (m, 2H), 7.39-7.41 (m, 1H), 7.64-7.67 (m, 1H), 7.79-7.84 (m, 2H), 7.89-7.91 (m, 1H), 8.36 (s, 1H). m/z=402.07 (M+H−HCl).

EXAMPLE 88

2-[(4-Bromophenyl)sulfonyl]-4-(1,4-diazepan-1-yl)thieno[3,2-c]pyridine hydrochloride Trifluoroacetic acid (1 mL) was added slowly to a solution of tert-butyl 4-{2-[(4-bromophenyl)thio]thieno[3,2-c]pyridin-4-yl}-1,4-diazepane-1-carboxylate (26 mg, 0.047 mmol) in CH$_2$Cl$_2$ at 0° C. The reaction mixture was allowed to reach room temperature, stirred for 40 min and then concentrated in vacuo. The residue was twice re-dissolved in MeOH and concentrated in vacuo. The residue was again dissolved in MeOH and an excess of 1M HCl in diethyl ether (4 mL) was slowly added to the solution. Removal of the solvents in vacuo afforded the title compound (21 mg, 91%) as a yellowish solid. $^1$H NMR (270 MHz, CH$_3$OH-d$_4$) δ 8.41 (s, 1H), 8.06-7.99 (m, 2H), 7.92 (d, J=6.86 Hz, 1H), 7.87-7.80 (m, 2H), 7.66 (d, J=6.86 Hz, 1H), 4.38-4.31 (m, 2H), 4.22-4.14 (m, 2H), 3.74-3.67 (m, 2H), 3.50-3.42 (m, 2H), 2.51-2.39 (m, 2H); MS m/z 452 (M+1).

EXAMPLE 89

2-(Phenylsulfonyl)-4-piperazin-1-ylthieno[3,2-c]pyridine hydrochloride

To a stirred solution of tert-butyl 4-[2-(phenylthio)thieno[3,2-c]pyridin-4-yl]piperazine-1-carboxylate (350 mg, 0.819 mmol) in ethanol was added oxone in water solution. The reaction was monitored by LCMS. When all starting material was consumed, the chromatogram showed two major peaks, the product and the N-oxide. After purification by preparative HPLC, the resulting Boc-material was treated with HCl in ether. The solution was centrifugated and the supernatant was removed. Ether was added, then centrifugated and decanted (repeated three times) to remove the excess HCl. The remaining ether was finally evaporated in a SpeedVac concentrator. Yield 18%, HPLC purity=98%, m/z=360.0 (M+H). $^1$H NMR (270 MHz, CH$_3$OH-d$_4$) δ ppm 3.56 (m, 4H) 4.08 (m, 4H) 7.68 (m, 4H) 7.77 (dd, J=6.60, 0.79 Hz, 1H) 8.04 (d, J=6.33 Hz, 1H) 8.12 (m, 2H) 8.39 (d, J=0.79 Hz, 1H).

EXAMPLE 90

2-(3-Methoxy-benzenesulfonyl)-4-piperazin-1-yl-thieno[3,2-c]pyridine hydrochloride 4-[2-(3-Methoxy-phenylsulfanyl)-thieno[3,2-c]pyridin-4-yl]-piperazine-1-carboxylic acid tert-butyl ester was obtained from 3-methoxythiophenol (130 µl, 1 mmol) and tert-Butyl 4-(2-bromothieno[3,2-c]pyridin-4-yl)piperazine-1-carboxylate (215 mg, 0.52 mmol). 120 mg, 50%) were obtained by the application of the general Method M described above. $^1$H NMR (270 MHz, CDCl$_3$) δ 1.48 (s, 9H), 3.42-3.51 (m, 4H), 3.58-3.67 (m, 4H), 3.74 (s, 3H), 6.76 (dd, J=8.18, 2.38 Hz, 1H), 6.84-6.92 (m, 2H), 7.16-7.23 (m, 2H), 7.51 (s, 1H), 8.04 (d, J=5.81 Hz, 1H); MS m/z 458 (M+1). The title compound was therefore obtained from 4-[2-(3-methoxy-phenylsulfanyl)-thieno[3,2-c]pyridin-4-yl]-piperazine-1-carboxylic acid tert-butyl (7 mg, 7%), after triturating with diethyl ether, as a beige solid, by the application of the general procedures B and C described above. $^1$H NMR (270 MHz, CD$_3$OD) δ 8.31 (s, 1H), 8.09 (d, J=6.33 Hz, 1H), 7.71-7.62 (m, 2H), 7.59-7.50 (m, 2H), 7.30-7.23 (m, 1H), 3.98-3.92 (m, 4H), 3.87 (s, 3H), 3.54-3.48 (m, 4H); MS m/z 390 (M+1).

EXAMPLE 91

2-(4-Methoxy-benzenesulfonyl)-4-piperazin-1-yl-thieno[3,2-c]pyridine hydrochloride 4-[2-(4-Methoxy-phenylsulfanyl)-thieno[3,2-c]pyridin-4-yl]-piperazine-1-carboxylic acid tert-butyl ester was obtained from 4-methoxythiophenol (130 ul, 1 mmol) and tert-butyl 4-(2-bromothieno[3,2-c]pyridin-4-yl)piperazine-1-carboxylate (215 mg, 0.52 mmol). 100 mg, 42% were isolated by the application of the general Method M described above. $^1$H NMR (270 MHz, CDCl$_3$) δ 1.48 (s, 9H), 3.40-3.47 (m, 4H), 3.58-3.65 (m, 4H), 3.79 (s, 3H), 6.83-6.89 (m, 2H), 7.15 (d, J=5.54 Hz, 1H), 7.35 (s, 1H), 7.38-7.43 (m, 2H), 7.99 (d, J=5.81 Hz, 1H); MS m/z 458 (M+1).

4-[2-(4-methoxy-phenylsulfanyl)-thieno[3,2-c]pyridin-4-yl]-piperazine-1-carboxylic acid tert-butyl ester was obtained (25 mg, 23%) as a clear liquid by the application of the general procedure B described above. $^1$H NMR (270 MHz, CDCl$_3$) δ 1.48 (s, 9H), 3.67-3.91 (m, 11H), 7.01 (d, J=8.97 Hz, 2H), 7.27-7.37 (m, 1H), 7.93 (d, J=8.97 Hz, 2H), 8.01-8.19 (m, 2H); MS m/z 490 (M+1). The title compound was thereby obtained following Procedure C): $^1$H NMR (CD$_3$OD) δ 8.25 (s, 1H), 8.09-7.89 (m, 3H), 7.69 (d, J=6.33 Hz, 1H), 7.17-7.10 (m, 2H), 4.00-3.93 (m, 4H), 3.87 (s, 3H), 3.55-3.48 (m, 4H); MS m/z 390 (M+1).

EXAMPLE 92

4-Piperazin-1-yl-2-{[4-trifluoromethyl)phenyl]sulfonyl}thieno[3,2-c]pyridine hydrochloride 2-{[4-(Trifluoromethyl)phenyl]thio}-4-piperazin-1-ylthieno[3,2-c]pyridine (0.42 mmol) was dissolved in TFA (1.5 mL) at 0° C., stirred for 15 min and H$_2$O$_2$ (100 µL) was added. The mixture was stirred at room temperature over night. NaOH (2 M) was added, extraction with ethyl acetate (3×), washed with brine, dried over NaSO$_4$, The solvent was removed and the product was purified by preparative HPLC to afford 154.7 mg (86.2%). $^1$H NMR (270 MHz, DMSO-d$_6$) δ ppm 9.79 (s, 1H) 8.56 (s, 1H) 8.35 (d, J=8.44 Hz, 2H) 8.12-8.05 (m, 3H) 7.79 (d, J=6.33 Hz, 1H) 3.98-3.96 (m, 4H) 3.32-3.31 (m, 4H); LC-MS 428 (M−H)$^+$; Purity (HPLC) 95%

EXAMPLE 93

2-[[2-tert-Butylphenyl)sulfonyl]-4-piperazin-1-ylthieno[3,2-c]pyridine hydrochloride The title compound was prepared following Method M-O. Yield: 10.6 mg (6.3%) of 2-[[2-tert-butylphenyl)sulfonyl]-4-piperazin-1-ylthieno[3,2-c]pyridine hydrochloride. $^1$H NMR (270 MHz, DMSO-d$_6$) δ ppm 9.57 (s, 1H) 8.42 (s, 1H) 8.26-8.22 (m, 1H) 8.06-8.04 (m, 1H) 7.68-7.55 (m, 4H) 3.87-3.86 (m, 4H) 3.34-3.33 (m, 4H) 1.51-1.43 (m, 9H); LC-MS 400 (M−H)$^+$; Purity (HPLC) 90%.

EXAMPLE 94

2-[(3,4-Dichlorophenyl)sulfonyl]-4-piperazin-1-ylthieno[3,2-c]pyridine-2-sulfonamide hydrochloride The title compound was prepared following Method M-O. Yield: 47.9 mg (22.9%). $^1$H NMR (270 MHz, DMSO-d$_6$) δ ppm 9.36 (s, 1H) 8.51 (s, 1H) 8.38 (d, J=2.11 Hz, 1H 8.06-7.94 (m, 3H) 7.70-7.68 (m, 1H) 3.81-3.77 (m, 4H) 3.31-3.29 (m, 4H); LC-MS 427 (M−H)$^+$; Purity (HPLC) 95%.

EXAMPLE 95

2-[(4-tert-Butylphenyl)sulfonyl]-4-piperazin-1-ylthieno[3,2-c]pyridine hydrochloride Oxone (0.52 g, 0.84 mmol) in water (4 mL), buffered to pH ~6 with sodium oxide acetate, was added to 2-[(4-tert-butylphenyl)thio]-4-piperazin-1-ylthieno[3,2-c]pyridine (0.42 mmol) in ethanol (30 mL). The mixture was stirred in room temperature for 2 h and more oxone (0.52 g, 0.84 mmol) was added. The reaction was stirred over night. Water was added to the mixture, extraction with dichloromethane (2×20 mL) and the solvent was removed. The products were purified by preparative HPLC. Yield: 41.9 mg (22.0%). $^1$H NMR (500 MHz, CH$_3$OH-d$_4$) δ ppm 8.38 (s, 1H) 8.05-8.01 (m, 3H) 7.80 (d, J=6.59 Hz, 1H) 7.71-7.69 (m, 2H) 4.15-4.13 (m, 4H) 3.59-3.57 (4H) 1.37-1.33 (m, 9H); LC-MS 416 (M−H)$^+$; Purity (HPLC) 95%.

EXAMPLE 96

2-(1-Naphthylsulfonyl)-4-piperazin-1-ylthieno[3,2-c]pyridine hydrochloride

The title compound was prepared following Method M-O. Yield: 3.4 mg (0.2%). $^1$H NMR (270 MHz, DMSO-d$_6$) δ ppm 9.34 (s, 1H) 8.82 (s, 1H) 8.44 (s, 1H) 8.26-8.06 (m, 5H) 7.79-7.65 (m, 3H) 3.79-3.78 (m, 4H) 3.32-3.30 (m, 4H); LC-MS 410 (M−H)$^+$; Purity (HPLC) 95%.

EXAMPLE 97

2-[(3-Fluorophenyl)sulfonyl]-4-piperazin-1-ylthieno[3,2-c]pyridine-2-sulfonamide hydrochloride 2-Bromo-4-chlorothieno[3,2-c]pyridine (190 mg, 0.50 mmol) in DMF (1 mL) was added to 3-fluorobenzenethiol (95.5 mg, 1.0 mmol), KOH (56 mg, 0.2 mmol) and Cu$_2$O (71 mg, 0.5 mmol) in DMF (1 mL). The reaction was heated to 120° C. over night. The mixture was filtrated through a silica plug and the solvent was removed. The product was dissolved in TFA (1.5 mL) at 0° C. and the solution were stirred for 15 min, H$_2$O$_2$ (100 μL) was added and the mixture was stirred at room temperature over night. 2M NaOH was added, extraction with etylacetate, washed with brine and solvent was removed. The product was purified by preparative HPLC. Yield: 30.1 mg (16.1%) $^1$H NMR (270 MHz, DMSO-d$_6$) δ ppm 9.34 (s, 1H) 8.45 (s, 1H) 8.16 (d, J=5.69 Hz, 1H) 7.97-7.93 (m, 2H) 7.76-7.62 (m, 3H) 3.30 (s, 4H) (4H obscured by solvent signal); LC-MS 378 (M−H)$^+$; Purity (HPLC) 99%.

EXAMPLE 98

2-(Mesitylsulfonyl)-4-piperazin-1-ylthieno[3,2-c]pyridine hydrochloride

The title compound was prepared following Method M-O. Yield: 32.0 mg (16.1%). $^1$H NMR (270 MHz, DMSO-d$_6$) δ ppm 9.32 (s, 1H) 8.20-8.14 (m, 2H) 7.66 (d, J=5.69 Hz, 1H) 7.14 (s, 2H) 3.29 (s, 4H) 2.65 (s, 6H) 2.28 (s, 3H) (4H obscured by solvent signal); LC-MS 402 (M−H)$^+$; Purity (HPLC) 95%.

EXAMPLE 99

2-[(2-Methoxyphenyl)sulfonyl]-4-piperazin-1-ylthieno[3,2-c]pyridine hydrochloride The title compound was prepared following Method M-O. Yield: 14.7 mg (7.6%). $^1$H NMR (270 MHz, DMSO-d$_6$) δ ppm 9.33 (s, 1H) 8.24 (s, 1H) 8.15 (d, J=5.94 Hz, 1H) 8.00 (dd, J=7.92, 1.48 Hz, 1H) 7.77-7.68 (m, 2H) 7.28-7.18 (m, 2H) 3.30 (s, 4H) (7H obscured by solvent signal); LC-MS 390 (M−H)+Purity (HPLC) 99%.

EXAMPLE 100

2-[(2,4-Dimethoxyphenyl)sulfonyl]-4-piperazin-1-ylthieno[3,2-c]pyridine hydrochloride The title compound was prepared following Method M-O. Yield: 42.7 mg (20.5%). $^1$H NMR (270 MHz, DMSO-d$_6$) δ ppm 9.39 (s, 1H) 8.37 (s, 1H) 8.13 (d, J=5.69 Hz, 1H) 7.68-7.66 (m, 2H) 7.54 (d, J=2.23 Hz, 1H) 7.19 (d, J=8.66 Hz, 1H) 3.29 (s, 4H) (10H obscured by solvent signal); LC-MS 420 (M−H)$^+$; Purity (HPLC) 98%.

EXAMPLE 101

2-[(2,4-Dimethylphenyl)sulfonyl]-4-piperazin-1-ylthieno[3,2-c]pyridine hydrochloride The title compound was prepared following Method M-O. Yield: 17.8 mg (9.3%). $^1$H NMR (270 MHz, DMSO-d$_6$) δ ppm 9.32 (s, 1H) 8.27 (s, 1H) 8.15 (d, J=5.94 Hz, 1H) 8.00 (d, J=8.17 Hz, 1H) 7.67 (d, J=5.94 Hz, 1H) 7.35-7.26 (m, 2H) 3.29 (s, 4H) 2.34 (s, 3H) (7H obscured by solvent signal); LC-MS 388 (M−H)+Purity (HPLC) 98%.

EXAMPLE 102

2-[(2,5-Dimethylphenyl)sulfonyl]-4-piperazin-1-ylthieno[3,2-c]pyridine hydrochloride The title compound was prepared following Method M-O. Yield: 16.9 mg (8.8%). $^1$H NMR (270 MHz, DMSO-d$_6$) δ ppm 9.17 (s, 1H) 8.29 (s, 1H) 8.18-18.15 (m, 1H) 7.94 (s, 1H) 7.66 (d, J=5.69 Hz, 1H) 7.47 (d, J=7.67 Hz, 1H) 7.32 (d, J=8.16 Hz, 1H) 3.29 (s, 2H) 2.42 (s, 3H) (7H obscured by solvent signal); LC-MS 388 (M−H)$^+$; Purity (HPLC) 99%.

EXAMPLE 103

2-[(2-Ethylphenyl)sulfonyl]-4-piperazin-1-ylthieno[3,2-c]pyridine hydrochloride

The title compound was prepared following Method M-O. Yield: 22.6 mg (11.2%). $^1$H NMR (270 MHz, DMSO-d$_6$) δ ppm 9.19 (s, 1H) 8.32 (s, 1H) 8.17 (d, J=5.69 Hz, 1H) 8.08 (d, J=7.92 Hz, 1H) 7.73-7.66 (m, 2H) 7.52 (t, J=7.67 Hz, 2H) 3.29 (s, 4H) 3.00 (q, J=7.34 Hz, 2H) 1.10 (m, 3H) (4H obscured by solvent signal); LC-MS 388 (M−H)$^+$; Purity (HPLC) 100%.

Scheme 7

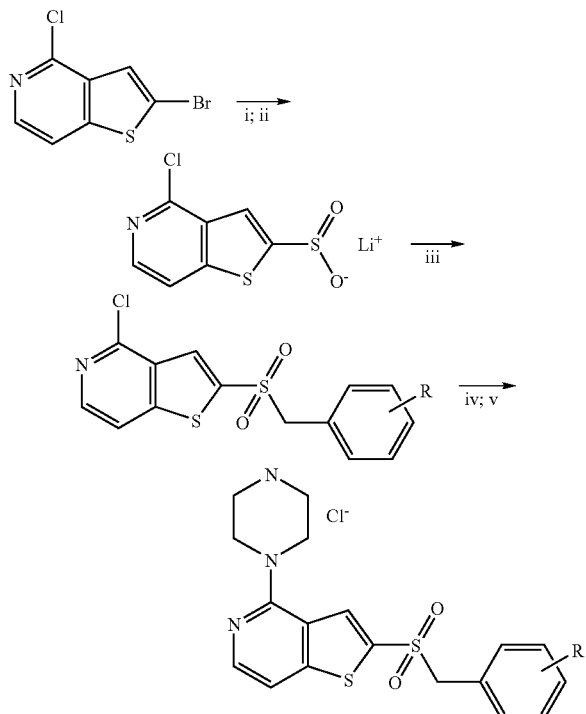

Legend to Scheme 7: i) nBuLi, diethyl ether; ii) SO₂ gas; iii) benzylbromine(s), DMF, heat; iv) diamine(s), K₂CO₃, DMF, heat; v) HCl, diethyl ether.

INTERMEDIATE 70

Lithium 4-chlorothieno[3,2-c]pyridine-2-sulfinate

2-Bromo-4-chlorothieno[3,2-c]pyridine (5.00 g, 20.1 mmol) was suspended in dry ether (100 ml) and the mixture was cooled to −78° C. under N₂-atmosphere. n-BuLi (1.6M in hexane, 15 mL) was added and the reaction mixture was stirred at −78° C. for 2 h. SO₂ (g) was then bubbled threw the reaction mixture for 1 h. After the gas bubbling had stopped the reaction mixture was stirred fore one more hour at −78° C. and was then allowed to warm to room temperature. The precipitate that had formed was filtered and washed with ether to give the sulfonate lithium salt (3.59 g, 74%) that was used in the next step without further purification. $^1$H NMR (270 MHz, DMSO-d₆) δ ppm 7.26 (s, 1H) 7.99 (d, J=5.54 Hz, 1H) 8.14 (d, J=5.54 Hz, 1H). MS (M−Li+1) 234.

Benzylation of Sulfinate Salts (Method P)

To a suspension of lithium 4-chlorothieno[3,2-c]pyridine-2-sulfinate (100 mg, 0.42 mmol) in dry DMF (2 mL) was added a benzylbromide (0.83 mmol, 2 equiv.) and the mixture heated with stirring for 16 h at 110° C. Analysis by LCMS showed desired product and no starting material remaining. The mixture was treated with polystyrene-thiophenol (200 mg) and was rolled for 16 h. The suspension was filtered washing with further DMF (2 mL). This material was reacted further without purification.

Nucleophilic Substitution of Chlorine (Method Q)

To a crude solutions of benzylsulfone in DMF (4 mL) are added potassium carbonate (172 mg, 1.25 mmol) and tert-butyl-piperazine-1-carboxylate (155 mg, 0.84 mmol). The resulting mixtures are heated for 16 h at 110° C. LCMS shows desired compound and no starting material. The reaction mixtures are filtered and then the solvent removed under reduced pressure. The desired compounds are isolated pure following preparative HPLC.

BOC-Deprotection (Method R)

The BOC N-protected piperazine derivatives are dissolved in HCl/diethyl ether (1 mL, 1.0M) at room temperature and stirred for 16 h. Removal of the solvent under reduced pressure gave the crude hydrochloride salts. Trituration with acetonitrile gives the desired compound as a white solid.

INTERMEDIATE 71 tert-Butyl-4-[2-(benzylsulfonyl)thieno[3,2-c]pyridin-4-yl]piperazine-1-carboxylate Lithium 4-chlorothieno[3,2-c]pyridine-2-sulfinate (0.44 mmol) was treated with benzylbromide (0.59 mmol) as described in Method P above and then reacted further with tert-butyl-piperazine-1-carboxylate as described in Method Q. Yield 0.009 g (7% over two steps).
$^1$H NMR (300 MHz, CDCl₃) δ 8.14 (d, J=5.5 Hz 1H), 7.27-7.40 (m, 5H), 7.15-7.21 (m, 2H), 4.45 (s, 2H), 3.50-3.56 (m, 4H), 3.40-3.45 (m, 4H), 1.49 (s, 9H); MS (ESI+) for C23H27N3O4S₂ m/z 474 (M+H)⁺. HPLC 77%, R$_T$ 3.93 min (ACE3 C8 50×4 mm, 5-50% acetonitrile in 3 min).

INTERMEDIATE 72 tert-Butyl-4-(2-{[4-(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 4-(trifluoromethyl)benzylbromide (0.59 mmol) as described in Method P above and then reacted further with tert-butyl-piperazine-1-carboxylate as described in Method QF. Yield 0.02 g (16% over two steps). Beige solid. $^1$H NMR (300 MHz, CDCl₃) δ 8.16 (d, J=6 Hz 1H), 7.53-7.61 (d, J=9 Hz 2H), 7.49 (s, 1H), 7.26-7.36 (m, 4H), 4.51 (s, 2H), 3.49-3.60 (m, 4H), 3.36-3.49 (m, 4H), 1.49 (s, 9H); MS (ESI+) for C24H26F3N3O4S₂ m/z 542 (M+H)⁺. HPLC 71%, R$_T$ 4.07 min (ACE3 C8 50×4 mm, 5-50% acetonitrile in 3 min).

INTERMEDIATE 73 tert-Butyl-4-{2-[(3-bromobenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 3-bromobenzylbromide (0.59 mmol) as described in Method P above and then reacted further with tert-butyl-piperazine-1-carboxylate as described in Method Q. Yield 0.023 g (10% over two steps). Beige solid. $^1$H NMR (300 MHz, CDCl₃) δ 8.16 (d, J=6 Hz, 1H), 7.50-7.55 (m, 2H), 7.32-7.40 (m, 2H), 7.10-7.24 (m, 3H), 4.44 (s, 2H), 3.61-3.73 (m, 8H), 1.50 (s, 9H); MS (ESI+) for C23H26BrN3O4S₂ m/z 554 (M+H)⁺. HPLC 77%, R$_T$ 4.07 min (ACE3 C8 50×4.6 mm, 5-50% acetonitrile in 3 min).

INTERMEDIATE 74 tert-Butyl-4-(2-{[3-(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 3-(trifluoromethyl)benzylbromide (0.59 mmol) as described in Method P above and then reacted further with tert-butyl-piperazine-1-carboxylate as described in Method Q. Yield 0.023 g (10% over two steps). Beige solid. $^1$H NMR (300 MHz, CDCl$_3$) δ 8.14 (d, J=6 Hz, 1H), 7.85-7.91 (m, 1H), 7.61-7.72 (m, 2H), 7.50-7.60 (m, 1H), 7.12-7.31 (m, 2H), 4.74 (s, 2H), 3.52-3.71 (m, 8H), 1.50 (s, 9H); MS (ESI+) for C24H26F3N3O4S$_2$ m/z 542 (M+H)$^+$. HPLC 85%, R$_T$ 2.13 min (YMC ODS AQ, 33×3 mm, 10-90% acetonitrile in 3 min).

INTERMEDIATE 75 tert-Butyl-4-(2-{[2,5-bis(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 2,5-bis(trifluoromethyl)benzylbromide (0.59 mmol) as described in Method P above and then reacted further with tert-butyl-piperazine-1-carboxylate as described in Method Q. Yield 0.01 g (4% over two steps). Beige solid. $^1$H NMR (300 MHz, CDCl$_3$) δ 8.16 (d, J=5.8 Hz 1H), 8.00 (s, 1H), 7.74-7.85 (m, 3H), 4.76 (s, 2H), 3.56-3.64 (m, 4H), 3.47-3.56 (m, 4H), 1.49 (s, 9H); MS (ESI+) for C25H25F6N3O4S$_2$ m/z 610 (M+H)$^+$. HPLC 73%, R$_T$ 2.36 min (YMC ODS AQ, 33×3 mm, 10-90% acetonitrile in 3 min).

INTERMEDIATE 76 tert-Butyl 4-{2-[(4-methylbenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 4-methylbenzylbromide (0.59 mmol) as described in Method P above and then reacted further with tert-butyl-piperazine-1-carboxylate as described in Method Q. Yield 0.005 g (3% over two steps). Beige solid. $^1$H NMR (300 MHz, CDCl$_3$) δ 8.15 (d, J=6 Hz 1H), 7.40 (s, 1H), 7.00-7.16 (m, 4H), 4.42 (s, 2H), 3.46-3.60 (m, 4H), 3.37-3.46 (m, 4H), 2.34 (s, 3H), 1.49 (s, 9H); MS (ESI+) for C24H29N3O4S$_2$ m/z 488 (M+H)$^+$. HPLC 69%, R$_T$ 2.06 min (YMC ODS AQ, 33×3 mm, 10-90% acetonitrile in 3 min).

INTERMEDIATE 77 tert-Butyl 4-(2-{[5-chloro-2-(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 5-chloro-2-(trifluoromethyl)benzylbromide (0.59 mmol) as described in Method P above and then reacted further with tert-butyl-piperazine-1-carboxylate as described in Method Q. Yield 0.019 g (7.5% over two steps). Beige solid. $^1$H NMR (300 MHz, CDCl$_3$) δ 8.12-8.14 (m, 1H), 7.80-7.88 (m, 2H), 7.47-7.66 (m, 2H), 4.71 (s, 2H), 3.74-3.83 (m, 4H), 3.63-3.72 (m, 4H), 1.49 (s, 9H); MS (ESI+) for C24H25ClF3N3O4S$_2$ m/z 576 (M+H)$^+$. HPLC 74%, R$_T$ 2.30 min (YMC ODS AQ, 33×3 mm, 10-90% acetonitrile in 3 min).

INTERMEDIATE 78 tert-Butyl 4-{2-[(3,4-difluorobenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 3,4-bis(trifluoromethyl)benzylbromide (0.59 mmol) as described in Method P above and then reacted further with tert-butyl-piperazine-1-carboxylate as described in Method Q. Yield 0.014 g (6% over two steps). Beige solid. $^1$H NMR (300 MHz, CDCl$_3$) δ 8.17-8.21 (m, 1H), 7.71 (s, 1H), 7.07-7.39 (m, 4H), 4.59 (s, 2H), 3.55-3.68 (m, 8H), 1.49 (s, 9H); MS (ESI+) for C23H25F2N3O4S$_2$ m/z 510 (M+H)$^+$. HPLC 64%, R$_T$ 2.02 min (YMC ODS AQ, 33×3 mm, 10-90% acetonitrile in 3 min).

INTERMEDIATE 79 tert-Butyl 4-{2-[(3,5-dimethoxybenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 3,5-dimethoxybenzylbromide (0.59 mmol) as described in Method P above and then reacted further with tert-butyl-piperazine-1-carboxylate as described in Method Q. Yield 0.02 g (10% over two steps). Beige solid. $^1$H NMR (300 MHz, CDCl$_3$) δ 8.14-8.18 (m, 1H), 7.55 (s, 1H), 6.40-6.45 (m, 1H), 6.26-6.34 (m, 2H), 4.39 (s, 2H), 3.54-3.72 (m, 14H), 1.50 (s, 9H); MS (ESI+) for C25H31N3O6S$_2$ m/z 534 (M+H)$^+$. HPLC 69%, R$_T$ 1.99 min (YMC ODS AQ, 33×3 mm, 10-90% acetonitrile in 3 min).

EXAMPLE 104

4-(Piperazinyl)-2-(3-methoxybenzyl-sulfonyl)-thienopyridine

A 1:1 mixture of lithium 4-chloro-thienopyridine-2-sulfinate (0.176 g, 0.734 mmol) and 2-methoxybenzylbromide (0.295 g, 1.47 mmol) in DMF (5 mL) was heated at 100° C. for 2 h. To the mixture was added Boc-piperazine (546 mg, 2.94 mmol) and the reaction was heated at 110° C. for 1.5 h. The solvent was removed and the crude product was purified by preparative HPLC to obtain 17.4 mg of 4-(4-t-butyl-oxycarbonyl-piperazinyl)-2-(3-methoxybenzylsulfonyl)-thienopyridine. The boc-protected product was dissolved in 2 mL of MeOH and 4 mL of HCl/ether was added to obtain 21.9 mg of 4-(piperazinyl)-2-(3-methoxybenzylsulfonyl)-thienopyridine. $^1$HNMR (CD$_3$OD/D$_2$O 1:1) δ 6.42-6.38 (m, 1H), 7.51-7.48 (m, 1H), 7.39-7.35 (m, 1H), 6.92-6.85 (m, 1H), 6.64-6.59 (m, 1H), 6.48-6.39 (m, 2H), 3.64-3.58 (m, 4H), 3.19-3.13 (m, 4H), 2.96 (s, 3H), 2.92 (s, 2H); MS (ESI) 404 (M+H)$^+$; Purity (HPLC, column YMC) 94%.

INTERMEDIATE 80 tert-Butyl-4-[2-(benzylsulfonyl)thieno[3,2-c]pyridin-4-yl]piperazine-1-carboxylate Lithium 4-chlorothieno[3,2-c]pyridine-2-sulfinate (0.44 mmol) was treated with benzylbromide (0.59 mmol) as described in Method P above and then reacted further with tert-butyl-piperazine-1-carboxylate as described in Method Q. Yield 0.00 g (7% over two steps). Beige solid. $^1$H NMR (300 MHz, CDCl$_3$) δ 8.14 (d, J=5.5 Hz 1H), 7.27-7.40 (m, 5H), 7.15-7.21 (m, 2H), 4.45 (s, 2H), 3.50-3.56 (m, 4H), 3.40-3.45 (m, 4H), 1.49 (s, 9H); MS (ESI+) for C23H27N3O4S$_2$ m/z 474 (M+H)$^+$. HPLC 77%, R$_T$ 3.93 min (ACE3 C8 50×4 mm, 5-50% acetonitrile in 3 min).

EXAMPLE 105

2-(Benzylsulfonyl)-4-piperazin-1-ylthieno[3,2-c]pyridine hydrochloride tert-Butyl 4-[2-(benzylsulfonyl)thieno[3,2-c]pyridin-4-yl]piperazine-1-carboxylate (0.01 g, 0.02 mmol) was treated as described in Method R to give the desired product as a white solid. Yield 0.009 g, (100%). White solid. $^1$H NMR (300 MHz, DMSO-d6) δ 8.98 (s, 1H), 8.13-8.20 (d, J=8 Hz 1H), 8.00 (s, 1H), 7.64-7.71 (m, 1H), 7.18-7.35 (m, 5H), 4.93 (s, 2H), 3.60-3.70 (m, 4H), 3.22. 3.34 (m, 4H); MS (ESI+) for C18H19N3O2S2. C1 H m/z 374 (M+H)$^+$. HPLC 90%, R$_T$ 2.91 min (ACE3 C8 50×4.6 mm, 5-50% acetonitrile in 3 min).

INTERMEDIATE 81 tert-Butyl-4-(2-{[4-(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 4-(trifluoromethyl)benzylbromide (0.59 mmol) as described in Method P above and then reacted further with tert-butyl-piperazine-1-carboxylate as described in Method Q. Yield 0.02 g (16% over two steps). Beige solid. $^1$H NMR (300 MHz, CDCl$_3$) δ 8.16 (d, J=6 Hz 1H), 7.53-7.61 (d, J=9 Hz 2H), 7.49 (s, 1H), 7.26-7.36 (m, 4H), 4.51 (s, 2H), 3.49-3.60 (m, 4H), 3.36-3.49 (m, 4H), 1.49 (s, 9H); MS (ESI+) for C24H26F3N3O4S$_2$ m/z 542 (M+H)$^+$. HPLC 71%, R$_T$ 4.07 min (ACE3 C8 50×4 mm, 5-50% acetonitrile in 3 min).

EXAMPLE 106

4-Piperazin-1-yl-2-{[4-(trifluoromethyl)benzyl]sulfonyl}thieno[3,2-c]pyridine hydrochloride tert-Butyl 4-(2-{[4-(trifluoromethyl)benzyl]sulfonyl}thieno[3,2-c]pyridin-4-yl)piperazine-1-carboxylate (0.02 g, 0.03 mmol) was treated as described in Method R to give the desired product as a white solid. Yield 0.014 g (100%) White solid. $^1$H NMR (300 MHz, DMSO-d6) δ 9.25 (s, 1H), 8.12-8.22 (m, 2H), 7.66-7.77 (m, 4H), 7.41-7.52 (m, 2H), 5.12 (s, 2H), 3.22-3.35 (m, 4H); MS (ESI+) for C19H18F3N3O2S2. C1 H m/z 442 (M+H)$^+$. HPLC 90%, R$_T$ 3.53 min (ACE3 C8 50×4.6 mm, 5-50% acetonitrile in 3 min).

INTERMEDIATE 82 tert-Butyl-4-{2-[(3-bromobenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 3-bromobenzylbromide (0.59 mmol) as described in Method P above and then reacted further with tert-butyl-piperazine-1-carboxylate as described in Method Q. Yield 0.023 g (10% over two steps). Beige solid. $^1$H NMR (300 MHz, CDCl$_3$) δ 8.16 (d, J=6 Hz, 1H), 7.50-7.55 (m, 2H), 7.32-7.40 (m, 2H), 7.10-7.24 (m, 3H), 4.44 (s, 2H), 3.61-3.73 (m, 8H), 1.50 (s, 9H); MS (ESI+) for C23H26BrN3O4S$_2$ m/z 554 (M+H)$^+$. HPLC 77%, R$_T$ 4.07 min (ACE3 C8 50×4.6 mm, 5-50% acetonitrile in 3 min).

EXAMPLE 107

2-[(3-Bromobenzyl)sulfonyl]-4-piperazin-1-ylthieno[3,2-c]pyridine hydrochloride tert-Butyl 4-{2-[(3-bromobenzyl)sulfonyl]thieno[3,2-c]pyridin-4-yl}piperazine-1-carboxylate (0.023 g, 0.04 mmol) was treated as described in Method R to give the desired product as a white solid. Yield 0.013 g (67%) White solid. $^1$H NMR (300 MHz, DMSO-d6) δ 9.19 (s, 1H), 8.18 (d, J=6 Hz, 1H), 8.05 (s, 1H), 7.70 (d, J=6 Hz, 1H), 7.53-7.58 (m, 1H), 7.43-7.45 (m, 1H), 7.19-7.32 (m, 2H), 4.98 (s, 2H), 3.24-3.35 (m, 4H); MS (ESI+) for C18H18BrN3O2S2. C1 H m/z 452 (M+H)$^+$. HPLC 90%, R$_T$ 3.30 min (ACE3 C8 50×4.6 mm, 5-50% acetonitrile in 3 min).

INTERMEDIATE 83 tert-Butyl 4-{2-[(3,4-difluorobenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 3,4-bis(trifluoromethyl)benzylbromide (0.59 mmol) as described in Method P above and then reacted further with tert-butyl-piperazine-1-carboxylate as described in Method Q. Yield 0.014 g (6% over two steps). Beige solid. $^1$H NMR (300 MHz, CDCl$_3$) δ 8.17-8.21 (m, 1H), 7.71 (s, 1H), 7.07-7.39 (m, 4H), 4.59 (s, 2H), 3.55-3.68 (m, 8H), 1.49 (s, 9H); MS (ESI+) for C23H25F2N3O4S$_2$ m/z 510 (M+H)$^+$. HPLC 64%, R$_T$ 2.02 min (YMC ODS AQ, 33×3 mm, 10-90% acetonitrile in 3 min).

EXAMPLE 108

2-[(2,3-Difluorobenzyl)sulfonyl]-4-piperazin-1-ylthieno[3,2-c]pyridine hydrochloride The BOC group was removed from tert-butyl 4-{2-[(3,4-difluorobenzyl)sulfonyl]thieno[3,2-c]pyridin-4-yl}piperazine-1-carboxylate using Method R. Yield 0.068 g (100%). White solid. $^1$H NMR (300 MHz, DMSO-d$_6$) δ 9.34 (s, 1H), 8.22 (s, 1H), 8.18 (d, J=5.5 Hz, 1H), 7.70 (d, J=5.5 Hz, 1H), 7.26-7.35 (m, 1H), 7.15-7.22 (m, 1H), 7.05-7.14 (m, 1H), 5.08 (s, 2H), 3.34-3.42 (m, 4H), 3.25-3.34 (m, 4H); MS (ESI+) for C18H17F2 N3O2S2. C1 H m/z 410 (M+H)$^+$. HPLC 90%, R$_T$ 1.07 min (YMC ODS AQ, 33×3 mm, 20-50% acetonitrile in 1.5 min).

EXAMPLE 109

2-[(4-Bromobenzyl)sulfonyl]-4-piperazin-1-ylthieno[3,2-c]pyridine hydrochloride

Lithium 4-chlorothieno[3,2-c]pyridine-2-sulfinate (0.42 mmol) was treated with 4-bromobenzylbromide (0.59 mmol) as described in Method P above and then reacted further with tert-butyl-piperazine-1-carboxylate as described in Method Q. The BOC protecting group was removed using Method R. Yield 0.024 g (12% over three steps). White solid. $^1$H NMR (300 MHz, DMSO-d6) δ 8.99 (s, 1H), 8.18 (d, J=5.5 Hz, 1H), 8.02 (s, 1H), 7.69 (d, J=5.5 Hz, 1H), 7.53 (d, J=8.5 Hz, 2H), 7.17 (d, J=8.5 Hz, 2H), 4.95 (s, 2H), 3.62-3.68 (m, 4H), 3.27-3.32 (m, 4H); MS (ESI+) for C18H18BrN3O2S2. C1 H m/z 454 (M+H)$^+$. HPLC 90%, R$_T$ 1.24 min (YMC ODS AQ, 33×3 mm, 20-50% acetonitrile in 1.5 min).

INTERMEDIATE 84 tert-Butyl-4-(2-{[2,5-bis(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 2,5-bis(trifluoromethyl)benzylbromide (0.59 mmol) as described in Method P above and then reacted further with tert-butyl-piperazine-1-carboxylate as described in Method Q. Yield 0.01 g (4% over two steps).

Beige solid. $^1$H NMR (300 MHz, CDCl$_3$) δ 8.16 (d, J=5.8 Hz 1H), 8.00 (s, 1H), 7.74-7.85 (m, 3H), 4.76 (s, 2H), 3.56-3.64 (m, 4H), 3.47-3.56 (m, 4H), 1.49 (s, 9H); MS (ESI+) for C25H25F6 N3O4S$_2$ m/z 610 (M+H)$^+$. HPLC 73%, R$_T$ 2.36 min (YMC ODS AQ, 33×3 mm, 10-90% acetonitrile in 3 min).

EXAMPLE 110

2-{[2,5-Bis(trifluoromethyl)benzyl]sulfonyl}-4-piperazin-1-ylthieno[3,2-c]pyridine hydrochloride The BOC group was removed from tert-butyl 4-(2-{[2,5-(trifluoromethyl)benzyl]sulfonyl}thieno[3,2-c]pyridin-4-yl)piperazine-1-carboxylate using Method R. Yield 0.024 g (100%). White solid. $^1$H NMR (300 MHz, DMSO-d$_6$) δ 9.30 (s, 1H), 8.25 (s, 1H), 8.19 (d, J=5.5 Hz, 1H), 8.00-8.07 (m, 2H), 7.85 (s, 1H), 7.69 (d, J=5.5 Hz, 1H), 5.22 (s, 2H), 3.24-3.33 (m, 4H); MS (EST+) for C20H17F6N3O2S2. C1 H m/z 510 (M+H)$^+$. HPLC 90%, R$_T$ 1.08 min (YMC ODS AQ, 33×3 mm, 30-60% acetonitrile in 1.5 min).

INTERMEDIATE 85 tert-Butyl 4-{2-[(4-methylbenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 4-methylbenzylbromide (0.59 mmol) as described in Method P above and then reacted further with tert-butyl-piperazine-1-carboxylate as described in Method Q. Yield 0.005 g (3% over two steps). Beige solid. $^1$H NMR (300 MHz, CDCl$_3$) δ 8.15 (d, J=6 Hz 1H), 7.40 (s, 1H), 7.00-7.16 (m, 4H), 4.42 (s, 2H), 3.46-3.60 (m, 4H), 3.37-3.46 (m, 4H), 2.34 (s, 3H), 1.49 (s, 9H); MS (ESI+) for C24H29N3O4S$_2$ m/z 488 (M+H)$^+$. HPLC 69%, R$_T$ 2.06 min (YMC ODS AQ, 33×3 mm, 10-90% acetonitrile in 3 min).

EXAMPLE 111

2-[(4-Methylbenzyl)sulfonyl]-4-piperazin-1-ylthieno[3,2-c]pyridine hydrochloride The BOC group was removed from tert-butyl 4-{2-[(4-methylbenzyl)sulfonyl]thieno[3,2-c]pyridin-4-yl}piperazine-1-carboxylate using Method R. Yield 0.05 g (75%). White solid. $^1$H NMR (300 MHz, DMSO-d6) δ 9.18 (s, 1H), 8.17 (d, J=5.5 Hz, 1H), 8.01 (s, 1H), 7.67 (d, J=5.5 Hz, 1H), 7.38 (s, 1H), 7.19 (s, 1H), 7.11 (s, 1H), 7.00 (s, 1H), 4.86 (s, 2H); MS (ESI+) for C19H21N3O2S2. C1 H m/z 388 (M+H)$^+$. HPLC 90%, R$_T$ 1.65 min (ACE3 C8 50×3.0 mm, 10-97% acetonitrile in 3 min).

INTERMEDIATE 86 tert-Butyl 4-(2-{[5-chloro-2-(trifluoromethyl)benzyl]sulfonyl}thieno[3,2-c]pyridin-4-yl)piperazine-1-carboxylate Lithium 4-chlorothieno[3,2-c]pyridine-2-sulfinate (0.44 mmol) was treated with 5-chloro-2-(trifluoromethyl)benzylbromide (0.59 mmol) as described in Method P above and then reacted further with tert-butyl-piperazine-1-carboxylate as described in Method Q. Yield 0.019 g (7.5% over two steps). Beige solid. $^1$H NMR (300 MHz, CDCl$_3$) δ 8.12-8.14 (m, 1H), 7.80-7.88 (m, 2H), 7.47-7.66 (m, 2H), 4.71 (s, 2H), 3.74-3.83 (m, 4H), 3.63-3.72 (m, 4H), 1.49 (s, 9H); MS (ESI+) for C24H25ClF3 N3O4S$_2$ m/z 576 (M+H)$^+$. HPLC 74%, R$_T$ 2.30 min (YMC ODS AQ, 33×3 mm, 10-90% acetonitrile in 3 min).

EXAMPLE 112

2-{[5-Chloro-2-(trifluoromethyl)benzyl]sulfonyl}-4-piperazin-1-ylthieno[3,2-c]pyridine hydrochloride The BOC group was removed from tert-butyl 4-(2-{[5-chloro-2-(trifluoromethyl)benzyl]sulfonyl}thieno[3,2-c]pyridin-4-yl)piperazine-1-carboxylate using Method r. Yield 0.012 g (92%). White solid. $^1$H NMR (300 MHz, DMSO-d$_6$) δ 9.05 (s, 1H), 8.18-8.23 (m, 2H), 7.78-7.83 (m, 1H), 7.72-7.76 (m, 1H), 7.69 (d, J=5.5 Hz, 1H), 7.62-7.65 (m, 1H), 5.07 (s, 2H), 3.65-3.72 (m, 4H), 7.25-7.34 (m, 4H); MS (ESI+) for C19H17ClF3N3O2S2. C1 H m/z 476 (M+H)$^+$. HPLC 90%, R$_T$ 1.65 min (ACE3 C8 50×3.0 mm, 10-97% acetonitrile in 3 min).

INTERMEDIATE 87 tert-Butyl 4-{2-[(3,5-dimethoxybenzyl)sulfonyl]thieno[3,2-c]pyridin-4-yl}piperazine-1-carboxylate Lithium 4-chlorothieno[3,2-c]pyridine-2-sulfinate (0.44 mmol) was treated with 3,5-dimethoxybenzylbromide (0.59 mmol) as described in Method P above and then reacted further with tert-butyl-piperazine-1-carboxylate as described in Method Q. Yield 0.02 g (10% over two steps). Beige solid. $^1$H NMR (300 MHz, CDCl$_3$) δ 8.14-8.18 (m, 1H), 7.55 (s, 1H), 6.40-6.45 (m, 1H), 6.26-6.34 (m, 2H), 4.39 (s, 2H), 3.54-3.72 (m, 14H), 1.50 (s, 9H); MS (ESI+) for C25H31N3O6S$_2$ m/z 534 (M+H)$^+$. HPLC 69%, R$_T$ 1.99 min (YMC ODS AQ, 33×3 mm, 10-90% acetonitrile in 3 min).

EXAMPLE 113

2-[(3,5-Dimethoxybenzyl)sulfonyl]-4-piperazin-1-ylthieno[3,2-c]pyridine hydrochloride The BOC group was removed from tert-butyl 4-{2-[(3,5-dimethoxybenzyl)sulfonyl]thieno[3,2-c]pyridin-4-yl}piperazine-1-carboxylate using Method R. Yield 0.01 g (62%). White solid. $^1$H NMR (300 MHz, DMSO-d$_6$) δ 9.09 (s, 1H), 8.18 (d, J=6.7 Hz, 1H), 8.02 (s, 1H), 7.69 (d, J=6.7 Hz, 1H), 6.45-6.48 (m, 1H), 6.35-6.38 (m, 2H), 4.84 (s, 2H), 3.61-3.67 (m, 4H), 3.58 (s, 6H), 3.24-3.33 (m, 4H). MS (ESI+) for C$_{20}$H$_{22}$N$_3$O$_4$S$_2$ m/z 434 (M+H)$^+$. HPLC 90%, R$_T$ 1.60 min (ACE3 C8 50×3.0 mm, 10-97% acetonitrile in 3 min).

EXAMPLE 114

2-[(2-Naphthylmethyl)sulfonyl]-4-piperazin-1-ylthieno[3,2-c]pyridine hydrochloride 2-(Bromomethyl)naphthalene was used according to Method P-R to give 12.4 mg of the desired product. $^1$H NMR (270 MHz, CH$_3$OH-d$_4$) δ ppm (obscured by CH$_3$OH, 4H) 3.70-3.79 (m, 4H) 4.95 (s, 2H) 7.36-7.58 (m, 3H) 7.70-7.91 (m, 6H) 8.02 (d, J=6.60 Hz, 1H). MS (M+1) 424.

EXAMPLE 115

4-Piperazin-1-yl-2-{[4-(1,2,3-thiadiazol-4-yl)benzyl]sulfonyl}thieno[3,2-c]pyridine hydrochloride 4-[4-(Bromomethyl)phenyl]-1,2,3-thiadiazole was used according to Method P-R to give 4.8 mg of the desired product. ¹H NMR (270 MHz, CH₃OH-d₄) δ ppm 3.41-3.50 (m, 4H) 3.54 (s, 2H) 3.89-3.98 (m, 4H) 7.45 (d, J=8.44 Hz, 2H) 7.75 (d, J=6.33 Hz, 1H) 7.96-8.13 (m, 4H) 9.31 (s, 1H). MS (M+1) 458.

EXAMPLE 116

1-(4-Pyrrolidin-1-ylphenyl)-2-[(4-piperazine-1-ylthieno[3,2-c]pyridin-2-yl)sulfonyl]ethanone hydrochloride 2-Bromo-1-(4-pyrrolidin-1-ylphenyl)ethanone was used according to Method P-R to give 19.6 mg of the desired product. ¹H NMR (270 MHz, CH₃OH-d₄) δ ppm 2.02-2.12 (m, 4H) 2.69 (s, 1H) 3.37 (t, J=6.73 Hz, 4H) 3.54 (s, 1H) 3.56-3.64 (m, 4H) 4.12-4.22 (m, 4H) 6.55 (d, J=8.97 Hz, 2H) 7.78-7.90 (m, 3H) 8.03 (d, J=6.86 Hz, 1H) 8.41 (s, 1H). MS (M+1) 471.

EXAMPLE 117

1-[4-(Diethylamino)phenyl]-2-[(4-piperazine-1-ylthieno[3,2-c]pyridin-2-yl)sulfonyl]ethanone hydrochloride 2-Bromo-1-[4-(diethylamino)phenyl]ethanone ethanone was used according to Method P-R to give 9.0 mg of the desired product. ¹H NMR (500 MHz, CH₃OH-d₄) δ ppm 1.16 (t, J=7.06 Hz, 6H) 3.49-3.66 (m, 10H) 4.14-4.27 (m, 4H) 7.13 (br. s, 2H) 7.85 (d, J=6.59 Hz, 1H) 7.98 (d, J=8.48 Hz, 2H) 8.03 (d, J=6.59 Hz, 1H) 8.47 (s, 1H). MS (M+1) 473.

EXAMPLE 118

1-(4-Bromophenyl)-2-[(4-piperazin-1-ylthieno[3,2-c]pyridin-2-yl)sulfonyl]ethanone-2

Bromo-1-(4-bromophenyl)ethanone was used according to method A to give 3.4 mg of the desired product. ¹H NMR (270 MHz, CH₃OH-d₄) δ ppm 3.55 (s, 2H) 3.56-3.67 (m, 4H) 4.08-4.26 (m, 4H) 7.68 (d, J=8.44 Hz, 2H) 7.79-7.98 (m, 3H) 8.06 (d, J=6.60 Hz, 1H) 8.45 (s, 1H). MS (M+1) 481.

EXAMPLE 119

1-(3-Methoxyphenyl)-2-[(4-piperazin-1-ylthieno[3,2-c]pyridin-2-yl)sulfonyl]ethanone 2-bromo-1-(3-methoxyphenyl)ethanone was used according to method A to give 1.0 mg of the desired product. ¹H NMR (270 MHz, CH₃OH-d₄) δ ppm 3.54 (s, 2H) 3.55-6.62 (m, J=10.03 Hz, 4H) 3.82 (s, 3H) 4.06-4.18 (m, 4H) 7.20 (dd, J=8.05, 2.24 Hz, 1H) 7.34-7.49 (m, 2H) 7.57 (d, J=7.39 Hz, 1H) 7.84 (d, J=6.60 Hz, 1H) 8.06 (d, J=6.60 Hz, 1H) 8.41 (s, 1H). MS (M+1) 432.

EXAMPLE 120

1-Phenyl-2-[(4-piperazin-1-ylthieno[3,2-c]pyridin-2-yl)sulfonyl]ethanone

2-Bromo-1-phenylethanone was used according to method A to give 1.2 mg of the desired product. ¹H NMR (270 MHz, CH₃OH-d₄) δ ppm 3.55 (s, 2H) 3.57-3.66 (m, 4H) 4.10-4.24 (m, 4H) 7.46-4.57 (m, 2H) 7.66 (t, J=7.39 Hz, 1H) 7.86 (d, J=6.60 Hz, 1H) 8.02 (dd, J=14.12, 6.99 Hz, 3H) 8.46 (s, 1H). MS (M+1) 402.

TABLE 6

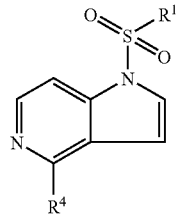

| EXAMPLE | | R¹ | R⁴ |
|---|---|---|---|
| 121 | 4-Piperazin-1-yl-1-(toluene-4-sulfonyl)-1H-pyrrolo[3,2-c]pyridine hydrochloride | 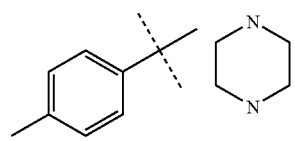 | |
| 122 | 1-(3-Chloro-2-methyl-benzenesulfonyl)-4-piperazin-1-yl-1H-pyrrolo[3,2-c]pyridine hydrochloride | 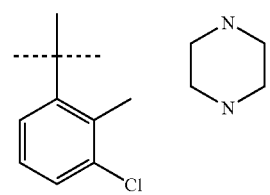 | |

TABLE 6-continued

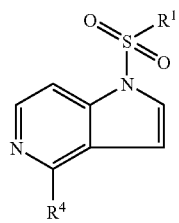

| EXAMPLE | | R¹ | R⁴ |
|---|---|---|---|
| 123 | 1-(3,4-Dimethoxy-benzenesulfonyl)-4-piperidine-1-yl-1H-pyrrolo[3,2-c]-pyridine hydrochloride | 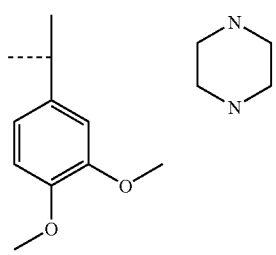 | |
| 124 | 4-(4-Piperazin-1-yl-pyrrolo[3,2-c]-pyridine-1-sulfonyl)-benzonitrile hydrochloride | 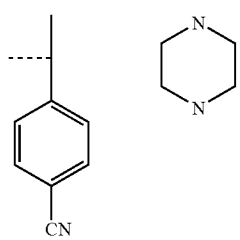 | |
| 125 | 1-(4,5-Dichloro-thiophene-2-sulfonyl)-4-piperazin-1-yl-1H-pyrrolo[3,2-c]pyridine hydrochloride | 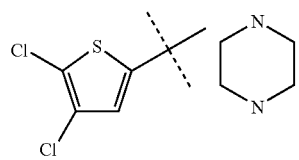 | |
| 126 | 1-(2-Chloro-4-fluoro-benzenesulfonyl)-4-piperazin-1-yl-1H-pyrrolo[3,2-c]pyridine hydrochloride | 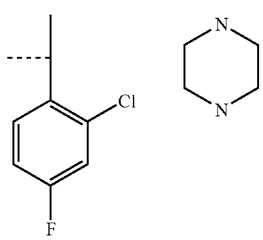 | |
| 127 | 1-Phenylmethanesulfonyl-4-piperazin-1-yl-1H-pyrrolo [3,2-c]pyridine hydrochloride | 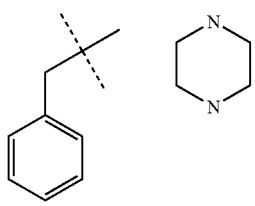 | |
| 128 | 1-(5-Chloro-thiophene-2-sulfonyl)-4-piperazin-1-yl-1H-pyrrolo[3,2-c]-pyridine hydrochloride | 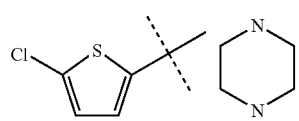 | |

TABLE 6-continued

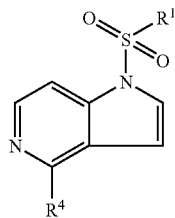

| EXAMPLE | | R¹ | R⁴ |
|---|---|---|---|
| 129 | 1-(4-Butyl-benzenesulfonyl)-4-piperazin-1-yl-1H-pyrrolo(3,2-c)pyridine hydrochloride | 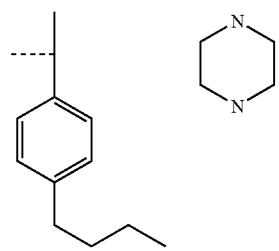 | |
| 130 | 1-(4-Phenoxy-benzenesulfonyl)-4-piperazin-1-yl-1H-pyrrolo(3,2-c)pyridine hydrochloride | 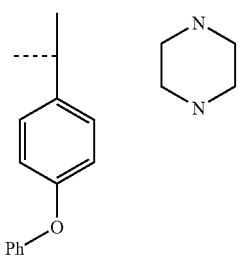 | |
| 131 | 1-(Phenylsulfonyl)-4-piperazin-1-yl-1H-pyrrolo[3,2-c]pyridine hydrochloride | 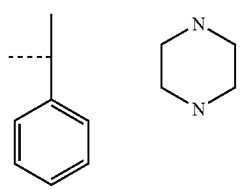 | |
| 132 | 1-[(4-Chlorophenyl)sulfonyl]-4-piperazin-1-yl-1H-pyrrolo[3,2-c]pyridine hydrochloride | 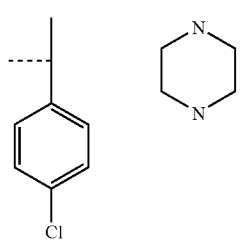 | |
| 133 | 1-[(4-Methoxyphenyl)sulfonyl]-4-piperazin-1-yl-1H-pyrrolo[3,2-c]pyridine hydrochloride | 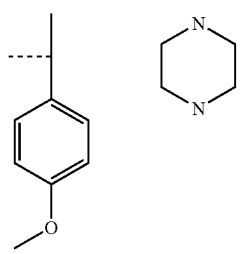 | |

TABLE 6-continued

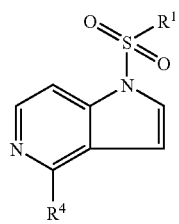

| EXAMPLE | | R¹ | R⁴ |
|---|---|---|---|
| 134 | 1-[(2-Methoxy-5-methylphenyl)sulfonyl]-4-piperazin-1-yl-1H-pyrrolo[3,2-c]pyridine hydrochloride | 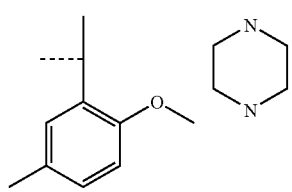 | |
| 135 | 4-Piperazin-1-yl-1-{[2-(trifluoromethyl)phenyl]-sulfonyl}-1H-pyrrolo[3,2-c]pyridine hydrochloride | 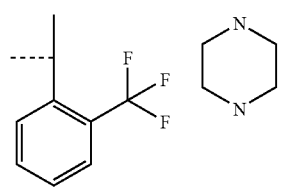 | |

Scheme 8

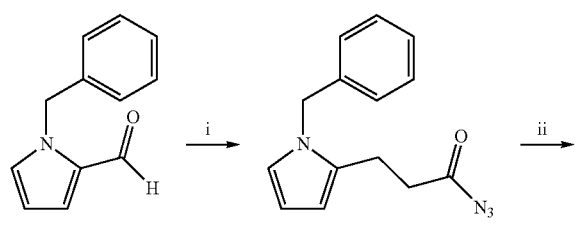

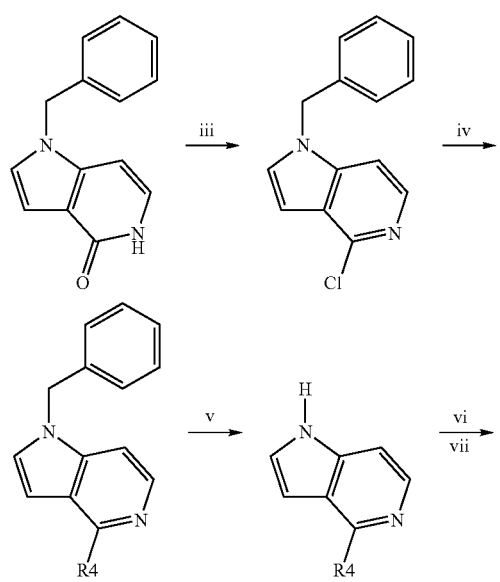

Legend to Scheme 8: i) Ethylchloroformate, TEA, acetone, NaN₃; ii) Bu₃N, DCM and diphenylether; iii) POCl₃, NaOH; iv) BOC protected amines (R⁴), K₂CO₃, DMSO; v) NH₃ gas Na, NH₄Cl, THF vi) Sulphonyl chlorides (R¹), NaH, THF; vii) HCl/diethyl ether, methanol.

INTERMEDIATE 88

(2E)-3-(1-Benzyl-1H-pyrrol-2-yl)acryloyl Azide

To a mixture of 1-benzyl-1H-pyrrole-2-carbaldehyde (28.4 g, 0.125 mol) and TEA (13.5 mL, 0.187 mol) in acetone (300 mL) was added ethylchloroformate (17.9 mL, 0.87 mol) dropwise. The reaction was stirred for 1.5 h after which NaN₃ (13 g, 0.200 mol) in H₂O (100 mL) was added. After 2 h, the reaction was diluted with water and left overnight. The acetone was removed and the product was filtered off to afford 21.4 g of a light brown solid. This compound was taken to the next step.

INTERMEDIATE 89

1-Benzyl-1,5-dihydro-pyrrolo[3,2-c]pyridin-4-one was prepared by the literature procedure according to C. Ducrocq; E. Bisangi; J-M, Lhoste; J. Mispelter; Tetrahedron, Vol 32, pp 773-780, (1976).

To a stirred solution of n-tributylamine (30 mL) in diphenyl ether (150 mL) heated to 195° C. was slowly added during 30 minutes a solution of the acyl azide dissolved in DCM (150 mL). The reaction mixture was stirred at 195° C. for 1 hour and then cooled to room temperature. Pentane (1.0 L) and ether (1.0 L) was added to the reaction mixture and the precipitate was collected by filtration. The crude solid was triturated with ether to give 6.89 g (81%) of the pure product. Purity HPLC>95%; MS (ESI) m/z 225 (m+H); $^1$H NMR (DMSO-d6, 25° C., 270.16) δ 10.84 (br s, 1H), 7.43-7.14 (m, 6H), 7.00 (d, J=7.12 Hz, 1H), 6.57-6.49 (m, 2H), 5.83 (s, 2H).

INTERMEDIATE 90

1-Benzyl-4-chloro-1H-indole

POCl$_3$ (3.11 mL, 33.4 mmol) was added to 1-benzyl-1,5-dihydro-4H-pyrrolo[3,2-c]pyridin-4-one (3.75 g, 16.7 mmol) and the reaction was stirred at 120° C. for 2 h. NaOH (1M) was added and the mixture was extracted with DCM three times. The organic layers were dried (MgSO$_4$), filtered and the solvent was removed. Flash chromatography (DCM/Heptane/MeOH 4:15:1) gave 1.17 g (29%) of product. The product was taken to the next step.

INTERMEDIATE 91 tert-Butyl 4-(1-benzyl-1H-pyrrolo[3,2-c]pyridin-4-yl)piperazine-1-carboxylate

A mixture of 1-benzyl-4-chloro-1H-indole (1.17 g, 4.82 mmol), K$_2$CO$_3$ (2.0 g, mmol) and Boc-piperazine (1.79 g, 9.64 mmol) in DMSO (75 mL) was stirred at 120° C. for 48 h. Additional of Boc-piperazine (4 equiv.) was added and the reaction was run for another 48 h. The reaction was diluted with ethyl acetate (200 mL) and the mixture was washed with several portions of water. Flash chromatography (DCM/MeOH/Heptane 4:1:15) gave 0.51 g of starting material and 0.38 g of product. $^1$HNMR (CD$_3$OD) δ 7.87-7.85 (m, 1H), 7.25-7.24 (m, 3H), 7.04-6.98 (m, 3H), 6.73-6.71 (m, 1H), 6.53-6.52 (m, 1H), 5.19 (s, 2H), 3.63-3.59 (m, 8H), 1.47 (s, 9H); MS (ESI) 393 (M+H)$^+$; Purity (HPLC, column ACE) 95%

INTERMEDIATE 92 tert-Butyl 4-(1H-pyrrolo[3,2-c]pyridin-4-yl)piperazine-1-carboxylate tert-Butyl 4-(1-benzyl-1H-pyrrolo[3,2-c]pyridin-4-yl)piperazine-1-carboxylate (383 mg, 0.488 mmol) was dissolved in THF (6 mL) and liquid ammonia (10 mL) in a 30 mL vial. Na (67 mg, 2.93 mmol) was added in portions and the reaction turned violet. After 30 min NH$_4$Cl (sat) was added and the reaction was let to room temperature The THF was removed and the residue was extracted with DCM. Recrystallization (DCM/Heptane) gave 112 mg of a white solid. $^1$HNMR (CD$_3$OD) δ 8.66 (s, 1H), 7.89 (d, 1H, J=5.80 Hz), 7.13-7.11 (m, 1H), 6.89-6.86 (m, 1H), 6.57-6.56 (m, 1H), 3.67-3.60 (m, 8H), 1.48 (s, 9H); MS (ESI) 303 (M+H)$^+$; Purity (HPLC, column ACE) 95%.

Method S for sulphonylation: tert-butyl 4-(1H-pyrrolo[3,2-c]pyridin-4-yl)piperazine-1-carboxylate (total 1.391 mmol, 1 equiv.) dissolved in THF (14 mL) and dispense to 10 mL vials with screwcap. A suspension of NaH (0.1488 mmol, 1.5 equiv.) in THF (15 mL) was dispense evenly to the vials containing the solution of tert-butyl 4-(1H-pyrrolo[3,2-c]pyridin-4-yl)piperazine-1-carboxylate and stirred for approximately for 15 min. Different sulfonylchlorides were dissolved in THF (2 mL) each and added drop-wise to the reaction mixtures. The reactions were quenched with MeOH (100 µL) and PS-Trisamine (3 equiv.) was added to each vial and shake for 2 hours. The mixtures were filtered and the filtrates were concentrate under vacuum. The products that were not pure enough (Purity <90%) were purified by preparative chromatography using acetonitrile-water gradients containing 0.1% trifluoroacetic acid. After HPLC analysis fractions that were ≧90% pure were collected and concentrated.

Method T BOC deprotection; The Boc-protected compound was dissolved in MeOH (2 mL) and HCL/ether (2 mL) was added. After 45 min the solvent was removed.

INTERMEDIATE 93 tert-Butyl-4-[1-(phenylsulfonyl)-1H-pyrrolo[3,2-c]pyridin-4-yl]piperazine-1-carboxylate Purification by recrystallization gave 16 mg (56%) after Boc-deprotection.
$^1$HNMR (CDCl$_3$) δ 8.03-8.01 (m, 1H), 7.89-7.86 (m, 2H), 7.57-7.39 (m, 5H), 6.67-6.64 (m, 1H), 3.55-3.52 (m, 8H), 1.47 (s, 9H); MS (ESI) 443 (M+H)$^+$; Purity (HPLC, column ACE) 95%.

INTERMEDIATE 94 tert-Butyl-4-{1-[(4-chlorophenyl)sulfonyl]-1H-pyrrolo[3,2-c]pyridin-4-yl}piperazine-1-carboxylate Purification by preparative HPLC gave 4 mg (11%) after Boc-deprotection.
$^1$HNMR (CDCl$_3$) δ 8.03-7.51 (m, 7H), 6.89-6.87 (m, 1H), 3.91-3.66 (m, 8H), 1.47 (s, 9H); MS (ESI) 377 (M+H)$^+$; Purity (HPLC, column ACE) 95%.

INTERMEDIATE 95 tert-Butyl-4-{1-[(4-methoxyphenyl)sulfonyl]-1H-pyrrolo[3,2-c]pyridin-4-yl}piperazine-1-carboxylate Purification by recrystallization (MeOH/Ether) gave 21 mg (67%) after boc-deprotection. $^1$HNMR (CDCl$_3$) δ 8.02-8.00 (m, 1H), 7.84-7.80 (m, 2H), 7.48-7.46 (m, 1H), 7.41-7.38 (m, 1H), 6.92-6.86 (m, 2H), 6.64-6.62 (m, 1H), 3.79 (s, 3H), 3.57-3.52 (m, 8H), 1.48 (s, 9H); MS (ESI) 473 (M+H)$^+$; Purity (HPLC, column ACE) 95%.

INTERMEDIATE 96 tert-Butyl 4-(1-{[2-(trifluoromethyl)phenyl]sulfonyl}-1H-pyrrolo[3,2-c]pyridin-4-yl)piperazine-1-carboxylate Purification by preparative HPLC gave 8.6 mg (25%) after boc-deprotection. $^1$HNMR (CDCl$_3$) δ 8.14-8.11 (m, 1H), 8.01-7.94 (m, 2H), 7.89-7.72 (m, 3H), 7.37-7.34 (m, 1H), 6.89-6.88 (m, 1H), 3.93-3.89 (m, 4H), 3.71-3.67 (m, 4H), 1.47 (s, 9H); MS (ESI) 511 (M+H)$^+$; Purity (HPLC, column ACE) 95%.

INTERMEDIATE 97 tert-Butyl 4-{1-[(2-methoxy-5-methylphenyl)sulfonyl]-1H-pyrrolo[3,2-c]pyridin-4-yl} piperazine-1-carboxylate Purification by preparative HPLC gave 10.3 mg (32%) after boc-deprotection. $^1$HNMR (CDCl$_3$) δ 7.95-7.92 (m, 2H), 7.74-7.72 (m, 1H), 7.44-7.40 (m, 2H), 6.85-6.77 (m, 2H), 3.92-3.88 (m, 4H), 3.70 (s, 3H), 3.69-3.66 (m, 4H), 2.39 (s, 3H), 1.47 (s, 9H); MS (ESI) 487 (M+H)+; Purity (HPLC, column ACE) 95%.

EXAMPLE 121

4-Piperazin-1-yl-1-(toluene-4-sulfonyl)-1H-pyrrolo[3,2-c]pyridine hydrochloride p-Toulenesulfonyl chloride (24.6 mg) was added to tert-butyl 4-(1H-pyrrolo[3,2-c]pyridin-4-yl)piperazine-1-carboxylate the title compound (4.3 mg). LC/MS $R_T$: 1.374 (System 10 till 40% MeCN over 1.5 min, ACE C8), Purity. 91%. MS: 357 (M+1) $^1$HNMR (CD$_3$OD) δ ppm 2.39 (s, 3H) 3.48 (m, 4H) 4.06 (m, 4H) 7.22 (d, J=3.71 Hz, 1H) 7.43 (d, J=8.16 Hz, 2H) 7.95 (m, 5H).

EXAMPLE 122

1-(3-Chloro-2-methyl-benzenesulfonyl)-4-piperazin-1-yl-1H-pyrrolo[3,2-c]pyridine hydrochloride 3-Chloro-2-methylbenzenesulfonyl chloride (29.0 mg) was added to tert-butyl 4-(1H-pyrrolo[3,2-c]pyridin-4-yl)piperazine-1-carboxylate the title compound (6.3 mg). LC/MS $R_T$: 1.563 (System 10 till 40% MeCN over 1.5 min, ACE C8), Purity. 96%. MS: 392 (M+1).

EXAMPLE 123

1-(3,4-Dimethoxy-benzenesulfonyl)-4-piperazin-1-yl-1H-pyrrolo[3,2-c]pyridine hydrochloride 3,4-Dimethoxybenzenulfonyl chloride (30.5 mg) was added to tert-butyl 4-(1H-pyrrolo[3,2-c]pyridin-4-yl)piperazine-1-carboxylate the title compound (8.5 mg). LC/MS $R_T$: 1.284 (System 10 till 40% MeCN over 1.5 min, ACE C8), Purity. 92%. MS: 404 (M+1) $^1$HNMR (CD$_3$OD) δ ppm 3.50 (m, J=4.21 Hz, 2H) 3.85 (d, J=3.22 Hz, 4H) 4.10 (m, J=3.96 Hz, 2H) 7.11 (d, J=8.66 Hz, 1H) 7.23 (d, J=3.46 Hz, 1H) 7.48 (d, J=1.73 Hz, 1H) 7.74 (dd, J=8.54, 1.86 Hz, 1H) 7.92 (s, 2H) 8.07 (d, J=3.46 Hz, 1H).

EXAMPLE 124

4-(4-Piperazin-1-yl-pyrrolo[3,2-c]pyridine-1-sulfonyl)-benzonitrile hydrochloride 4-Cyanobenzenesulfonyl chloride (26.0 mg) was added to tert-butyl 4-(1H-pyrrolo[3,2-c]pyridin-4-yl)piperazine-1-carboxylate the title compound (9.1 mg). LC/MS $R_T$: 1.150 (System 10 till 40% MeCN over 1.5 min, ACE C8), Purity. 93%. MS: 369 (M+1) $^1$HNMR (CD$_3$OD) δ ppm 3.50 (m, 4H) 4.08 (m, 4H) 7.29 (d, J=3.71 Hz, 2H) 7.98 (m, 4H) 8.29 (d, J=8.66 Hz, 2H).

EXAMPLE 125

1-(4,5-Dichloro-thiophene-2-sulfonyl)-4-piperazin-1-yl-1H-pyrrolo[3,2-c]pyridine hydrochloride 4,5-Dichloro-thiophene-2-sulfonyl chloride (32.4 mg) was added to tert-butyl 4-(1H-pyrrolo[3,2-c]pyridin-4-yl)piperazine-1-carboxylate the title compound (0.3 mg). LC/MS $R_T$: 1.119 (System 10 till 40% MeCN over 1.5 min, ACE C8), Purity. 92%. MS: 418 (M+1).

EXAMPLE 126

1-(2-Chloro-4-fluoro-benzenesulfonyl)-4-piperazin-1-yl-1H-pyrrolo[3,2-c]pyridine hydrochloride 2-Chloro-4-flourobenzenesulfonyl chloride (29.5 mg) was added to tert-butyl 4-(1H-pyrrolo[3,2-c]pyridin-4-yl)piperazine-1-carboxylate the title compound (2.4 mg). LC/MS $R_T$: 1.361 (System 10 till 40% MeCN over 1.5 min, ACE C8), Purity. 90%. MS: 396 (M+1)
$^1$HNMR (CD$_3$OD) δ ppm 3.51 (m, 4H) 4.08 (m, 4H) 7.23 (dd, J=3.96, 0.49 Hz, 1H) 7.47 (m, 1H) 7.55 (dd, J=8.41, 2.47 Hz, 2H) 7.62 (d, J=6.93 Hz, 1H) 7.91 (d, J=7.18 Hz, 1H) 8.06 (d, J=3.96 Hz, 1H).

EXAMPLE 127

1-Phenylmethanesulfonyl-4-piperazin-1-yl-1H-pyrrolo[3,2-c]pyridine hydrochloride Phenyl-methanesulfonyl chloride (24.6 mg) was added to tert-butyl 4-(1H-pyrrolo[3,2-c]pyridin-4-yl)piperazine-1-carboxylate the title compound (0.2 mg). LC/MS $R_T$: 1.007 (System 10 till 40% MeCN over 1.5 min, ACE C8), Purity. 90%. MS: 357 (M+1).

EXAMPLE 128

1-(5-Chloro-thiophene-2-sulfonyl)-4-piperazin-1-yl-1H-pyrrolo[3,2-c]pyridine hydrochloride 5-Chlorothiophene-2-sulfonyl chloride (28.0 mg) was added to tert-butyl 4-(1H-pyrrolo[3,2-c]pyridin-4-yl)piperazine-1-carboxylate the title compound (7.2 mg). LC/MS $R_T$: 1.381 (System 10 till 40% MeCN over 1.5 min, ACE C8), Purity. 97%. MS: 483 (M+1).

EXAMPLE 129

1-(4-Butyl-benzenesulfonyl)-4-piperazin-1-yl-1H-pyrrolo(3,2-c)pyridine hydrochloride 4-N-Butylbenzenesulfonylchloride (30.0 mg) was added to tert-butyl 4-(1H-pyrrolo[3,2-c]pyridin-4-yl)piperazine-1-carboxylate the title compound (11.9 mg). LC/MS $R_T$: 1.904 (System 10 till 40% MeCN over 1.5 min, ACE C8), Purity. 95%. MS: 400 (M+1) $^1$HNMR (CD$_3$OD) δ ppm 0.90 (t, J=7.18 Hz, 3H) 1.31 (m, 2H) 1.55 (m, 2H) 2.67 (m, 2H) 3.50 (m, 4H) 4.09 (m, J=3.96 Hz, 4H) 7.25 (d, J=3.71 Hz, 2H) 7.44 (d, J=8.16 Hz, 2H) 7.91 (m, 2H) 8.02 (m, 2H).

EXAMPLE 130

1-(4-Phenoxy-benzenesulfonyl)-4-piperazin-1-yl-1H-pyrrolo(3,2-c)pyridine hydrochloride (4-Phenoxy)benzene)sulfonyl chloride (34.7 mg) was added to tert-butyl 4-(1H-pyrrolo[3,2-c]pyridin-4-yl)piperazine-1-carboxylate the title compound (12.8 mg). LC/MS $R_T$: 1.839 (System 10 till 40% MeCN over 1.5 min, ACE C8), Purity. 95%. MS: 436 (M+1) $^1$HNMR (CD$_3$OD) δ ppm 3.50 (m, J=3.96 Hz, 4H) 4.09 (m, J=4.45 Hz, 4H) 7.05 (dd, J=8.16, 6.43 Hz, 2H) 7.26 (m, 2H) 7.44 (t, J=7.79 Hz, 2H) 7.90 (m, 3H) 8.01 (d, J=3.71 Hz, 2H) 8.07 (d, J=8.91 Hz, 2H).

EXAMPLE 131

1-(Phenylsulfonyl)-4-piperazin-1-yl-1H-pyrrolo[3,2-c]pyridine hydrochloride

Purification by recrystallization gave 16 mg (56%) after Boc-deprotection. MS (ESI) 343.1 (M+H)$^+$; Purity (HPLC, column ACE) 94%.

EXAMPLE 132

1-[(4-Chlorophenyl)sulfonyl]-4-piperazin-1-yl-1H-pyrrolo[3,2-c]pyridine hydrochloride Purification by preparative HPLC gave 4 mg (11%) after Boc-deprotection. MS (ESI) 377 (M+H)$^+$; Purity (HPLC, column ACE) 96%.

EXAMPLE 133

1-[(4-Methoxyphenyl)sulfonyl]-4-piperazin-1-yl-1H-pyrrolo[3,2-c]pyridine hydrochloride Purification by recrystallization (MeOH/Ether) gave 21 mg (67%) after Boc-deprotection. MS (ESI) 373 (M+H)$^+$; Purity (HPLC, column ACE) 92%

EXAMPLE 134

1-[(2-Methoxy-5-methylphenyl)sulfonyl]-4-piperazin-1-yl-1H-pyrrolo[3,2-c]pyridine hydrochloride Purification by preparative HPLC gave 10.3 mg (32%) after Boc-deprotection. MS (ESI) 387 (M+H)$^+$; Purity (HPLC, column ACE) 95%.

EXAMPLE 135

4-Piperazin-1-yl-1-{[2-(trifluoromethyl)phenyl]sulfonyl}-1H-pyrrolo[3,2-c]pyridine hydrochloride Purification by preparative HPLC gave 8.6 mg (25%) after Boc-deprotection. MS (ESI) 411 (M+H)$^+$; Purity (HPLC, column ACE) 94%.

Biological Tests

The ability of a compound according to the invention to bind a 5-HT$_6$ receptor, and to be pharmaceutically useful, can be determined using in vivo and in vitro assays known in the art.

(a) 5-HT$_6$ Binding Assay

Binding affinity experiment for the 5-HT$_6$ receptor are performed in HEK293 cells transfected with 5-HT$_6$ receptor using (3H)-LSD as labeled ligand according to the general method as described by Boess F. G et al. Neuropharmacology vol. 36(4/5) 713-720, 1997.

Materials
Cell Culture

The HEK-293 cell line transfected with the 5-HT$_6$ receptor was cultured in Dulbeccos Modified Eagles Medium containing 5% dialyzed foetal bovine serum, (Gibco BRL 10106-169), 0.5 mM sodium pyruvate and 400 µg/ml Geneticin (G-418) (Gibco BRL10131-019). The cells were passaged 1:10, twice a week.

Chemicals

The radioligand [$^3$H] LSD 60-240 Ci/mmol, obtained from Amersham Pharmacia Biotech, (Buckinghamshire, England) was in ethanol and stored at −20° C. The unlabelled ligands, representing different selectivity profiles, are presented in Table 1. The compounds were dissolved in 100% DMSO and diluted with binding buffer.

Disposable

Compounds were diluted in Costar 96 well V-bottom polypropylene plates (Corning Inc. Costar, N.Y., USA). Samples were incubated in Packard Optiplate (Packard Instruments B. V., Groningen, The Netherlands). The total amount of added radioligand was measured in Packard 24-well Barex plates (Packard Instruments B. V., Groningen, The Netherlands) in the presence of Microscint™ 20 scintillation fluid (Packard Bioscience, Meriden, Conn., USA).

Buffer

The binding buffer consisted of 20 mM HEPES, 150 mM NaCl, 10 mM MgCl$_2$, and 1 mM, EDTA, pH 7.4.

Methods
Membrane Preparation

Cells were grown to approximately 90% confluence on 24.5×24.5 NUNC culture dishes. The medium was aspirated, and after rinsing with ice-cold PBS, the cells were scraped off using 25 ml Tris buffer (50 mM Tris-HCl, 1 mM EDTA, 1 mM EGTA, pH 7.4) and a window scraper. The cells were then broken with a Polytron homogeniser, and remaining particulate matter was removed by low-speed centrifugation, 1000×g for 5 min. Finally, the membranes were collected by high-speed centrifugation (20 000×g), suspended in binding buffer, and frozen in aliquots at −70° C.

Radioligand Binding

Frozen cell membranes were thawed, immediately rehomogenized with a Polytron homogenizer, and coupled to SPA wheat germ agglutinin beads (Amersham Life Sciences, Cardiff, England) for 30 min under continuous shaking of the tubes. After coupling, the beads were centrifuged for 10 minutes at 1000 g, and subsequently suspended in 20 ml of binding buffer per 96-well plate The binding reaction was then initiated by adding radioligand and test compounds to the bead-membrane suspension. Following incubation at room temperature, the assay plates were subjected to scintillation counting.

The original SPA method was followed except for that membranes were prepared from HEK293 cells expressing the human 5-HT$_6$ receptor instead of from HeLa cells (Dinh D M, Zaworski P G, Gill G S, Schlachter S K, Lawson C F, Smith M W. Validation of human 5-HT$_6$ receptors expressed in HeLa cell membranes: saturation binding studies, pharmacological profiles of standard CNS agents and SPA development. The Upjohn Company Technical Report 7295-95-064 1995; 27 Dec.). The specific binding of [$^3$H]LSD was saturable, while the non-specific binding increased linearly with the concentration of added radioligand. [$^3$H] LSD bound with high affinity to 5-HT$_6$ receptors. The K$_d$ value was estimated to 2.61 0.2 nM based on four separate experiments.

The total binding at 3 nM of [$^3$H] LSD, the radioligand concentration used in the competition experiments, was typically 6000 dpm, and the specific binding more than 70%. 5-HT caused a concentration dependent inhibition of [$^3$H] LSD binding with an over all average Ki value of 236 nM when tested against two different membrane preparations. The inter assay variability over three experiments showed a CV of 10% with an average K$_i$ values of 173 nM (SD 30) and a Hill coefficient of 0.94 (SD 0.09). The intra assay variation was 3% (n—4). Ki values for a limited set of reference compounds with reported binding affinities at 5-HT$_6$ receptor are presented in Table 7. All unlabelled ligands displaced the specific binding of [$^3$H] LSD in a concentration-dependent manner, albeit at different potencies. The rank order of potency for the compounds was methiothepin (2 nM)>mianserin (190 nM)≈5-HT (236 nM)>methysergide (482 nM)>mesulergide (1970 nM).

Protein Determination

Protein concentrations were determined with BioRad Protein Assay (Bradford MM. A rapid and sensitive method for the quantitation of microgram quantities of protein utilizing the principle of protein-dye binding. Anal Biochem 1976; 72:248-54). Bovine serum albumin was used as standard.

Scintillation Counting

The radioactivity was determined in a Packard TopCount™ scintillation counter (Packard Instruments, Meriden, Conn., USA) at a counting efficiency of approximately 20%. The counting efficiency was determined in separate sets of experiments.

Saturation Experiments

At least 6 concentrations in duplicates of radioligand (0.1-20 nM of [$^3$H] LSD) were used in saturation experiments. The specific binding was calculated as the difference between total binding and non-specific binding, which was determined as the binding of radioligand in the presence of 5 μM lisuride. $B_{max}$ and the dissociation constant, $K_d$, were determined from the non-linear regression analysis using equation 1. $L_u$ is the unbound concentration of radioligand, and is y is the amount bound.

$$y = \frac{B_{max} \cdot Lu}{Lu + Kd} \quad \text{(equation 1)}$$

Competition Experiments

Total- and non-specific binding of radioligand was defined in eight replicates of each. Samples containing test compound were run in duplicate at 11 concentrations. Incubations were carried out at room temperature for 3 hours. The $IC_{50}$ value, i.e. the concentration of test compound that inhibited 50% of the specific binding of radioligand, was determined with non linear regression analysis and the $K_i$ value was calculated using the method of [Cheng Y. C. Biochem. Pharmacol. 22, 3099-3108, 1973S] equation 2.

$$Ki = \frac{IC_{50}}{1 + \frac{L}{K_d}} \quad \text{(equation 2)}$$

L=concentration of radioligand
$K_d$=Affinity of radioligand (b) 5-HT$_6$ Intrinsic Activity Assay Antagonists to the 5-HT$_6$ receptor were characterized by measuring inhibition of 5-HT induced increase in cAMP in HEK 293 cells expressing the human 5-HT$_6$ receptor (see Boess et al. (1997) Neuropharmacology 36: 713-720). Briefly, HEK293/5-HT$_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% $CO_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 μl dissolved in assay medium, the cells were incubated for 10 min at 37° C. in a 5% $CO_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times $EC_{50}$) evoked increase in cAMP, using the formula $IC_{50, corr}$=$IC_{50}/(1+[5HT]/EC_{50})$.

The compounds in accordance with the invention have a selective affinity to 5-HT$_6$ receptors with $K_i$ and $IC_{50,corr}$ values between 0.5 nM and 5 μM or display a % inhibition of [$^3$H] LSD≧20% at 50 nM and are antagonists, agonist or partial agonist at 5-HT$_6$. The compounds show good selectivity over 5-HT$_{1a}$, 5-HT$_{2a}$, 5-HT$_{2a}$, 5-HT$_{2b}$, 5-HT$_{2c}$.

(c) In Vivo Assay of Reduction of Food Intake

For a review on serotonin and food intake, see Blundell, J. E. and Halford, J. C. G. (1998) Serotonin and Appetite Regulation. Implications for the Pharmacological Treatment of Obesity. CNS Drugs 9:473-495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57B1/6JBom; Bomholtsgaard, Denmark) 8-9 weeks with an average body weight of 50 g (obese) and 25 g (lean) are used in all the studies. The animals are housed singly in cages at 23±1° C., 40-60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulfonic acid, polyethylene glycol/methane sulfonic acid, saline. Fresh solutions are made for each study. Doses of 30, 50 and 100 mg kg$^{-1}$day$^{-1}$ are used. The purity of the test compounds is of analytical grade.

The animals are weighed at the start of the study and randomized based on body weight. Alzet osmotic minipumps (Model 2001D; infusion rate 8 μl/h) are used and loaded essentially as recommended by the Alzet technical information manual (Alza Scientific Products, 1997; Theeuwes, F. and Yam, S. I. Ann. Biomed. Eng. 4(4). 343-353, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min. It takes about 3 h to reach steady state delivery of the compound.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring. A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean±SD and ±SEM from eight animals per dose group. Statistical evaluation is performed by Kruskal-Wallis one-way ANOVA using the percent basal values. If statistical significance is reached at the level of p<0.05, Mann-Whitney U-test for statistical comparison between control and treatment groups is performed.

The compounds according to the invention show an effect in the range of 5-200 mg/kg.

TABLE 7

Biological data

In vitro binding at the human 5-HT6 receptor

| EXAMPLE | $K_i$ (nM) human 5-HT$_6$ |
|---|---|
| 1 | 10 |
| 11 | 6.5 |
| 20 | 10.5 |
| 40 | 7.5 |
| 43 | 4.5 |
| 68 | 13 |
| 85 | 32 |
| 131 | 5 |

In vivo efficacy data

| EXAMPLE | % FI reduction* | Css, u (uM) |
|---|---|---|
| 1 | 12 | 0.44 |
| 11 | 47.1 | 0.02 |
| 40 | 44 | 0.2 |

*Effect on Food Intake reduction In Ob/ob mice Single administration 50 mg/kg/d measured at steady state

The invention claimed is:

1. A compound of the formula (I):

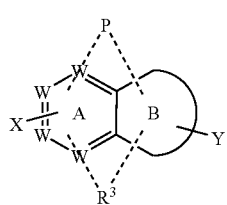

or a pharmaceutically acceptable salt thereof, wherein:
ring B is

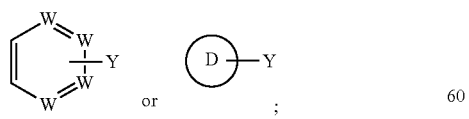

in which D is a five-membered heterocyclic or heteroaryl ring, said ring comprising one or two atoms selected from the group consisting of nitrogen, sulfur and oxygen, with the proviso that when D contains an oxygen atom, D is heteroaryl;

each W is independently —N—, —(CH)—, or —C— provided that not more than three groups W are —N— in both rings A and B together;

P is any one of formula (a), (b) or (c)

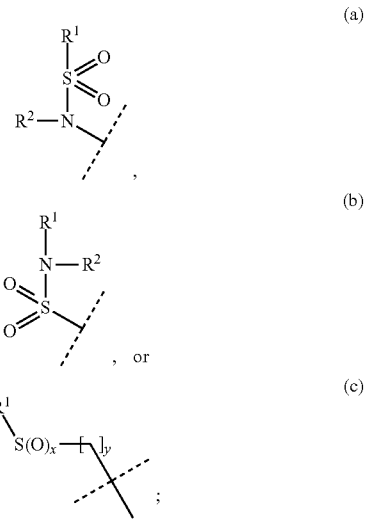

wherein x=0, 1, or 2 and y=0, 1, or 2;

and P and $R^3$ can be attached to any carbon atom that allows the substitution in one of either the A- or B-ring, or when ring A contains at least one nitrogen atom and P is (c), then P can alternatively be attached to any nitrogen in ring B that allows the substitution;

the dashed bonds denote that P and $R^3$, respectively, may be attached to either the A or B ring; but each of P or $R^3$ may not be simultaneously bound to both rings A and B;

$R^1$ is
(a) $C_{1-6}$ alkyl,
(b) $C_{1-6}$ alkoxyalkyl,
(c) straight-chained or branched $C_{1-6}$ hydroxyalkyl,
(d) straight-chained or branched $C_{1-6}$ alkylhalides,
(e) aryl carbonylmethyl,
(f) $C_{3-7}$ cycloalkyl, which is optionally partially unsaturated,
(g) $C_{3-7}$ cycloalkyl-$C_{1-6}$ alkyl, wherein the cyclic ring is optionally partially unsaturated, or
(h) a group Ar;
wherein Ar is
(a) phenyl,
(b) 1-naphthyl,
(c) 2-naphthyl,
(d) aryl-$C_{1-6}$ alkyl,
(e) cinnamyl,
(f) a 5 to 7-membered, optionally aromatic, partially saturated or completely saturated, mono- or bi-cyclic heterocyclic ring, each containing 1 to 4 heteroatoms, selected from oxygen, sulfur, and nitrogen,
(g) a bicyclic ring system comprising at least one heterocyclic ring according to (f) and a group Ar,
wherein the group Ar is substituted in one or more positions with
(a) H, X or Y, or
(b) a 5 to 7-membered, optionally aromatic, partially saturated or completely saturated, heterocyclic ring each containing 1 to 4 heteroatoms selected from oxygen, nitrogen and sulfur;

$R^2$ is
 (a) H,
 (b) $C_{1-6}$ alkyl,
 (c) $C_{2-6}$ alkoxyalkyl,
 (d) straight or branched $C_{1-6}$ hydroxyalkyl, or
 (e) straight or branched $C_{1-6}$ alkylhalides;
 (f) a group Ar,
or $R^1$ and $R^2$ are linked to form a group —$CH_2CH_2OCH_2CH_2$—
or, when P is —$SO_2NR^1R^2$, $NR^1R^2$ is:

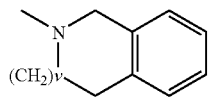

wherein v is 0-2,

X and Y are independently
 (a) H,
 (b) halogen,
 (c) $C_{1-6}$ alkyl,
 (d) $CF_3$,
 (e) hydroxy,
 (f) $C_{1-6}$ alkoxy,
 (g) $C_{2-6}$ alkenyl,
 (h) phenyl,
 (i) phenoxy,
 (j) benzyloxy,
 (k) benzoyl,
 (l) —$OCF_3$,
 (m) —CN,
 (n) straight or branched $C_{1-6}$ hydroxyalkyl,
 (o) straight or branched $C_{1-6}$ alkylhalides,
 (p) —$NH_2$,
 (q) —$NHR^4$,
 (r) —$NR^4R^5$,
 (s) —$NO_2$,
 (t) —$CONR^4R^5$,
 (u) —$NHSO_2R^4$,
 (v) —$NR^4COR^5$,
 (x) —$SO_2NR^4R^5$,
 (z) —C(=O)$R^4$,
 (aa) —$CO_2R^4$, or
 (ab) —$S(O)_nR^4$, wherein n is 0, 1, 2 or 3,
 (ac) —S—($C_{1-6}$)alkyl, or
 (ad) —$SCF_3$; and $R^4$ and $R^5$ are independently
 (a) H,
 (b) $C_{1-6}$ alkyl,
 (c) $C_{3-7}$ cycloalkyl, or
 (d) Ar, as defined above for $R^1$;

alternatively, $R^4$ and $R^5$ are linked to form a group —$CH_2OCH_2$—, —$CH_2CH_2OCH_2CH_2$— or $(CH_2)_{3-5}$;

$R^3$ is a group selected from the group consisting of

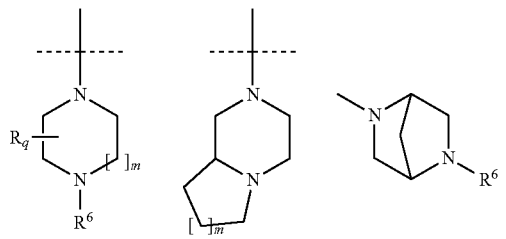

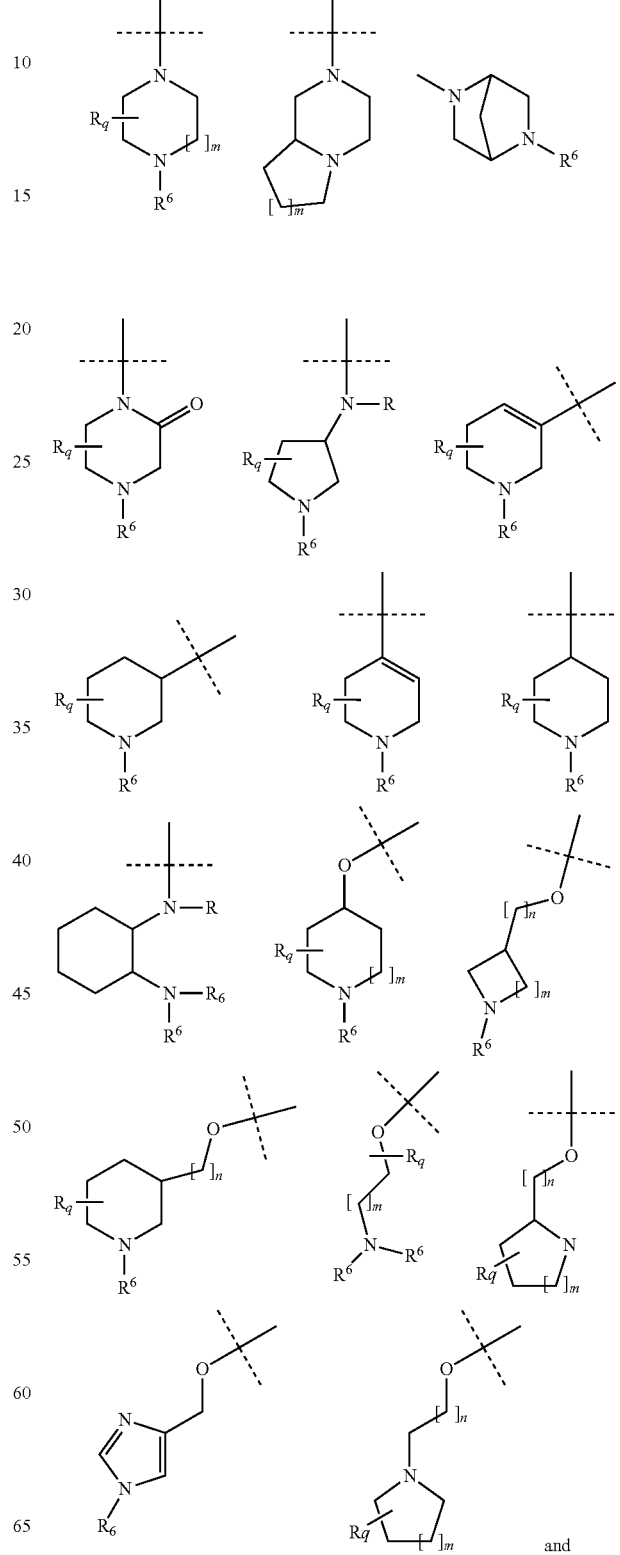

and

-continued

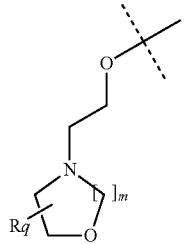

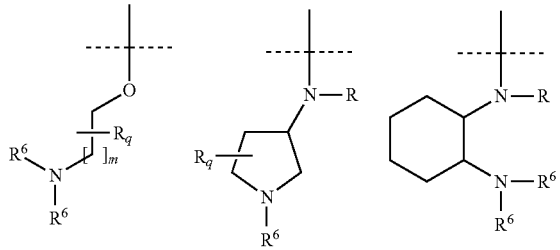

wherein R³ is optionally substituted on each carbon atom that allows the substitution with one, two, three, four, five, or six Rq groups, wherein each Rq is (C$_{1-6}$) alkyl, and wherein two Rq groups can be present on the same carbon atom simultaneously, wherein R is H or C$_{1-6}$ alkyl;

m=1 or 2, and n=0, 1 or 2;

each R⁶ is independently
  (a) H,
  (b) linear or branched C$_{1-6}$ alkyl,
  (c) benzyl,
  (d) —CH$_2$—CH$_2$—OH, or
  (e) —CH$_2$—CH$_2$—O—C$_{1-6}$ alkyl;

P and R³ can be attached to the same ring or to different rings of rings A and B; provided that:

(1) when the compound is a compound according to formula (I) wherein P is

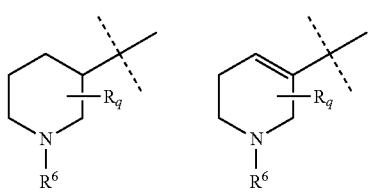

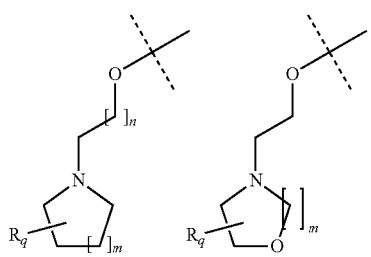

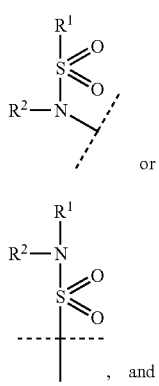

(a)

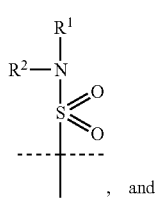

or (b)

P and R³ both are attached to ring A in the meta- or para-position relative to one another then R³ is selected from the group consisting of:

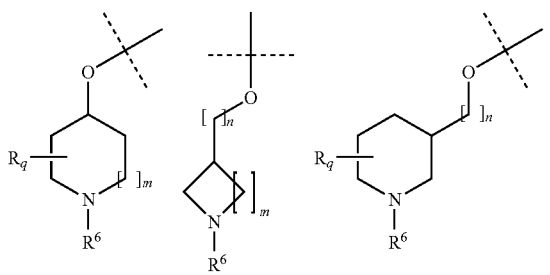

(2) when ring B is

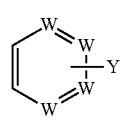

and P is (a)

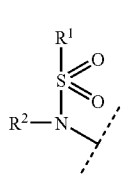

then P and R³ are simultaneously attached to the same ring A or B;

(3) when ring B is

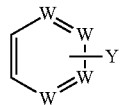

and P is

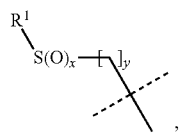

wherein y=0, then P and $R^3$ are attached to the different rings of rings A and B;

(4) when the ring system A+B is benzofuran or benzothiophene, and P is:

(c)

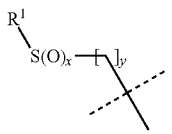

and attached to position 3 in the A+B ring system, and $R^3$ is a group selected from the group consisting of:

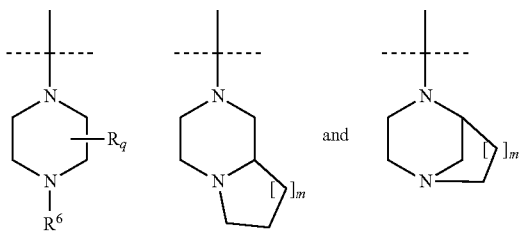

and attached to position 7 in the A+B ring system, then y=1 or 2;

(5) when the ring system A+B is indole, and P is:

(c)

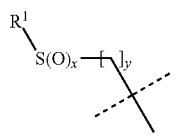

and P is attached to position 3 in the A+B ring system, and $R^3$ is a group selected from the group consisting of:

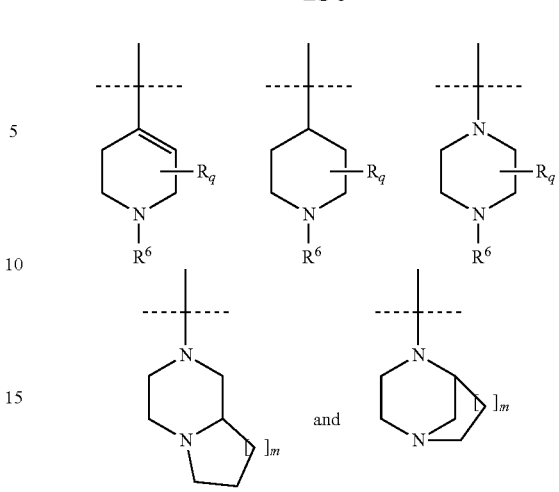

and $R^3$ is attached to any one of positions 5, 6 or 7 in the A+B ring system, then y=1 or 2;

(6) when ring B is

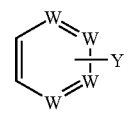

and $R^1$ is Ar and is a partially saturated bi-cyclic heterocyclic ring containing a N atom, the N atom in Ar cannot be attached to the S atom in P;

(7) when rings A and B are both phenyl, together forming a naphthalene ring, and P is any one of formula (a) or (c) substituted in position 7 on the naphthalene ring, then $R^3$ is not substituted in position 1 on the naphthalene ring; and (8) when ring D is a pyrrole ring, P is of the formula (c), then $R^3$ is not of the formula:

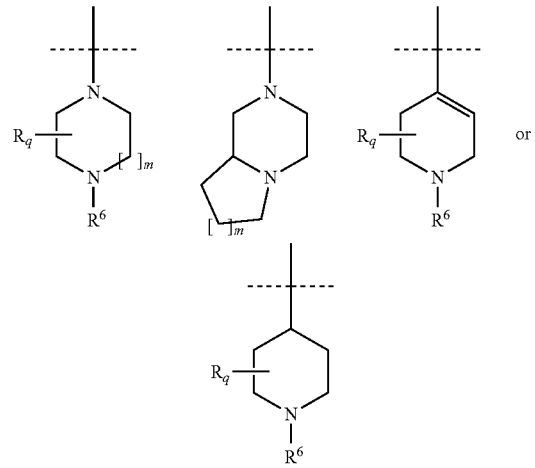

substituted in position 3 on the pyrrole ring.

2. The compound according to claim 1, or pharmaceutically acceptable salt thereof, wherein
$R^1$ is
(a) $C_{1-6}$ alkyl, or
(e) a group Ar;

Ar is
- (a) phenyl,
- (b) 1-naphthyl,
- (c) 2-naphthyl, or
- (f) a 5 to 7-membered, optionally aromatic, partially saturated or completely saturated, heterocyclic ring containing 1 to 4 heteroatoms, selected from oxygen, nitrogen and sulfur, wherein the group Ar is substituted in one or more positions with
- (a) H,
- (b) halogen,
- (c) $C_{1-6}$ alkyl,
- (d) —$CF_3$,
- (f) $C_{1-6}$ alkoxy,
- (g) $C_{2-6}$ alkenyl,
- (l) —$OCF_3$,
- (m) straight or branched $C_{1-6}$ hydroxyalkyl,
- (n) phenyloxy,
- (o) benzyloxy,
- (v) —$NR^4COR^5$,
- (x) —$SO_2NR^4R^5$,
- (z) —$C(=O)R^4$,
- (ab) —$S(O)_nR^4$, wherein n is 0, 1, 2 or 3;
- (ac) —S—($C_{1-6}$) alkyl, or
- (ad) —$SCF_3$;

$R^2$ is
- (a) H, or
- (b) $C_{1-6}$ alkyl;

or $R^1$ and $R^2$ are linked to form a group —$CH_2CH_2OCH_2CH_2$—;

X and Y are H;

$R^4$ and $R^5$ are each independently H or $C_{1-3}$ alkyl; and $R^3$ is selected from the group consisting of

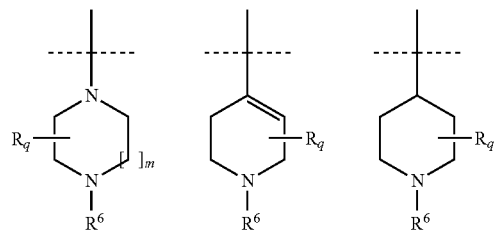

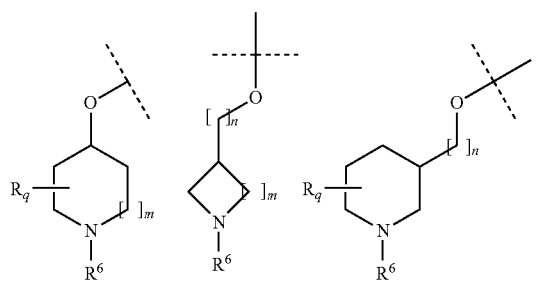

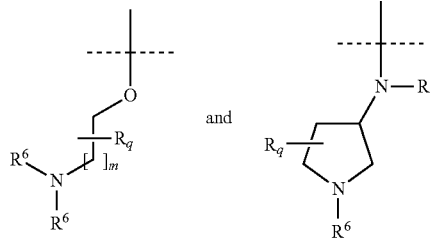

wherein $R^3$ is optionally substituted on each carbon atom that allows the substitution with one or two Rq groups, wherein each Rq is $C_{1-6}$ alkyl, and wherein two Rq groups can be present on the same carbon atom simultaneously, wherein R is H or $C_{1-6}$ alkyl;

m=1 or 2, n=0, and each $R^6$ is independently
- (a) H,
- (b) $C_{1-6}$ alkyl, in particular methyl,
- (d) —$CH_2$—$CH_2$—OH, or
- (e) —$CH_2$—$CH_2$—$OCH_3$.

3. The compound of claim 1, or pharmaceutically acceptable salt thereof, wherein $R^3$ is selected from the group consisting of:

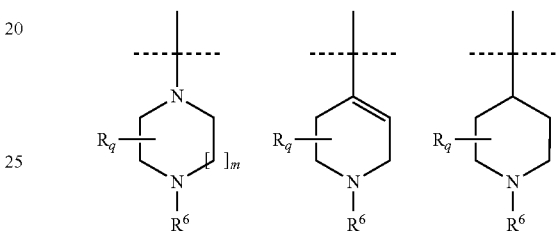

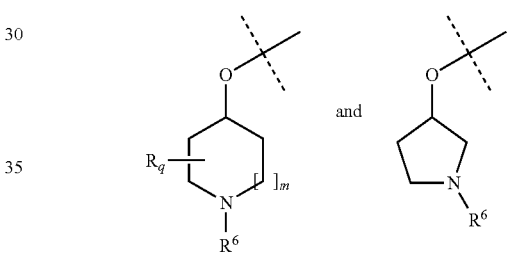

wherein $R^3$ is optionally substituted on each carbon atom that allows the substitution with one or two Rq groups, wherein each Rq is $C_{1-2}$ alkyl, and wherein two Rq groups can be present on the same carbon atom simultaneously, wherein m=1 or 2; and $R^6$ is
- (a) H,
- (b) $C_{1-3}$ alkyl,
- (d) —$CH_2$—$CH_2$—OH, or
- (e) —$CH_2$—$CH_2$—$OCH_3$.

4. The compound of claim 1, or pharmaceutically acceptable salt thereof; wherein $R^3$ is selected from the group consisting of:

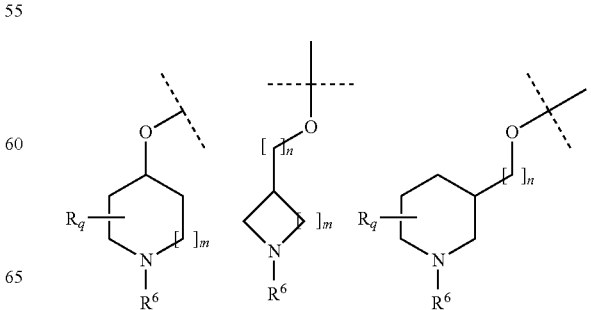

-continued

[chemical structures showing R³ substituent options with O-linker and pyrrolidine-N-R]

wherein R³ is optionally substituted on each carbon atom that allows the substitution with one or two Rq groups, wherein each Rq is $C_{1-6}$ alkyl, and wherein two Rq groups can be present on the same carbon atom simultaneously, wherein R is H or $C_{1-6}$ alkyl;
m=1 or 2,
n=0, and
each R⁶ is independently
  (a) H,
  (b) $C_{1-3}$ alkyl,
  (d) —CH₂—CH₂—OH, or
  (e) —CH₂—CH₂—OCH₃.

5. The compound of claim 1, or pharmaceutically acceptable salt thereof, wherein R³ is selected from:

[chemical structures: various piperazine, homopiperazine, piperidine, tetrahydropyridine rings with R⁶ substituents]

R⁶ is
(a) H,
(b) $C_{1-3}$ alkyl,
(d) —CH₂—CH₂—OH, or
(e) —CH₂—CH₂—OCH₃.

6. The compound of claim 1, or pharmaceutically acceptable salt thereof, wherein R⁶ is H or methyl.

7. The compound of claim 1, or pharmaceutically acceptable salt thereof, wherein R³ is piperazine; homopiperazine; 2,6-dimethylpiperazine; 3,5-dimethylpiperazine; 2,5-dimethylpiperazine; 2-methylpiperazine; 3-methylpiperazine; 2,2-dimethylpiperazine; 3,3-dimethylpiperazine; piperidine; 1,2,3,6-tetrahydro-pyrazine; or 4-pyrrolidin-3-yloxy.

8. The compound of claim 1, or pharmaceutically acceptable salt thereof, wherein the groups Y and X are attached to any unsubstituted carbon atom.

9. The compound of claim 1, or pharmaceutically acceptable salt thereof, wherein D is a pyrrole, thiophane, or furan ring.

10. The compound of claim 1, or pharmaceutically acceptable salt thereof, wherein P is (c)

[chemical structure showing R¹–S(O)ₓ–[ ]ᵧ group]

wherein R¹, x, and y are as defined in claim 1.

11. The compound of claim 1, or pharmaceutically acceptable salt thereof, wherein P is (a)

[chemical structure showing R²–N(R¹)–SO₂– group]

12. The compound of claim 11, or pharmaceutically acceptable salt thereof, wherein R² is H.

13. The compound of claim 10, or pharmaceutically acceptable salt thereof, wherein the compound is a compound having formula (II)

(II)

[chemical structure of formula (II): isoquinoline core with S(O)ₓ–R¹ substituent, X, Y, and R³ substituents]

wherein R¹, x, y, X, and Y are as defined in claim 1, and R³ is

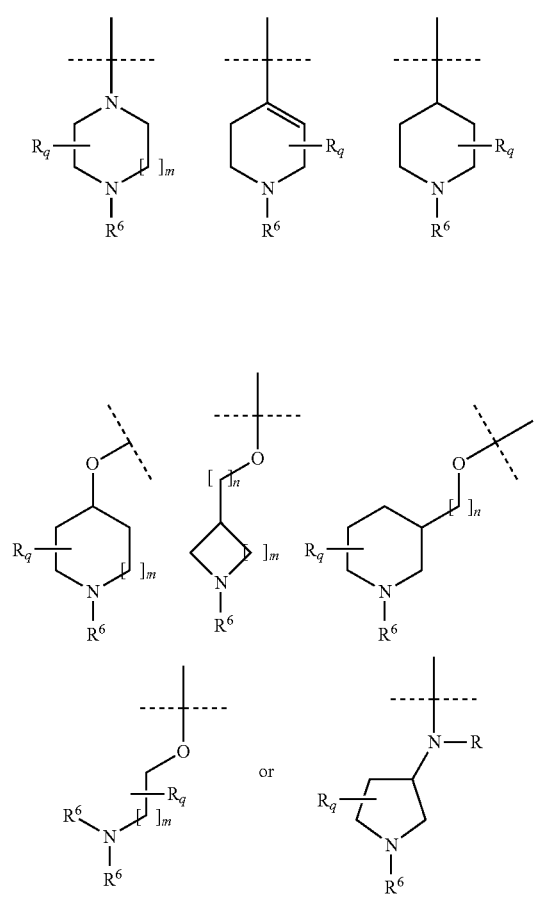

wherein $R^3$ is optionally substituted on each carbon atom that allows the substitution with one or two Rq groups, wherein each Rq is $C_{1-6}$ alkyl, and wherein two Rq groups can be present on the same carbon atom simultaneously, wherein R is H or $C_{1-6}$ alkyl, m=1 or 2, n=0; and $R^6$ is as defined in claim 1.

14. The compound of claim 13, or pharmaceutically acceptable salt thereof, wherein y=0 and x=2.

15. The compound of claim 10, or pharmaceutically acceptable salt thereof, wherein the compound is a compound having formula (III):

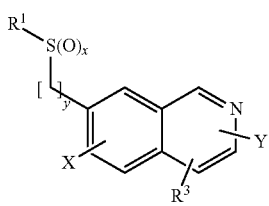

(III)

wherein $R^1$, x, y, X, and Y are as defined in claim 1, and $R^3$ is:

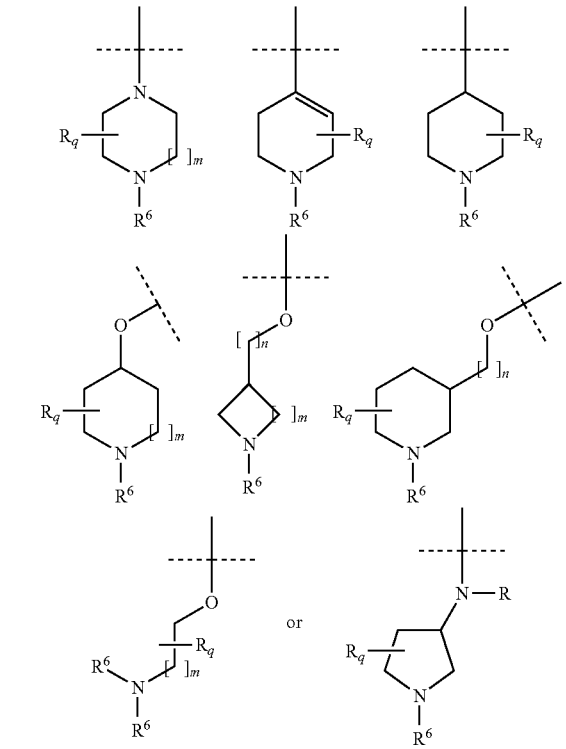

wherein $R^3$ is optionally substituted on each carbon atom that allows the substitution with one or two Rq groups, wherein Rq is independently H, or $C_{1-6}$ alkyl, and wherein two Rq groups can be present on the same carbon atom simultaneously, wherein R is H or $C_{1-6}$ alkyl, m=1 or 2, n=0; and $R^6$ is as defined in claim 1.

16. The compound of claim 15, or pharmaceutically acceptable salt thereof, wherein y=0 and x=2.

17. The compound of claim 10, or pharmaceutically acceptable salt thereof, wherein the compound is a compound having formula (IV):

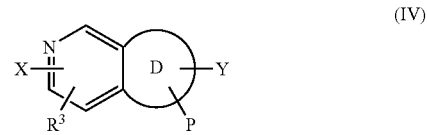

(IV)

wherein $R^1$, x, y, P, X, and Y are as defined in claim 1, and $R^3$ is

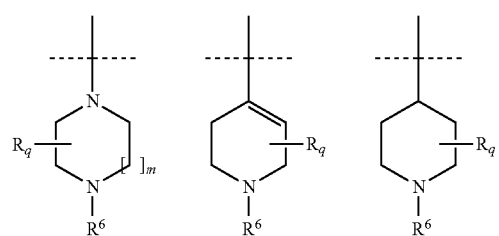

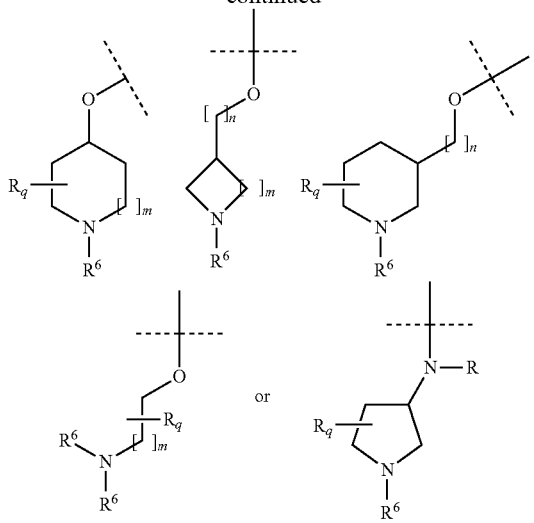

wherein R³ is optionally substituted on each carbon atom that allows the substitution with one or two Rq groups, wherein each Rq is C$_{1-6}$ alkyl, and wherein two Rq groups can be present on the same carbon atom simultaneously, wherein R is H or C$_{1-6}$ alkyl;
m=1 or 2,
n=0, and
wherein D is a five-membered heteroaryl ring, said ring comprising one or two atoms selected from the group consisting of nitrogen, sulfur and oxygen; and when the heteroaryl ring comprises one or two nitrogen atoms, a group R⁶ is attached at any nitrogen atom which allows the substitution; and R⁶ is as defined in claim 1.

18. The compound of claim 17, or pharmaceutically acceptable salt thereof, wherein D is a thiophene and P is attached to the D ring.

19. The compound of claim 17, or pharmaceutically acceptable salt thereof, wherein D is pyrrole and P is attached to the nitrogen atom in the D ring.

20. The compound of claim 17, or pharmaceutically acceptable salt thereof, wherein D is furan and P is attached to the D ring.

21. The compound of claim 10, or pharmaceutically acceptable salt thereof, wherein the compound is a compound having formula (V)

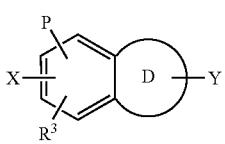

(V)

wherein R¹, x, y, P, X, Y, and R³ are as defined in claim 1, and
wherein D is a five-membered heteroaryl ring, said heteroaryl ring comprising one or two atoms selected from the group consisting of nitrogen, sulfur and oxygen; and when the heteroaryl ring comprises one or two nitrogen atoms, a group R⁶ is attached at any nitrogen atom which allows the substitution; and R⁶ is as defined in claim 1.

22. The compound of claim 11, or pharmaceutically acceptable salt thereof, wherein the compound is a compound having formula (V)

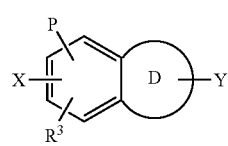

(V)

wherein P, X, Y, and R³ are as defined in claim 1, and
wherein D is a five-membered heteroaryl ring, said heteroaryl ring comprising one or two atoms selected from the group consisting of nitrogen, sulfur and oxygen; and when the heteroaryl ring comprises one or two nitrogen atoms, a group R⁶ is attached at any nitrogen atom which allows the substitution; and R⁶ is as defined in claim 1.

23. The compound of claim 11, or pharmaceutically acceptable salt thereof, wherein the compound is a compound having formula (VI)

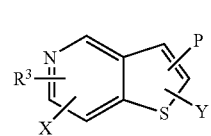

(VI)

wherein P, X and Y are as defined in claim 1, and R³ is

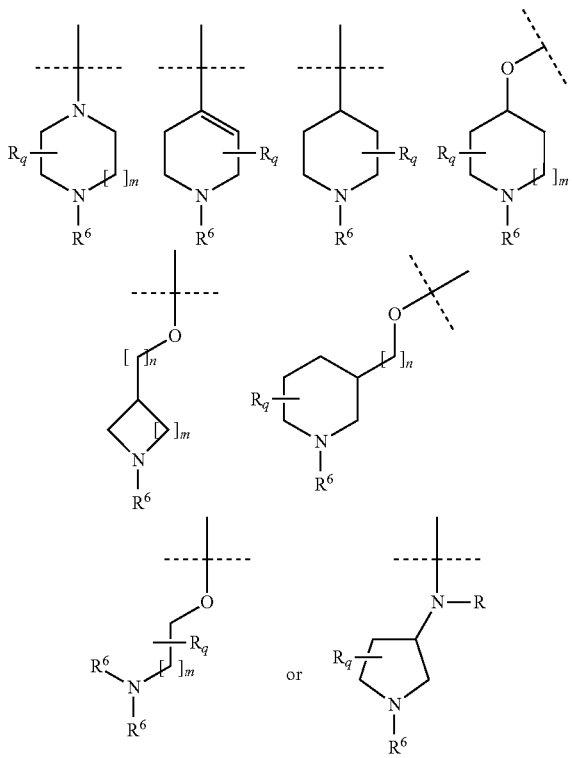

wherein R³ is optionally substituted on each carbon atom that allows the substitution with one or two Rq groups, wherein each Rq is $C_{1-6}$ alkyl, and wherein two Rq groups can be present on the same carbon atom simultaneously, wherein R is H, or $C_{1-6}$ alkyl, m=1 or 2, n=0; and $R^6$ is as defined in claim 1.

24. The compound of claim 11, or pharmaceutically acceptable salt thereof, wherein the compound is a compound having formula (VII):

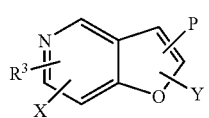
(VII)

wherein P, X and Y are as defined in claim 1, and $R^3$ is

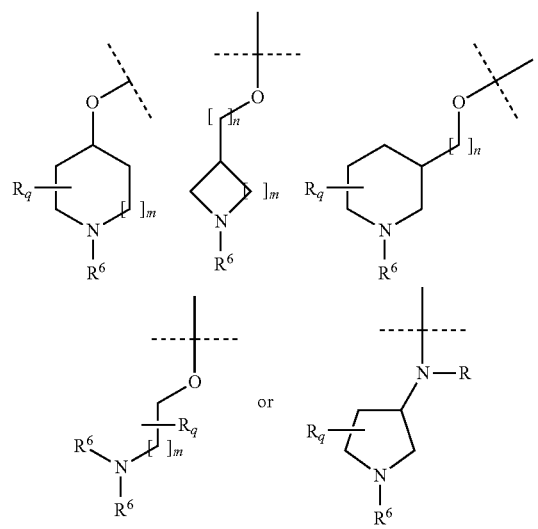

wherein $R^3$ is optionally substituted on each carbon atom that allows the substitution with one or two Rq groups, wherein each Rq is $C_{1-6}$ alkyl, and wherein two Rq groups can be present on the same carbon atom simultaneously, wherein R is H, or $C_{1-6}$ alkyl, m=1 or 2, n=0; and $R^6$ is as defined in claim 1.

25. The compound of claim 11, or pharmaceutically acceptable salt thereof, wherein the compound is a compound having formula (VIII)

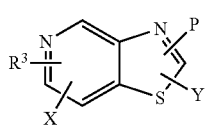
(VIII)

wherein P, X, Y, and $R^3$ are as defined in claim 1.

26. The compound of claim 11, or pharmaceutically acceptable salt thereof, wherein the compound is a compound having formula (IX)

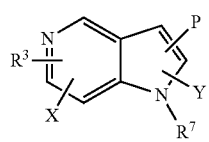
(IX)

wherein $R^7$ in formula (IX) is:
(a) H,
(b) $C_{1-6}$ alkyl,
(c) benzyl,
(d) —$CH_2$—$CH_2$—OH, or
(e) $CH_2$—$CH_2$-O—$CH_3$, and
wherein P, X, Y, and $R^3$ are as defined in claim 1.

27. The compound of claim 11, or pharmaceutically acceptable salt thereof, wherein the compound is a compound having formula (X)

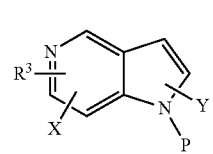
(X)

wherein P, X, Y, and $R^3$ are as defined in claim 1.

28. The compound of claim 12, or pharmaceutically acceptable salt thereof, wherein the compound is a compound having formula (XI)

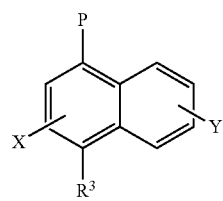
(XI)

wherein X and Y are as defined in claim 1, and $R^3$ is

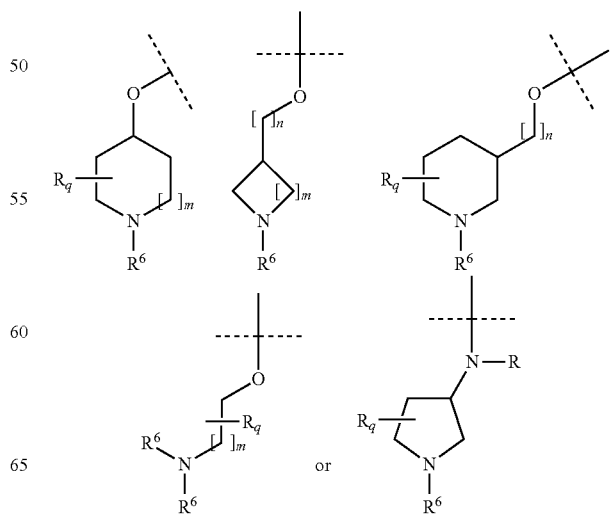

wherein R³ is optionally substituted on each carbon atom that allows the substitution with one or two Rq groups, wherein each Rq is C_{1-6} alkyl, and wherein two Rq groups can be present on the same carbon atom simultaneously, wherein
R is H, or C_{1-6} alkyl,
m=1 or 2,
n=0; and
R⁶ is as defined in claim 1.

29. The compound of claim 1, or pharmaceutically acceptable salt thereof, wherein the compound is a compound having formula (XII):

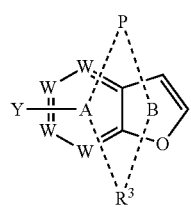

wherein P and R³ are attached to the same ring or to different rings of rings A and B, and wherein A, B, W, Y, P, and R₃ are as defined in claim 1, or a pharmaceutically acceptable salt thereof.

30. The compound of claim 13, or pharmaceutically acceptable salt thereof, wherein the compound is:
   6-Benzenesulfonyl-4-piperazin-1-yl-quinoline;
   6-[(2-Fluorophenyl)sulfonyl]-4-piperazin-1-ylquinoline;
   6-(1-Naphthylsulfonyl)-4-piperazin-1-ylquinoline;
   6-[(3,4-Dichlorophenyl)sulfonyl]-4-piperazin-1-ylquinoline;
   6-[(3,5-Dimethylphenyl)sulfonyl]-4-piperazin-1-ylquinoline;
   6-[(2-Chloro-6-methylphenyl)sulfonyl]-4-piperazin-1-ylquinoline;
   6-[(4-Chlorophenyl)sulfonyl]-4-piperazin-1-ylquinoline;
   6-[(2-Methyl-4-tert-butylphenyl)sulfonyl]-4-piperazin-1-ylquinoline;
   6-[(3,4-Dimethylphenyl)sulfonyl]-4-piperazin-1-ylquinoline;
   6-[(2,3-Dichlorophenyl)sulfonyl]-4-piperazin-1-ylquinoline;
   6-[(4-tert-Butylphenyl)sulfonyl]-4-piperazin-1-ylquinoline;
   6-[(4-Isopropylphenyl)sulfonyl]-4-piperazin-1-ylquinoline;
   4-Piperazin-1-yl-6-{4-(trifluoromethyl)phenyl]sulfonyl}quinoline;
   6-[(4-tert-Butylphenyl)sulfonyl]-4-(1,4-diazepan-1-yl)quinoline; or
   4-(1,4-Diazepan-1-yl)-6-[(4-isopropylphenyl)sulfonyl]quinoline;
   or a pharmaceutically acceptable salt of any thereof.

31. The compound of claim 15, or pharmaceutically acceptable salt thereof, wherein the compound is:
   7-(2-Chloro-6-methyl-benzenesulfonyl)-1-piperazin-1-yl-isoquinoline;
   7-(2-t-Butyl-benzenesulfonyl)-1-piperazin-1-yl-isoquinoline;
   7-(3,4-Dichloro-benzenesulfonyl)-1-piperazin-1-yl-isoquinoline;
   7-(2,4-Dimethyl-benzenesulfonyl)-1-piperazin-1-yl-isoquinoline;
   7-(2,5-Dimethyl-benzenesulfonyl)-1-piperazin-1-yl-isoquinoline;
   7-(p-Chloro-benzenesulfonyl)-1-piperazin-1-yl-isoquinoline;
   7-Benzenesulfonyl-1-[1,4]diazepan-1-yl-isoquinoline,hydrochloride;
   7-(4-tert-Butyl-benzenesulfonyl)-1-[1,4]diazepan-1-yl]-isoquinoline;
   7-(2-Chloro-6-methyl-benzenesulfonyl)-1-[1,4]diazepan-1-yl]-isoquinoline;
   7-(3,5-Dimethyl-benzenesulfonyl)-1-[1,4]diazepan-1-yl]-isoquinoline;
   7-(3,4-Dichloro-benzenesulfonyl)-1-[1,4]diazepan-1-yl]-isoquinoline;
   7-(4-Chloro-benzenesulfonyl)-1-[1,4]diazepan-1-yl]-isoquinoline;
   7-(3,4-Dimethyl-benzenesulfonyl)-1-[1,4]diazepan-1-yl]-isoquinoline;
   7-(2-tert-Butyl-benzenesulfonyl)-1-[1,4]diazepan-1-yl]-isoquinoline;
   7-Benzenesulfonyl-1-piperazin-yl-isoquinoline; or
   7-(4-tert-Butyl-benzenesulfonyl)-1-piperazin-yl-isoquinoline;
   or a pharmaceutically acceptable salt of any thereof.

32. The compound of claim 17, or pharmaceutically acceptable salt thereof, wherein the compound is:
   4-(1,4-Diazepan-1-yl)-2-(phenylsulfonyl)thieno[3,2-c]pyridine;
   4-(1,4-Diazepan-1-yl)-2-[(3,4-dichlorophenyl)sulfonyl]thieno[3,2-c]pyridine;
   4-(1,4-Diazepan-1-yl)-2-[4-tert-butylphenylsulfonyl)thieno[3,2-c]pyridine;
   4-(1,4-Diazepan-1-yl)-2-[4-tert-butylphenylsulfonyl)thieno[3,2-c]pyridine;
   4-(1,4-Diazepan-1-yl)-2-[3,4-dimethylphenylsulfonyl)thieno[3,2-c]pyridine;
   2-[(4-Bromophenyl)sulfonyl]-4-(1,4-diazepan-1-yl)thieno[3,2-c]pyridine;
   2-(Phenylsulfonyl)-4-piperazin-1-ylthieno[3,2-c]pyridine;
   2-(3-Methoxy-benzenesulfonyl)-4-piperazin-1-yl-thieno[3,2-c]pyridine;
   2-(4-Methoxy-benzenesulfonyl)-4-piperazin-1-yl-thieno[3,2-c]pyridine;
   4-Piperazin-1-yl-2-{[4-trifluoromethyl)phenyl]sulfonyl}thieno[3,2-c]pyridine;
   2-[(2-tert-Butylphenyl)sulfonyl]-4-piperazin-1-ylthieno[3,2-c]pyridine;
   2-[(3,4-Dichlorophenyl)sulfonyl]-4-piperazin-1-ylthieno[3,2-c]pyridine-2-sulfonamide;
   2-[(4-tert-Butylphenyl)sulfonyl]-4-piperazin-1-ylthieno[3,2-c]pyridine;
   2-(1-Naphthyl sulfonyl)-4-piperazin-1-ylthieno[3,2-c]pyridine;
   2-[(3-Fluorophenyl)sulfonyl]-4-piperazin-1-ylthieno[3,2-c]pyridine-2-sulfonamide;
   2-(Mesitylsulfonyl)-4-piperazin-1-ylthieno[3,2-c]pyridine;
   2-[(2-Methoxyphenyl)sulfonyl]-4-piperazin-1-ylthieno[3,2-c]pyridine;
   2-[(2,4-Dimethoxyphenyl)sulfonyl]-4-piperazin-1-ylthieno[3,2-c]pyridine;
   2-[(2,4-Dimethylphenyl)sulfonyl]-4-piperazin-1-ylthieno[3,2-c]pyridine;
   2-[(2,5-Dimethylphenyl)sulfonyl]-4-piperazin-1-ylthieno[3,2-c]pyridine;

2-[(2-Ethylphenyl)sulfonyl]-4-piperazin-1-ylthieno[3,2-c]pyridine;
4-(Piperazinyl)-2-(3-methoxybenzyl-sulfonyl)-thienopyridine;
2-(Benzylsulfonyl)-4-piperazin-1-ylthieno[3,2-c]pyridine;
4-Piperazin-1-yl-2-{[4-(trifluoromethyl)benzyl]sulfonyl}thieno[3,2-c]pyridine;
2-[(3-Bromobenzyl)sulfonyl]-4-piperazin-1-ylthieno[3,2-c]pyridine;
2-[(2,3-Difluorobenzyl)sulfonyl]-4-piperazin-1-ylthieno[3,2-c]pyridine;
2-[(4-Bromobenzyl)sulfonyl]-4-piperazin-1-ylthieno[3,2-c]pyridine;
2-{[2,5-bis(Trifluoromethyl)benzyl]sulfonyl}-4-piperazin-1-ylthieno[3,2-c]pyridine;
2-[(4-Methylbenzyl)sulfonyl]-4-piperazin-1-ylthieno[3,2-c]pyridine;
2-{[5-Chloro-2-(trifluoromethyl)benzyl]sulfonyl}-4-piperazin-1-ylthieno[3,2-c]pyridine;
2-[(3,5-Dimethoxybenzyl)sulfonyl]-4-piperazin-1-ylthieno[3,2-c]pyridine;
2-[(2-Naphthylmethyl)sulfonyl]-4-piperazin-1-ylthieno[3,2-c]pyridine;
4-Piperazin-1-yl-2-{[4-(1,2,3-thiadiazol-4-yl)benzyl]sulfonyl}thieno[3,2-c]pyridine;
1-(4-Pyrrolidin-1-ylphenyl)-2-[(4-piperazine-1-ylthieno[3,2-c]pyridin-2-yl)sulfonyl]ethanone; or
1-[4-(Diethylamino)phenyl]-2-[(4-piperazine-1-ylthieno[3,2-c]pyridin-2-yl)sulfonyl]ethanone;
or a pharmaceutically acceptable salt of any thereof.

33. The compound of claim 17, or pharmaceutically acceptable salt thereof, wherein the compound is:
1-(4-Methylphenylsulfonyl)-4-piperazin-1-yl-1H-pyrrolo[3,2-c]pyridine;
1-(3-Chloro-2-methylphenylsulfonyl)-4-piperazin-1-yl-1H-pyrrolo[3,2-c]pyridine;
1-(3,4-Dimethoxyphenylsulfonyl)-4-piperazin-1-yl-1H-pyrrolo[3,2-c]pyridine;
4-(4-Piperazin-1-yl-pyrrolo[3,2-c]pyridine-1-sulfonyl)-benzonitrile;
1-(4,5-Dichloro-thiophene-2-sulfonyl)-4-piperazin-1-yl-1H-pyrrolo[3,2-c]pyridine;
1-(2-Chloro-4-fluorophenylsulfonyl)-4-piperazin-1-yl-1H-pyrrolo[3,2-c]pyridine;
1-Phenylmethanesulfonyl-4-piperazin-1-yl-1H-pyrrolo[3,2-c]pyridine;
1-(5-Chloro-thiophene-2-sulfonyl)-4-piperazin-1-yl-1H-pyrrolo[3,2-c]pyridine;
1-(4-Butyl-benzenesulfonyl)-4-piperazin-1-yl-1H-pyrrolo[3,2-c]pyridine;
1-(4-Phenoxy-benzenesulfonyl)-4-piperazin-1-yl-1H-pyrrolo[3,2-c]pyridine;
1-(Phenylsulfonyl)-4-piperazin-1-yl-1H-pyrrolo[3,2-c]pyridine;
1-[(4-Chlorophenyl)sulfonyl]-4-piperazin-1-yl-1H-pyrrolo[3,2-c]pyridine;
1-[(4-Methoxyphenyl)sulfonyl]-4-piperazin-1-yl-1H-pyrrolo[3,2-c]pyridine;
1-[(2-Methoxy-5-methylphenyl)sulfonyl]-4-piperazin-1-yl-1H-pyrrolo[3,2-c]pyridine; or
4-Piperazin-1-yl-1-{[2-(trifluoromethyl)phenyl]sulfonyl}-1H-pyrrolo[3,2-c]pyridine;
or a pharmaceutically acceptable salt of any thereof.

34. The compound of claim 23, wherein the compound is:
N-(4-Methylphenyl)-4-(4-methylpiperazin-1-yl)thieno[3,2-c]pyridine-2-sulfonamide;
2-Bromo-4-(4-methylpiperazin-1-yl)-thieno[3,2-c]pyridine-3-sulfonic acid p-tolylamide;
4-(4-Methylpiperazin-1-yl)-n-phenylthieno[3,2-c]pyridine-2-sulfonamide;
4-Piperazin-1-yl-thieno[3,2-c]pyridine-2-sulfonic acid (3-fluoro-5-trifluoromethyl-phenyl)-amide;
4-Piperazin-1-yl-thieno[3,2-c]pyridine-2-sulfonic acid (4-chloro-phenyl)-amide;
4-Piperazin-1-yl-thieno[3,2-c]pyridine-2-sulfonic acid (4-isopropyl-phenyl)-amide;
4-Piperazin-1-yl-thieno[3,2-c]pyridine-2-sulfonic acid p-tolylamide;
4-(4-Methylpiperazin-1-yl)-N-(2-cyclohex-1-en-1-yl-ethyl)thieno[3,2-c]pyridine-2-sulfonamide;
2-(4-(4-Methylpiperazin-1-yl)thieno[3,2-c]pyridin-2-ylsulfonyl)-1,2,3,4-tetrahydroisoquinoline;
4-(4-Methylpiperazin-1-yl)-N-(2-thien-2-ylethyl)thieno[3,2-c]pyridine-2-sulfonamide;
4-(4-Methylpiperazin-1-yl)-N-[1-(1-naphthyl)ethyl]thieno[3,2-c]pyridine-2-sulfonamide;
4-(4-Methylpiperazin-1-yl)-N-(4-hexylphenyl)thieno[3,2-c]pyridine-2-sulfonamide;
N-(3-Chlorobenzyl)-4-(4-methylpiperazin-1-yl)thieno[3,2-c]pyridine-2-sulfonamide;
4-(4-Methylpiperazin-1-yl)-N-[1-(4-fluorophenyl)ethyl]thieno[3,2-c]pyridine-2-sulfonamide;
N-(2,3-Difluorobenzyl)-4-(4-methylpiperazin-1-yl)thieno[3,2-c]pyridine-2-sulfonamide;
4-(4-Methylpiperazin-1-yl)-N-(4-chloro-2,5-dimethoxyphenyl)thieno[3,2-c]pyridine-2-sulfonamide;
2-Bromo-4-(4-methylpiperazin-1-yl)-N-(2-cyclohex-1-en-1-ylethyl)thieno[3,2-c]pyridine-3-sulfonamide;
2-Bromo-4-(4-methylpiperazin-1-yl)-N-[(1S)-1-(2-naphthyl)ethyl]thieno[3,2-c]pyridine-3-sulfonamide;
2-Bromo-4-(4-methylpiperazin-1-yl)-N-[1-(4-fluorophenyl)ethyl]thieno[3,2-c]pyridine-3-sulfonamide;
2-Bromo-4-(4-methylpiperazin-1-yl)-N-(2,4,5-trimethoxyphenyl)thieno[3,2-c]pyridine-3-sulfonamide;
N-(3,4-Dichlorophenyl)-4-piperazin-1-ylthieno[3,2-c]pyridine-2-sulfonamide;
N-(2,4-Difluorophenyl)-4-piperazin-1-ylthieno[3,2-c]pyridine-2-sulfonamide;
4-Piperazin-1-yl-N-[-3-(trifluoromethyl)phenyl]thieno[3,2-c]pyridine-2-sulfonamide;
N-(3-Ethylphenyl)-4-piperazin-1-ylthieno[3,2-c]pyridine-2-sulfonamide;
N-(3,4-Dimethoxyphenyl)-4-piperazin-1-ylthieno[3,2-c]pyridine-2-sulfonamide;
N-(4-Bromo-2-methylphenyl)-4-piperazin-1-ylthieno[3,2-c]pyridine-2-sulfonamide;
2-(4-Piperazin-1-yl-thieno[3,2-c]pyridine-2-sulfonyl)-1,2,3,4-tetrahydro-isoquinoline;
4-Piperazin-1-yl-thieno[3,2-c]pyridine-2-sulfonic acid (2-thiophen-2-yl-ethyl)-amide;
4-Piperazin-1-yl-thieno[3,2-c]pyridine-2-sulfonic acid (4-chloro-2,5-dimethoxy-phenyl)-amide;
4-Piperazin-1-yl-thieno[3,2-c]pyridine-2-sulfonic acid phenethyl-amide;
4-Piperazin-1-yl-thieno[3,2-c]pyridine-2-sulfonic acid (2,6-diethyl-phenyl)-amide;
4-Piperazin-1-yl-thieno[3,2-c]pyridine-2-sulfonic acid (3-phenyl-propyl)-amide;
4-Piperazin-1-yl-thieno[3,2-c]pyridine-2-sulfonic acid (3,3-diphenyl-propyl)-amide;
4-Piperazin-1-yl-thieno[3,2-c]pyridine-2-sulfonic acid [2-(5-methoxy-1H-indol-3-yl)-ethyl]-amide;

4-Piperazin-1-yl-thieno[3,2-c]pyridine-2-sulfonic acid 4-trifluoromethyl-benzylamide;
4-Piperazin-1-yl-thieno[3,2-c]pyridine-2-sulfonic acid benzyl-ethyl-amide;
N-(3-Ethylphenyl)-4-piperazin-1-ylthieno[3,2-c]pyridine-3-sulfonamide;
N-(4-Isopropylphenyl)-4-piperazin-1-ylthieno[3,2-c]pyridine-3-sulfonamide;
N-(4-Methylphenyl)-4-(pyrrolidin-3-yloxy)thieno[3,2-c]pyridine-2-sulfonamide;
N-(4-Methylphenyl)-4-(piperidin-4-yloxy)thieno[3,2-c]pyridine-2-sulfonamide;
N-(2,3-Difluorobenzyl)-4-piperazin-1-ylthieno[3,2-c]pyridine-2-sulfonamide;
N-(3-Chlorobenzyl)-4-piperazin-1-ylthieno[3,2-c]pyridine-2-sulfonamide;
4-Piperazin-1-yl-thieno[3,2-c]pyridine-2-sulfonic acid phenylamide;
4-Piperazin-1-yl-thieno[3,2-c]pyridine-2-sulfonic acid (4-tert-butyl-phenyl)-amide;
4-(4-Methyl-piperazin-1-yl)-thieno[3,2-c]pyridine-2-sulfonic acid phenylamide;
4-(4-Methyl-piperazin-1-yl)-thieno[3,2-c]pyridine-2-sulfonic acid (3-chloro-phenyl)-amide;
2-Bromo-4-(4-methyl-piperazin-1-yl)-thieno[3,2-c]pyridine-3-sulfonic acid phenylamide;
4-(4-Methyl-piperazin-1-yl)-thieno[3,2-c]pyridine-3-sulfonic acid (4-methylphenyl)-amide; or
N-Phenyl-7-piperazin-1-ylthieno[2,3-c]pyridine-2-sulfonamide;
or a pharmaceutically acceptable salt of any thereof.

35. A compound of claim 24, or pharmaceutically acceptable salt thereof, wherein the compound is:
N-(4-methylphenyl)-4-piperazin-1-ylfuro[3,2-c]pyridine-2-sulfonamide;
N-phenyl-4-piperazin-1-ylfuro[3,2-c]pyridine-2-sulfonamide; or
N-phenyl-7-piperazin-1-ylfuro[2,3-c]pyridine-2-sulfonamide;
or a pharmaceutically acceptable salt of any thereof.

36. A compound according to claim 25, or pharmaceutically acceptable salt thereof, which is the compound
4-piperazin-1-yl-thiazolo[4,5-c]pyridine-2-sulfonic acid phenylamide;
or a pharmaceutically acceptable salt thereof.

37. A compound according to claim 26, or pharmaceutically acceptable salt thereof, which is the compound N-(4-methylphenyl)-4-piperazin-1-yl-1H-pyrrolo[3,2-c]pyridine-2-sulfonamide;
N-phenyl-4-piperazin-1-yl-1H-pyrrolo[3,2-c]pyridine-2-sulfonamide; or
N-phenyl-7-piperazin-1-yl-1H-pyrrolo[2,3-c]pyridine-2-sulfonamide;
or a pharmaceutically acceptable salt of any thereof.

38. A compound of claim 27, or pharmaceutically acceptable salt thereof, wherein the compound is:
4-Chloro-N-[4-(pyrrolidin-3-yloxy)-1-naphthyl]benzenesulfonamide;
4-Methoxy-N-[4-(pyrrolidin-3-yloxy)-1-naphthyl]benzenesulfonamide;
5-Chloro-N-[4-(pyrrolidin-3-yloxy)-1-naphthyl]thiophene-2-sulfonamide;
4-Chloro-N-[4-(piperidin-3-yloxy)-1-naphthyl]benzenesulfonamide;
4-Methoxy-N-[4-(piperidin-3-yloxy)-1-naphthyl]benzenesulfonamide;
5-Fluoro-2-methyl-N-[4-(piperidin-4-yloxy)-1-naphthyl]benzenesulfonamide;
5-Chloro-N-[4-(piperidin-4-yloxy)-1-naphthyl]thiophene-2-sulfonamide;
4-Chloro-N-{4-[(3S)-pyrrolidin-3-yloxy]-1-naphthyl}benzenesulfonamide; or
4-Chloro-N-{4-[(3R)-pyrrolidin-3-yloxy]-1-naphthyl}benzenesulfonamide;
or a pharmaceutically acceptable salt of any thereof.

39. A pharmaceutical composition comprising a compound of formula (I) of claim 1, or a pharmaceutically acceptable salt thereof, and a pharmaceutically acceptable diluent or carrier.

40. The compound of claim 1, or pharmaceutically acceptable salt thereof, wherein P is

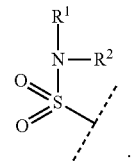

41. The compound of claim 40, or pharmaceutically acceptable salt thereof, wherein $R^2$ is H.

* * * * *